US012577195B2

(12) United States Patent
Ko et al.

(10) Patent No.: US 12,577,195 B2
(45) Date of Patent: Mar. 17, 2026

(54) LIGHT EMITTING ELEMENT AND DISPLAY DEVICE INCLUDING THE SAME

(71) Applicant: Samsung Display Co., Ltd., Yongin-si (KR)

(72) Inventors: Hyomin Ko, Suwon-si (KR); Ilsoo Oh, Seoul (KR); Bora Lee, Hwaseong-si (KR); Illhun Cho, Seoul (KR); Minji Kim, Hwaseong-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 953 days.

(21) Appl. No.: 17/835,229

(22) Filed: Jun. 8, 2022

(65) Prior Publication Data

US 2023/0129980 A1 Apr. 27, 2023

(30) Foreign Application Priority Data

Sep. 7, 2021 (KR) ........................ 10-2021-0119309

(51) Int. Cl.
*C07C 211/54* (2006.01)
*C07D 209/82* (2006.01)
(Continued)

(52) U.S. Cl.
CPC .......... *C07C 211/54* (2013.01); *C07D 209/82* (2013.01); *C07D 307/91* (2013.01); (Continued)

(58) Field of Classification Search
CPC ..... H10K 50/15; H10K 50/156; H10K 85/631
See application file for complete search history.

(56) References Cited

U.S. PATENT DOCUMENTS 8,809,079 B2 8/2014 Chen et al.
10,483,479 B2 11/2019 Tanaka
(Continued)

FOREIGN PATENT DOCUMENTS

KR 10-2019-0031602 3/2019
KR 10-2021-0004874 1/2021
KR 10-2021-0064485 6/2021

OTHER PUBLICATIONS

Amin Salehi et al., "Highly Efficient Organic Light-Emitting Diode Using A Low Refractive Index Electron Transport Layer", Advanced Optical Materials, May 2, 2017, pp. 1-7, vol. 5, No. 1700197.
(Continued)

*Primary Examiner* — Vu A Nguyen
(74) *Attorney, Agent, or Firm* — CANTOR COLBURN LLP

(57) ABSTRACT

A light emitting element includes a first electrode, a hole transport region disposed on the first electrode, an emission layer disposed on the hole transport region, an electron transport region disposed on the emission layer, and a second electrode disposed on the electron transport region, wherein the hole transport region includes a first hole transport layer disposed adjacent to the first electrode and including a first amine compound having a first refractive index, a second hole transport layer disposed between the first hole transport layer and the emission layer, and including a second amine compound having a second refractive index greater than the first refractive index, and a third hole transport layer disposed between the second hole transport layer and the emission layer, and including a third amine compound having a third refractive index less than the second refractive index, thereby having high luminous efficiency.

28 Claims, 10 Drawing Sheets

(51) Int. Cl.

| | |
|---|---|
| ***C07D 307/91*** | (2006.01) |
| ***C07D 333/76*** | (2006.01) |
| ***C07D 405/12*** | (2006.01) |
| ***C07D 409/12*** | (2006.01) |
| ***C07F 5/02*** | (2006.01) |
| ***H10K 50/15*** | (2023.01) |
| ***H10K 50/16*** | (2023.01) |
| ***H10K 50/818*** | (2023.01) |
| ***H10K 85/30*** | (2023.01) |
| ***H10K 85/60*** | (2023.01) |

(52) U.S. Cl.

CPC ......... *C07D 333/76* (2013.01); *C07D 405/12* (2013.01); *C07D 409/12* (2013.01); *C07F 5/027* (2013.01); *H10K 85/322* (2023.02); *H10K 85/615* (2023.02); *H10K 85/622* (2023.02); *H10K 85/624* (2023.02); *H10K 85/631* (2023.02); *H10K 85/633* (2023.02); *H10K 85/6572* (2023.02); *H10K 85/6574* (2023.02); *H10K 85/6576* (2023.02); *H10K 50/156* (2023.02); *H10K 50/16* (2023.02); *H10K 50/818* (2023.02)

(56) References Cited

U.S. PATENT DOCUMENTS

| | | | | |
|---|---|---|---|---|
| 12,275,683 | B2 * | 4/2025 | Ma ........................ | C07D 209/82 |
| 2021/0005814 | A1 | 1/2021 | Watabe et al. | |
| 2021/0159418 | A1 | 5/2021 | Ye et al. | |
| 2022/0278292 | A1 * | 9/2022 | Watabe ................ | H10K 50/818 |

OTHER PUBLICATIONS

Hyun Shin et al., "Sky-Blue Phosphorescent OLEDs with 34.1% External Quantum Efficiency Using a Low Refractive Index Electron Transporting Layer", Advanced Materials, Apr. 9, 2016, pp. 4920-4925, vol. 28.

* cited by examiner

LIGHT EMITTING ELEMENT AND DISPLAY DEVICE INCLUDING THE SAME

CROSS-REFERENCE TO RELATED APPLICATION(S)

This application claims priority to and benefits of Korean Patent Application No. 10-2021-0119309 under 35 U.S.C. § 119, filed on Sep. 7, 2021 in the Korean Intellectual Property Office, the entire contents of which are incorporated herein by reference.

BACKGROUND

1. Technical Field

The disclosure relates to a light emitting element including multiple hole transport layers and a display device including the same.

2. Description of the Related Art

Active development continues for organic electroluminescence display devices and the like as image display devices. The organic electroluminescence displays are display devices which include so-called self-luminescent light emitting elements in which holes and electrons respectively injected from a first electrode and a second electrode recombine in an emission layer, so that a luminescent material in the emission layer emits light to accomplish display.

In the application of light emitting elements to display devices, there is a demand for light emitting elements having a low driving voltage, high luminous efficiency, and a long life, and continuous development is required on materials for light emitting elements which are capable of stably attaining such characteristics.

Studies have been conducted regarding the optimization of structures in light emitting elements to obtain light emitting elements having high luminous efficiency.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

The disclosure provides a light emitting element exhibiting excellent luminous efficiency, and a display device including the same.

An embodiment provides a light emitting element which may include a first electrode, a hole transport region disposed on the first electrode, an emission layer disposed on the hole transport region, an electron transport region disposed on the emission layer, and a second electrode disposed on the electron transport region. The hole transport region may include a first hole transport layer disposed adjacent to the first electrode and including a first amine compound having a first refractive index, a second hole transport layer disposed between the first hole transport layer and the emission layer, and including a second amine compound having a second refractive index greater than the first refractive index, and a third hole transport layer disposed between the second hole transport layer and the emission layer, and including a third amine compound having a third refractive index less than the second refractive index. The first amine compound and the third amine compound may each independently be a compound represented by Formula 1.

[Formula 1]

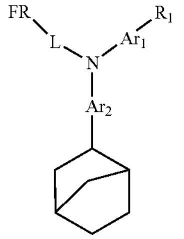

In Formula 1, $R_1$ may be a substituted or unsubstituted adamantyl group, a substituted or unsubstituted cyclohexyl group, or a substituted or unsubstituted bicycloheptyl group, $Ar_1$ and $Ar_2$ may each independently be a substituted or unsubstituted arylene group having 6 to 30 ring-forming carbon atoms, L may be a direct linkage, a substituted or unsubstituted arylene group having 6 to 30 ring-forming carbon atoms, or a substituted or unsubstituted heteroarylene group having 2 to 30 ring-forming carbon atoms, and FR may be a group represented by Formula 2.

[Formula 2]

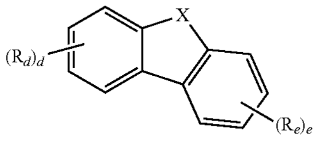

In Formula 2, X may be $C(R_a)(R_b)$, N, $N(R_c)$, O, or S, $R_a$ to $R_c$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring, d and e may each independently be an integer from 0 to 4, and $R_d$ and $R_e$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In an embodiment, a difference between the second refractive index and the first refractive index may be in a range of about 0.1 to about 1.1, and a difference between the second refractive index and the third refractive index may be in a range of about 0.1 to about 1.1.

In an embodiment, the first refractive index and the third refractive index may each independently be in a range of about 1.3 to about 1.8.

In an embodiment, the second refractive index may be in a range of about 1.8 to about 2.4.

In an embodiment, a thickness ratio of the first hole transport layer to the second hole transport layer to the third hole transport layer may be in a range of about 4.50:1.00:4.50 to about 0.125:1.00:0.125.

In an embodiment, the compound represented by Formula 1 may be represented by Formula 1-1 or Formula 1-2.

[Formula 1-1]

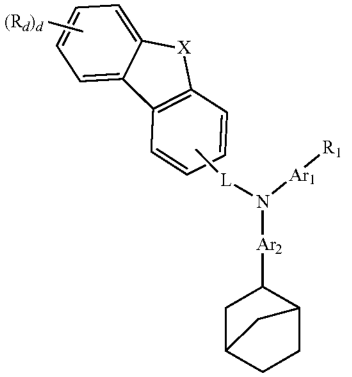

[Formula 1-2]

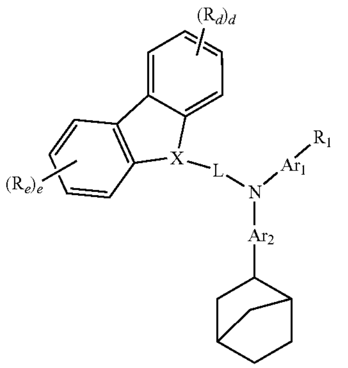

In Formulas 1-1 and 1-2, $R_1$, L, $Ar_1$, and $Ar_2$ are the same as defined in Formula 1, and X, $R_d$, $R_e$, d, and e are the same as defined in Formula 2.

In an embodiment, the compound represented by Formula 1-2 may be represented by Formula 1-2A.

[Formula 1-2A]

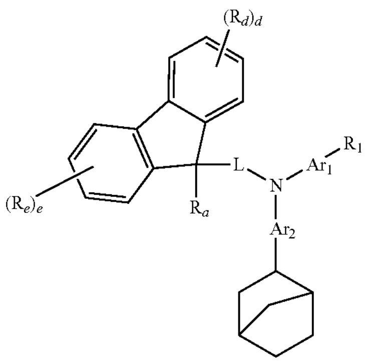

In Formulas 1-2A, $R_1$, L, $Ar_1$, and $Ar_2$ are the same as defined in Formula 1, and $R_a$, $R_d$, $R_e$, d, and e are the same as defined in Formula 2.

In an embodiment, the compound represented by Formula 1 may be represented by Formula 1A.

[Formula 1A]

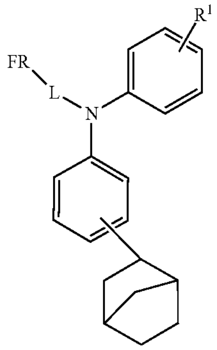

In Formula 1A, $R_1$, L, and FR are the same as defined in Formula 1.

In an embodiment, the first amine compound and the third amine compound may each independently be any one selected from Compound Group 1, which is explained below.

In an embodiment, the second amine compound may be represented by Formula 3.

[Formula 3]

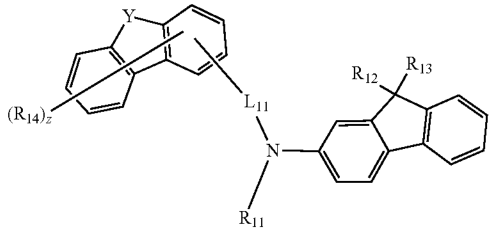

In Formula 3, z may be an integer from 0 to 7, Y may be $C(R_f)(R_g)$, $N(R_h)$, O, or S, $L_{11}$ may be a direct linkage, a substituted or unsubstituted arylene group having 6 to 30 ring-forming carbon atoms, or a substituted or unsubstituted heteroarylene group having 2 to 30 ring-forming carbon atoms, and $R_f$ to $R_h$ and $R_{11}$ to $R_{14}$ may each independently be a hydrogen atom, a deuterium atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In an embodiment, the second amine compound represented by Formula 3 may be represented by any one of Formulas 3-1 to 3-3.

[Formula 3-1]

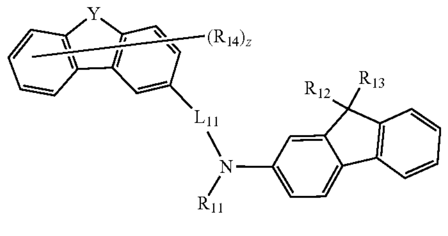

-continued

[Formula 3-2]

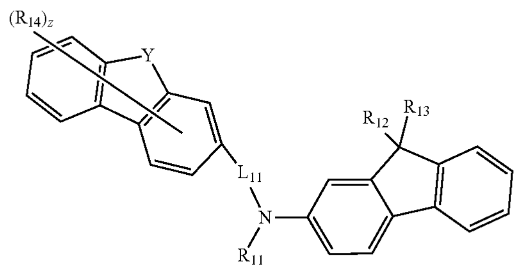

[Formula 3-3]

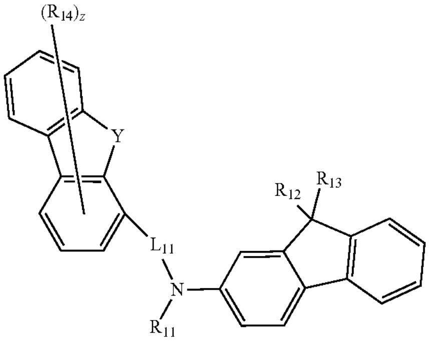

In Formulas 3-1 to 3-3, z, $L_{11}$, Y, and $R_{11}$ to $R_{14}$ are the same as defined in Formula 3.

In an embodiment, the second amine compound represented by Formula 2 may be any one selected from Compound Group 2, which is explained below.

In an embodiment, a light emitting element may include a first electrode, a hole transport region disposed on the first electrode, an emission layer disposed on the hole transport region, an electron transport region disposed on the emission layer, and a second electrode disposed on the electron transport region. The hole transport region may include a first hole transport layer disposed adjacent to the first electrode and including a first amine compound having a first refractive index, a second hole transport layer disposed between the first hole transport layer and the emission layer and including a second amine compound having a second refractive index, and a third hole transport layer disposed between the second hole transport layer and the emission layer and including a third amine compound having a third refractive index. The second amine compound may be represented by Formula 3, and the first amine compound and the third amine compound may each independently be a compound represented by Formula 4.

[Formula 3]

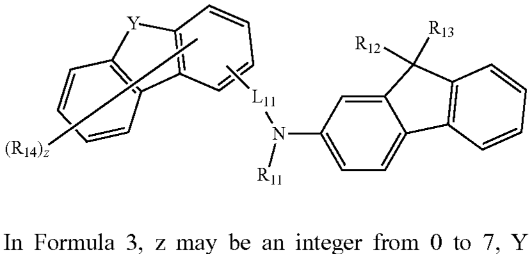

In Formula 3, z may be an integer from 0 to 7, Y is $C(R_f)(R_g)$, $N(R_h)$, O, or S, $L_{11}$ may be a direct linkage, a substituted or unsubstituted arylene group having 6 to 30 ring-forming carbon atoms, or a substituted or unsubstituted heteroarylene group having 2 to 30 ring-forming carbon atoms, and $R_f$ to $R_h$ and $R_{11}$ to $R_{14}$ are each independently a hydrogen atom, a deuterium atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

[Formula 4]

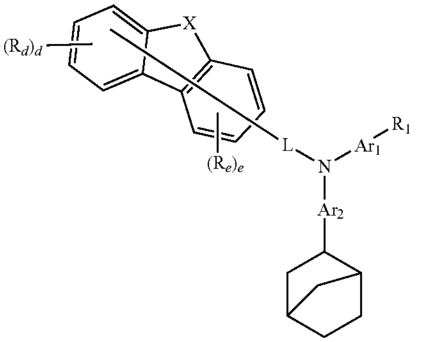

In Formula 4, $R_1$ may be a substituted or unsubstituted adamantyl group, a substituted or unsubstituted cyclohexyl group, or a substituted or unsubstituted bicycloheptyl group, $Ar_1$ and $Ar_2$ may each independently be a substituted or unsubstituted arylene group having 6 to 30 ring-forming carbon atoms, L may be a direct linkage, a substituted or unsubstituted arylene group having 6 to 30 ring-forming carbon atoms, or a substituted or unsubstituted heteroarylene group having 2 to 30 ring-forming carbon atoms, and X may be $C(R_a)(R_b)$, N, $N(R_c)$, O, or S, $R_a$ to $R_c$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring, d and e may each independently be an integer from 0 to 4, and $R_d$ and $R_e$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In an embodiment, the first refractive index and the third refractive index may each independently be in a range of about 1.3 to about 1.8, the second refractive index may be in a range of about 1.8 to about 2.4, and the first refractive index and the third refractive index may each be less than the second refractive index.

In an embodiment, a difference between the second refractive index and the first refractive index may be in a range of about 0.1 to about 1.1, and a difference between the second refractive index and the third refractive index may each be in a range of about 0.1 to about 1.1.

In an embodiment, the compound represented by Formula 4 may be represented by Formula 4-1 or Formula 4-2.

[Formula 4-1]

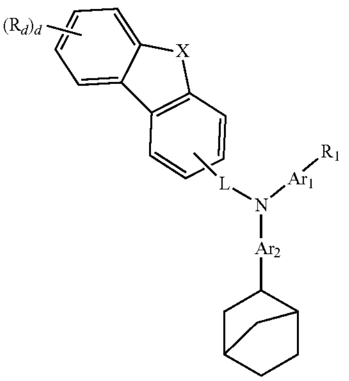

[Formula 4-2]

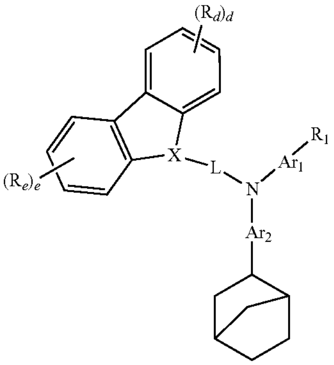

In Formulas 4-1 and 4-2, $R_1$, L, $Ar_1$, $Ar_2$, X, $R_d$, $R_e$, d, and e are the same as defined in Formula 4.

In an embodiment, the compound represented by Formula 4-2 may be represented by Formula 4-2A.

[Formula 4-2]

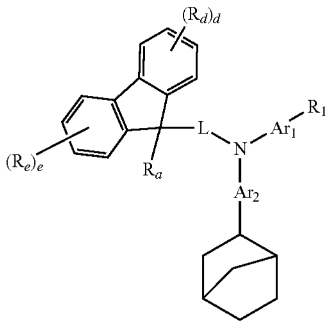

In Formulas 4-2A, $R_1$, L, $Ar_1$, $Ar_2$, $R_a$, $R_d$, $R_e$, d, and e are the same as defined in Formula 4.

In an embodiment, the compound represented by Formula 4 may be represented by Formula 4A.

[Formula 4A]

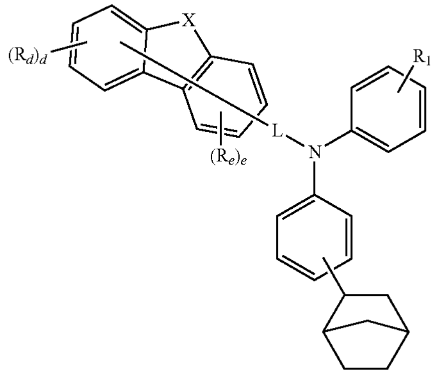

In Formula 4A, $R_1$, L, X, $R_d$, $R_e$, d, and e are the same as defined in Formula 4.

In an embodiment, the second amine compound represented by Formula 3 may be represented b an one of Formulas 3-1 to 3-3.

[Formula 3-1]

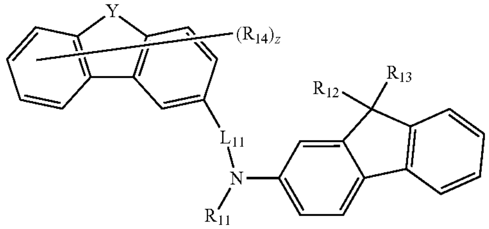

[Formula 3-2]

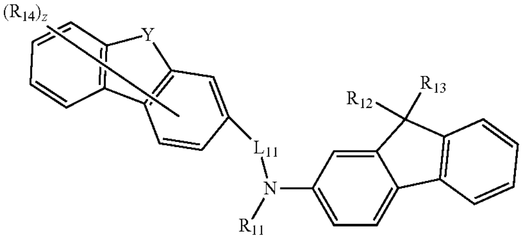

[Formula 3-3]

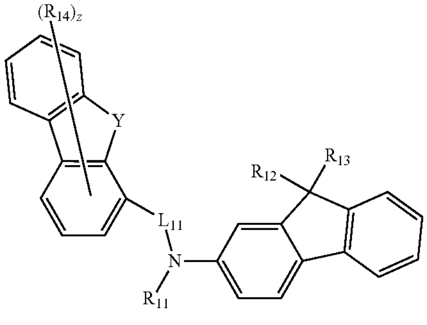

In Formulas 3-1 to 3-3, z, $L_{11}$, Y, and $R_{11}$ to $R_{14}$ are the same as defined in Formula 3.

In an embodiment, a display device may include multiple light emitting elements, wherein the light emitting elements may each include a first electrode, a hole transport region disposed on the first electrode, an emission layer disposed on the hole transport region, an electron transport region disposed on the emission layer, and a second electrode disposed on the electron transport region. The hole transport region may include a first hole transport layer disposed adjacent to the first electrode and including a first amine compound having a first refractive index, a second hole transport layer disposed between the first hole transport layer and the emission layer, and including a second amine compound having a second refractive index greater than the first refractive index, and a third hole transport layer disposed between the second hole transport layer and the emission layer, and including a third amine compound having a third refractive index less than the second refractive index. The first amine compound and the third amine compound may each independently be a compound represented by Formula 1.

[Formula 1]

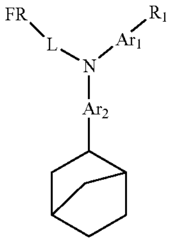

In Formula 1, $R_1$ may be a substituted or unsubstituted adamantyl group, a substituted or unsubstituted cyclohexyl group, or a substituted or unsubstituted bicycloheptyl group, $Ar_1$ and $Ar_2$ may each independently be a substituted or unsubstituted arylene group having 6 to 30 ring-forming carbon atoms, L may be a direct linkage, a substituted or unsubstituted arylene group having 6 to 30 ring-forming carbon atoms, or a substituted or unsubstituted heteroarylene group having 2 to 30 ring-forming carbon atoms, and FR may be a group represented by Formula 2.

[Formula 2]

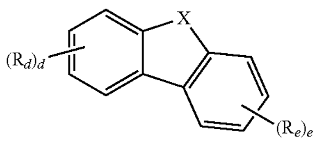

In Formula 2, X $C(R_a)(R_b)$, N, $N(R_c)$, O, or S, $R_a$ to $R_c$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring, d and e may each independently be an integer from 0 to 4, and $R_d$ and $R_e$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In an embodiment, the first refractive index and the third refractive index may each independently be in a range of about 1.3 to about 1.8, and the second refractive index may be in a range of about 1.8 to about 2.4.

In an embodiment, a difference between the second refractive index and the first refractive index may be in a range of about 0.1 to about 1.1.

In an embodiment, a difference between the second refractive index and the third refractive index may be in a range of about 0.1 to about 1.1.

In an embodiment, the light emitting elements may include a first light emitting element including a first emission layer emitting light of a first wavelength, a second light emitting element emitting light of a second wavelength different from the first wavelength and including a second emission layer spaced apart from the first emission layer in a plan view; and a third light emitting element emitting light of a third wavelength different from the first wavelength and the second wavelength, and including a third emission layer spaced apart from the first emission layer and the second emission layer in a plan view.

In an embodiment, at least one emission layer of the first to third emission layers may include a polycyclic compound represented by Formula F-c.

[Formula F-c]

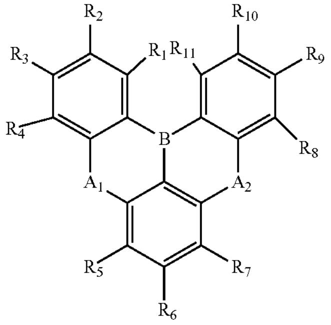

In Formula F-c, $A_1$ and $A_2$ may each independently be O, S, Se, or $N(R_m)$, $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In an embodiment, the first wavelength may be longer than the second wavelength, and the second wavelength may be longer than the third wavelength. The display device may further include a first resonance auxiliary layer disposed between the first emission layer and the hole transport region, a second resonance auxiliary layer disposed between the second emission layer and the hole transport region and having a smaller thickness than the first resonance auxiliary layer, and a third resonance auxiliary layer disposed between the third emission layer and the hole transport region and having a smaller thickness than the second resonance auxiliary layer.

In an embodiment, the first electrode may be a reflective electrode, and the second electrode may be a transflective electrode or a transmissive electrode.

BRIEF DESCRIPTION OF THE DRAWINGS

The accompanying drawings are included to provide a further understanding of the embodiments, and are incorporated in and constitute a part of this specification. The drawings illustrate embodiments of the disclosure and principles thereof. The above and other aspects and features of the disclosure will become more apparent by describing in detail embodiments thereof with reference to the attached drawings, in which.

DETAILED DESCRIPTION OF THE EMBODIMENTS

Figure 1:
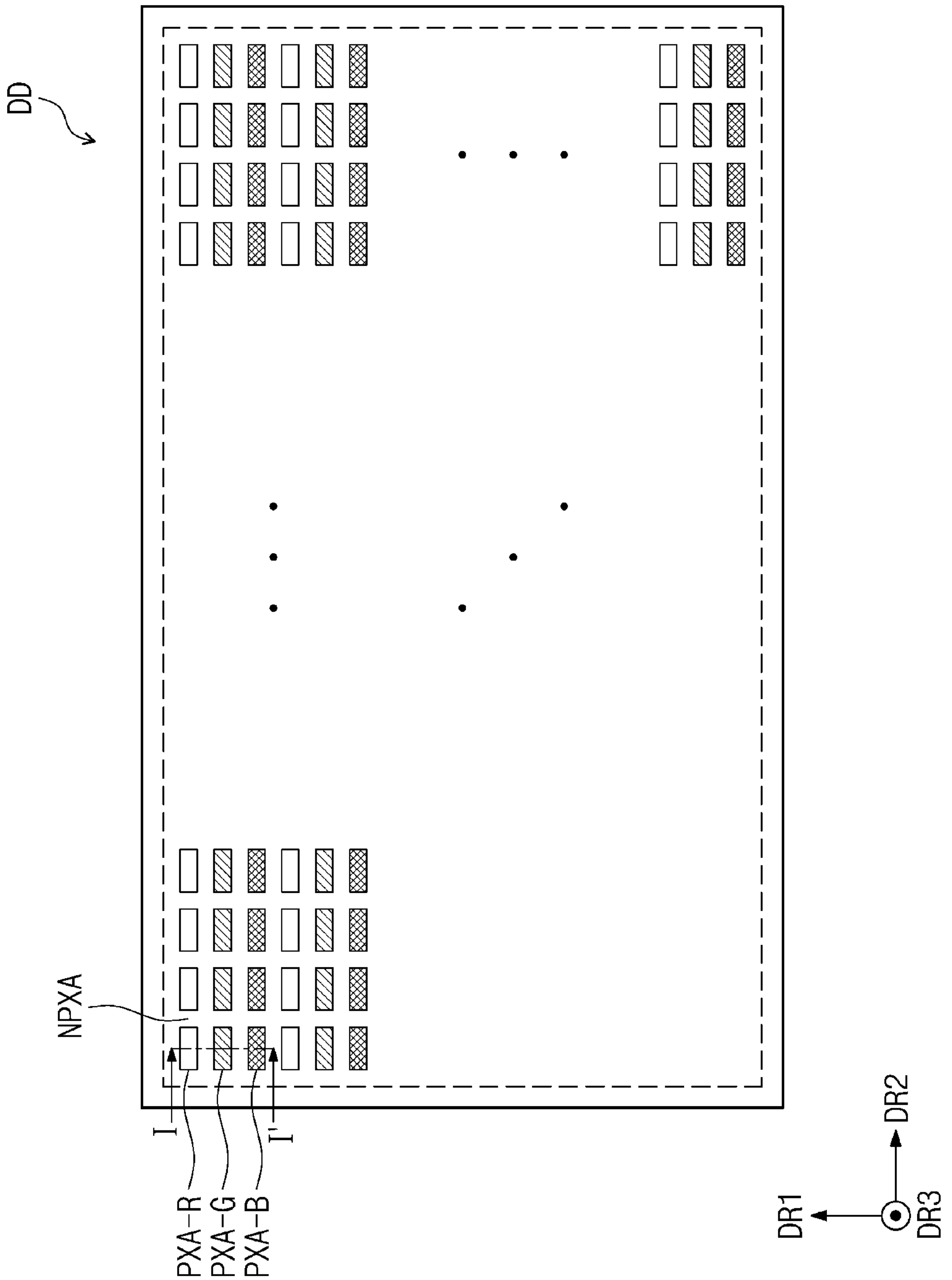
FIG. 1 is a plan view illustrating a display device according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the specification, it will be understood that when an element (or region, layer, part, etc.) is referred to as being "on", "connected to", or "coupled to" another element, it can be directly on, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the specification, when an element is "directly on," "directly connected to," or "directly coupled to" another element, there are no intervening elements present. For example, "directly on" may mean that two layers or two elements are disposed without an additional element such as an adhesion element therebetween.

As used herein, the expressions used in the singular such as "a," "an," and "the," are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from the group of" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, ±10%, or 5% of the stated value.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

In the specification, the term “substituted or unsubstituted” may mean a group that is substituted or unsubstituted with at least one substituent selected from the group consisting of a deuterium atom, a halogen atom, a cyano group, a nitro group, an amine group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. Each of the substituents listed above may itself be substituted or unsubstituted. For example, a biphenyl group may be interpreted as an aryl group, or may be interpreted as a phenyl group substituted with a phenyl group.

In the specification, the term “bonded to an adjacent group to form a ring” may mean a group that is bonded to an adjacent group to form a substituted or unsubstituted hydrocarbon ring or a substituted or unsubstituted heterocycle. The hydrocarbon ring may be an aliphatic hydrocarbon ring or an aromatic hydrocarbon ring. The heterocycle may be an aliphatic heterocycle or an aromatic heterocycle. The hydrocarbon ring and the heterocycle may each independently be monocyclic or polycyclic. A ring that is formed by adjacent groups being bonded to each other may itself be connected to another ring to form a spiro structure.

In the specification, the term “an adjacent group” may mean a substituent substituted for an atom which is directly connected to an atom substituted with a corresponding substituent, another substituent substituted for an atom which is substituted with a corresponding substituent, or a substituent sterically positioned at the nearest position to a corresponding substituent. For example, two methyl groups in 1,2-dimethylbenzene may be interpreted as mutually “adjacent groups” and two ethyl groups in 1,1-diethylcyclopentane may be interpreted as mutually “adjacent groups”. For example, two methyl groups in 4,5-dimethylphenanthrene may be interpreted as mutually “adjacent groups”.

In the specification, examples of a halogen atom may include a fluorine atom, a chlorine atom, a bromine atom, or an iodine atom.

In the specification, an alkyl group may be a linear, a branched, or a cyclic type. The number of carbon atoms in the alkyl group may be 1 to 50, 1 to 30, 1 to 20, 1 to 10, or 1 to 6. Examples of the alkyl group may include a methyl group, an ethyl group, an n-propyl group, an isopropyl group, an n-butyl group, a s-butyl group, a t-butyl group, an i-butyl group, a 2-ethylbutyl group, a 3,3-a dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but are not limited thereto.

In the specification, a hydrocarbon ring group may be any functional group or substituent derived from an aliphatic hydrocarbon ring. The hydrocarbon ring group may be a saturated hydrocarbon ring group having 5 to 20 ring-forming carbon atoms.

In the specification, an aryl group may be any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, etc., but are not limited thereto.

In the specification, a fluorenyl group may be substituted, and two substituents may be bonded to each other to form a spiro structure. Examples of substituted fluorenyl groups may include the following groups. However, embodiments are not limited thereto.

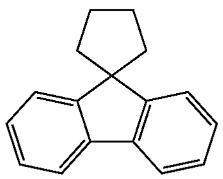
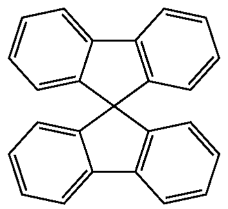
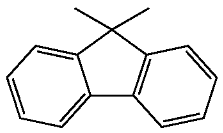
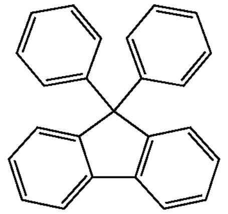

In the specification, a heterocyclic group may be any functional group or substituent derived from a ring containing at least one of B, O, N, P, Si, or S as a heteroatom. The heterocyclic group may be an aliphatic heterocyclic group or an aromatic heterocyclic group. The aromatic heterocyclic group may be a heteroaryl group. The aliphatic heterocycle and the aromatic heterocycle may each independently be monocyclic or polycyclic.

In the specification, a heterocyclic group may contain at least one of B, O, N, P, Si, or S as a heteroatom. When the heterocyclic group contains two or more heteroatoms, the two or more heteroatoms may be the same as or different from each other. The heterocyclic group may be a monocyclic heterocyclic group or a polycyclic heterocyclic group, and may include a heteroaryl group. The number of ring-forming carbon atoms in the heterocyclic group may be 2 to 30, 2 to 20, or 2 to 10.

In the specification, an aliphatic heterocyclic group may contain at least one of B, O, N, P, Si or S as a heteroatom. The number of ring-forming carbon atoms in the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., but are not limited to thereto In the specification, a heteroaryl group may include at least one of B, O, N, P, Si, or S as a heteroatom. When the heteroaryl group contains two or more heteroatoms, the two or more heteroatoms may be the same as or different from each other. The heteroaryl group may be a monocyclic heteroaryl group or a polycyclic heteroaryl group. The number of ring-forming carbon atoms in the heteroaryl group may be 2 to 30, 2 to 20, or 2 to 10. Examples of the heteroaryl group may include a thiophene group, a furan group, a pyrrole group, an imidazole group, a triazole group, a pyridine group, a bipyridine group, a pyrimidine, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazole group, a thiadiazole group, a phenothiazine group, a dibenzosilole group, a dibenzofuran group, etc., but are not limited thereto.

In the specification, the above description of the aryl group may be applied to an arylene group, except that the arylene group is a divalent group. The above description of the heteroaryl group may be applied to a heteroarylene group, except that the heteroarylene group is a divalent group.

In the specification, a silyl group may be an alkyl silyl group or an aryl silyl group. Examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., but are not limited thereto.

In the specification, the number of carbon atoms in an amino group is not particularly limited, but may be 1 to 30. The amino group may include an alkyl amino group, an aryl amino group, or a heteroaryl amino group. Examples of the amino group include a methylamino group, a dimethylamino group, a phenylamino group, a diphenylamino group, a naphthylamino group, a 9-methyl-anthracenylamino group, a triphenylamino group, etc., but are not limited thereto.

In the specification, the number of carbon atoms in a carbonyl group is not particularly limited, but may be 1 to 40, 1 to 30, or 1 to 20. For example, the carbonyl group may have one of the following structures, but is not limited thereto.

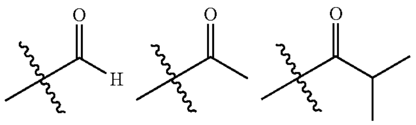

-continued

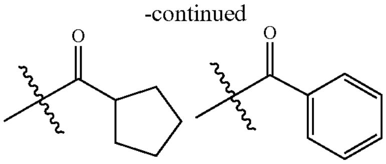

In the specification, the number of carbon atoms in a sulfinyl group or a sulfonyl group is not particularly limited, but may be 1 to 30. The sulfinyl group may be an alkyl sulfinyl group or an aryl sulfinyl group. The sulfonyl group may be an alkyl sulfonyl group or an aryl sulfonyl group.

In the specification, a thio group may be an alkyl thio group or an aryl thio group. The thio group may be a sulfur atom that is bonded to an alkyl group or an aryl group as defined above. Examples of the thio group may include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., but are not limited to thereto.

In the specification, an oxy group may be an oxygen atom that is bonded to an alkyl group or an aryl group as defined above. The oxy group may be an alkoxy group or an aryl oxy group. The alkoxy group may be linear, branched, or cyclic. The number of carbon atoms in the alkoxy group is not particularly limited, but may be, for example, 1 to 20, or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc., but are not limited thereto.

In the specification, a boron group may be a boron atom that is bonded to an alkyl group or an aryl group as defined above. The boron group may be an alkyl boron group or an aryl boron group. Examples of the boron group may include a trimethylboron group, a triethylboron group, a t-butyldimethylboron group, a triphenylboron group, a diphenylboron group, a phenylboron group, etc., but are not limited thereto.

In the specification, an alkenyl group may be linear or branched. The number of carbon atoms is not particularly limited, but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styryl vinyl group, etc., but are not limited thereto.

In the specification, the number of carbon atoms in an amine group is not particularly limited, but may be 1 to 30. The amine group may be an alkyl amine group or an aryl amine group. Examples of the amine group may include a methylamine group, a dimethylamine group, a phenylamine group, a diphenylamine group, a naphthylamine group, a 9-methyl-anthracenylamine group, a triphenylamine group, etc., but are not limited thereto.

In the specification, examples of the alkyl group may include an alkylthio group, an alkyl sulfoxy group, an alkylaryl group, an alkylamino group, an alkyl boron group, an alkyl silyl group, or an alkyl amine group.

In the specification, examples of the aryl group may include an aryloxy group, an arylthio group, an aryl sulfoxy group, an arylamino group, an aryl boron group, an aryl silyl group, or an aryl amine group.

In the specification, a direct linkage may be a single bond.

In the specification,

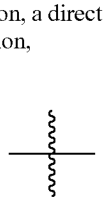 and each represent a bonding site to a neighboring atom.

Hereinafter, embodiments will be described with reference to the accompanying drawings.

Figure 2:
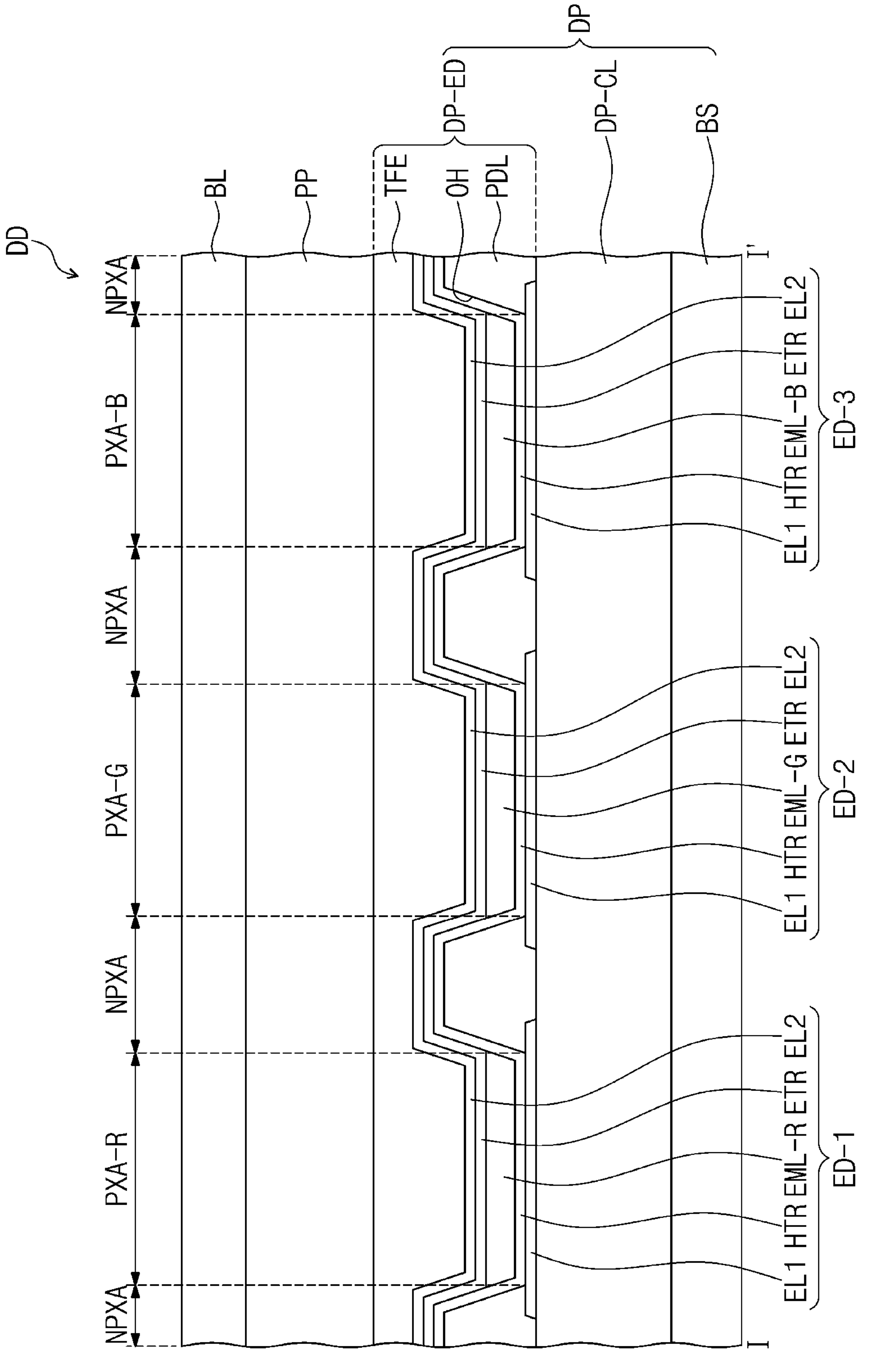
FIG. 2 is a schematic cross-sectional view of a display device according to an embodiment.

FIG. 1 is a plan view showing an embodiment of a display device DD. FIG. 2 is a schematic cross-sectional view of a display device DD of an embodiment. FIG. 2 is a schematic cross-sectional view showing a portion corresponding to line I-I' of FIG. 1.

The display device DD may include a display panel DP and an optical layer PP disposed on the display panel DP. The display panel DP includes light emitting elements ED-1, ED-2, and ED-3. The display device DD may include multiples of each of the light emitting elements ED-1, ED-2, and ED-3. The optical layer PP may be disposed on the display panel DP to control light reflected at the display panel DP from an external light. The optical layer PP may include, for example, a polarizing layer or a color filter layer. Although not shown in the drawings, in an embodiment, the optical layer PP may be omitted from the display device DD.

Abase substrate BL may be disposed on the optical layer PP. The base substrate BL may provide a base surface on which the optical layer PP is disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawings, in an embodiment, the base substrate BL may be omitted.

The display device DD according to an embodiment may further include a filling layer (not shown). The filling layer (not shown) may be disposed between a display element layer DP-ED and the base substrate BL. The filling layer (not shown) may be an organic material layer. The filling layer (not shown) may include at least one of an acrylic resin, a silicone-based resin, or an epoxy-based resin.

The display panel DP may include a base layer BS, a circuit layer DP-CL provided on the base layer BS, and a display element layer DP-ED. The display element layer DP-ED may include pixel defining films PDL, the light emitting elements ED-1, ED-2, and ED-3 disposed between the pixel defining films PDL, and an encapsulation layer TFE disposed on the light emitting elements ED-1, ED-2, and ED-3.

The base layer BS may provide a base surface on which the display element layer DP-ED is disposed. The base layer BS may be a glass substrate, a metal substrate, a plastic substrate, etc. However, embodiments are not limited thereto, and the base layer BS may include an inorganic layer, an organic layer, or a composite material layer.

In an embodiment, the circuit layer DP-CL may be disposed on the base layer BS, and the circuit layer DP-CL may include transistors (not shown). The transistors (not shown) may each include a control electrode, an input electrode, and an output electrode. For example, the circuit layer DP-CL may include a switching transistor and a driving transistor for driving the light emitting elements ED-1, ED-2, and ED-3 of the display element layer DP-ED.

The light emitting elements ED-1, ED-2, and ED-3 may each have a structure of a light emitting element ED of an embodiment according to FIGS. 3 to 6, which will be described later. The light emitting elements ED-1, ED-2, and ED-3 may each include a first electrode EL1, a hole transport region HTR, emission layers EML-R, EML-G, and EML-B, an electron transport region ETR, and a second electrode EL2.

FIG. 2 shows an embodiment in which the emission layers EML-R, EML-G, and EML-B of the light emitting elements ED-1, ED-2, and ED-3 are disposed in openings OH defined in the pixel defining films PDL, and the hole transport region HTR, the electron transport region ETR, and the second electrode EL2 are each provided as a common layer throughout the light emitting elements ED-1, ED-2, and ED-3. However, embodiments are not limited thereto. Although not shown in FIG. 2, in an embodiment, the hole transport region HTR and the electron transport region ETR may each be patterned and provided inside the openings OH defined in the pixel defining films PDL. For example, in an embodiment, the hole transport region HTR, the emission layers EML-R, EML-G, and EML-B, and the electron transport region ETR, etc., of the light emitting elements ED-1, ED-2, and ED-3 may each be patterned and provided through an inkjet printing method.

The encapsulation layer TFE may cover the light emitting elements ED-1, ED-2, and ED-3. The encapsulation layer TFE may seal the display element layer DP-ED. The encapsulation layer TFE may be a thin film encapsulation layer. The encapsulation layer TFE may be a single layer or a stack of multiple layers. The encapsulation layer TFE may include at least one insulating layer. The encapsulation layer TFE according to an embodiment may include at least one inorganic film (hereinafter, an encapsulation inorganic film). The encapsulation layer TFE according to an embodiment may include at least one organic film (hereinafter, an encapsulation organic film) and at least one encapsulation inorganic film.

The encapsulation inorganic film may protect the display element layer DP-ED from moisture and/or oxygen and the encapsulation organic film may protect the display element layer DP-ED from foreign substances such as dust particles. The encapsulation inorganic film may include silicon nitride, silicon oxy nitride, silicon oxide, titanium oxide, aluminum oxide, etc., but is not limited thereto. The encapsulation organic layer may include an acrylic compound, an epoxy-based compound, etc. The encapsulation organic layer may include a photopolymerizable organic material, without limitation.

The encapsulation layer TFE may be disposed on the second electrode EL2, and may be disposed to fill the openings OH.

Referring to FIGS. 1 and 2, the display device DD may include non-light emitting regions NPXA and light emitting regions PXA-R, PXA-G, and PXA-B. The light emitting regions PXA-R, PXA-G, and PXA-B may each be a region emitting light generated from each of the light emitting elements ED-1, ED-2, and ED-3, respectively. The light emitting regions PXA-R, PXA-G, and PXA-B may be spaced apart from each other in a plan view.

Each of the light emitting regions PXA-R, PXA-G, and PXA-B may be a region separated by the pixel defining films PDL. The non-light emitting regions NPXA may be regions between neighboring light emitting regions PXA-R, PXA-G, and PXA-B, and may correspond to the pixel defining films PDL. For example, in an embodiment, each of the light emitting regions PXA-R, PXA-G, and PXA-B may correspond to a pixel. The pixel defining films PDL may separate the light emitting elements ED-1, ED-2, and ED-3. The emission layers EML-R, EML-G, and EML-B of the light emitting elements ED-1, ED-2, and ED-3 may be disposed in openings OH defined by the pixel defining films PDL and separated from each other.

The light emitting regions PXA-R, PXA-G, and PXA-B may be divided into groups according to the color of light generated from each of the light emitting elements ED-1, ED-2, and ED-3. In the display device DD of an embodiment shown in FIGS. 1 and 2, three light emitting regions PXA-R, PXA-G, and PXA-B which respectively emit red light, green light, and blue light, are illustrated as an example. For example, the display device DD of an embodiment may include a red light emitting region PXA-R, a green light emitting region PXA-G, and a blue light emitting region PXA-B, which are distinct from one another.

In the display device DD according to an embodiment, the light emitting elements ED-1, ED-2, and ED-3 may each emit light having different wavelength ranges. For example, in an embodiment, the display device DD may include a first light emitting element ED-1 emitting red light, a second light emitting element ED-2 emitting green light, and a third light emitting element ED-3 emitting blue light. For example, the red light emitting region PXA-R, the green light emitting region PXA-G, and the blue light emitting region PXA-B of the display device DD may correspond to the first light emitting element ED-1, the second light emitting element ED-2, and the third light emitting element ED-3, respectively.

However, embodiments are not limited thereto, and the first to third light emitting elements ED-1, ED-2, and ED-3 may emit light in a same wavelength range, or at least one thereof may emit light in a different wavelength range. For example, the first to third light emitting elements ED-1, ED-2, and ED-3 may all emit blue light.

The light emitting regions PXA-R, PXA-G, and PXA-B in the display device DD according to an embodiment may be arranged in a stripe configuration. Referring to FIG. 1, the red light emitting regions PXA-R, the green light emitting regions PXA-G, and the blue light emitting regions PXA-B may each be arranged along a second directional axis DR2. In another embodiment, the red light emitting region PXA-R, the green light emitting region PXA-G, and the blue light emitting region PXA-B may be alternately arranged in turn along a first directional axis DR1.

FIGS. 1 and 2 illustrate that the light emitting regions PXA-R, PXA-G, and PXA-B are all similar in size. However, embodiments are not limited thereto, and the light emitting regions PXA-R, PXA-G and PXA-B may be different in size from each other according to a wavelength range of emitted light. The areas of the light emitting regions PXA-R, PXA-G, and PXA-B may be areas in a plan view that are defined by the first directional axis DR1 and the second directional axis DR2.

The arrangement of the light emitting regions PXA-R, PXA-G, and PXA-B is not limited to the one shown in FIG. 1, and the order in which the red light emitting region PXA-R, the green light emitting region PXA-G, and the blue light emitting region PXA-B are arranged may be provided in various combination according to display quality characteristics which are required for the display device DD. For example, the light emitting regions PXA-R, PXA-G, and PXA-B may be arranged in a PENTILE™ configuration or a diamond configuration.

In an embodiment, the areas of each of the light emitting regions PXA-R, PXA-G, and PXA-B may be different in size from one another. For example, in an embodiment, an area of the green light emitting region PXA-G may be smaller than an area of the blue light emitting region PXA-B in size, but embodiments are not limited thereto.

Hereinafter, FIGS. 3 to 6 are each a schematic cross-sectional view showing a light emitting element according to an embodiment. The light emitting element ED according to an embodiment may include a first electrode EL1, a second electrode EL2 facing the first electrode EL1, and at least one functional layer disposed between the first electrode EL1 and the second electrode EL2. The at least one functional layer may include a hole transport region HTR, an emission layer EML, and an electron transport region ETR, which are sequentially stacked. For example, the light emitting element ED of an embodiment may include a first electrode EL1, a hole transport region HTR, an emission layer EML, an electron transport region ETR, and a second electrode EL2, each disposed in that stated order.

Figure 3:
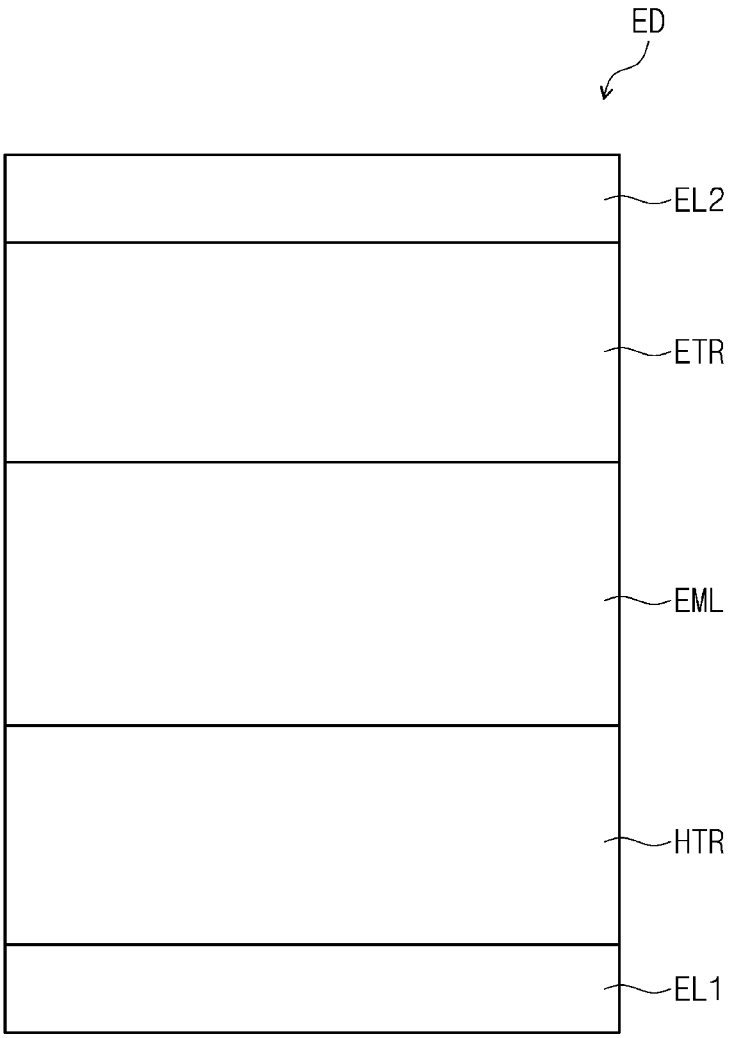
FIG. 3 is a schematic cross-sectional view showing a light emitting element according to an embodiment.
Figure 4:
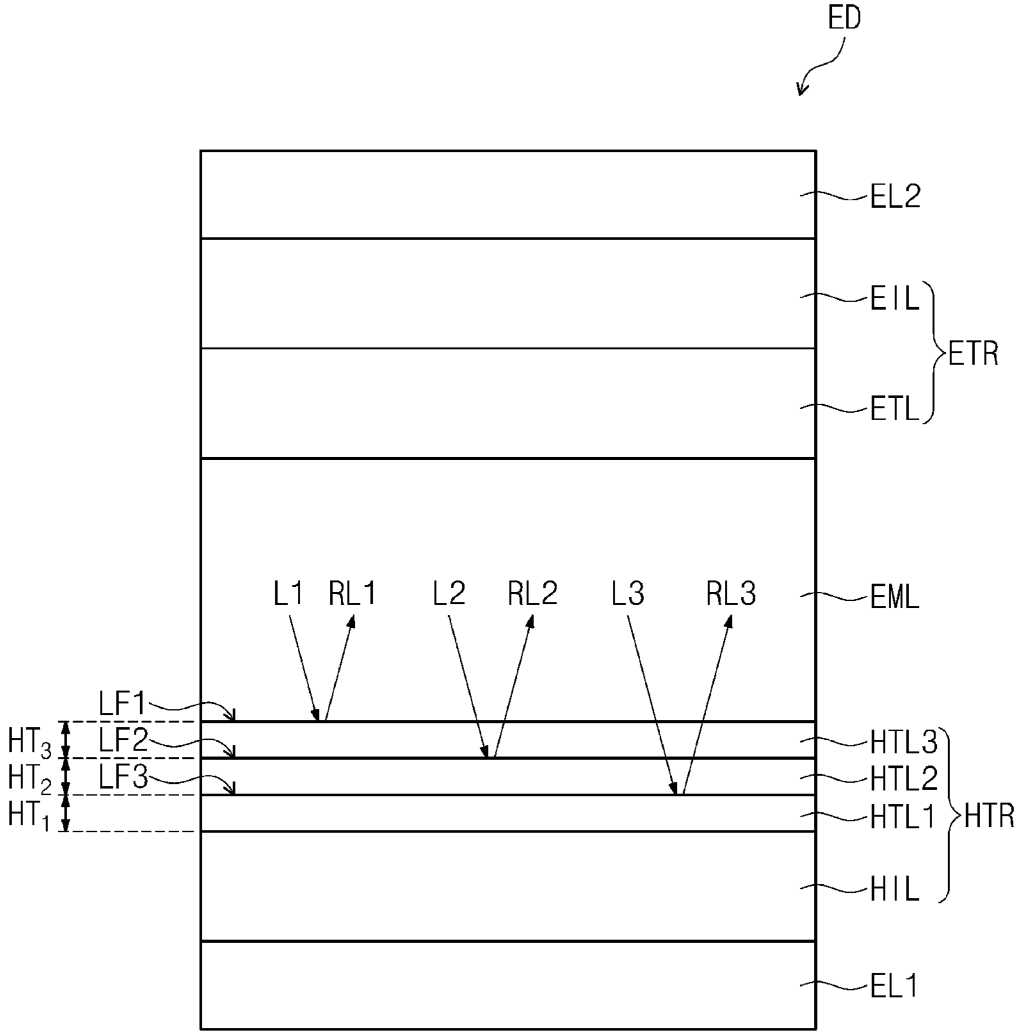
FIG. 4 is a schematic cross-sectional view showing a light emitting element according to an embodiment.
Figure 5:
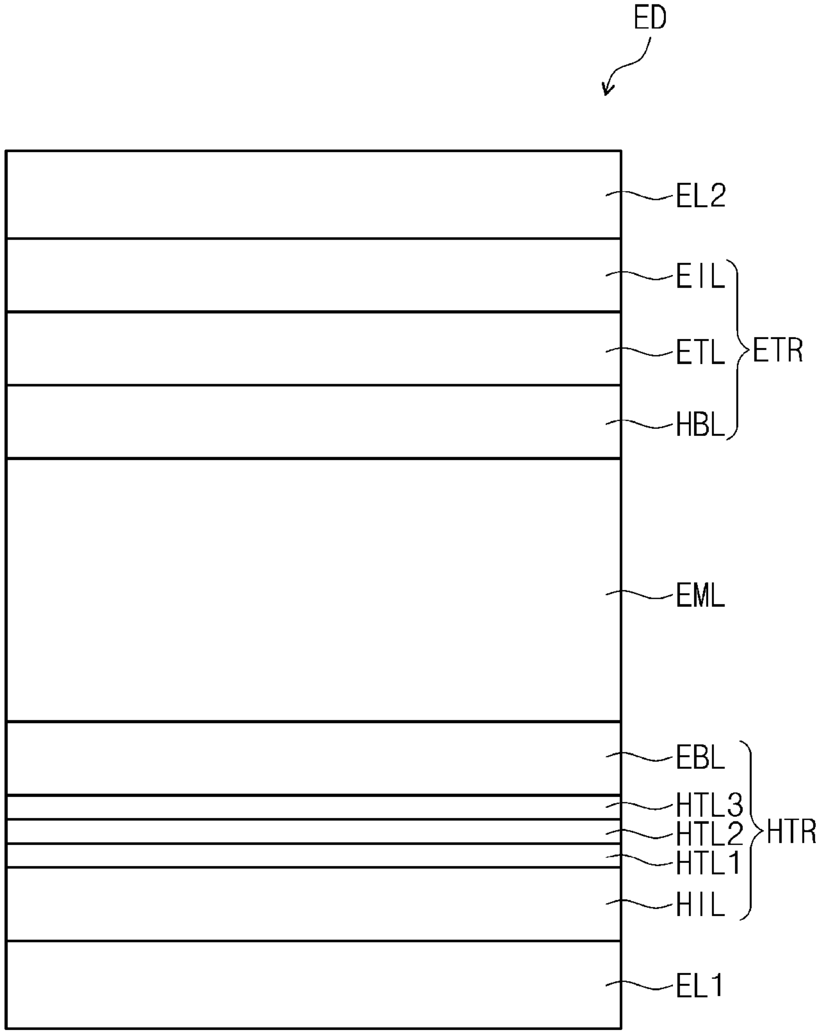
FIG. 5 is a schematic cross-sectional view showing a light emitting element according to an embodiment.
Figure 6:
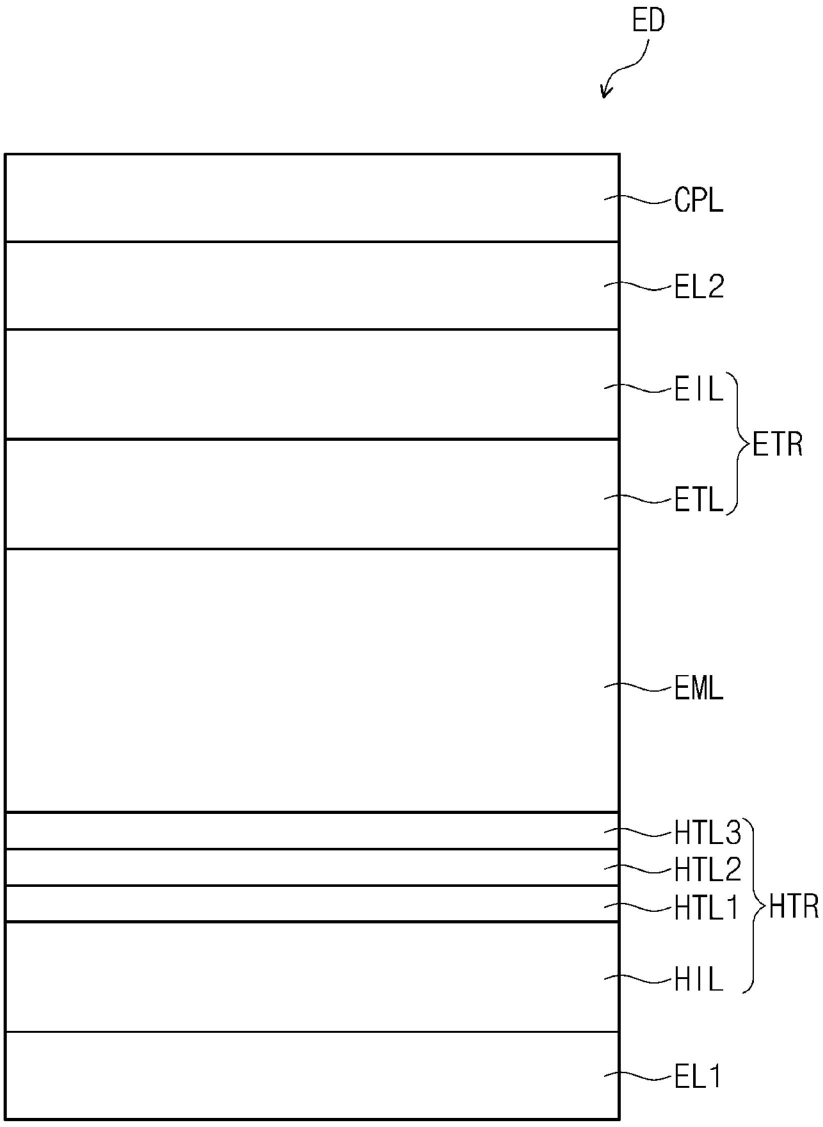
FIG. 6 is a schematic cross-sectional view showing a light emitting element according to an embodiment.

In comparison to FIG. 3, FIG. 4 shows a schematic cross-sectional view of a light emitting element ED of an embodiment in which the hole transport region HTR includes a hole injection layer HIL, a first hole transport layer HTL1, a second hole transport layer HTL2, and a third hole transport layer HTL3, and the electron transport region ETR includes an electron injection layer EIL and an electron transport layer ETL. In comparison to FIG. 3, FIG. 5 shows a schematic cross-sectional view of a light emitting element ED of an embodiment in which the hole transport region HTR includes a hole injection layer HIL, a first hole transport layer HTL1, a second hole transport layer HTL2, and a third hole transport layer HTL3, and an electron blocking layer EBL, and the electron transport region ETR includes an electron injection layer EIL, an electron transport layer ETL, and a hole blocking layer HBL. In comparison to FIG. 4, FIG. 6 shows a schematic cross-sectional view of a light emitting element ED of an embodiment that includes a capping layer CPL disposed on the second electrode EL2.

The light emitting element ED according to an embodiment may include a first amine compound of an embodiment, a second amine compound of an embodiment, and a third amine compound of an embodiment, which will each be described later in the hole transport region HTR.

In the light emitting element ED according to an embodiment, the first electrode EL1 has conductivity. The first electrode EL1 may be formed of a metal material, a metal alloy, or a conductive compound. The first electrode EL1 may be an anode or a cathode. However, embodiments are not limited thereto. For example, the first electrode EL1 may be a pixel electrode. The first electrode EL1 may be a transmissive electrode, a transflective electrode, or a reflective electrode. When the first electrode EL1 is a transmissive electrode, the first electrode EL1 may include a transparent metal oxide such as indium tin oxide (ITO), indium zinc oxide (IZO), zinc oxide (ZnO), or indium tin zinc oxide (ITZO). When the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, W, a compound thereof, or a mixture thereof (e.g., a mixture of Ag and Mg). In another embodiment, the first electrode EL1 may have a multilayer structure including a reflective film or a transflective film formed of the above-described materials, and a transparent conductive film formed of indium tin oxide (ITO), indium zinc oxide (IZO), zinc oxide (ZnO), indium tin zinc oxide (ITZO), etc. For example, the first electrode EL1 may have a three-layer structure of ITO/Ag/ITO. However, embodiments are not limited thereto. The first electrode EL1 may include the above-described metal materials, a combination of two or more metal materials selected from the above-described metal materials, or oxides of the above-described metal materials. The first electrode EL1 may have a thickness in a range of about 700 Å to about 10,000 Å. For example, the first electrode EL1 may have a thickness in a range of about 1,000 Å to about 3,000 Å.

The hole transport region HTR is provided on the first electrode EL1. The hole transport region HTR may include the first hole transport layer HTL1, the second hole transport layer HTL2, and the third hole transport layer HTL3.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

FIGS. 4 to 6 each illustrate that the hole transport region HTR includes the hole injection layer HIL and the hole transport layers HTL1, HTL2, and HTL3, but in an embodiment, in the hole transport region HTR, the hole transport layers HTL1, HTL2, and HTL3 may be directly disposed on the first electrode EL1 without the hole injection layer HIL. In an embodiment, the hole transport region HTR may include a buffer layer (not shown) that is disposed above the hole transport layer HTL, or may include an electron blocking layer EBL that is disposed above the hole transport layer HTL.

The first hole transport layer HTL1 may include a first amine compound having a first refractive index. The second hole transport layer HTL2 may include a second amine compound having a second refractive index greater than the first refractive index. The third hole transport layer HTL3 may include a third amine compound having a third refractive index less than the second refractive index. For example, the second refractive index may be greater than each of the first refractive index and the third refractive index. The first refractive index may be the same as or different from the third refractive index.

The first to third hole transport layers HTL1, HTL2, and HTL3 may include the first to third amine compounds, respectively, and thus, may have the first to third refractive indices.

In the light emitting element ED according to an embodiment, the first hole transport layer HTL1 and the third hole transport layer HTL3, which have a relatively low refractive index may respectively be disposed on an upper side and a lower side, with respect to the second hole transport layer HTL2 having a relatively higher refractive index than the other hole transport layers HTL1 and HTL3. In the light emitting element ED of an embodiment, the hole transport region HTR may include three hole transport layers HTL1, HTL2, and HTL3, which are disposed in the order of a low refractive hole transport layer/high refractive hole transport layer/low refractive hole transport layer in the thickness direction.

A difference between the second refractive index of the second hole transport layer HTL2 and the first refractive index of the first hole transport layer HTL1 may be in a range of about 0.1 to about 1.1. A difference between the second refractive index of the second hole transport layer HTL2 and the third refractive index of the third hole transport layer HTL3 may be in a range of about 0.1 to about 1.1. A difference between the second refractive index and the first refractive index may be the same as or different from a difference between the second refractive index and the third refractive index.

The first refractive index and the third refractive index may each independently be in a range of about 1.3 to about 1.8. The first refractive index and the third refractive index may be the same as or different from each other. The second refractive index may be in a range of about 1.8 to about 2.4. For example, the first refractive index and the third refractive index may each independently be in a range of about 1.3 to about 1.8, and the second refractive index may be in a range of about 1.8 to about 2.4. The first refractive index and the third refractive index are each less than the second refractive index, and thus, when the second refractive index is 1.8, the first refractive index and the third refractive index may each independently be in a range of about 1.3 to about 1.7. The light emitting element ED of an embodiment includes three hole transport layers HTL1, HTL2, and HTL3, which are disposed in the order of a low refractive hole transport layer/high refractive hole transport layer/low refractive hole transport layer, and these hole transport layers bring about constructive interference of light to increase light extraction efficiency.

The hole transport region HTR may have, for example, a thickness of about 50 Å to about 15,000 Å. A thickness ratio of the first hole transport layer HTL1 to the second hole transport layer HTL2 to the third hole transport layer HTL3 included in the hole transport region HTR may be expressed as $HT_1$:$HT_2$:$HT_3$ and may be in a range of about 4.50:1.00:4.50 to about 0.125:1.00:0.125. For example, the thickness $HT_1$ of the first hole transport layer HTL1 may substantially be the same as the thickness $HT_3$ of the third hole transport layer HTL3, and the thickness $HT_2$ of the second hole transport layer HTL2 may be different from each of the thickness $HT_1$ of the first hole transport layer HTL1 and the thickness $HT_3$ of the third hole transport layer HTL3. However, this is presented as an example, and the embodiment is not limited thereto, and the thickness $HT_1$ of the first hole transport layer HTL1 and the thickness $HT_3$ of the third hole transport layer HTL3 may be different from each other. The thickness ratio $HT_1$:$HT_2$:$HT_3$ of the first to third hole transport layers HTL1, HTL2, and HTL3 may be controlled to be in an optimum range according to a wavelength range of light emitted from the emission layer EML, according to a display quality required for the display device DD (FIG. 2), and according to a hole transport material used in each of the hole transport layers HTL1, HTL2, and HTL3 of the hole transport region HTR.

In an embodiment, the first hole transport layer HTL1 may be directly disposed on an upper side of the first electrode EL1. The third hole transport layer HTL3 may be directly disposed on a lower side of the emission layer EML. The third refractive index of the third hole transport layer HTL3 may be less than a refractive index of the emission layer EML.

A portion of first incident light L1 incident in the direction of the third hole transport layer HTL3 may be reflected in the direction of the emission layer EML from a first interface LF1 between the emission layer EML and the third hole transport layer HTL3. A portion of second incident light L2 incident in the direction of the second hole transport layer HTL2 from the emission layer EML by passing through the third hole transport layer HTL3 may be reflected in the direction of the emission layer EML from a second interface LF2 between the third hole transport layer HTL3 and the second hole transport layer HTL2. A portion of third incident light L3 incident in the direction of the first hole transport layer HTL1 from the emission layer EML by passing through the third hole transport layer HTL3 and through the second hole transport layer HTL2 may be reflected in the direction of the emission layer EML from a third interface LF3 between the second hole transport layer HTL2 and the first hole transport layer HTL1. In the light emitting element ED of an embodiment, constructive interference may occur among the first reflected light RL1 reflected from the first interface LF1, the second reflected light RL2 reflected from the second interface LF2, and the third reflected light RL3 reflected from the third interface LF3. Accordingly, the light emitting element ED of an embodiment may exhibit high external light extraction efficiency.

The light emitting element ED of an embodiment may include the hole transport layers HTL1, HTL2, and HTL3, which are disposed in the order of a low refractive hole transport layer/high refractive hole transport layer/low refractive hole transport layer, and thus may exhibit increased luminous efficiency. The light emitting element ED of an embodiment includes the hole transport layers HTL1, HTL2, and HTL3 of the hole transport region HTR having different refractive indices to minimize light emitted from functional layers inside to disappear due to destructive interference, and to create constructive interference of light by the hole transport layers HTL1, HTL2, and HTL3 having different refractive indices, thereby achieving high light extraction efficiency.

In the light emitting element ED according to an embodiment, the first amine compound included in the first hole transport layer HTL1 and the third amine compound included in the third hole transport layer HTL3 may each independently be a compound represented by Formula 1.

[Formula 1]

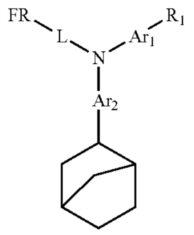

In Formula 1, $R_1$ may be a substituted or unsubstituted adamantyl group, a substituted or unsubstituted cyclohexyl group, or a substituted or unsubstituted bicycloheptyl group, and FR may be a group represented by Formula 2.

[Formula 2]

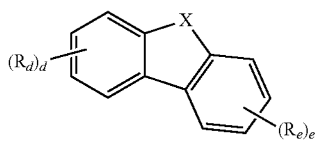

For example, the amine compound of an embodiment may include a first substituent of a bicycloheptyl group, a second substituent selected from an adamantyl group, a cyclohexyl group, or a bicycloheptyl group, and a third substituent selected from a fluorenyl group or a dibenzoheterole group, each bonded to an N atom. For example, the bicycloheptyl group used as a substituent in the amine compound of an embodiment may be an unsubstituted bicyclo[2,2,1]heptyl group (bicyclo[2,2,1]heptyl). For example, in the amine compound of an embodiment, $R_1$ may be an unsubstituted adamantyl group, an unsubstituted cyclohexyl group, or an unsubstituted bicyclo[2,2,1]heptyl group (bicyclo[2,2,1]heptyl).

In Formula 1, FR may be a group represented by Formula 2 which may be bonded to L of Formula 1 or to the N atom of Formula 1 at the X position or at a position of any one of ring-forming atoms of a benzene ring as represented by Formula 2A or Formula 2B. In Formulas 2A and 2B, represents a bonding site to a neighboring atom.

[Formula 2A]

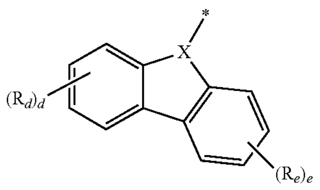

[Formula 2B]

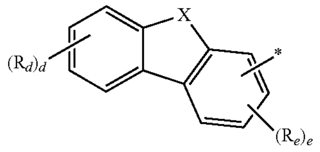

In Formula 1, $Ar_1$ and $Ar_2$ may each independently be a substituted or unsubstituted arylene group having 6 to 30 ring-forming carbon atoms. For example, $Ar_1$ and $Ar_2$ may each independently be a substituted or unsubstituted phenylene group.

In Formula 1, L may be a direct linkage, a substituted or unsubstituted arylene group having 6 to 30 ring-forming carbon atoms, or a substituted or unsubstituted heteroarylene group having 2 to 30 ring-forming carbon atoms. When L is a direct linkage, the nitrogen atom (N) of Formula 1 and FR of Formula 1 may be directly bonded with a single bond. In an embodiment, L may be a substituted or unsubstituted phenylene group.

In Formula 2, X may be $C(R_a)(R_b)$, N, $N(R_c)$, O, or S. For example, the FR group represented by Formula 2 may be a substituted or unsubstituted fluorene derivative, a substituted or unsubstituted carbazole derivative, a substituted or unsubstituted dibenzofuran derivative, or a substituted or unsubstituted dibenzothiophene derivative.

In Formula 2, $R_a$ to $R_c$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula 2, d and e may each independently be an integer from 0 to 4. In Formula 2, $R_d$ and $R_e$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula 2, when d is 0, $R_d$ may not be present in Formula 2, and when e is 0, $R_e$ may not be present in Formula 2. For example, when d and e are both 0 in Formula 2, the benzene rings of Formula 2 may be unsubstituted. In Formula 2, when d is 2 or greater, multiple $R_d$ groups may all be the same or at least one may be different from the others. In Formula 2, when e is 2 or greater, multiple $R_e$ groups may all be the same or at least one may be different from the others.

In an embodiment, in Formula 2, when X is represented by $C(R_a)(R_b)$, $R_a$ and $R_b$ may each independently be a linear alkyl group, a cyclic alkyl group, or an aryl group. For example, $R_a$ and $R_b$ may be bonded to each other to form a ring. When $R_a$ and $R_b$ are bonded to each other to form a fluorene ring, the FR group represented by Formula 2 may have a spiro structure.

In Formula 2, when X is represented by $C(R_a)(R_b)$, $R_a$ or $R_b$ may be directly bonded to L, or $R_a$ or $R_b$ may be directly bonded to the nitrogen atom (N) of Formula 1.

In an embodiment, the compound represented by Formula 1 may be represented by Formula 1-1 or Formula 1-2. In Formulas 1-1 and 1-2, $R_1$, L, $Ar_1$, and $Ar_2$ are the same as defined in Formula 1, and X, $R_d$, $R_e$, d, and e are the same as defined in Formula 2.

[Formula 1-1]

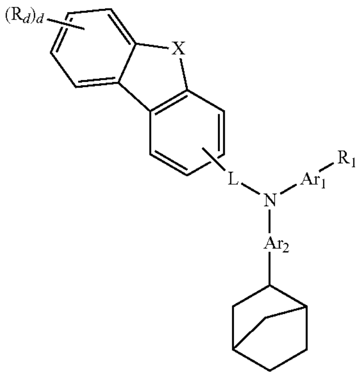

[Formula 1-2]

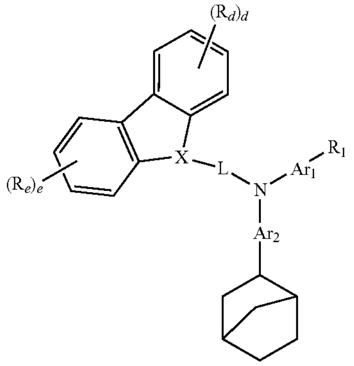

In an embodiment, the compound represented by Formula 1-2 may be represented by Formula 1-2A. In Formula 1-2A, $R_1$, L, $Ar_1$, and $Ar_2$ are the same as defined in Formula 1, and $R_a$, $R_d$, $R_e$, d, and e are the same as defined in Formula 2.

[Formula 1-2A]

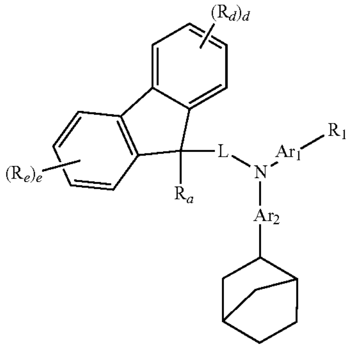

In an embodiment, the compound represented by Formula 1 may be represented by Formula 1A. For example, in the compound represented by Formula 1, $Ar_1$ and $Ar_2$ may each be an unsubstituted phenylene group. In Formula 1A, $R_1$, L, and FR are the same as defined in Formula 1.

[Formula 1A]

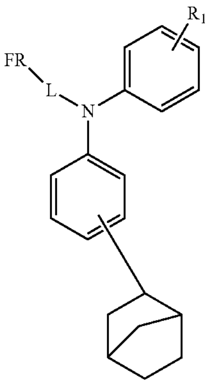

In an embodiment, the compound represented by Formula 1A may be represented by Formula 1A-1. For example, in the compound represented by Formula 1, a bicycloheptyl group and a substituent represented by $R_1$ may each respectively be bonded to a phenylene group at a para position with respect to the nitrogen atom (N) of Formula 1. However, embodiments are not limited thereto.

[Formula 1A-1]

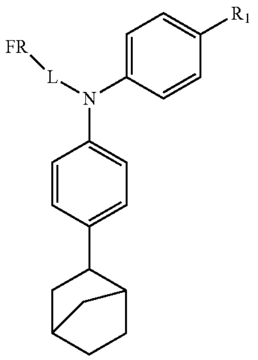

In Formula 1A-1, $R_1$, L, and FR are the same as defined in Formula 1.

The first amine compound and the third amine compound of an embodiment represented by Formula 1 may each independently be any one selected from Compound Group 1. The first hole transport layer HTL1 and the third hole transport layer HTL3 of the light emitting element ED according to an embodiment may include at least one of the amine compounds disclosed in Compound Group 1.

[Compound Group 1]

1

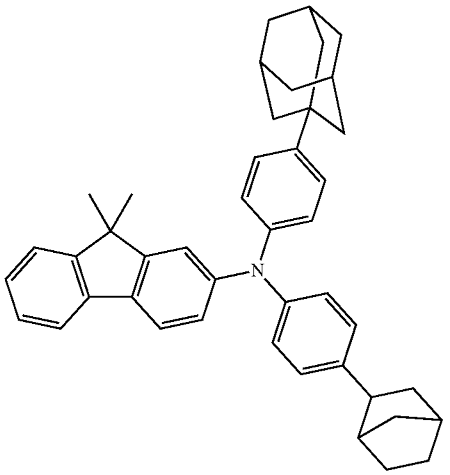

2

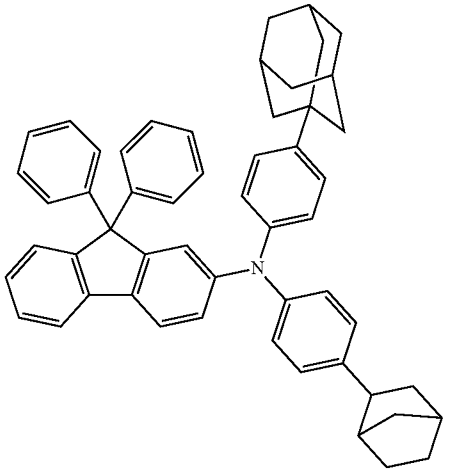

-continued

3

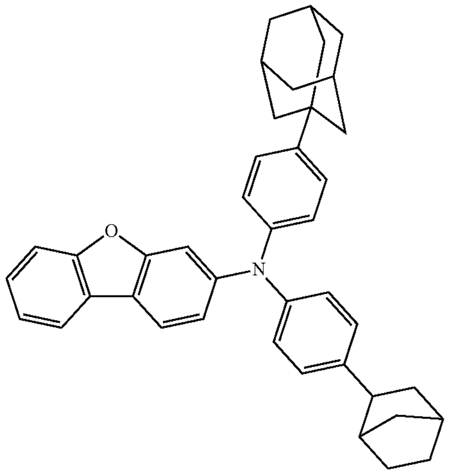

4

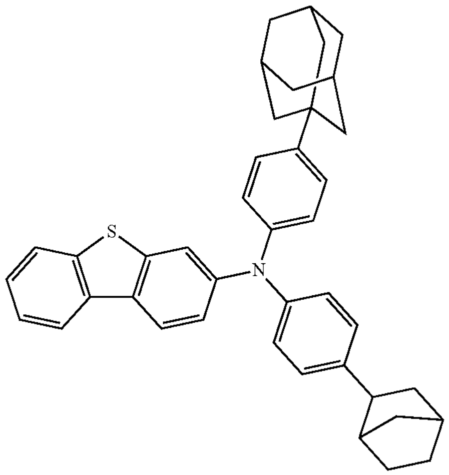

5

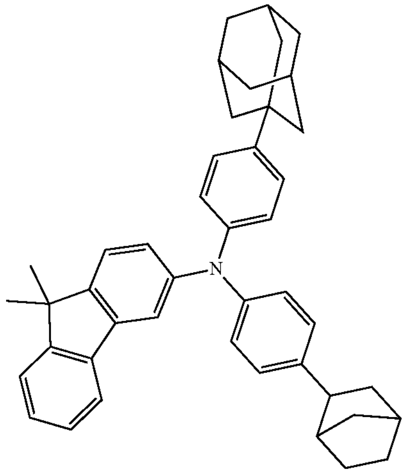

-continued
6
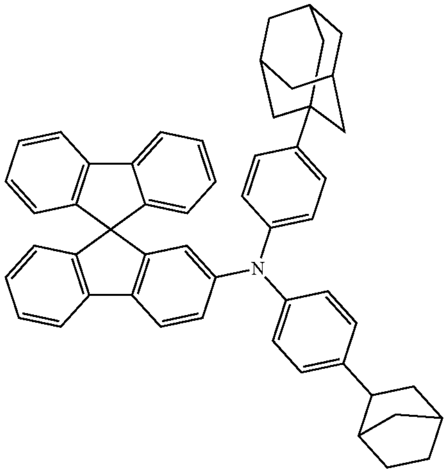
7
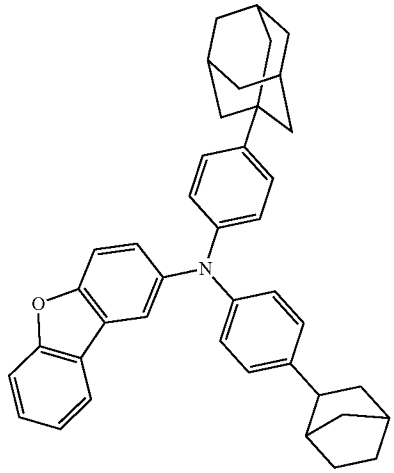
8
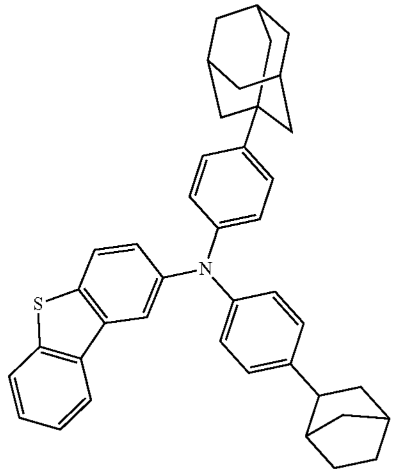
-continued
9
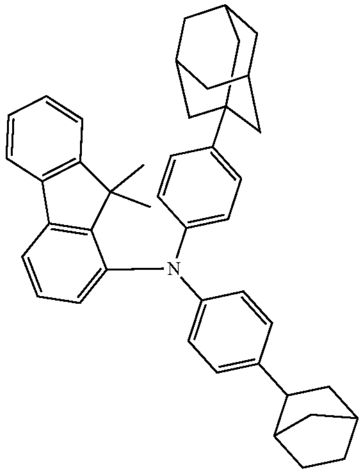
10
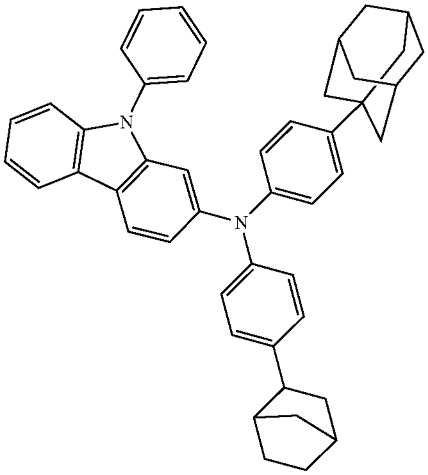
11
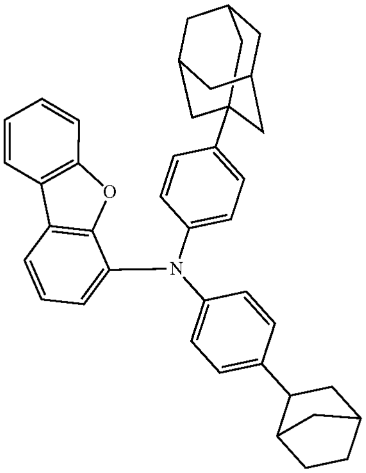

-continued
12
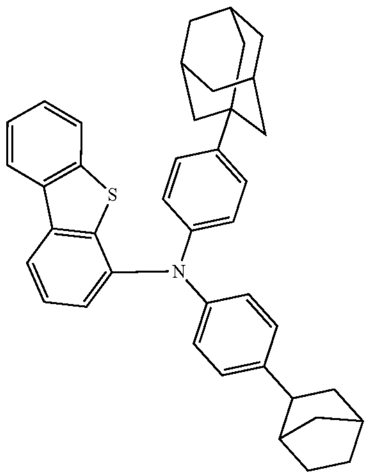
13
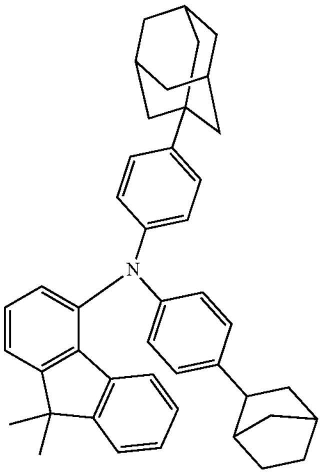
14
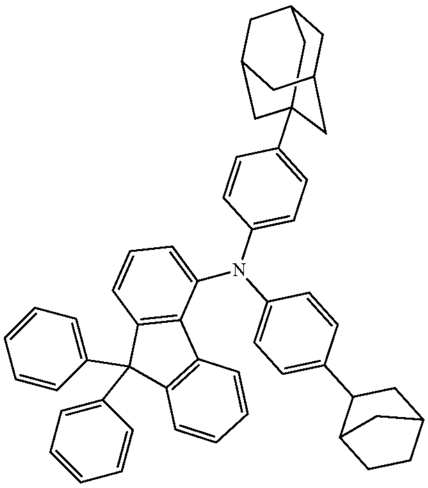
-continued
15
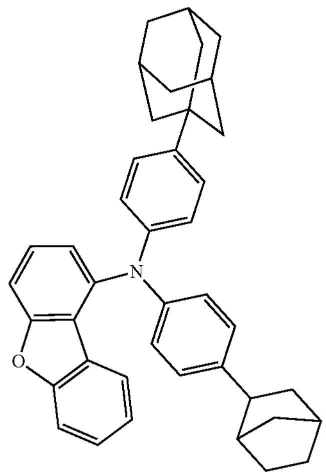
16
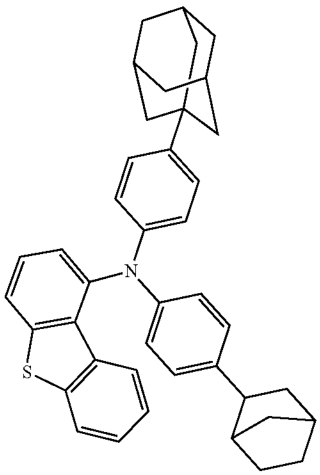
17
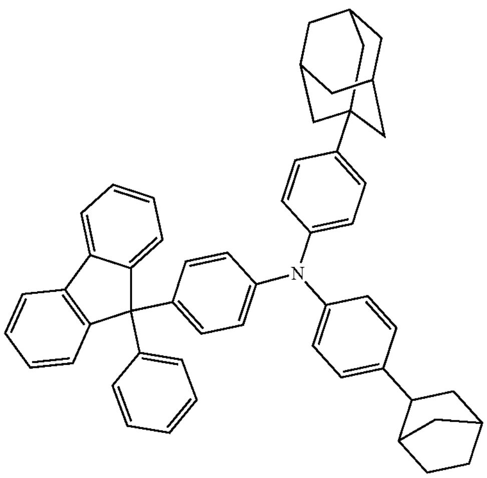

-continued
18
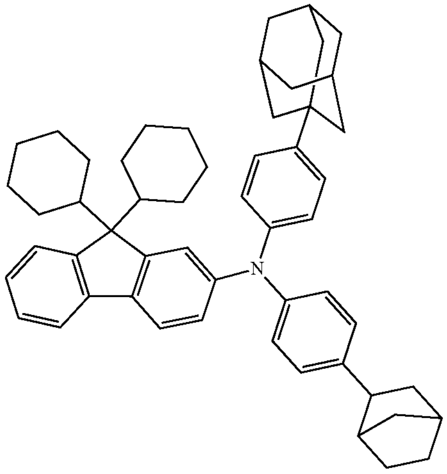
19
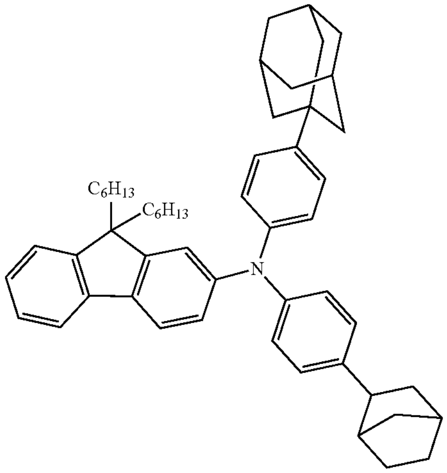
20
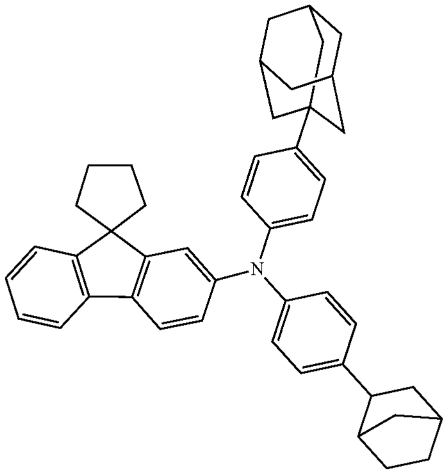
-continued
21
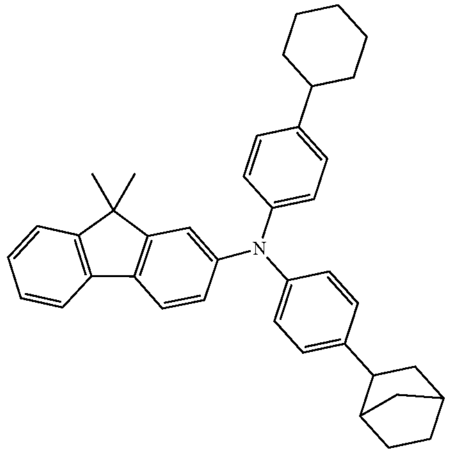
22
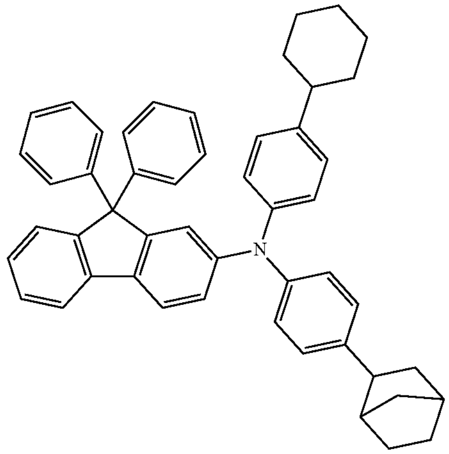
23
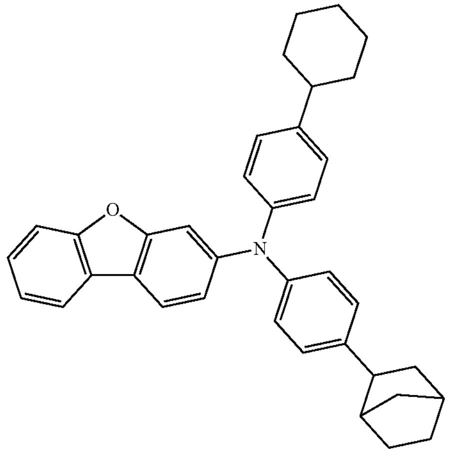

24
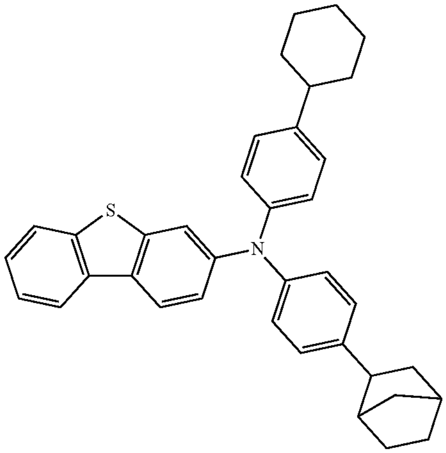
25
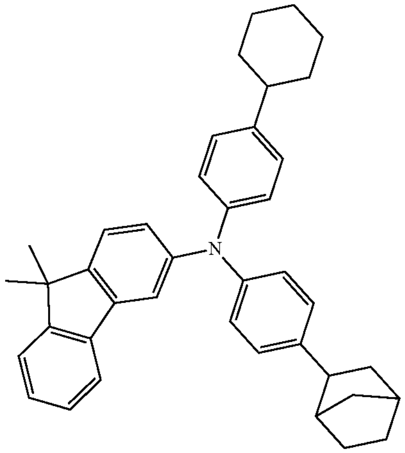
26
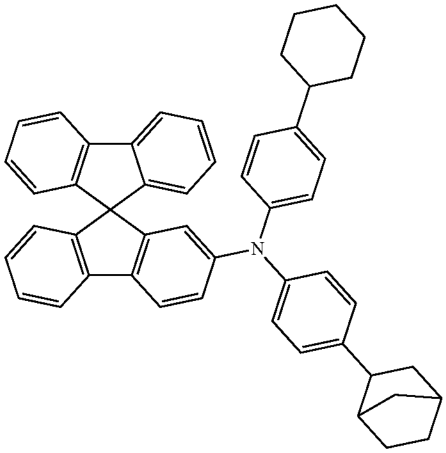
27
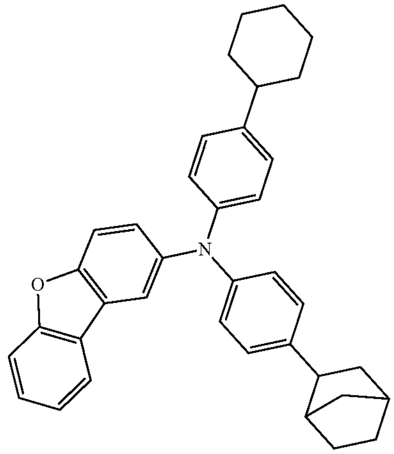
28
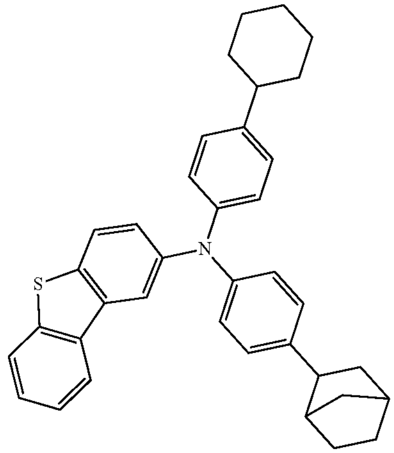
29
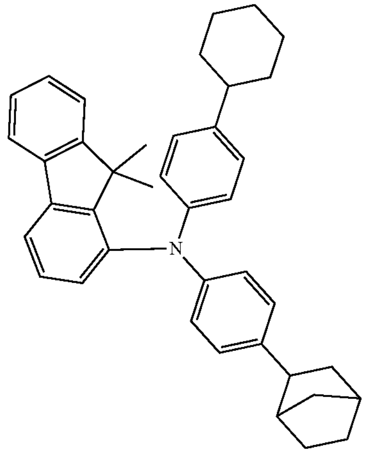

-continued
30
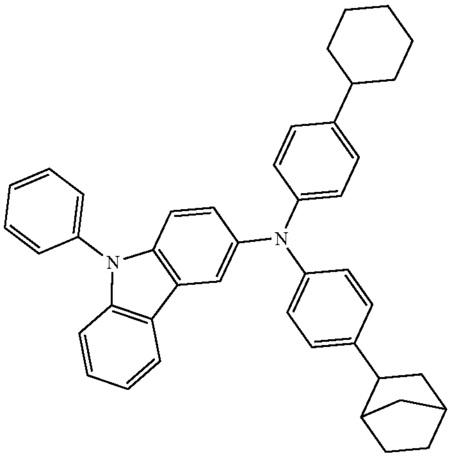
31
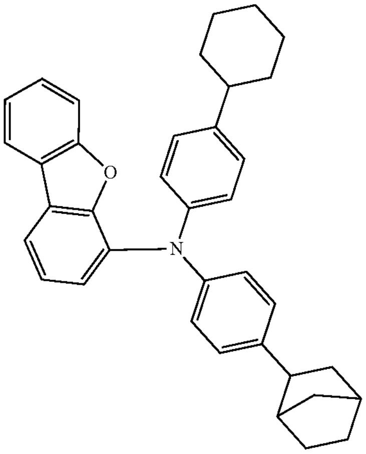
32
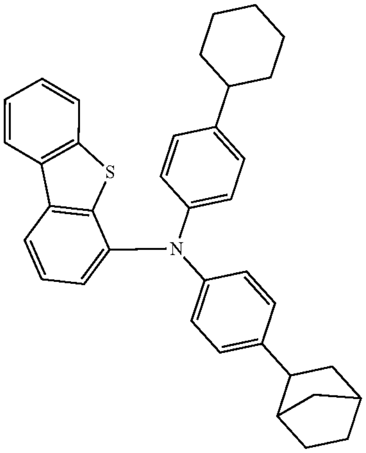
-continued
33
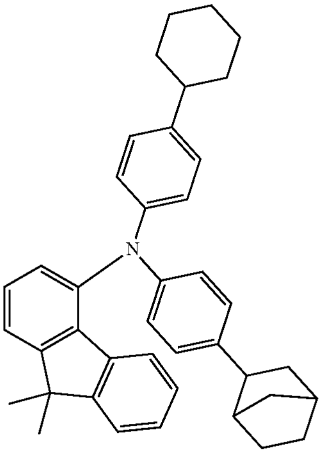
34
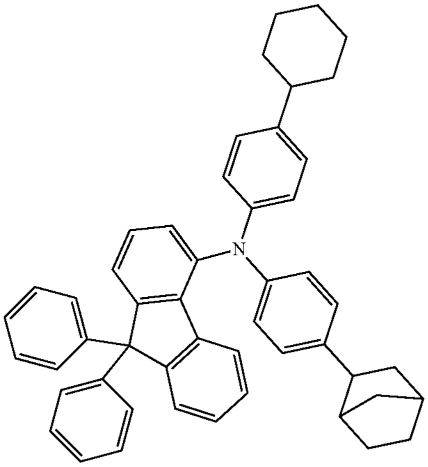
35
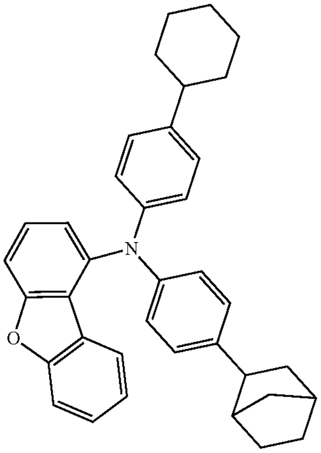

-continued
36
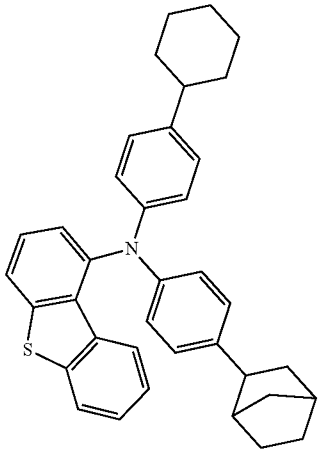
37
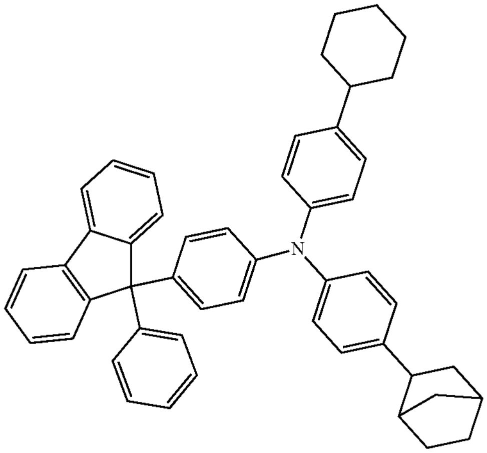
38
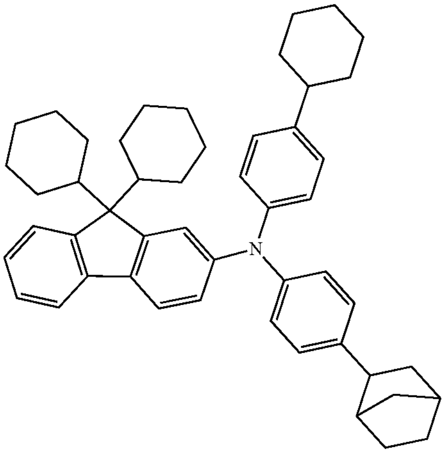
-continued
39
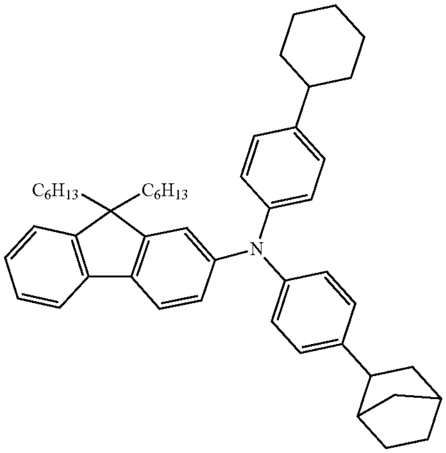
40
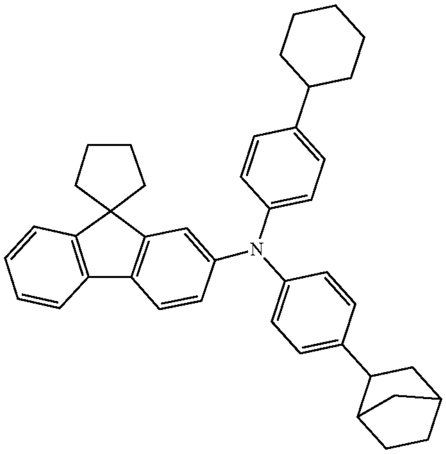
41
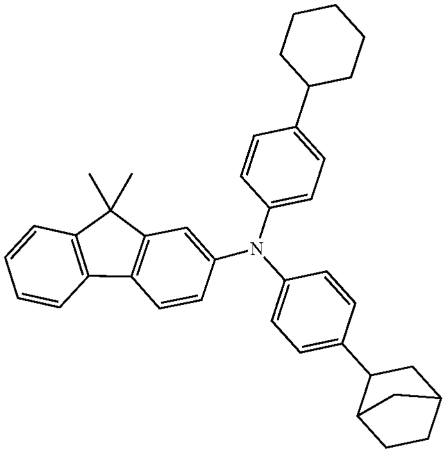

-continued
42
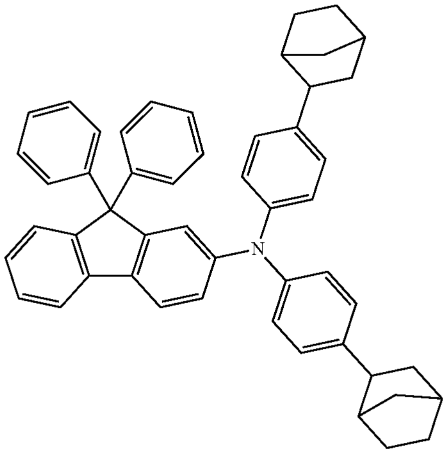
43
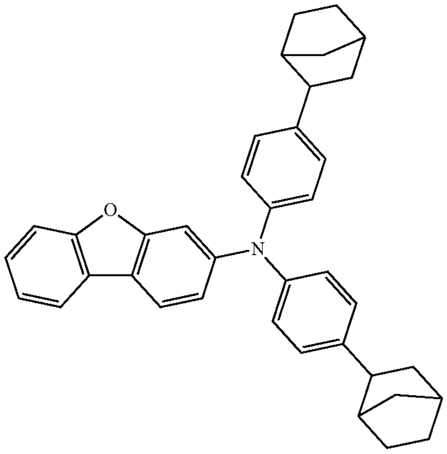
44
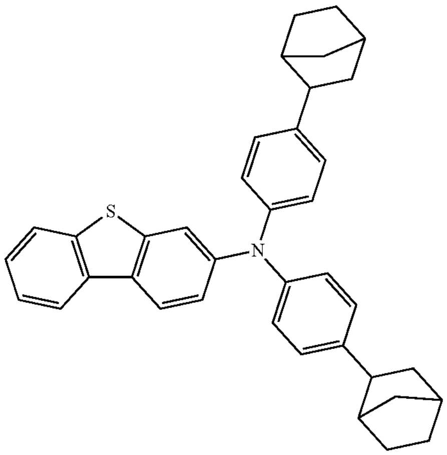
-continued
45
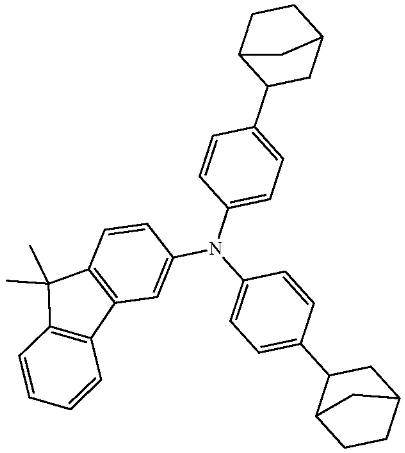
46
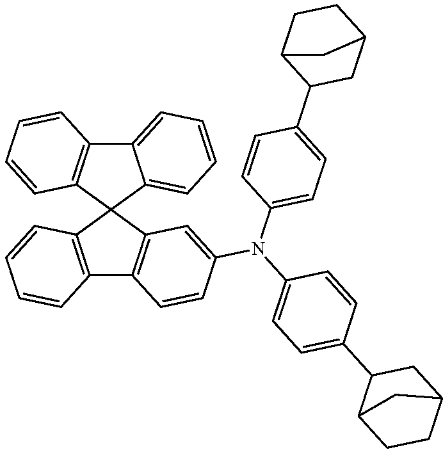
47
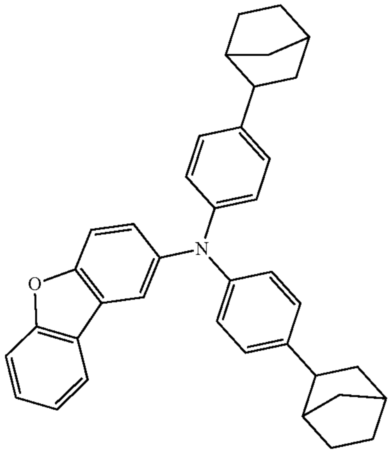

-continued
48
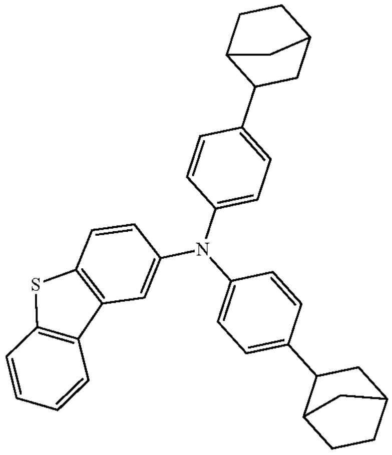
49
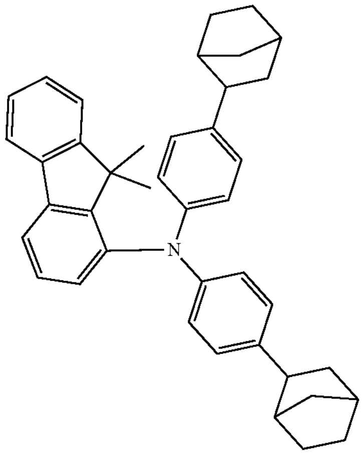
50
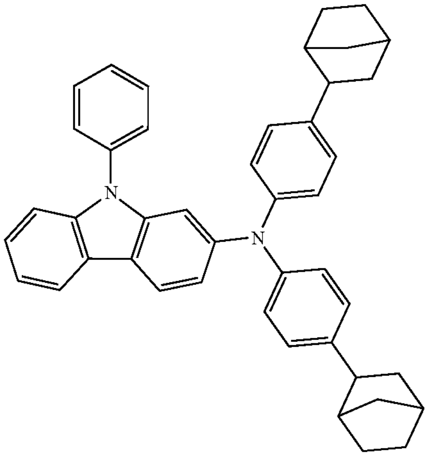
-continued
51
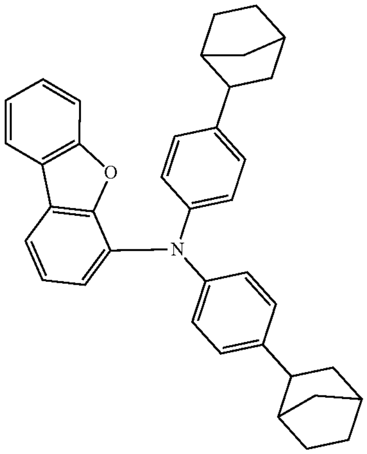
52
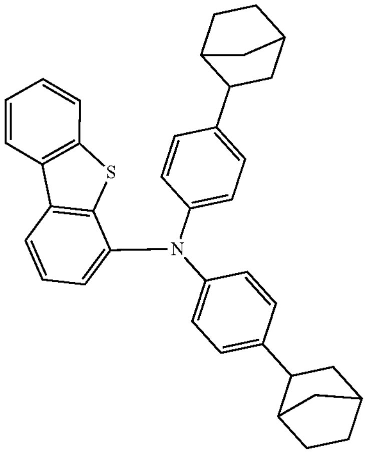
53
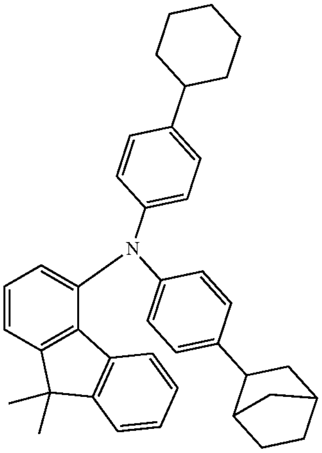

-continued
54
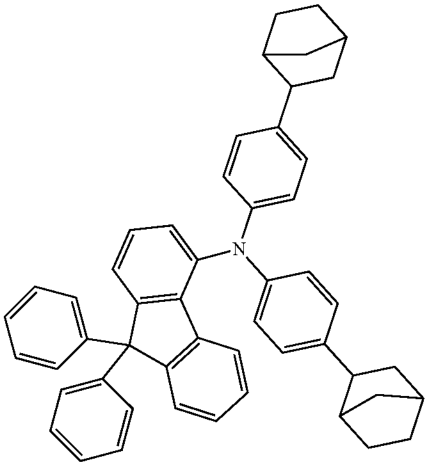
55
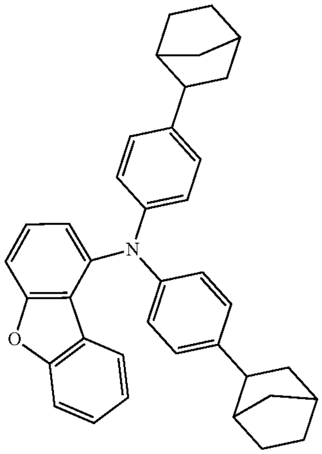
56
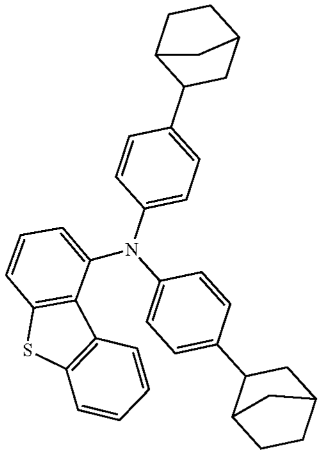
-continued
57
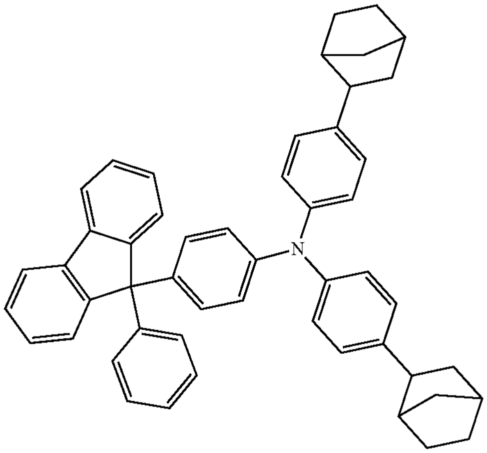
58
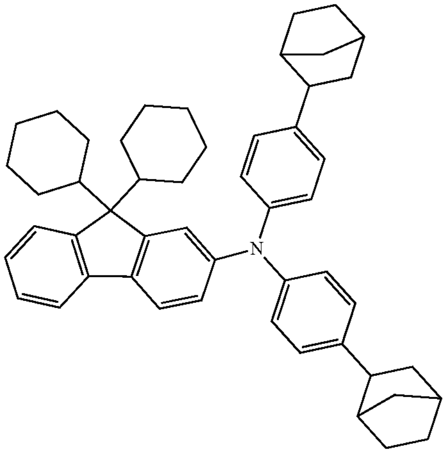
59
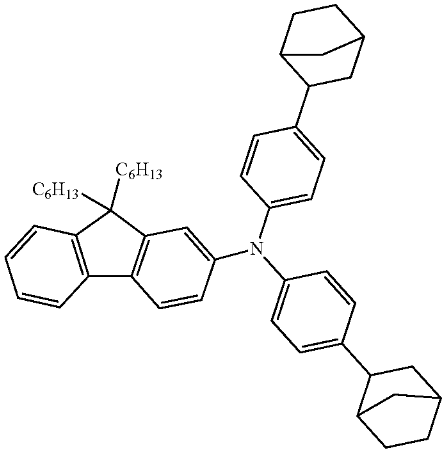

-continued
60
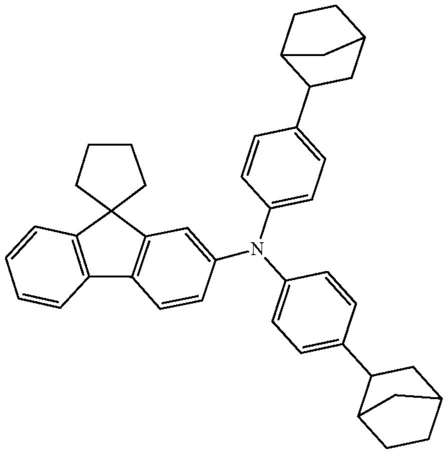
61
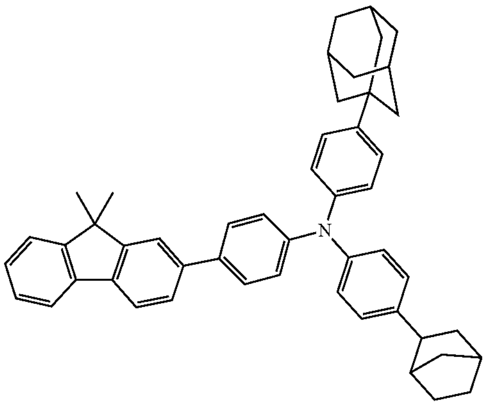
62
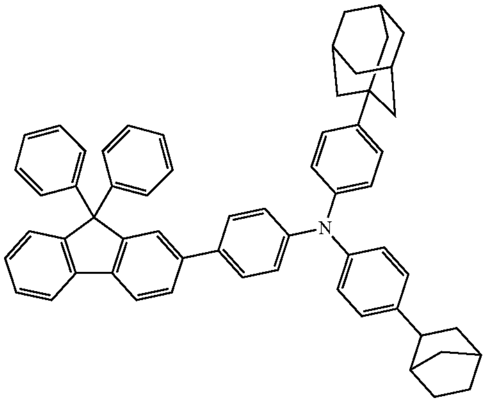
-continued
63
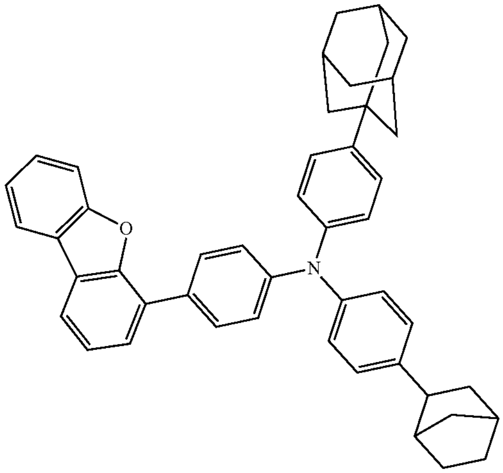
64
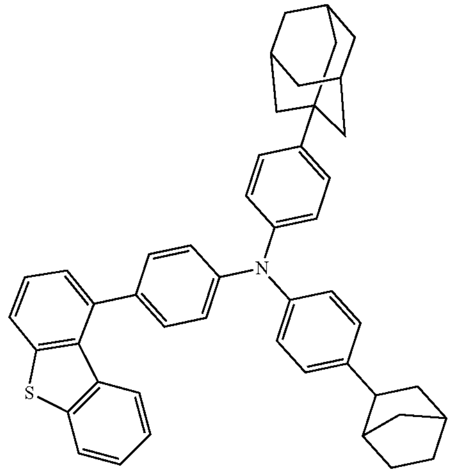
65
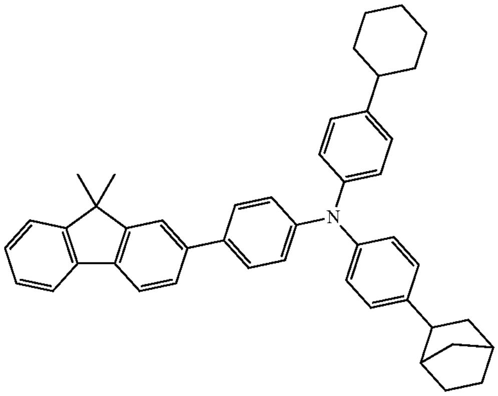

-continued
66
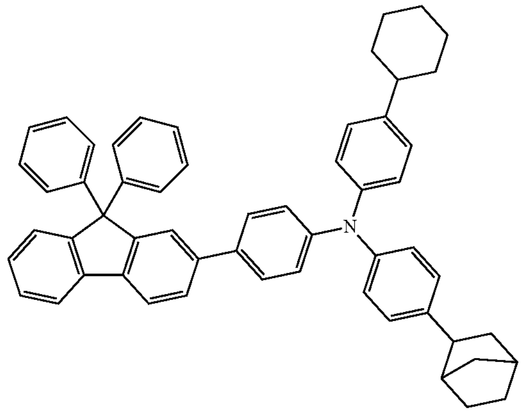
67
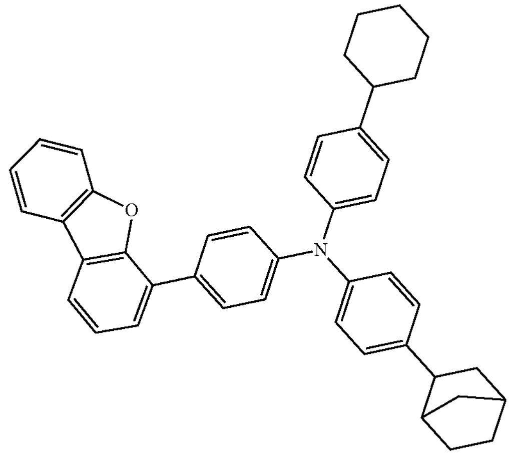
68
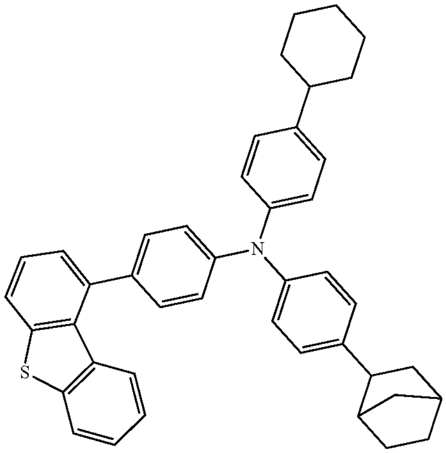
-continued
69
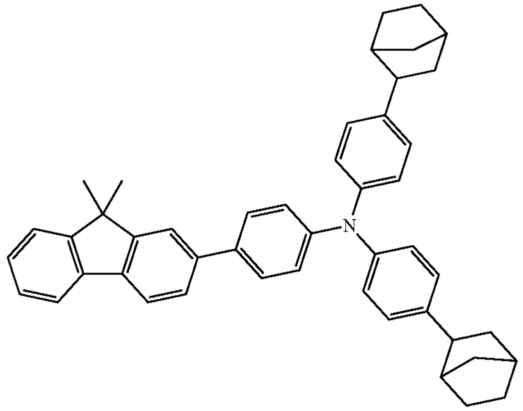
70
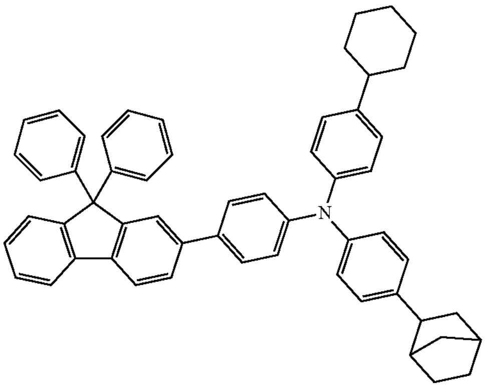
71
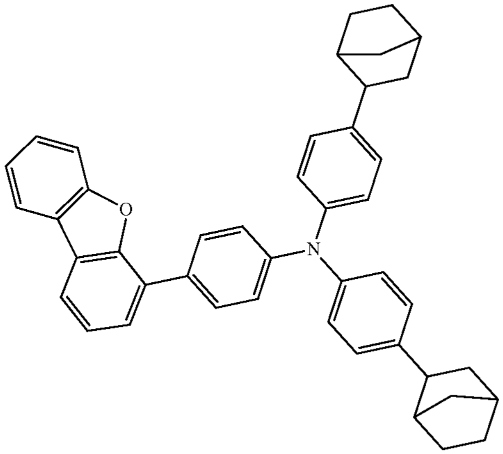

-continued

72

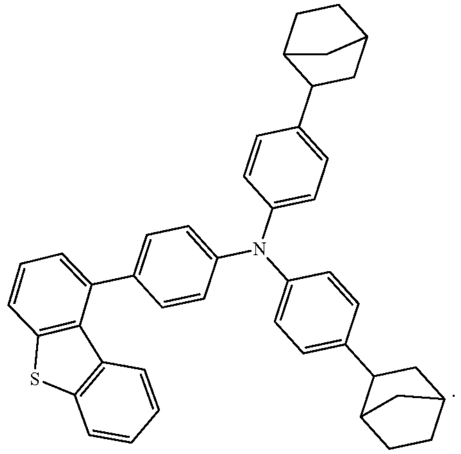

The first amine compound and the third amine compound according to an embodiment represented by Formula 1 may have a structure of a substituent essentially containing one unsubstituted bicycloheptyl group, as well as essentially containing one of a substituted or unsubstituted bicycloheptyl group, a substituted or unsubstituted cyclohexyl group, or a substituted or unsubstituted adamantyl group, thereby having a low refractive index.

In an embodiment, the first amine compound and the third amine compound may each independently be a compound represented by Formula 4.

[Formula 4]

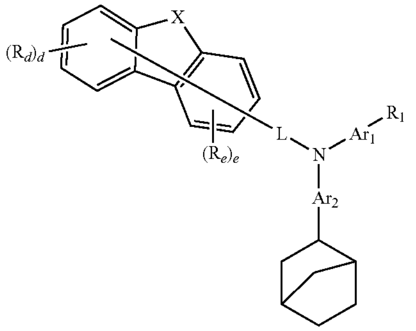

In Formula 4, $R_1$ may be a substituted or unsubstituted adamantyl group, a substituted or unsubstituted cyclohexyl group, or a substituted or unsubstituted bicycloheptyl group.

For example, the amine compound of an embodiment represented by Formula 4 may include a first substituent of a bicycloheptyl group, a second substituent selected from an adamantyl group, a cyclohexyl group, or a bicycloheptyl group, and a third substituent selected from a fluorenyl group or a dibenzoheterole group, each bonded to an N atom. For example, the bicycloheptyl group used as a substituent in the amine compound of an embodiment may be an unsubstituted bicyclo[2,2,1]heptyl group (bicyclo[2,2,1]heptyl). For example, in the amine compound of an embodiment, $R_1$ may be an unsubstituted adamantyl group, an unsubstituted cyclohexyl group, or an unsubstituted bicyclo[2,2,1]heptyl group (bicyclo[2,2,1]heptyl).

In Formula 4, $Ar_1$ and $Ar_2$ may each independently be a substituted or unsubstituted arylene group having 6 to 30 ring-forming carbon atoms. For example, $Ar_1$ and $Ar_2$ may each independently be a substituted or unsubstituted phenylene group.

In Formula 4, L may be a direct linkage, a substituted or unsubstituted arylene group having 6 to 30 ring-forming carbon atoms, or a substituted or unsubstituted heteroarylene group having 2 to 30 ring-forming carbon atoms. When L is a direct linkage, the nitrogen atom (N) of Formula 4 and a group represented by

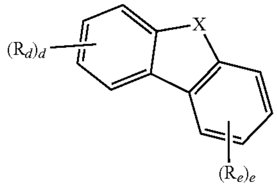

may be directly bonded with a single bond. In another embodiment, L may be a substituted or unsubstituted phenylene group.

In Formula 4, X may be $C(R_a)(R_b)$, N, $N(R_c)$, O, or S. For example, in Formula 4, a group represented by

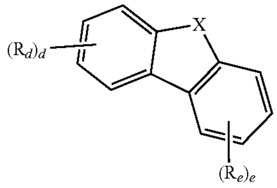

may be a substituted or unsubstituted fluorene derivative, a substituted or unsubstituted carbazole derivative, a substituted or unsubstituted dibenzofuran derivative, or a substituted or unsubstituted dibenzothiophene derivative.

In Formula 4, $R_a$ to $R_c$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring, In Formula 4, d and e may each independently be an integer from 0 to 4. In Formula 4, $R_d$ and $R_e$ may each independently be a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula 4, when d is 0, $R_d$ may not be present, and when e is 0, $R_e$ may not be present. For example, when d and e are each 0 in Formula 4, the benzene rings of the group represented by

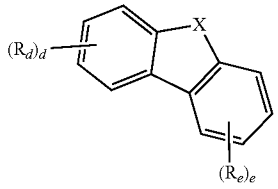

may be unsubstituted. In Formula 4, when d is 2 or greater, multiple $R_d$ groups may all be the same or at least one may be different from the others. In Formula 4, when e is 2 or greater, multiple $R_e$ groups may all be the same or at least one may be different from the others.

In an embodiment, in Formula 4, when X is represented by $C(R_a)(R_b)$, $R_a$ and $R_b$ may each independently be a linear alkyl group, a cyclic alkyl group, or an aryl group. For example, $R_a$ and $R_b$ may be bonded to each other to form a ring. When $R_a$ and $R_b$ are bonded to each other to form a fluorene ring, the group represented by

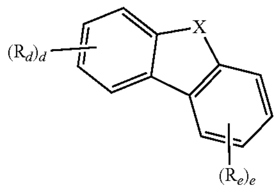

may have a spiro structure.

In Formula 4, when X is represented by $C(R_a)(R_b)$, $R_a$ or $R_b$ may be directly bonded to L, or $R_a$ or $R_b$ may be directly bonded to the nitrogen atom (N) of Formula 4.

In an embodiment, the second hole transport layer HTL may be disposed between the first hole transport layer HTL1 and the third hole transport layer HTL3 and may include a second amine compound represented by Formula 3.

[Formula 3]

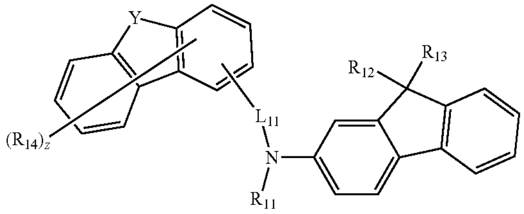

In Formula 3, $L_{11}$ may be a direct linkage, a substituted or unsubstituted arylene group having 6 to 30 ring-forming carbon atoms, or a substituted or unsubstituted heteroarylene group having 2 to 30 ring-forming carbon atoms. For example, $L_{11}$ may be a direct linkage or a substituted or unsubstituted phenylene group. However, embodiments are not limited thereto.

In Formula 3, z may be an integer from 0 to 7. When z is 2 or greater, all $R_{14}$ groups may be the same, or at least one $R_{14}$ group may be different from the others.

In Formula 3, Y may be $C(R_f)(R_g)$, $N(R_h)$, O, or S. In Formula 3, when Y is represented by $C(R_f)(R_g)$ or $N(R_h)$, $R_f$ to $R_h$ may each independently be a hydrogen atom, a deuterium atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula 3, $R_{11}$ to $R_{14}$ may each independently be a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In the second amine compound represented by Formula 3, $R_{11}$ may be an aryl group or a heteroaryl group. For example, $R_{11}$ may be a substituted or unsubstituted phenyl group, a substituted or unsubstituted naphthyl group, a substituted or unsubstituted fluorene group, a substituted or unsubstituted biphenyl group, a substituted or unsubstituted dibenzofuran group, or a substituted or unsubstituted dibenzothiophene group.

In an embodiment, the second amine compound represented by Formula 3 may be represented by any one of Formulas 3-1 to 3-3. In Formulas 3-1 to 3-3, z, $L_{11}$, Y, and $R_{11}$ to $R_{14}$ are the same as defined in Formula 3.

[Formula 3-1]

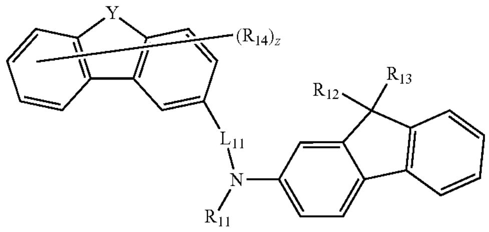

[Formula 3-2]

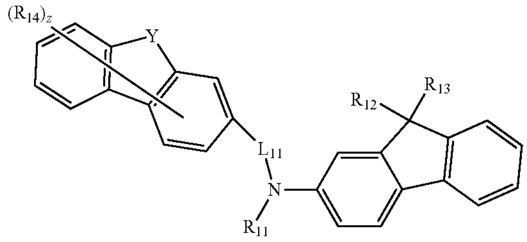

[Formula 3-3]

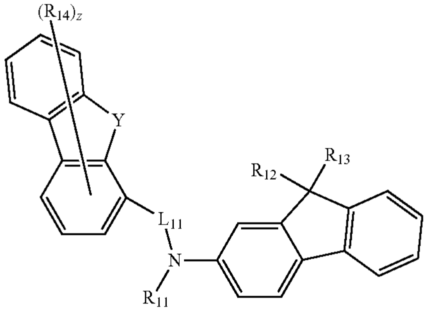

The light emitting element ED of an embodiment may include the first amine compound of an embodiment described above in the first hole transport layer HTL1, and the second amine compound represented by Formula 3-1, the second amine compound represented by Formula 3-2, or the second amine compound represented by Formula 3-3 in the second hole transport layer HTL2, and the third amine compound of an embodiment described above in the third hole transport layer HTL3.

The second amine compound represented by Formula 3 may be any one selected from Compound Group 2. For example, the second hole transport layer HTL2 may include at least one compound selected from Compound Group 2.

[Compound Group 2]

73

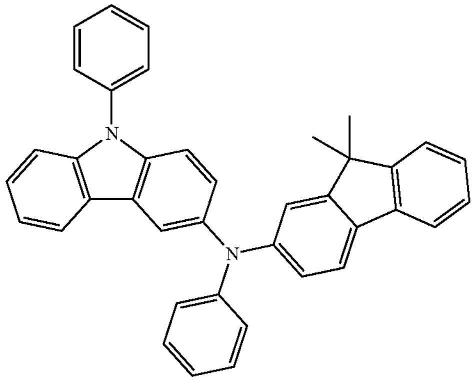

74

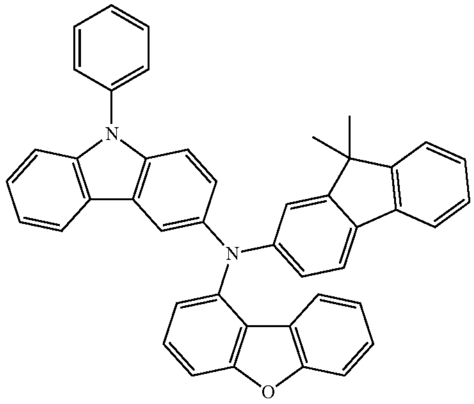

75

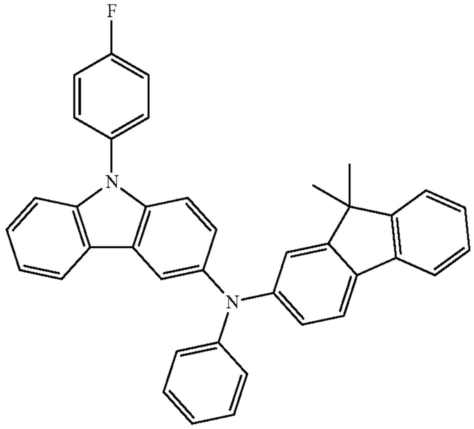

-continued

76

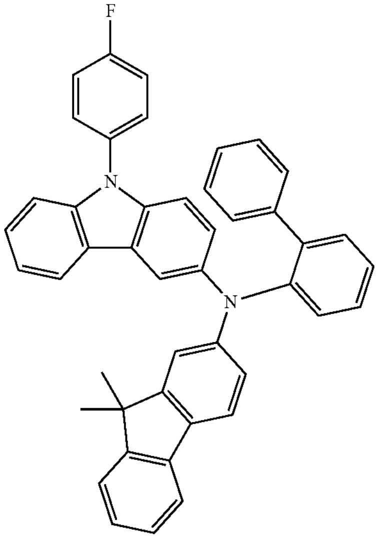

77

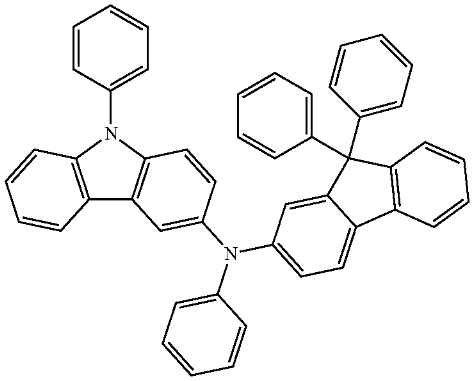

78

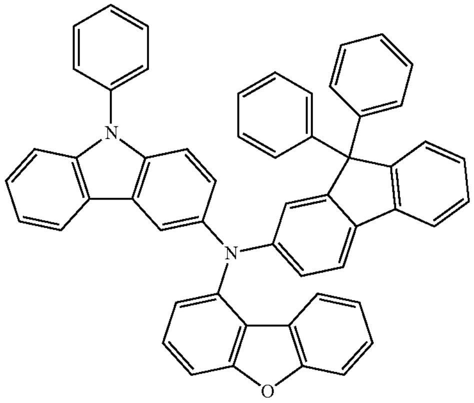

-continued
79
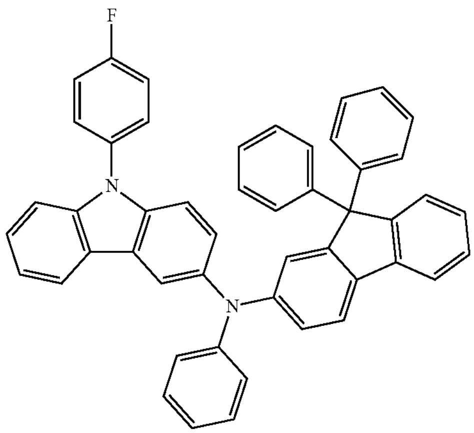
80
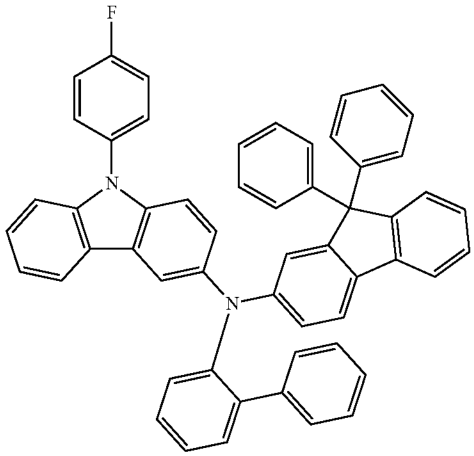
81
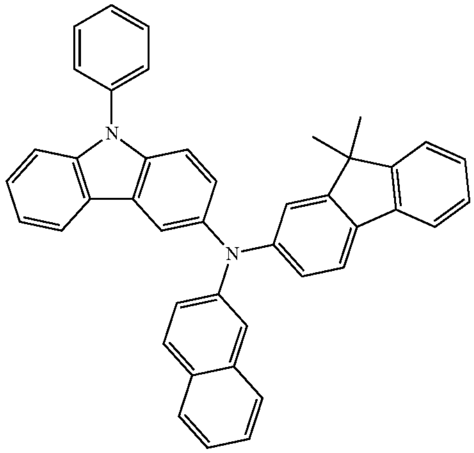
-continued
82
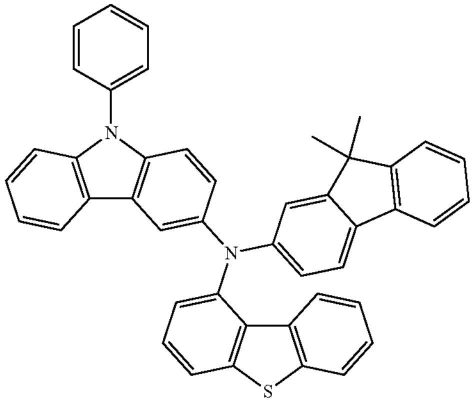
83
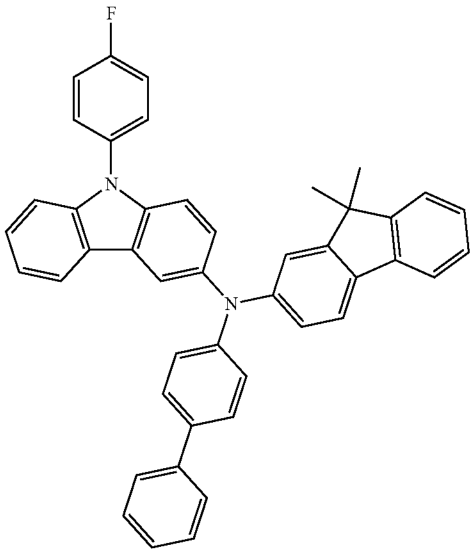
84
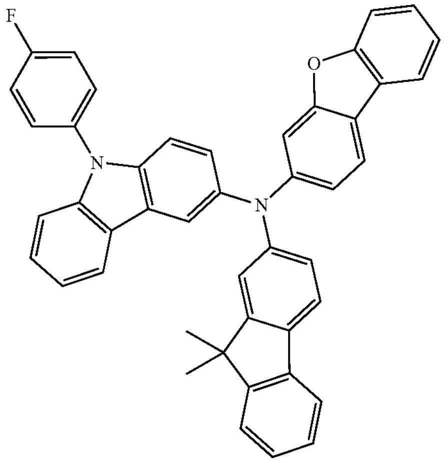

-continued
85
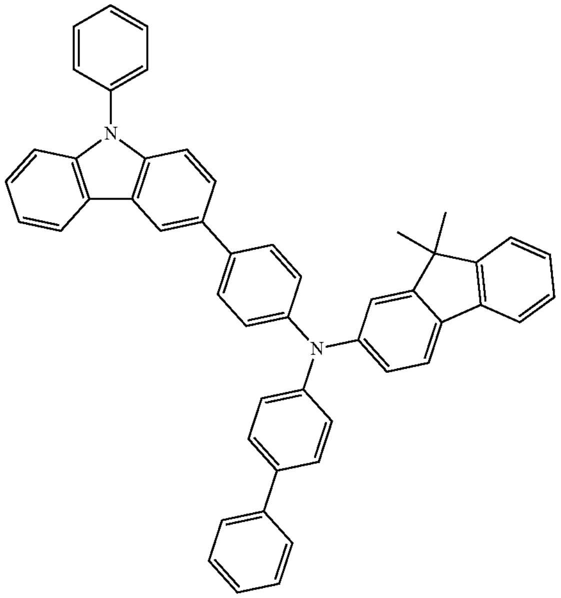
86
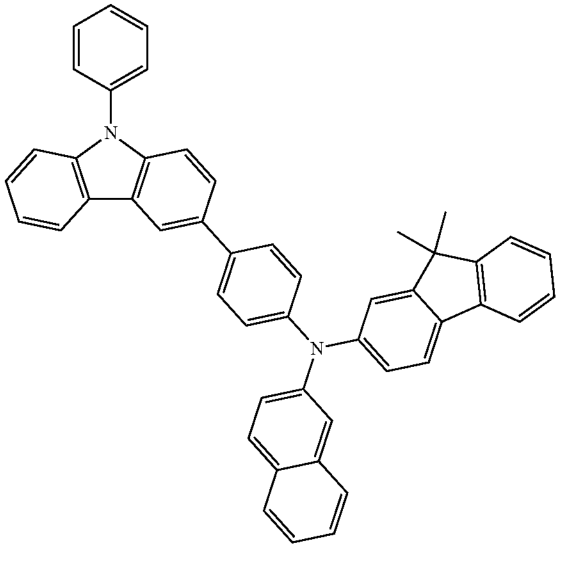
-continued
87
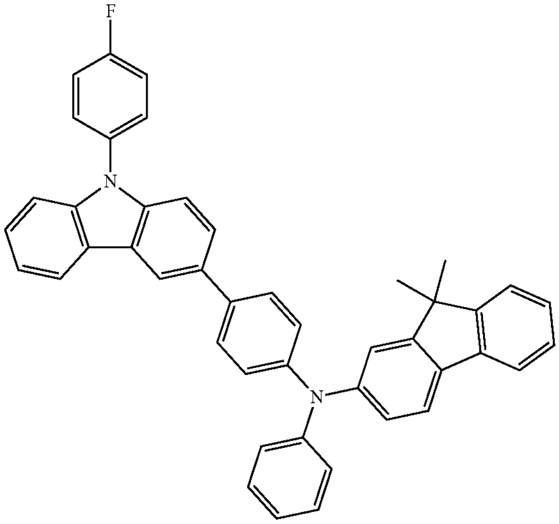
88
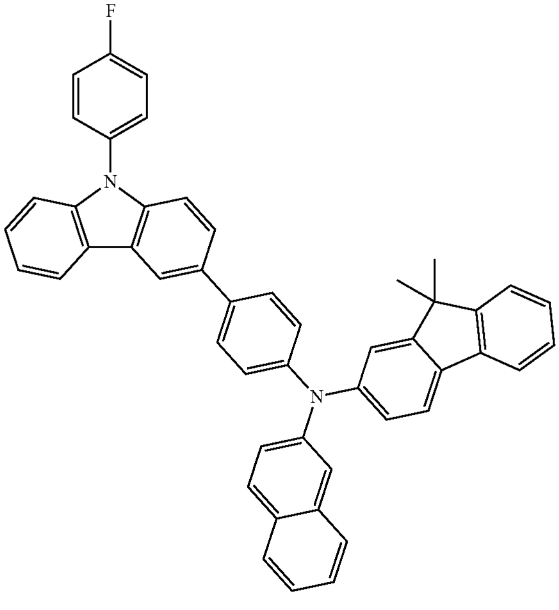

-continued
89
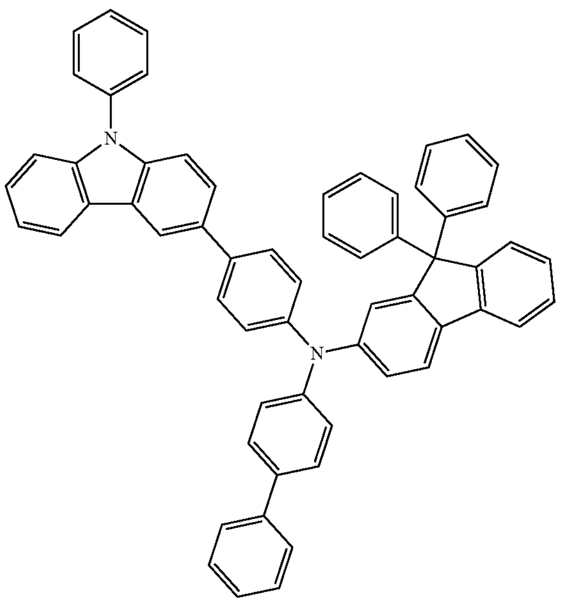
90
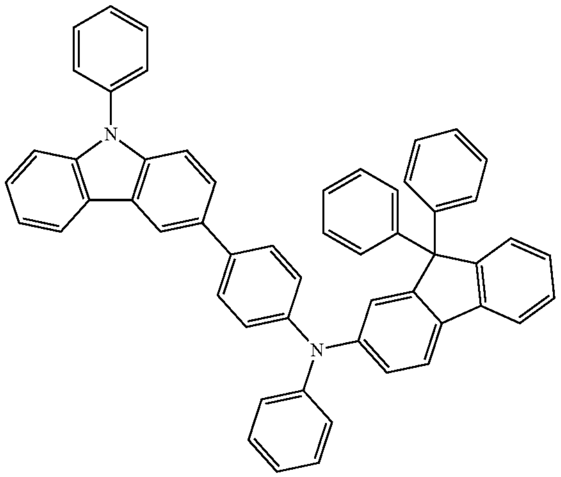
91
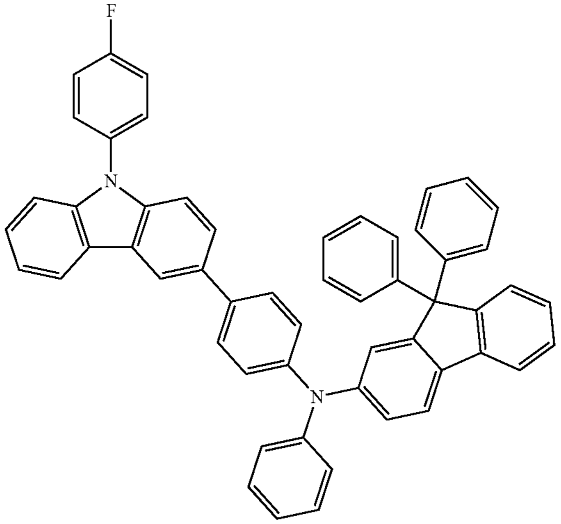
-continued
92
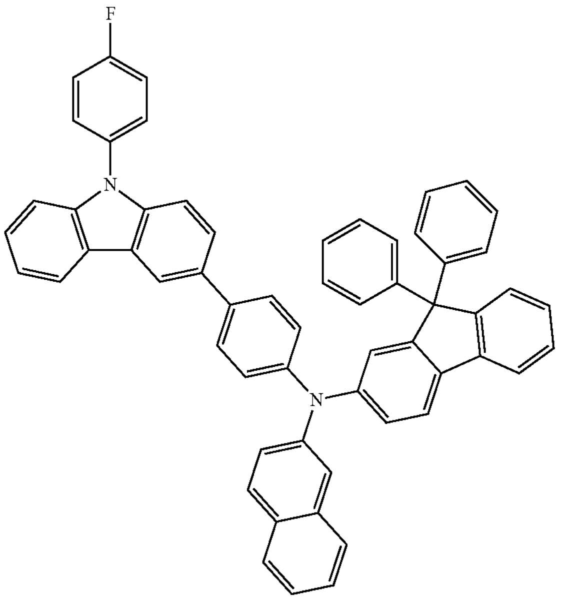
93
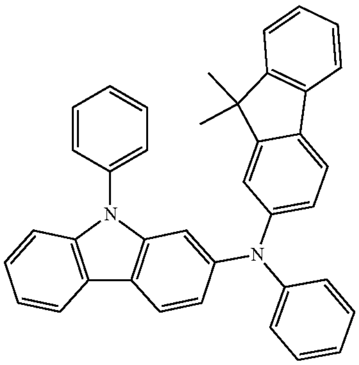
94
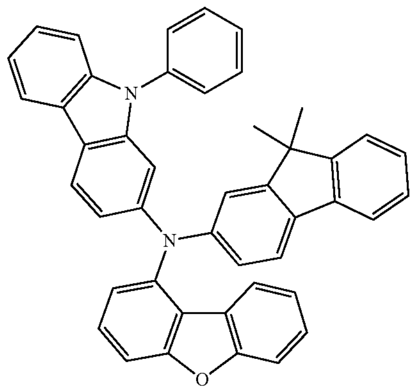

-continued
95
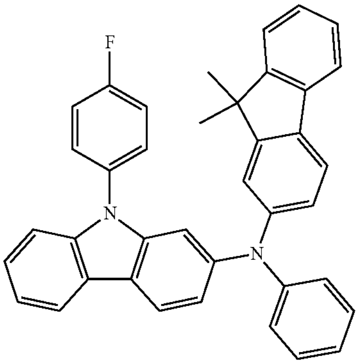
96
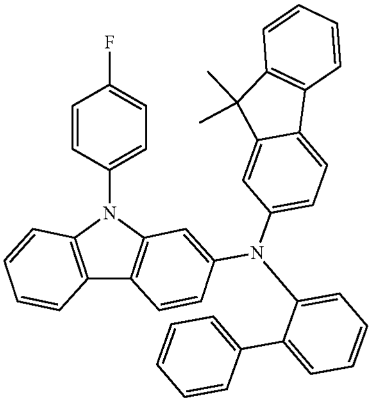
97
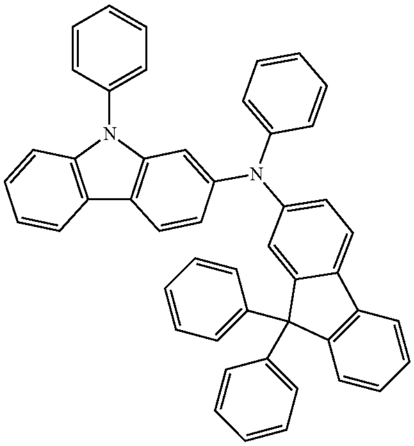
98
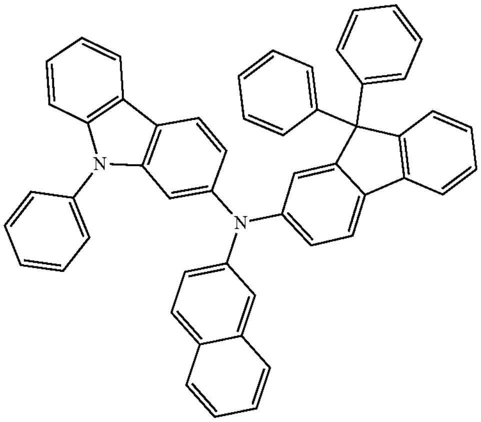
-continued
99
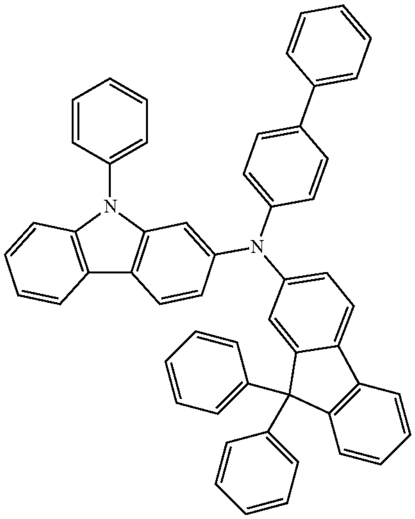
100
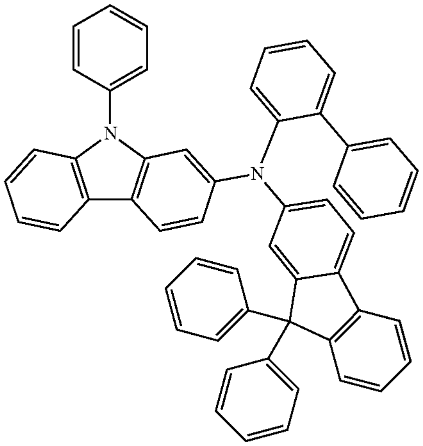
101
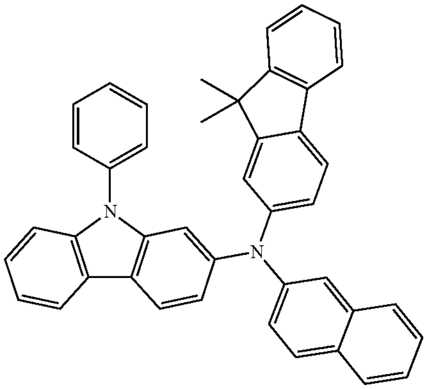

-continued
102
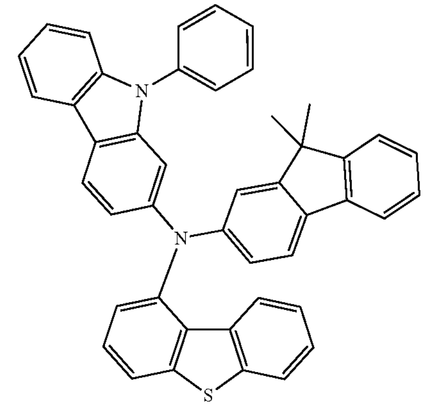
103
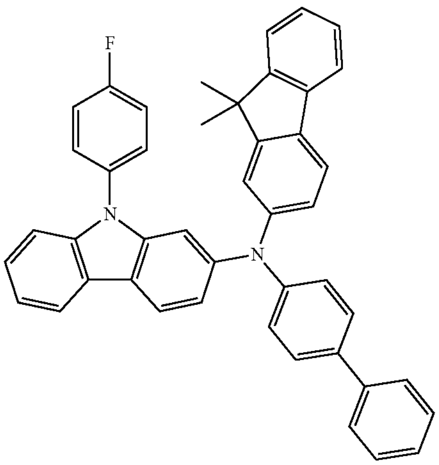
104
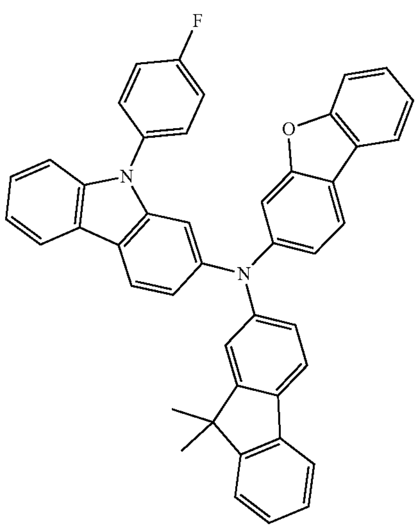
-continued
105
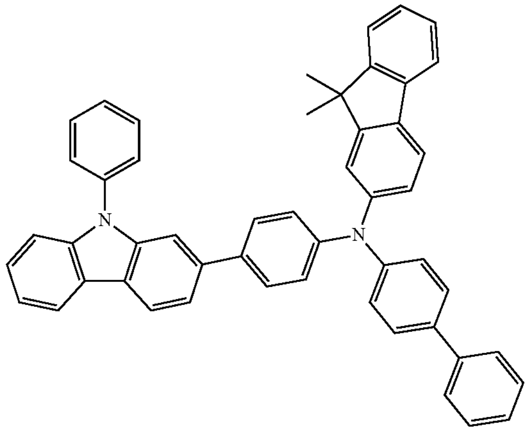
106
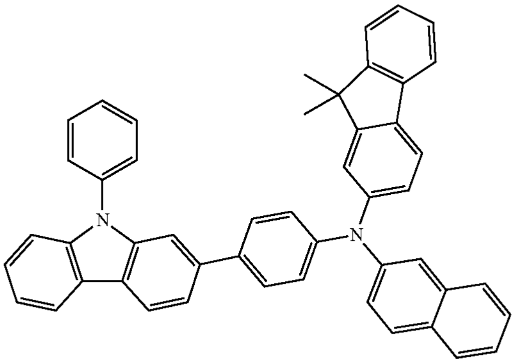
107
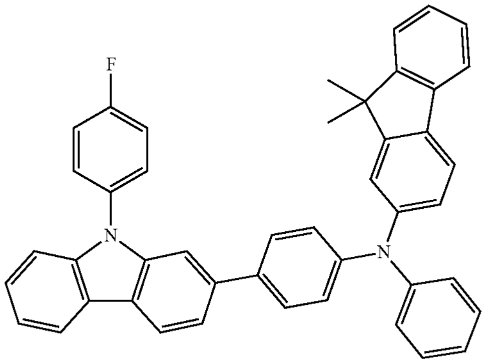
108
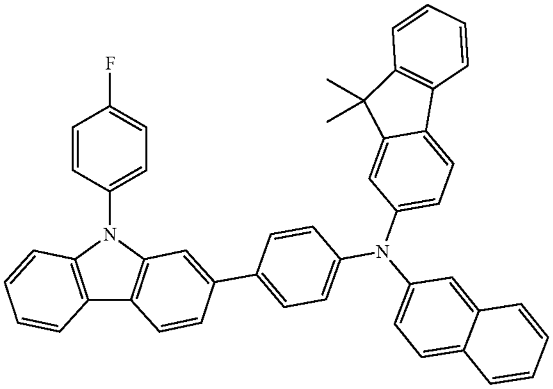

-continued
109
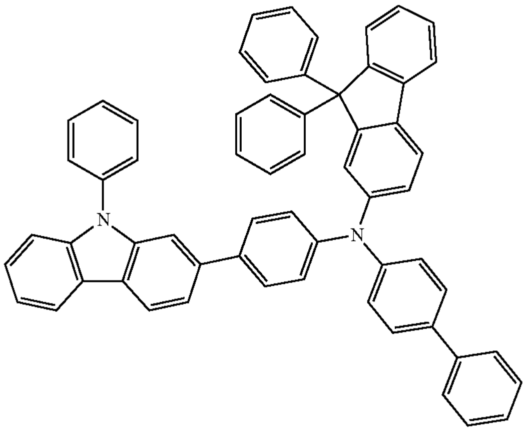
110
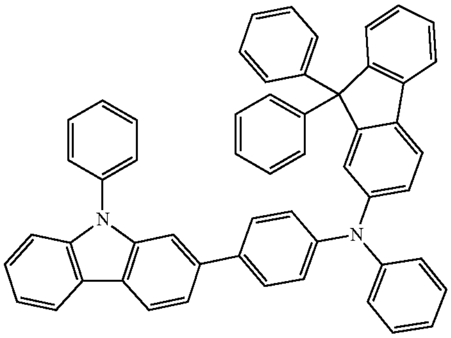
111
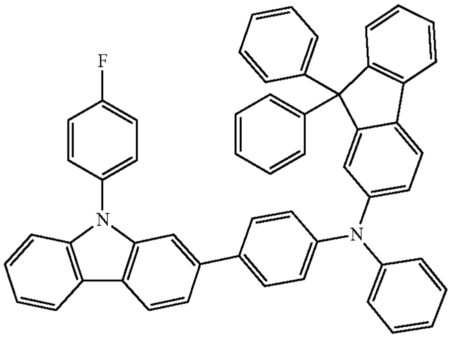
112
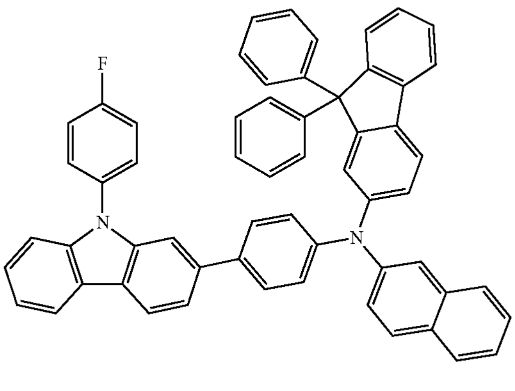
-continued
113
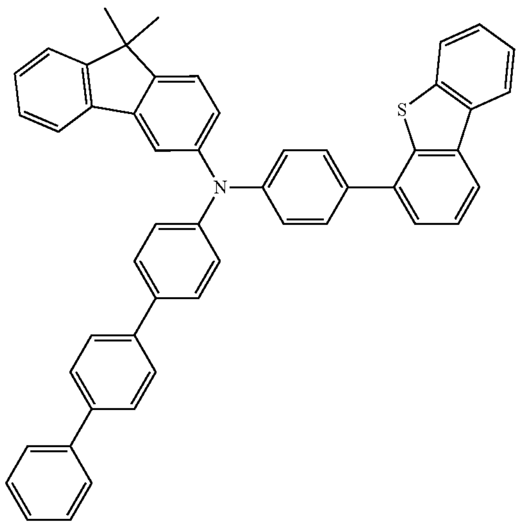
114
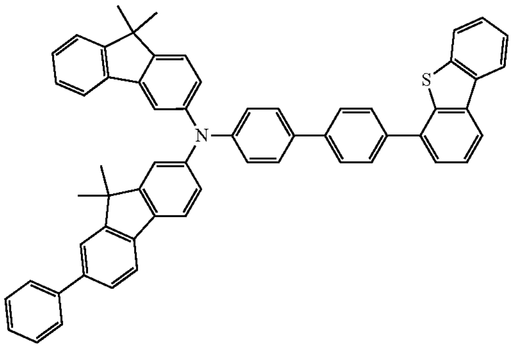
115
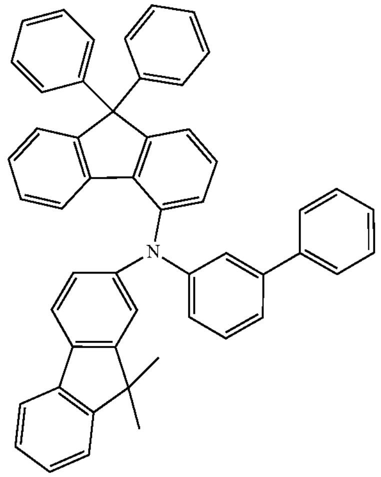

-continued

116

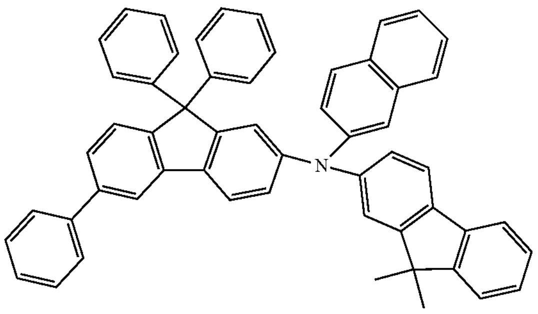

117

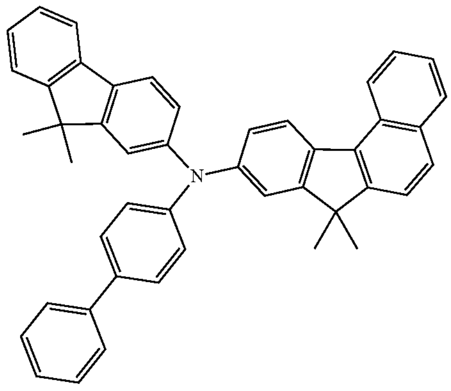

118

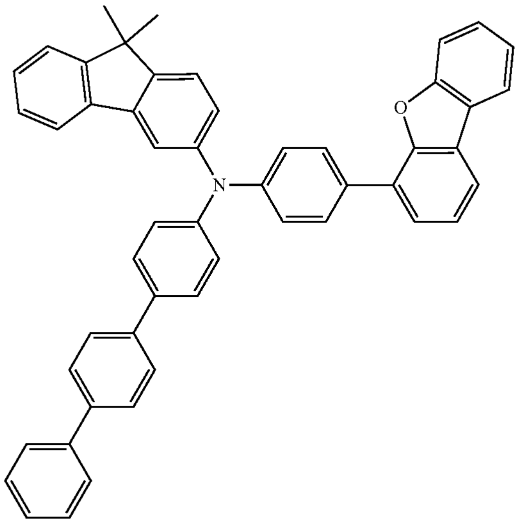

119

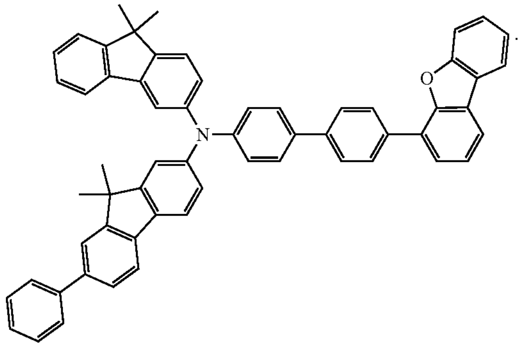

The light emitting element ED of an embodiment may further include the first amine compound and the third amine compound each independently represented by Formula 1 of an embodiment described above, the second amine compound represented by Formula 3, and materials of a hole transport region, which will be described later.

The hole transport region HTR may include a compound represented by Formula H-1. For example, the second hole transport layer HTL2 may include compounds having a refractive index greater than the refractive index of the compound included in the first hole transport layer HTL1 and the refractive index of the compound included in the third hole transport layer HTL3 each among compounds represented by Formula H-1. For example, the second hole transport layer HTL2 may include compounds having a refractive index in a range of about 1.8 to about 2.4 among the compounds represented by Formula H-1.

[Formula H-1]

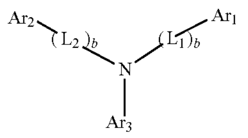

In Formula H-1, $L_1$ and $L_2$ may each independently be a direct linkage, a substituted or unsubstituted arylene group having 6 to 30 ring-forming carbon atoms, or a substituted or unsubstituted heteroarylene group having 2 to 30 ring-forming carbon atoms. In Formula H-1, a and b may each independently be an integer from 0 to 10. When a or b is 2 or greater, multiple $L_1$ groups and multiple $L_2$ groups may each independently be a substituted or unsubstituted arylene group having 6 to 30 ring-forming carbon atoms, or a substituted or unsubstituted heteroarylene group having 2 to 30 ring-forming carbon atoms.

In Formula H-1, $Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. In Formula H-1, $Ar_3$ may be a substituted or unsubstituted aryl group having 6 to 30 ring-forming carbon atoms.

A compound represented by Formula H-1 may be a monoamine compound. In another embodiment, the compound represented by Formula H-1 may be a diamine compound in which at least one of $Ar_1$ to $Ar_3$ includes an amine group as a substituent. In still another embodiment, the compound represented by Formula H-1 may be a carbazole-based compound including a substituted or unsubstituted carbazole group in at least one of $Ar_1$ or $Ar_2$ includes a substituted or unsubstituted fluorene group.

The compound represented by Formula H-1 may be any one selected from Compound Group H. However, the compounds listed in Compound Group H are only presented as examples, and the compound represented by Formula H-1 is not limited to those shown in Compound Group H.

[Compound Group H]
H-1-1
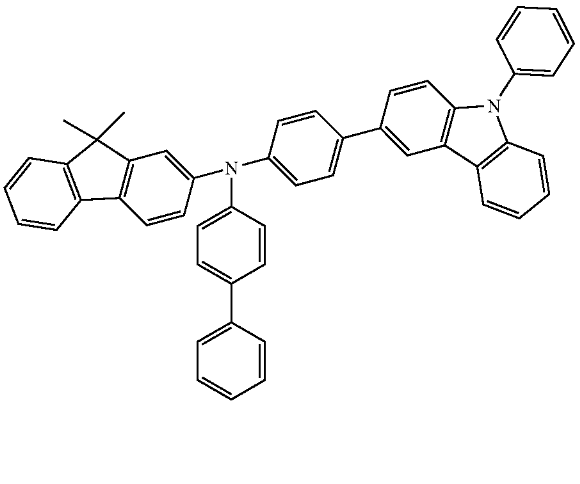
H-1-2
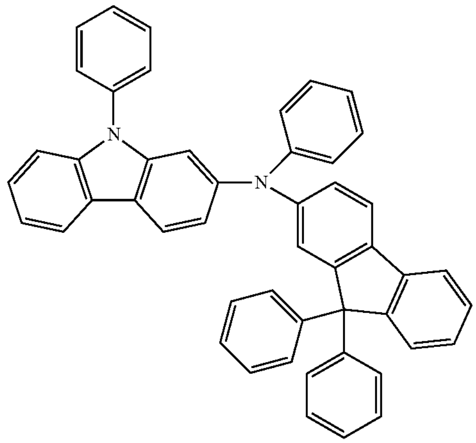
H-1-3
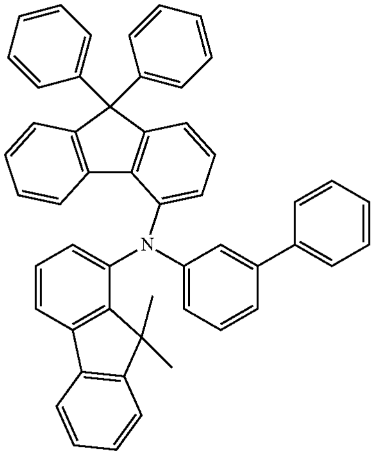
-continued
H-1-4
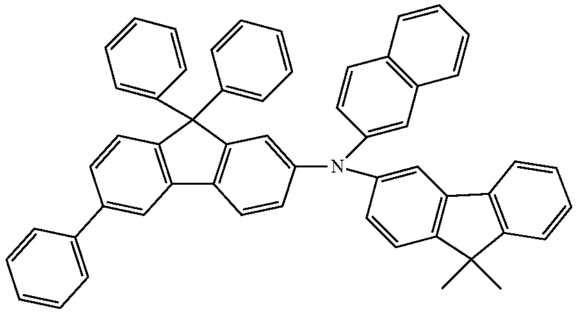
H-1-5
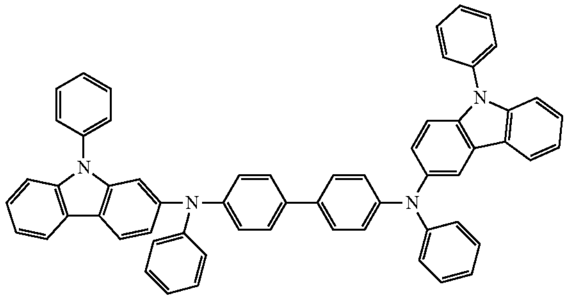
H-1-6
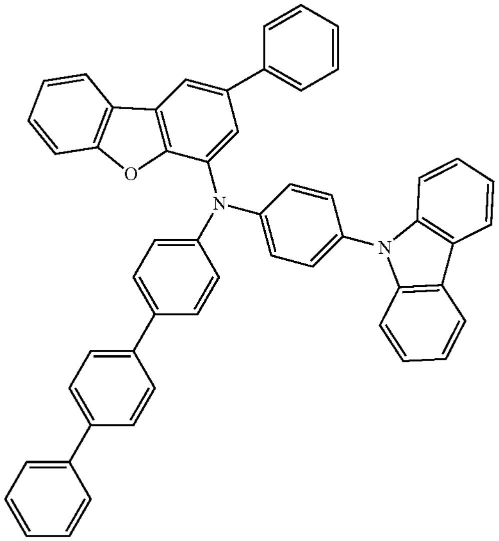

-continued
H-1-7
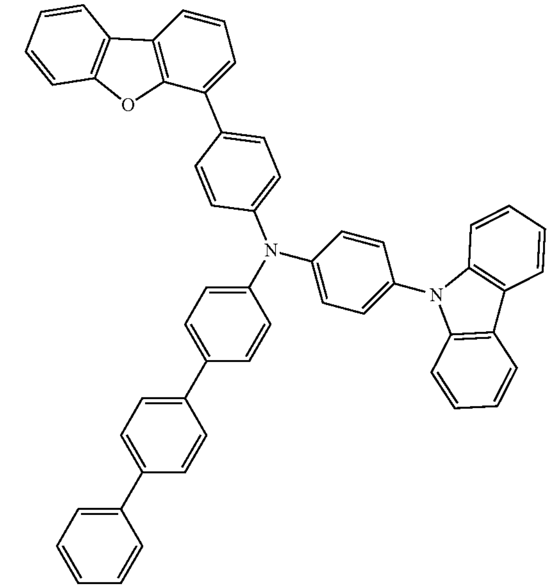
H-1-8
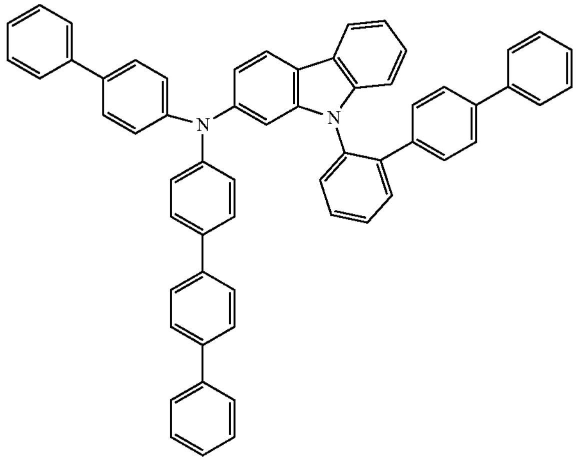
H-1-9
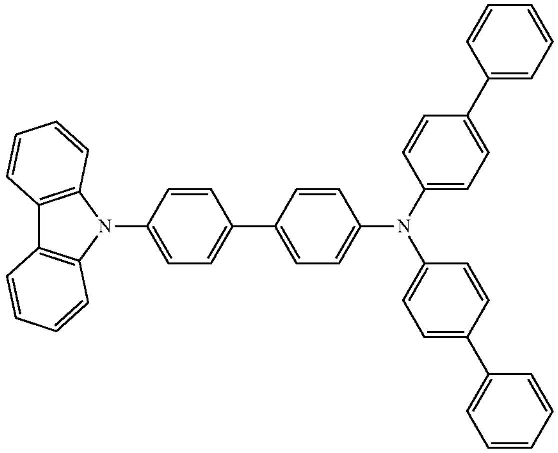
-continued
H-1-10
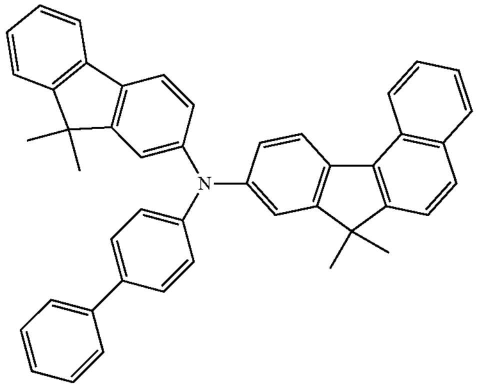
H-1-14
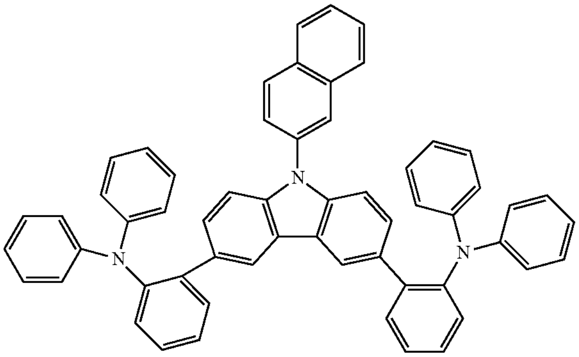
H-1-15
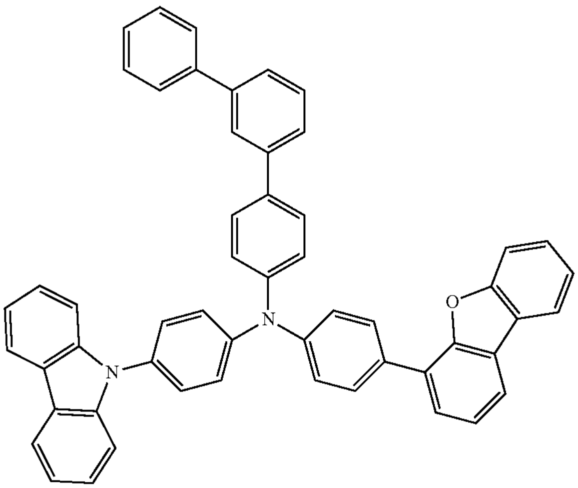

-continued

H-1-16

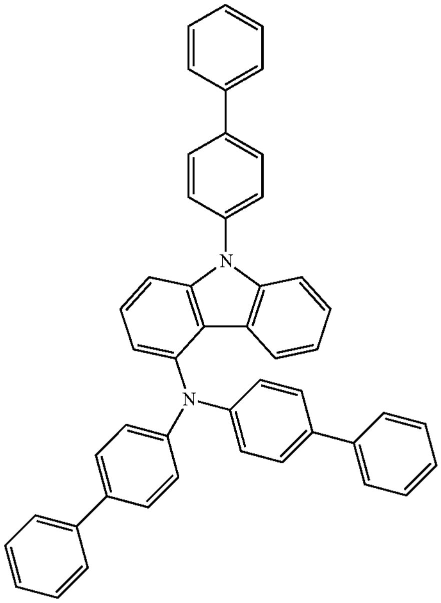

H-1-17

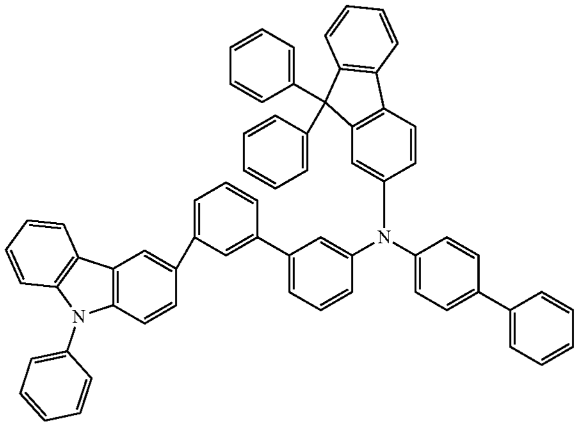

H-1-18

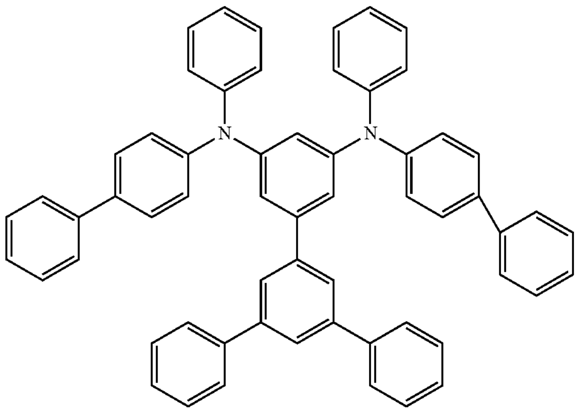

-continued

H-1-19

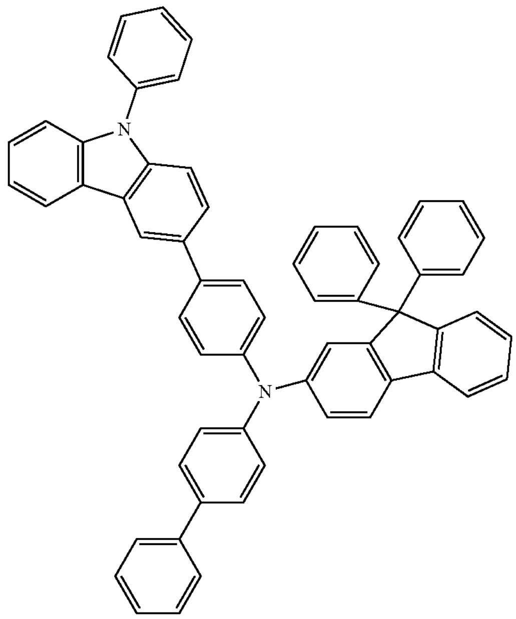

The hole transport region HTR may include a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-[tris(3-methylphenyl)phenylamino]triphenylamine] (m-MTDATA), 4,4',4"-tris(N,N-diphenylamino)triphenylamine (TDATA), 4,4',4"-tris{N,-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyetherketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport region HTR may include carbazole-based derivatives such as N-phenyl carbazole and polyvinyl carbazole, fluorene-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl)triphenylamine (TCTA), N,N'-di(1-naphtalene-1-yl)-N,N'-diphenyl-benzidine (NPB), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The hole transport region HTR may include 9-(4-tert-Butylphenyl)-3,6-bis(triphenylsilyl)-9H-carbazole (CzSi), 9-phenyl-9H-3,9'-bicarbazole (CCP), 1,3-Bis(N-carbazolyl)benzene (mCP), 1,3-bis(1,8-dimethyl-9H-carbazol-9-yl)benzene (mDCP), etc.

The hole transport region HTR may include the compounds of the hole transport region described above in at least one of the hole injection layer HIL, the hole transport layer HTL, or the electron blocking layer EBL.

The hole transport region HTR may have a thickness in a range of about 100 Å to about 10,000 Å. For example, the hole transport region HTR may have a thickness in a range of about 100 Å to about 5,000 Å. When the hole transport region HTR includes a hole injection layer HIL, the hole injection layer HIL may have a thickness, for example, in a range of about 30 Å to about 1,000 Å. When the hole transport region HTR includes a hole transport layer HTL, the hole transport layer HTL may have a thickness in a range of about 30 Å to about 1,000 Å. When the hole transport region HTR includes an electron blocking layer EBL, the electron blocking layer EBL may have a thickness, for example, in a range of about 10 Å to about 1,000 Å. When the thicknesses of the hole transport region HTR, the hole injection layer HIL, the hole transport layer HTL, and the electron blocking layer EBL satisfy the above-described ranges, satisfactory hole transport properties may be obtained without a substantial increase in driving voltage.

The hole transport region HTR may further include, in addition to the above-described materials, a charge generation material to increase conductivity. The charge generation material may be uniformly or non-uniformly dispersed in the hole transport region HTR. The charge generation material may be, for example, a p-dopant. The p-dopant may include at least one of halogenated metal compounds, quinone derivatives, metal oxides, or cyano group-containing compounds, but is not limited thereto. For example, the p-dopant may include halogenated metal compounds such as CuI and RbI, quinone derivatives such as tetracyanoquinodimethane (TCNQ) and 2,3,5,6-tetrafluoro-7,7,8,8-tetracyanoquinodimethane (F4-TCNQ), metal oxides such as tungsten oxides and molybdenum oxides, cyano group-containing compounds such as dipyrazino[2,3-f: 2',3'-h] quinoxaline-2,3,6,7,10,11-hexacarbonitrile (HATCN) and 4-[[2,3-bis[cyano-(4-cyano-2,3,5,6-tetrafluorophenyl)methylidene] cyclopropylidene]-cyanomethyl]-2,3,5,6-tetrafluorobenzonitrile (NDP9), etc., but is not limited thereto.

As described above, the hole transport region HTR may further include at least one of a buffer layer (not shown) or an electron blocking layer EBL, in addition to the hole injection layer HIL and the hole transport layer HTL. The buffer layer (not shown) may compensate for a resonance distance according to a wavelength of light emitted from an emission layer EML, and may thus increase luminous efficiency. Materials which may be included in the hole transport region HTR may be used as materials included in the buffer layer (not shown). The electron blocking layer EBL may prevent electrons from being injected from the electron transport region ETR to the hole transport region HTR.

The emission layer EML is provided on the hole transport region HTR. The emission layer EML may have, for example, a thickness in a range of about 100 Å to about 1.000 Å. For example, the emission layer EML may have a thickness in a range of about 100 Å to about 300 Å. The emission layer EML may be a layer formed of a single material, a layer formed of different materials, or a multilayer structure having layers formed of different materials.

In the light emitting element ED of an embodiment, the emission layer EML may include an anthracene derivative, a pyrene derivative, a fluoranthene derivative, a chrysene derivative, a dihydrobenzanthracene derivative, or a triphenylene derivative. For example, the emission layer EML may include an anthracene derivative or a pyrene derivative.

In the light emitting element ED of an embodiment shown in FIGS. 3 to 6, the emission layer EML may include a host and a dopant, and the emission layer EML may include a compound represented by Formula E-1. The compound represented by Formula E-1 may be used as a fluorescent host material.

[Formula E-1]

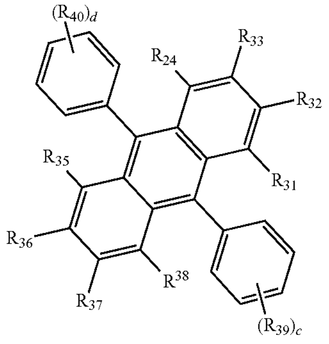

In Formula E-1, $R_{31}$ to $R_{40}$ may each independently be a hydrogen atom, a deuterium atom, a halogen atom, a substituted or unsubstituted silyl group, a substituted or unsubstituted thio group, a substituted or unsubstituted oxy group, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In Formula E-1, $R_{31}$ to $R_{40}$ may be bonded to an adjacent group to form a saturated hydrocarbon ring, an unsaturated hydrocarbon ring, a saturated heterocycle, or an unsaturated heterocycle.

In Formula E-1, c and d may each independently be an integer from 0 to 5.

The compound represented by Formula E-1 may be any one selected from Compounds E1 to E19.

E1

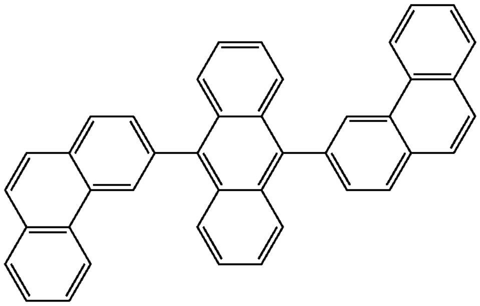

E2

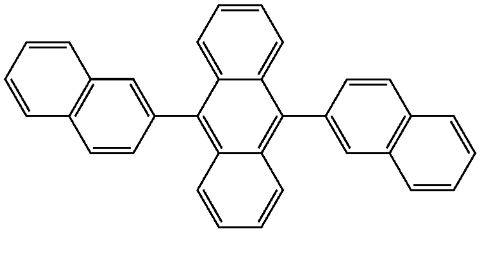

-continued
E3
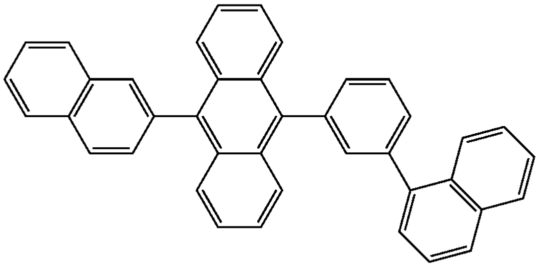
E4
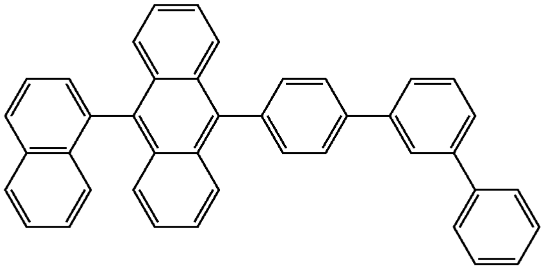
E5
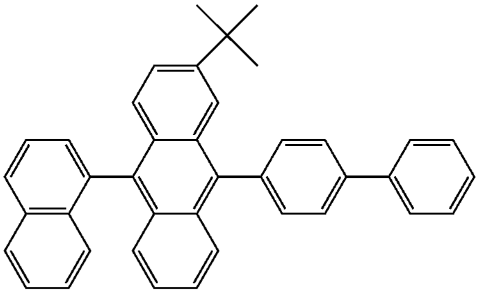
E6
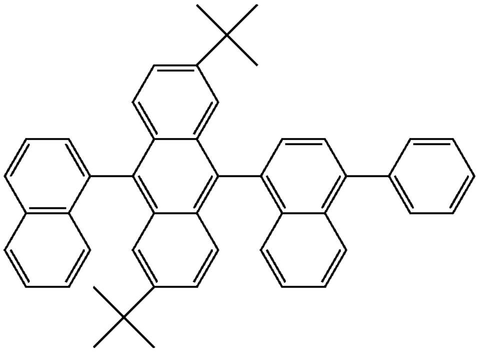
E7
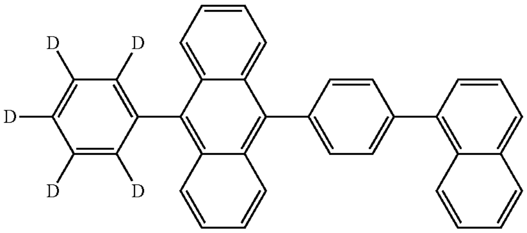
-continued
E8
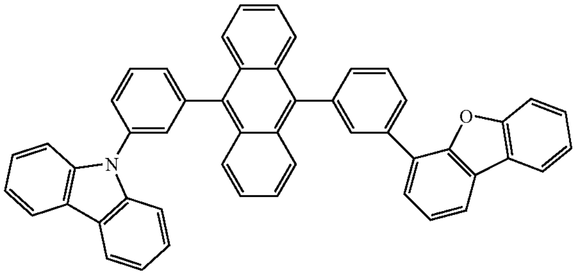
E9
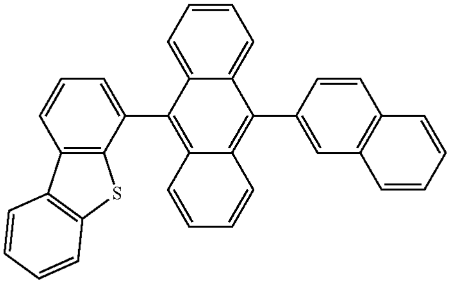
E10
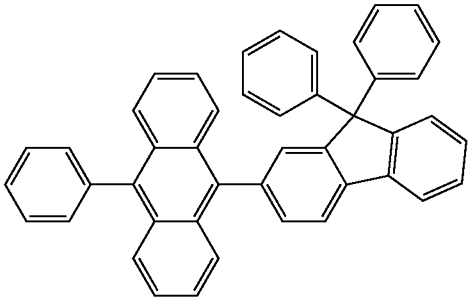
E11
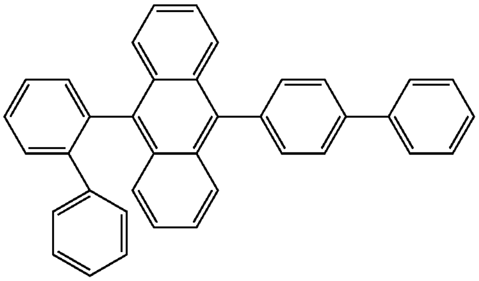
E12
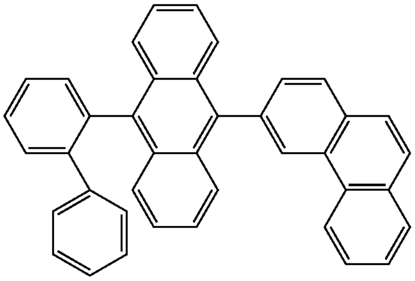

-continued
E13
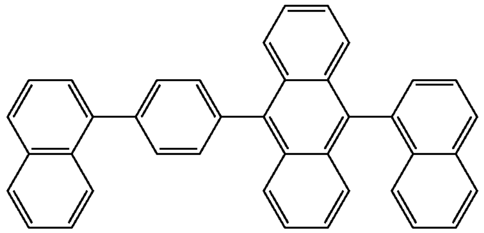
E14
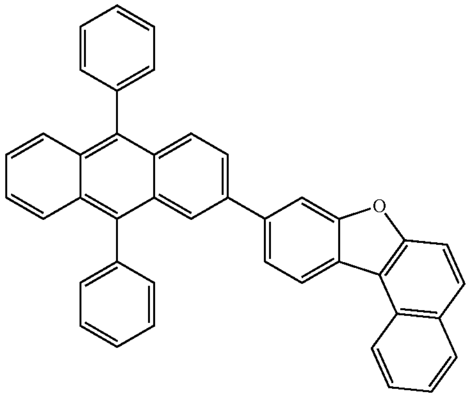
E15
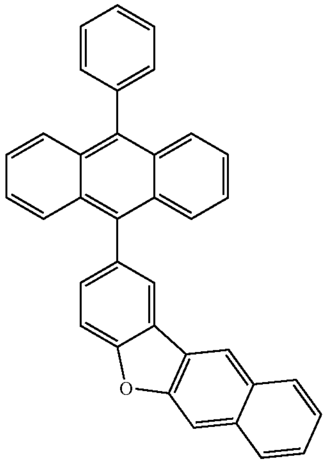
E16
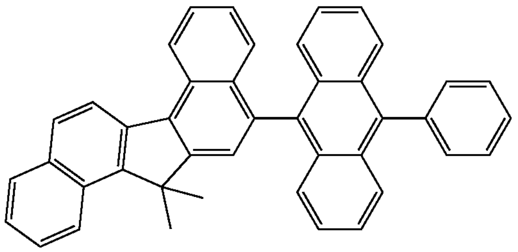
-continued
E17
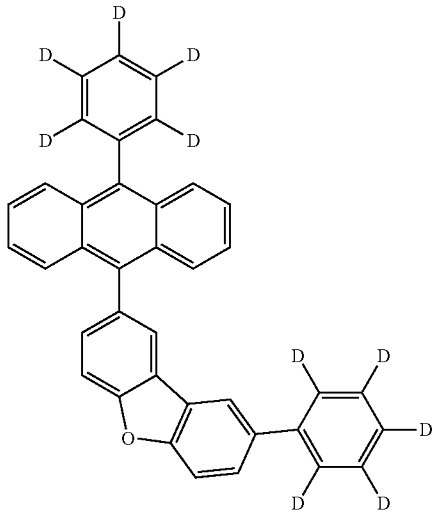
E18
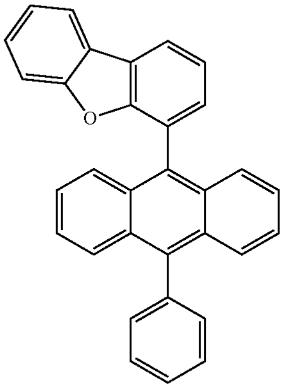
E19
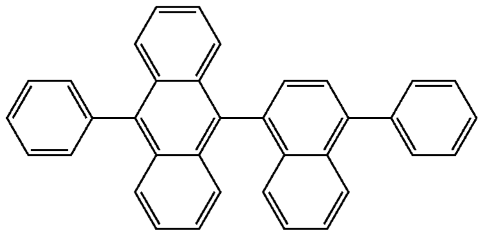
In an embodiment, the emission layer EML may include a compound represented by Formula E-2a or Formula E-2b. The compound represented by Formula E-2a or Formula E-2b may be used as a phosphorescent host material.

[Formula E-2a]

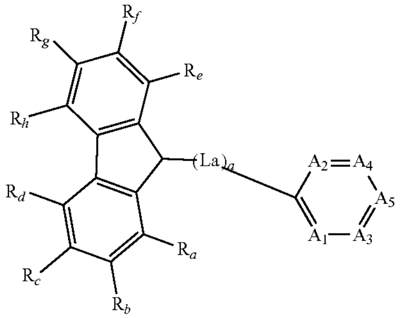

In Formula E-2a, a may be an integer from 0 to 10, and $L_a$ may be a direct linkage, a substituted or unsubstituted arylene group having 6 to 30 ring-forming carbon atoms, or a substituted or unsubstituted heteroarylene group having 2 to 30 ring-forming carbon atoms. When a is 2 or greater, multiple $L_a$ groups may each independently be a substituted or unsubstituted arylene group having 6 to 30 ring-forming carbon atoms, or a substituted or unsubstituted heteroarylene group having 2 to 30 ring-forming carbon atoms.

In Formula E-2a, $A_1$ to $A_5$ may each independently be N or $C(R_i)$. $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. $R_a$ to $R_i$ may be bonded to an adjacent group to form a hydrocarbon ring or a heterocycle containing N, O, S, etc. as a ring-forming atom.

In Formula E-2a, two or three of $A_1$ to $A_5$ may be N, and the remainder of $A_1$ to $A_5$ may be $C(R_i)$.

[Formula E-2b]

$$(Cbz1)-(L_b)_b-(Cbz2)$$

In Formula E-2b, Cbz1 and Cbz2 may each independently be an unsubstituted carbazole group or a carbazole group substituted with an aryl group having 6 to 30 ring-forming carbon atoms. $L_b$ may be a direct linkage, a substituted or unsubstituted arylene group having 6 to 30 ring-forming carbon atoms, or a substituted or unsubstituted heteroarylene group having 2 to 30 ring-forming carbon atoms, In Formula E-2b, b may be an integer from 0 to 10, and when b is 2 or greater, multiple $L_b$ groups may each independently be a substituted or unsubstituted arylene group having 6 to 30 ring-forming carbon atoms, or a substituted or unsubstituted heteroarylene group having 2 to 30 ring-forming carbon atoms.

The compound represented by Formula E-2a or Formula E-2b may be any one selected from Compound Group E-2. However, the compounds listed in Compound Group E-2 are only presented as examples, and the compound represented by Formula E-2a or Formula E-2b is not limited to those listed in Compound Group E-2.

E-2-1

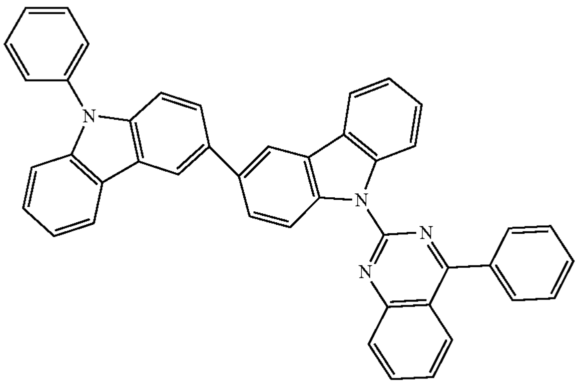

E-2-2

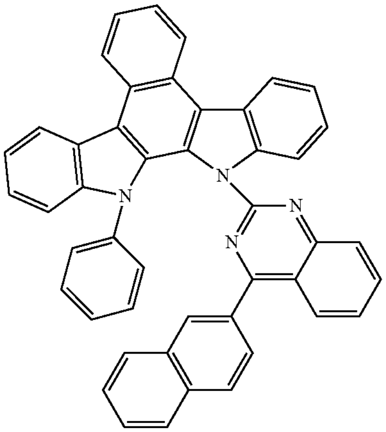

E-2-3

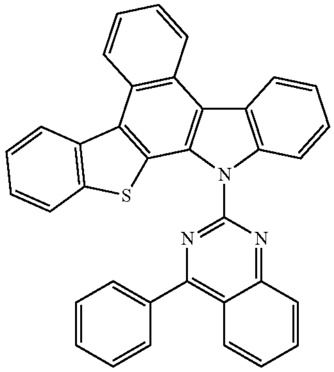

E-2-4

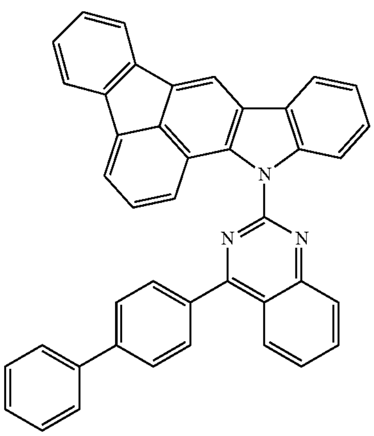

-continued
E-2-5
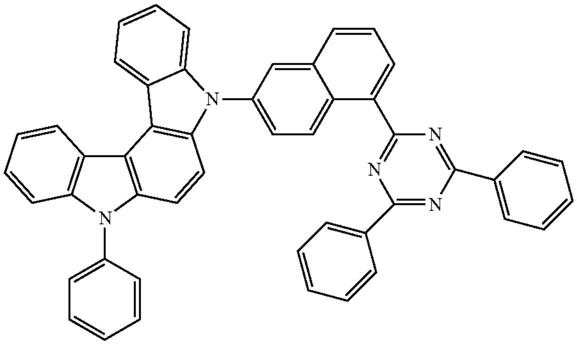
E-2-6
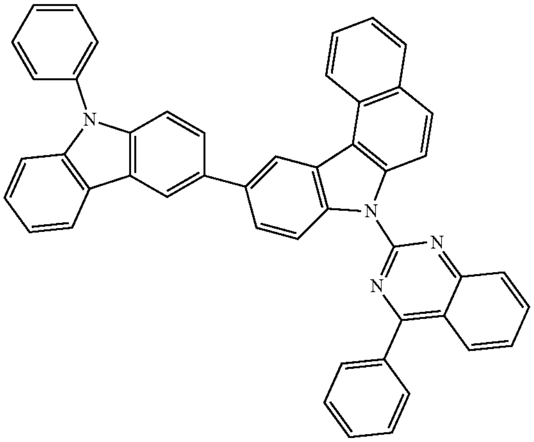
E-2-7
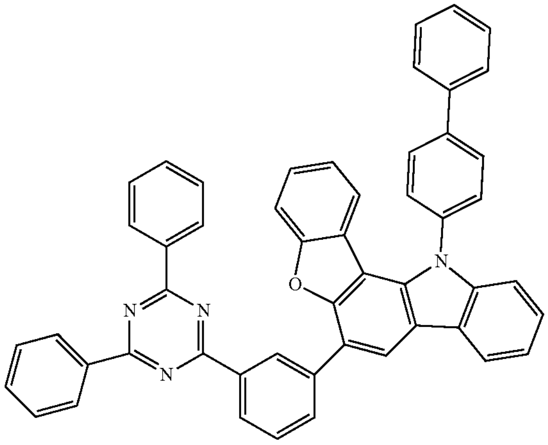
-continued
E-2-8
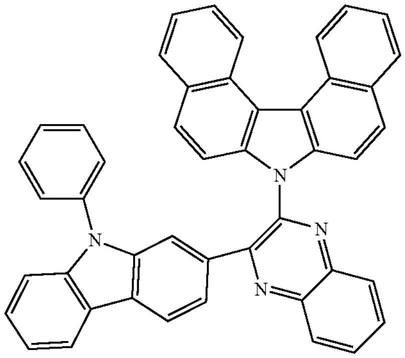
E-2-9
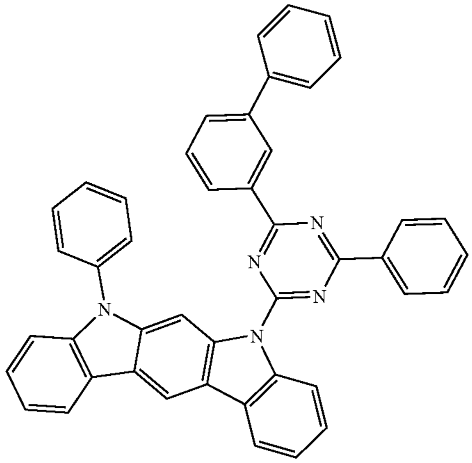
E-2-10
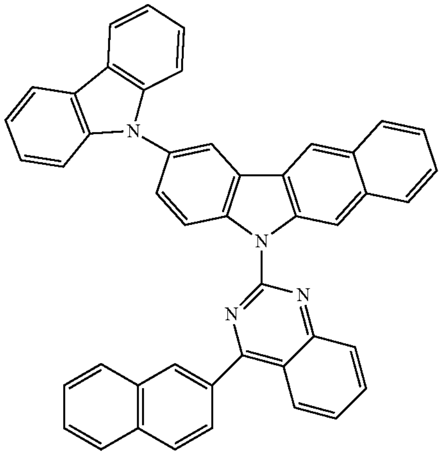

-continued
E-2-11
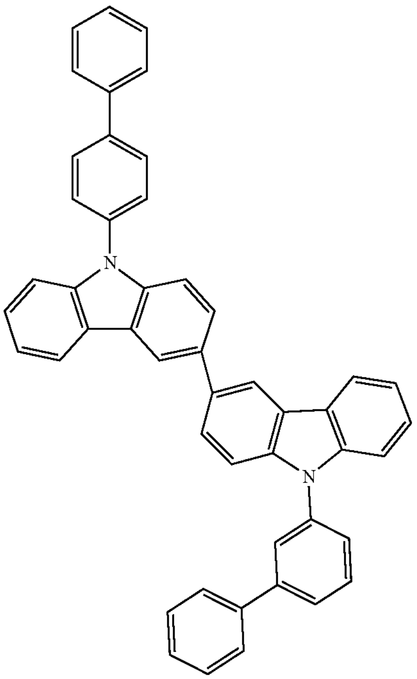
E-2-12
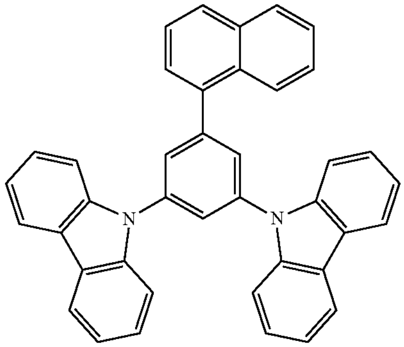
E-2-13
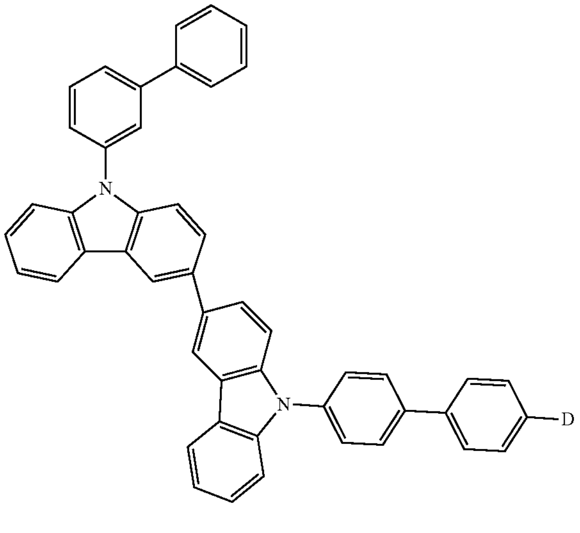
-continued
E-2-14
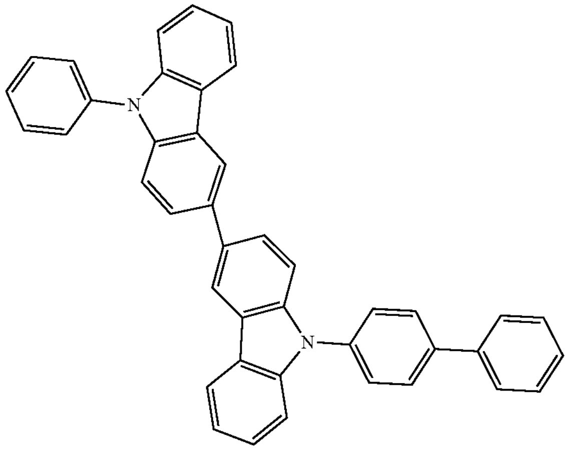
E-2-15
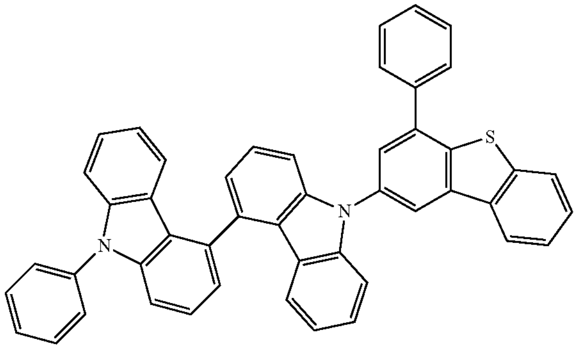
E-2-16
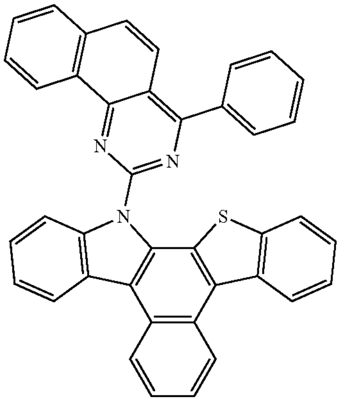

-continued
E-2-17
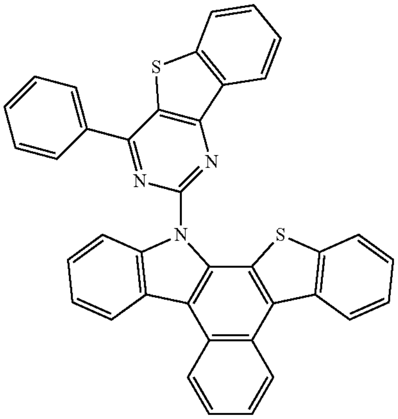
E-2-18
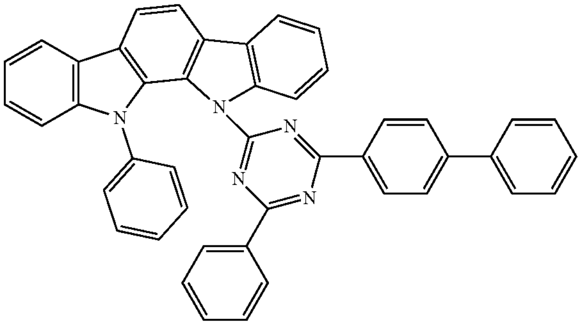
E-2-19
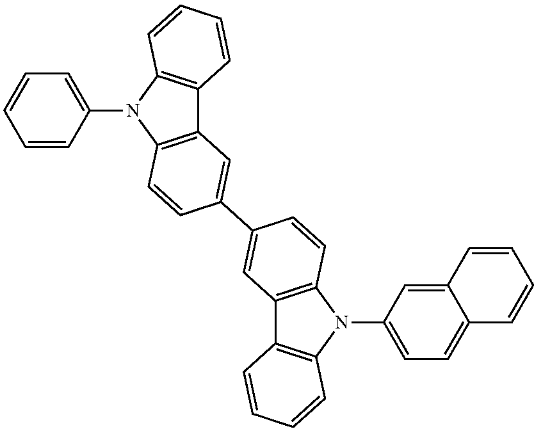
E-2-20
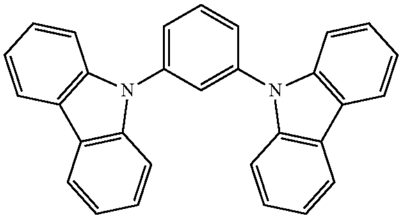
-continued
E-2-21
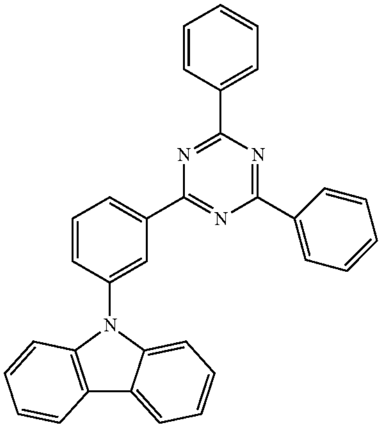
E-2-22
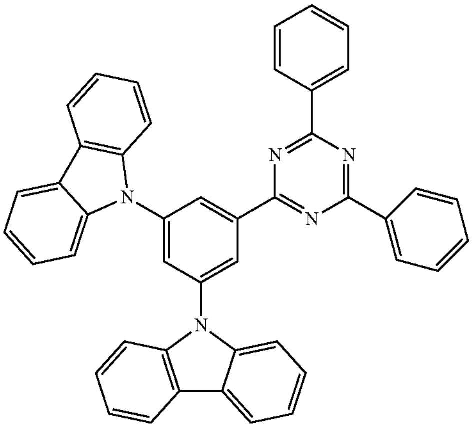
E-2-23
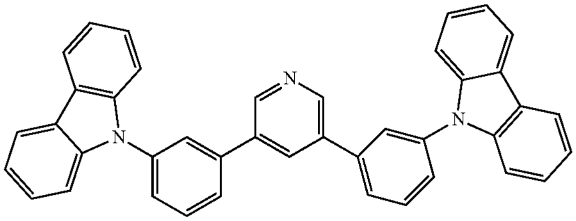

-continued

E-2-24

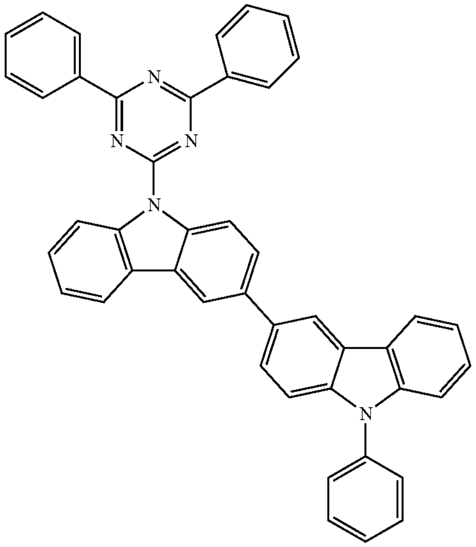

The emission layer EML may further include a material of the art as a host material. For example, the emission layer EML may include, as a host material, at least one among bis[2-(diphenylphosphino)phenyl]ether oxide (DPEPO), 4,4'-bis(N-carbazolyl)-1,1'-biphenyl (CBP), 1,3-bis(carbazolyl-9-yl)benzene (mCP), 2,8-bis(diphenylphosphoryl) dibenzofuran (PPF), 4,4',4"-tris(carbazol-9-yl)-triphenylamine (TCTA), and 1,3,5-tris(1-phenyl-1H-benzo[d]imidazol-2-yl) benzene (TPBi). However, embodiments are not limited thereto, and for example, tris(8-hydroxyquinolino) aluminum ($Alq_3$), 9,10-di(naphthalene-2-yl)anthracene (ADN), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), etc. may be used as a host material.

The emission layer EML may include a compound represented by Formula M-a or Formula M-b. The compound represented by Formula M-a or Formula M-b may be used as a phosphorescent dopant material.

[Formula M-a]

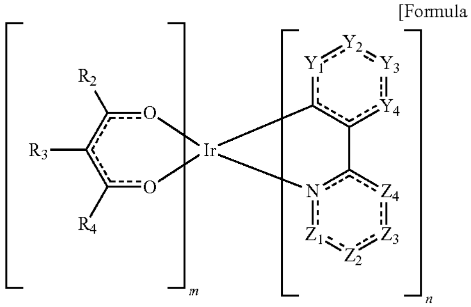

In Formula M-a, $Y_1$ to $Y_4$ and $Z_1$ to $Z_4$ may each independently be $C(R_1)$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In Formula M-a, m may be 0 or 1, and n may be 2 or 3. In Formula M-a, when m is 0, n may be 3, and when m is 1, n may be 2.

The compound represented by Formula M-a may be used as a phosphorescent dopant.

The compound represented by Formula M-a may be any one selected from Compounds M-a1 to M-a25. However, Compounds M-a1 to M-a25 are only examples, and the compound represented by Formula M-a is not limited to Compounds M-a1 to M-a25.

M-a1

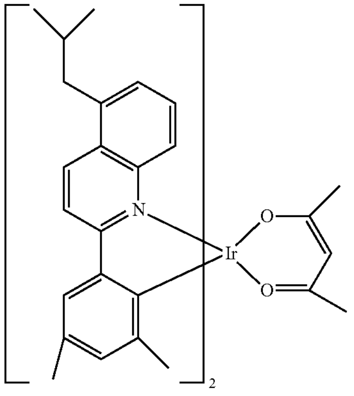

M-a2

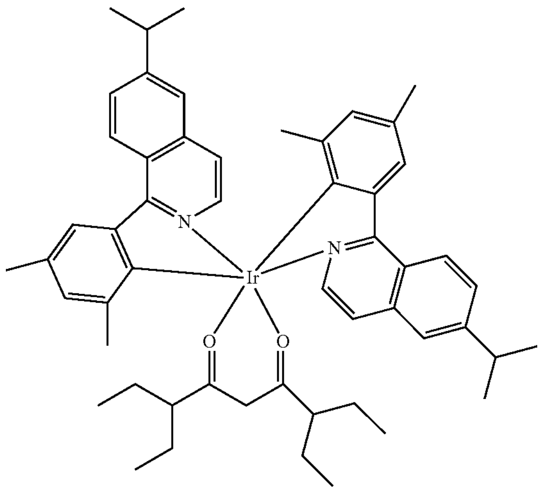

M-a3

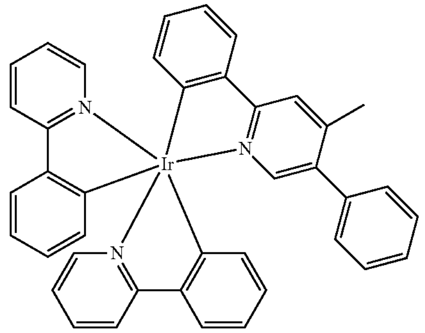

-continued
M-a4
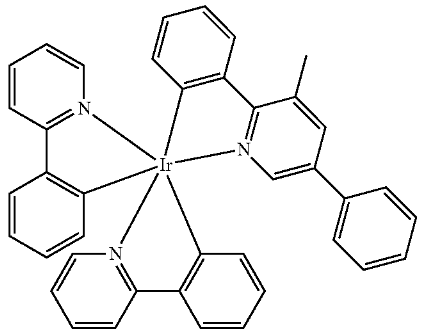
M-a5
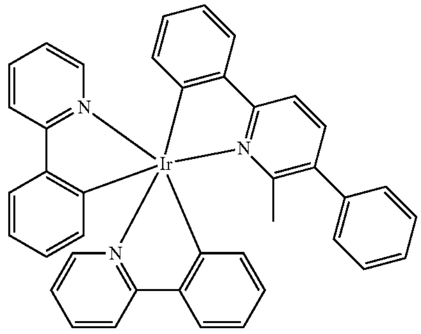
M-a6
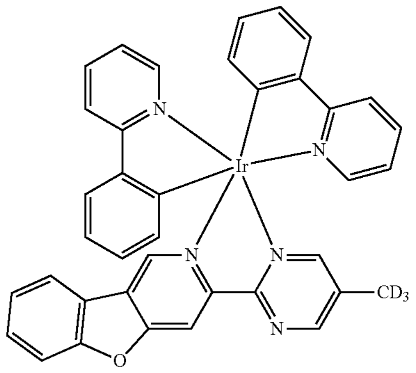
M-a7
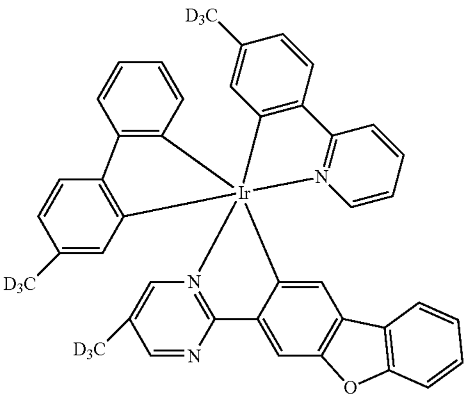
-continued
M-a8
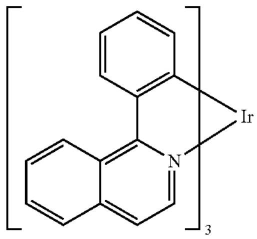
M-a9
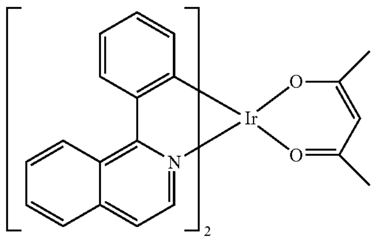
M-a10
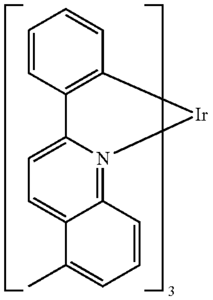
M-a11
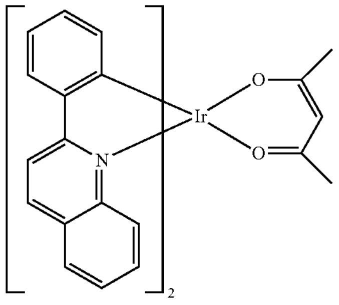
M-a12
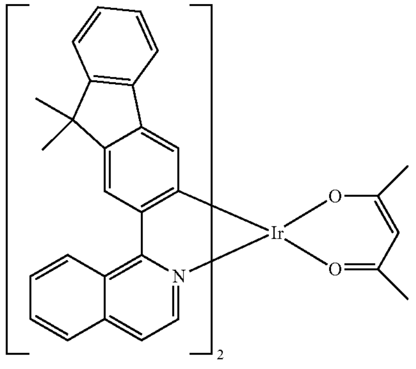

-continued
M-a13
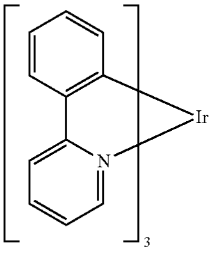
M-a14
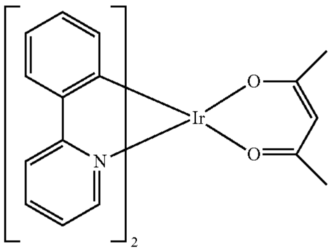
M-a15
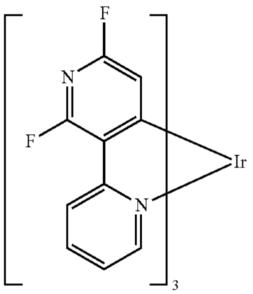
M-a16
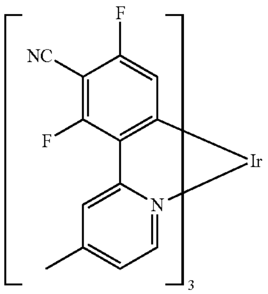
M-a17
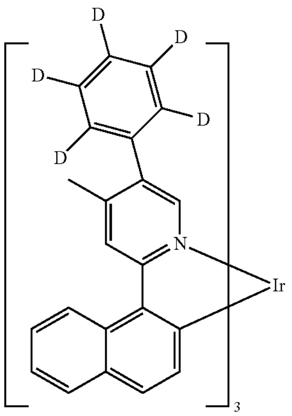
-continued
M-a18
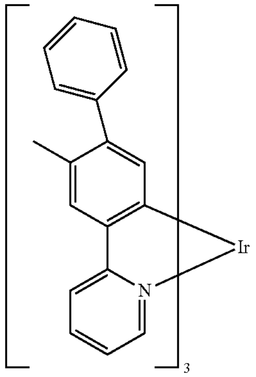
M-a19
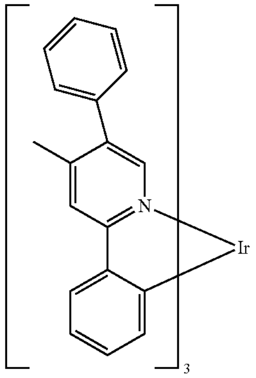
M-a20
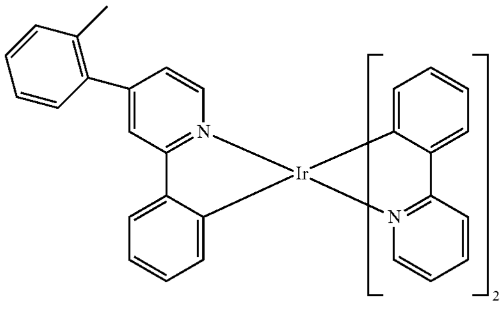
M-a21
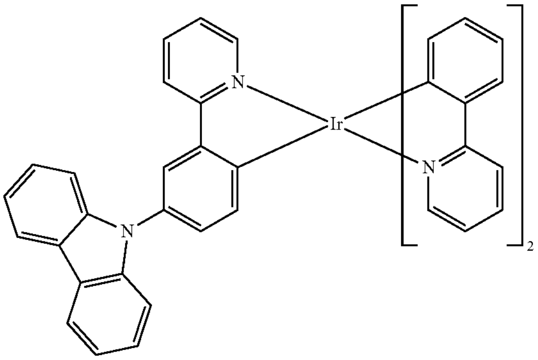

-continued

M-a22

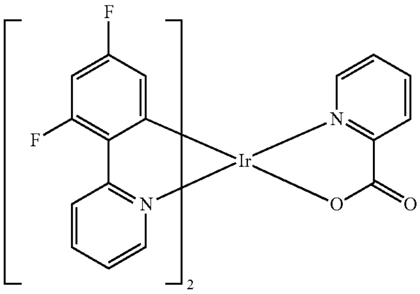

M-a23

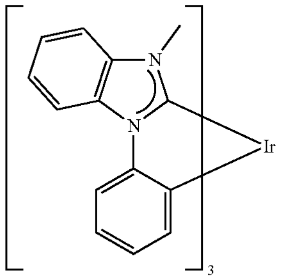

M-a24

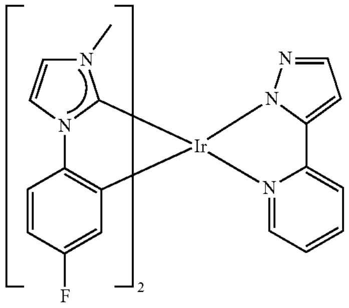

M-a25

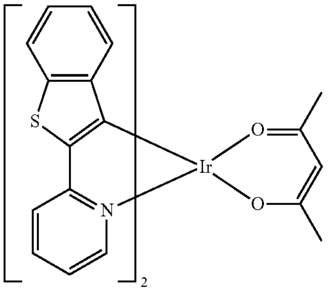

Compounds M-a1 and M-a2 may be used as a red dopant material, and Compounds M-a3 to M-a7 may be used as a green dopant material.

[Formula M-b]

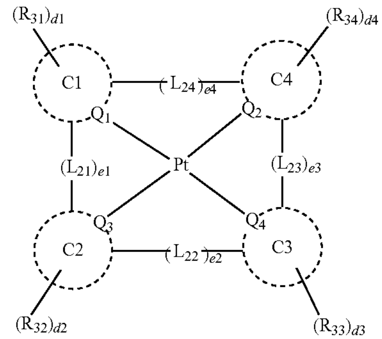

In Formula M-b, $Q_1$ to $Q_4$ may each independently be C or N, and C1 to C4 may each independently be a substituted or unsubstituted hydrocarbon ring having 5 to 30 ring-forming carbon atoms, or a substituted or unsubstituted heterocycle having 2 to 30 ring-forming carbon atoms. In Formula M-b, $L_{21}$ to $L_{24}$ may each independently be a direct linkage,

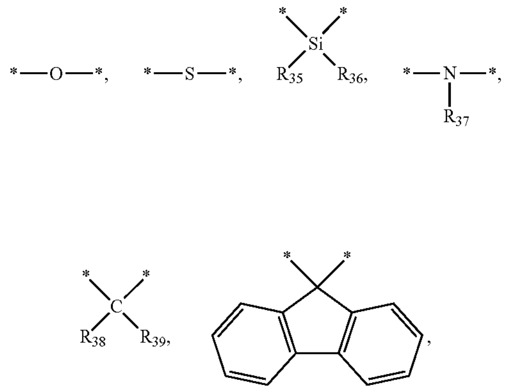

a substituted or unsubstituted divalent alkyl group having 1 to 20 carbon atoms, a substituted or unsubstituted arylene group having 6 to 30 ring-forming carbon atoms, or a substituted or unsubstituted heteroarylene group having 2 to 30 ring-forming carbon atoms, and e1 to e4 may each independently be 0 or 1. In Formula M-b, $R_{31}$ to $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring, and d1 to d4 may each independently be an integer from 0 to 4.

The compound represented by Formula M-b may be used as a blue phosphorescent dopant or as a green phosphorescent dopant.

The compound represented by Formula M-b may be any one selected from Compounds M-b-1 to M-b-12. However, Compounds M-b-1 to M-b-12 are only examples, and the compound represented by Formula M-b is not limited to Compounds M-b-1 to M-b-12.

-continued
M-b-1
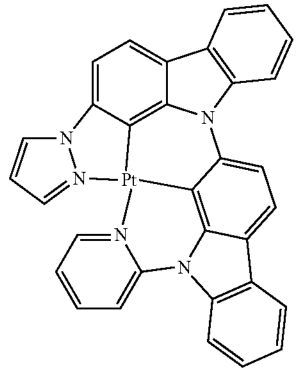
M-b-2
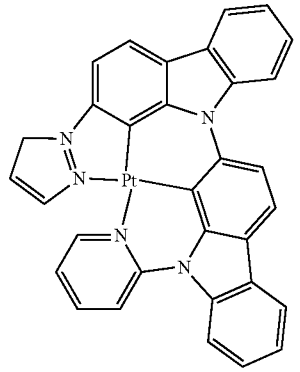
M-b-3
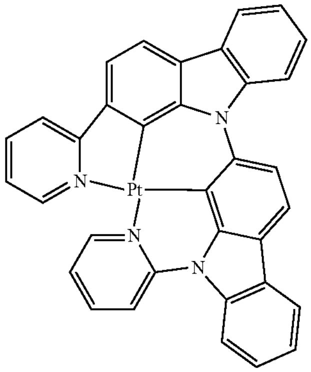
M-b-4
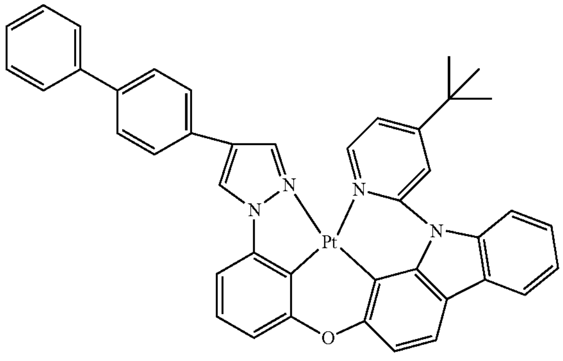
M-b-5
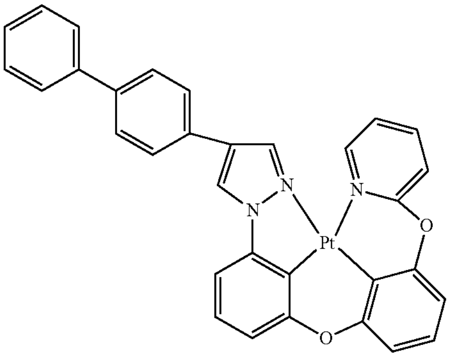
M-b-6
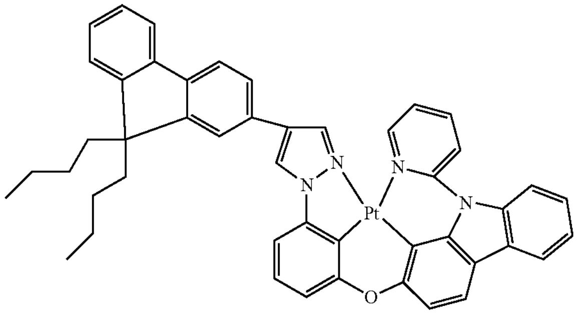
M-b-7
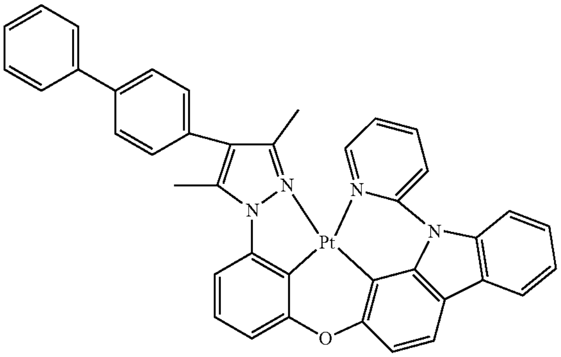
M-b-8
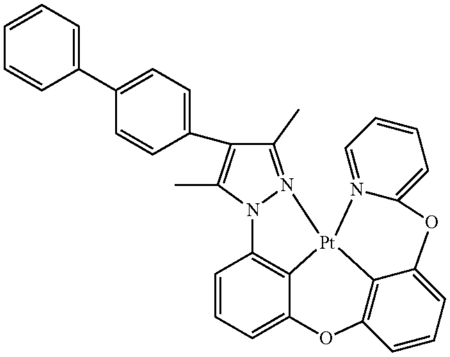

-continued

M-b-9

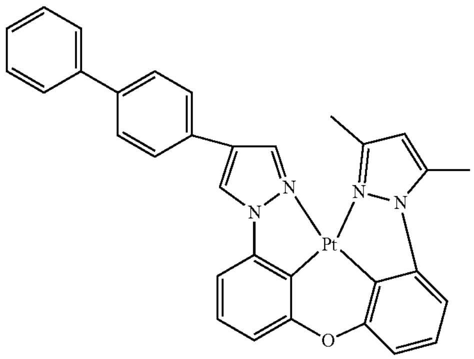

M-b-10

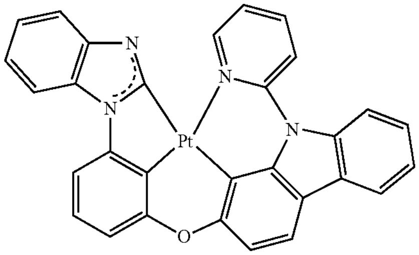

M-b-11

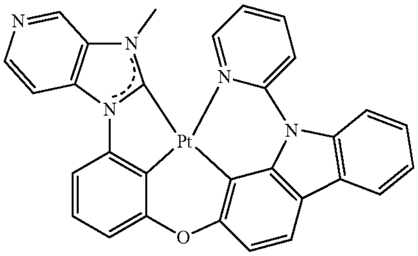

M-b-12

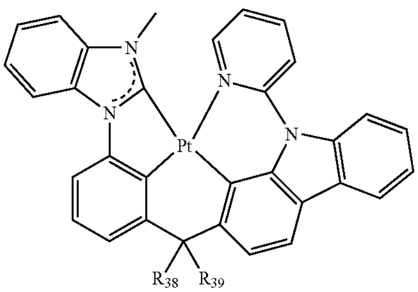

In Compounds M-b-1 to M-b-12, R, $R_{38}$, and $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

The emission layer EML may include a compound represented by any one of Formulas F-a to F-c. The compounds represented by Formulas F-a to F-c may be used as a fluorescent dopant material.

[Formula F-a]

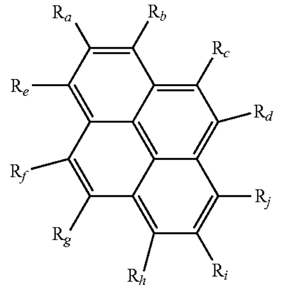

In Formula F-a, two of $R_a$ to $R_j$ may each independently be substituted with a group represented by $$*-NAr_1Ar_2.$$

The remainder of $R_a$ to $R_j$ not substituted with the group represented by $$*-NAr_1Ar_2$$

may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In the group represented by $$*-NAr_1Ar_2,$$

$Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. For example, at least one of $Ar_1$ or $Ar_2$ may be a heteroaryl group containing O or S as a ring-forming atom.

[Formula F-b]

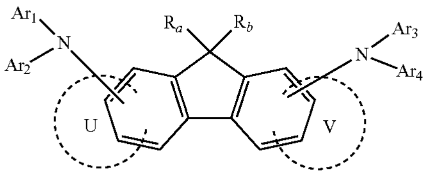

In Formula F-b, $R_a$ and $R_b$ may each independently be a hydrogen atom, a deuterium atom, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula F-b, U and V may each independently be a substituted or unsubstituted hydrocarbon ring having 5 to 30 ring-forming carbon atoms, or a substituted or unsubstituted heterocycle having 2 to 30 ring-forming carbon atoms.

In Formula F-b, the number of rings represented by U and V may each independently be 0 or 1. For example, in Formula F-b, when the number of U or V is 1, a condensed ring may be present at a portion indicated by U or V, and when the number of U or V is 0, a ring may not be present at a portion indicated by U or V. For example, when the number of U is 0 and the number of V is 1, or when the number of U is 1 and the number of V is 0, a condensed ring having a fluorene core of Formula F-b may be a cyclic compound having four rings. When both U and V are 0, a condensed ring having a fluorene core of Formula F-b may be a cyclic compound having three rings. When U and V are each 1, a condensed ring having a fluorene core of Formula F-b may be a cyclic compound having five rings.

[Formula F-c]

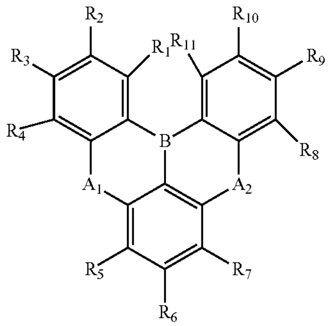

In Formula F-c, $A_1$ and $A_2$ may each independently be O, S, Se, or $N(R_m)$, and $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In Formula F-c, $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula F-c, $A_1$ and $A_2$ may each independently be bonded to substituents of neighboring rings to form a condensed ring. For example, when $A_1$ and $A_2$ are each independently $N(R_m)$, $A_1$ may be bonded to $R_4$ or $R_5$ to form a ring. For example, $A_2$ may be bonded to $R_7$ or $R_8$ to form a ring.

The emission layer EML may include, as a dopant material, styryl derivatives (e.g., 1,4-bis[2-(3-N-ethylcarbazoryl) vinyl]benzene (BCzVB), 4-(di-p-tolylamino)-4"-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi)), perylene and derivatives thereof (e.g., 2,5,8,11-tetra-t-butylperylene (TBP)), pyrene and derivatives thereof (e.g., 1,1-dipyrene, 1,4-dipyrenylbenzene, 1,4-bis(N,N-diphenylamino)pyrene), etc.

The emission layer EML may include a phosphorescent dopant material. For example, as a phosphorescent dopant, a metal complex including iridium (Ir), platinum (Pt), osmium (Os), gold (Au), titanium (Ti), zirconium (Zr), hafnium (Hf), europium (Eu), and terbium (Tb), or thulium (Tm) may be used. For example, iridium(III) bis(4,6-difluorophenylpyridinato-N,C2')picolinate (FIrpic), bis(2,4-difluorophenylpyridinato)-tetrakis(1-pyrazolyl)borate iridium (III) (Fir6), platinum octaethyl porphyrin (PtOEP), etc. may be used as a phosphorescent dopant. However, embodiments are not limited thereto.

The emission layer EML may include a quantum dot. The quantum dot may be a Group II-VI compound, a Group III-VI compound, a Group I-III-VI compound, a Group III-V compound, a Group III-II-V compound, a Group IV-VI compound, a Group IV element, a Group IV compound, or a combination thereof.

The Group II-VI compound may be selected from: a binary compound selected from the group consisting of CdSe, CdTe, CdS, ZnS, ZnSe, ZnTe, ZnO, HgS, HgSe, HgTe, MgSe, MgS, and a mixture thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof; a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof; or any combination thereof.

The Group III-VI compound may include a binary compound such as $In_2S_3$ and $In_2Se_3$; a ternary compound such as $InGaS_3$ and $InGaSe_3$; or any combination thereof.

The Group I-III-VI compound may include: a ternary compound selected from the group consisting of AgInS, $AgInS_2$, CuInS, $CuInS_2$, $AgGaS_2$, $CuGaS_2$ $CuGaO_2$, $AgGaO_2$, $AgAlO_2$, or any mixture thereof; a quaternary compound such as $AgInGaS_2$ and $CuInGaS_2$; or any combination thereof.

The Group III-V compound may be selected from: a binary compound selected from the group consisting of GaN, GaP, GaAs, GaSb, AlN, AlP, AlAs, AlSb, InN, InP, InAs, InSb, and a mixture thereof; a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof; a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof; or any combination thereof. The Group III-V compound may further include a Group II metal. For example, InZnP, etc. may be selected as a Group III-II-V compound.

The Group IV-VI compound may be selected from: a binary compound selected from the group consisting of SnS, SnSe, SnTe, PbS, PbSe, PbTe, and a mixture thereof; a ternary compound selected from the group consisting of SnSeS, SnSeTe, SnSTe, PbSeS, PbSeTe, PbSTe, SnPbS, SnPbSe, SnPbTe, and a mixture thereof; a quaternary compound selected from the group consisting of SnPbSSe, SnPbSeTe, SnPbSTe, and a mixture thereof; or any combination thereof. The Group IV element may be selected from the group consisting of Si, Ge, and a mixture thereof. The Group IV compound may be a binary compound selected from the group consisting of SiC, SiGe, and a mixture thereof.

A binary compound, a ternary compound, or a quaternary compound may be present in particles at a uniform concentration distribution, or may be present in particles at a partially different concentration distribution. In an embodiment, the quantum dot may have a core/shell structure in which a quantum dot surrounds another quantum dot. A quantum dot having a core/shell structure may have a concentration gradient in which the concentration of an element that is present in the shell decreases towards the core.

In embodiments, a quantum dot may have a core/shell structure including a core having nano-crystals, and a shell surrounding the core, which are described above. The shell of the quantum dot may function as a protection layer that prevents chemical deformation of the core so as to maintain semiconductor properties, and/or may function as a charging layer that imparts electrophoretic properties to the quantum dot. The shell may be a single layer or multiple layers. Examples of the shell of the quantum dot may include a metal oxide, a non-metal oxide, a semiconductor compound, or a combination thereof.

For example, the metal oxide or the non-metal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, NiO; or a ternary compound such as $MgAl_2O_4$, $CoFe_2O_4$, $NiFe_2O_4$, and $CoMn_2O_4$, but embodiments are not limited thereto.

The semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments are not limited thereto.

A quantum dot may have a full width of half maximum (FWHM) of a light emission wavelength spectrum equal to or less than about 45 nm. For example, the quantum dot may have a FWHM of a light emission wavelength spectrum equal to or less than about 40 nm. For example, the quantum dot may have a FWHM of a light emission wavelength spectrum equal to or less than about 30 nm. Color purity or color reproducibility may be enhanced in the above ranges. Light emitted through the quantum dot may be emitted in all directions, so that a wide viewing angle may be improved.

The form of a quantum dot is not particularly limited as long as it is a form used in the art. For example, a quantum dot may have a spherical shape, a pyramidal shape, a multi-arm shape, or a cubic shape, or the quantum dot may be in the form of nanoparticles, nanotubes, nanowires, nanofibers, nanoplatelets, etc.

The quantum dot may control the color of emitted light according to a particle size thereof, and thus the quantum dot may have various colors of emitted light such as blue, red, green, etc.

In the light emitting element ED of an embodiment illustrated in FIGS. 3 to 6, an electron transport region ETR is provided on the emission layer EML. The electron transport region ETR may include at least one of a hole blocking layer HBL, an electron transport layer ETL, or an electron injection layer EIL, but embodiments are not limited thereto.

The electron transport region ETR may be a layer formed of a single material, a layer formed of different materials, or a multilayer structure having layers formed of different materials.

For example, the electron transport region ETR may have a single layer structure of an electron injection layer EIL or an electron transport layer ETL, or may have a single layer structure formed of an electron injection material and an electron transport material. In other embodiment, the electron transport region ETR may have a single layer structure formed of different materials, or may have a structure in which an electron transport layer ETL/electron injection layer EIL, or a hole blocking layer HBL/electron transport layer ETL/electron injection layer EIL are stacked in its respective stated order from the emission layer EML, but embodiments are not limited thereto. The electron transport region ETR may have a thickness, for example, in a range of about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, a laser induced thermal imaging (LITI) method, etc.

The electron transport region ETR may include a compound represented by Formula ET-1.

[Formula ET-1]

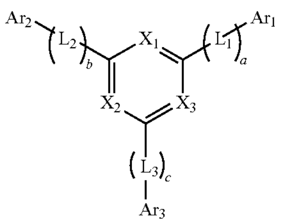

In Formula ET-1, at least one of $X_1$ to $X_3$ may be N and the remainder of $X_1$ to $X_3$ may be $C(R_a)$. $R_a$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In Formula ET-1, $Ar_1$ to $Ar_3$ may each independently be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula ET-1, a to c may each independently be an integer from 0 to 10. In Formula ET-1, $L_1$ to $L_3$ may each independently be a direct linkage, a substituted or unsubstituted arylene group having 6 to 30 ring-forming carbon atoms, or a substituted or unsubstituted heteroarylene group having 2 to 30 ring-forming carbon atoms. When a to c are 2 or greater, $L_1$ to $L_3$ may each independently be a substituted or unsubstituted arylene group having 6 to 30 ring-forming carbon atoms, or a substituted or unsubstituted heteroarylene group having 2 to 30 ring-forming carbon atoms.

The electron transport region ETR may include an anthracene-based compound. However, embodiments are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate ($Bebq_2$), 9,10-di(naphthalene-2-yl) anthracene (ADN), 1,3-bis[3,5-di(pyridin-3-yl)phenyl] benzene (BmPyPhB), or a mixture thereof.

The electron transport region ETR may include halogenated metals such as LiF, NaCl, CsF, RbCl, RbI, CuI, and KI, lanthanide metals such as Yb, co-deposition materials of a halogenated metal and a lanthanide metal. For example, the electron transport region ETR may include KI:Yb, RbI:Yb, LiF:Yb, etc. as a co-deposition material. The electron transport region ETR may include a metal oxide such as $Li_2O$ and BaO, or 8-hydroxyl-lithium quinolate (Liq), etc., but embodiments are not limited thereto. The electron transport region ETR may also be formed of a mixture material of an electron transport material and an insulating organo-metal salt. The organo-metal salt may be a material having an energy band gap equal to or greater than about 4 eV. For example, the organo-metal salt may include metal acetates, metal benzoates, metal acetoacetates, metal acetylacetonates, or metal stearates.

The electron transport region ETR may further include, for example, at least one of 2,9-dimethyl-4,7-diphenyl-1,10-phenanthroline (BCP) or 4,7-diphenyl-1,10-phenanthroline (Bphen) in addition to the materials described above, but embodiments are not limited thereto.

The electron transport region ETR may include the compounds of the electron transport region described above in at least one of the electron injection layer EIL, the electron transport layer ETL, or the hole blocking layer HBL.

When the electron transport region ETR includes an electron transport layer ETL, the electron transport layer ETL may have a thickness in a range of about 100 Å to about 1,000 Å. For example, the electron transport layer ETL may have a thickness in a range of about 150 Å to about 500 Å. When the thickness of the electron transport layer ETL satisfies the above-described range, satisfactory electron transport properties may be obtained without a substantial increase in driving voltage. When the electron transport region ETR includes an electron injection layer EIL, the electron injection layer EIL may have a thickness in a range of about 1 Å to about 100 Å. For example, the electron injection layer EIL may have a thickness in a range of about 3 Å to about 90 Å. When the thickness of the electron injection layer EIL satisfies the above-described ranges, satisfactory electron injection properties may be obtained without a substantial increase in driving voltage.

The second electrode EL2 is provided on the electron transport region ETR. The second electrode EL2 may be a common electrode. The second electrode EL2 may be a cathode or an anode but embodiments are not limited thereto. For example, when the first electrode EL1 is an anode, the second electrode EL2 may be a cathode, and when the first electrode EL1 is a cathode, the second electrode EL2 may be an anode.

The second electrode EL2 may be a transmissive electrode, a transflective electrode, or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, a compound thereof, or a mixture thereof (e.g., AgMg, AgYb, or MgAg). In another embodiment, the second electrode EL2 may have a multilayer structure including a reflective film or a transflective film formed of the above-described materials, and a transparent conductive film formed of indium tin oxide (ITO), indium zinc oxide (IZO), zinc oxide (ZnO), indium tin zinc oxide (ITZO), etc. For example, the second electrode EL2 may include the above-described metal materials, a combination of two or more metal materials selected from the above-described metal materials, or oxides of the above-described metal materials.

Although not shown in the drawings, the second electrode EL2 may be electrically connected to an auxiliary electrode. When the second electrode EL2 is electrically connected to the auxiliary electrode, the resistance of the second electrode EL2 may decrease.

In an embodiment, the light emitting element ED may further include a capping layer CPL disposed on the second electrode EL2. The capping layer CPL may be a multilayer or a single layer. In an embodiment, the capping layer CPL may include an amine compound of an embodiment described above.

In an embodiment, the capping layer CPL may include an organic layer or an inorganic layer. For example, when the capping layer CPL includes an inorganic material, the inorganic material may include an alkali metal compound such as LiF, an alkaline earth metal compound such as $MgF_2$, SiON, $SiN_x$, SiOy, etc.

For example, when the capping layer CPL includes an organic material, the organic material may include α-NPD, NPB, TPD, m-MTDATA, $Alq_3$ CuPc, N4,N4,N4',N4'-tetra (biphenyl-4-yl) biphenyl-4,4'-diamine (TPD15), 4,4',4"-tris (carbazol sol-9-yl)triphenylamine (TCTA), etc., or may include epoxy resins or acrylates such as methacrylates. However, embodiments are not limited thereto, and the capping layer CPL may include at least one of Compounds P1 to P5.

P1

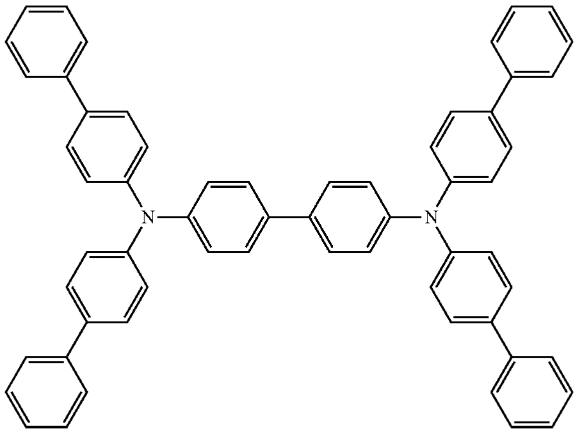

-continued

P2

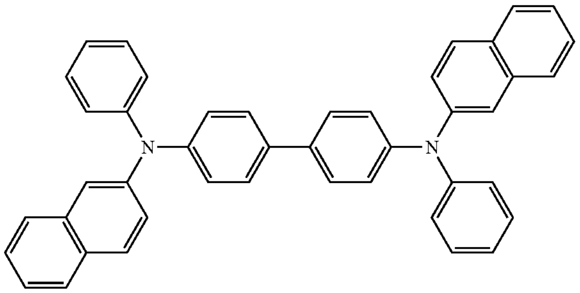

P3

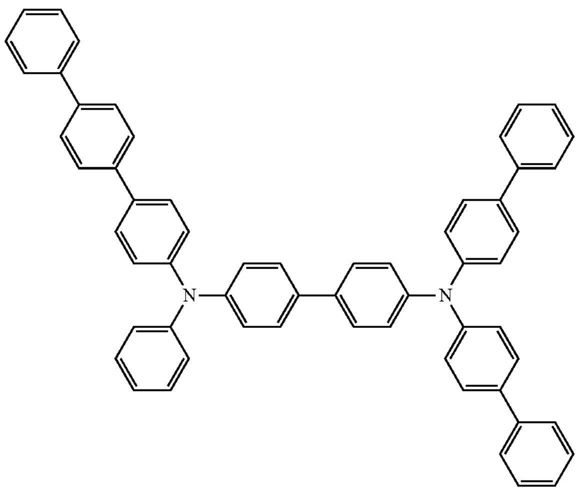

P4

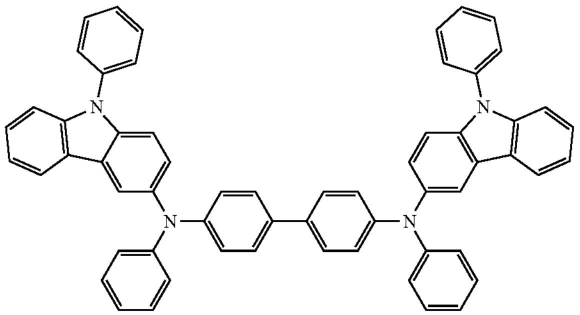

-continued

P5

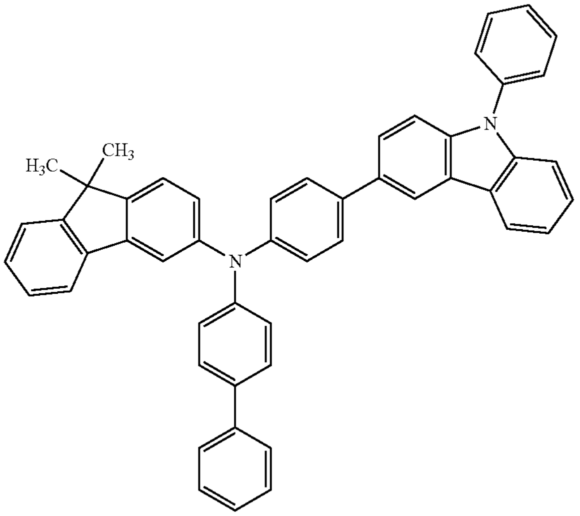

The capping layer CPL may have a refractive index equal to or greater than about 1.6. For example, the capping layer CPL may have a refractive index equal to or greater than about 1.6 with respect to light in a wavelength range of about 550 nm to about 660 nm.

Figure 7:
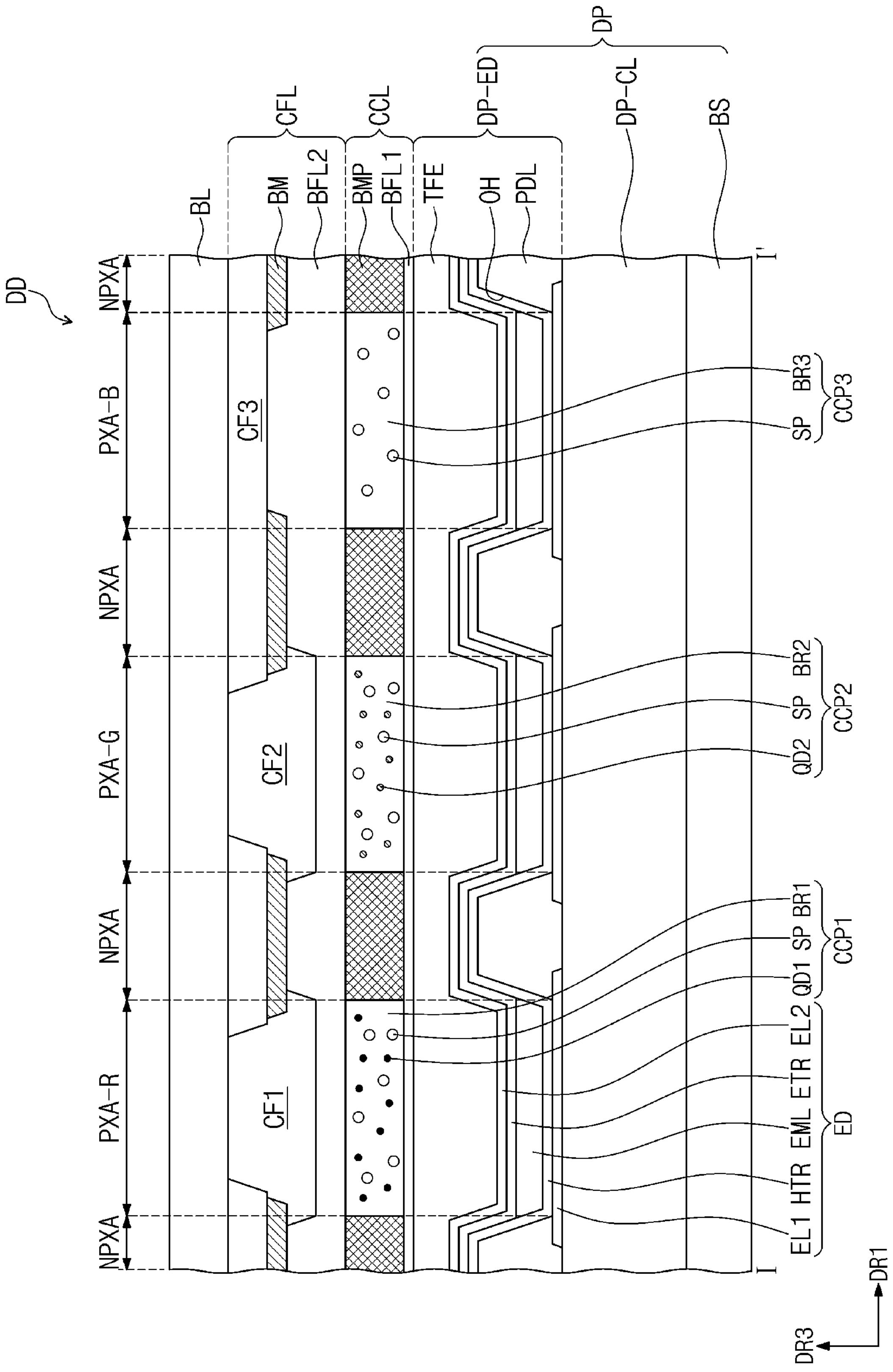
FIG. 7 is a schematic cross-sectional view of a display device according to an embodiment.
Figure 8:
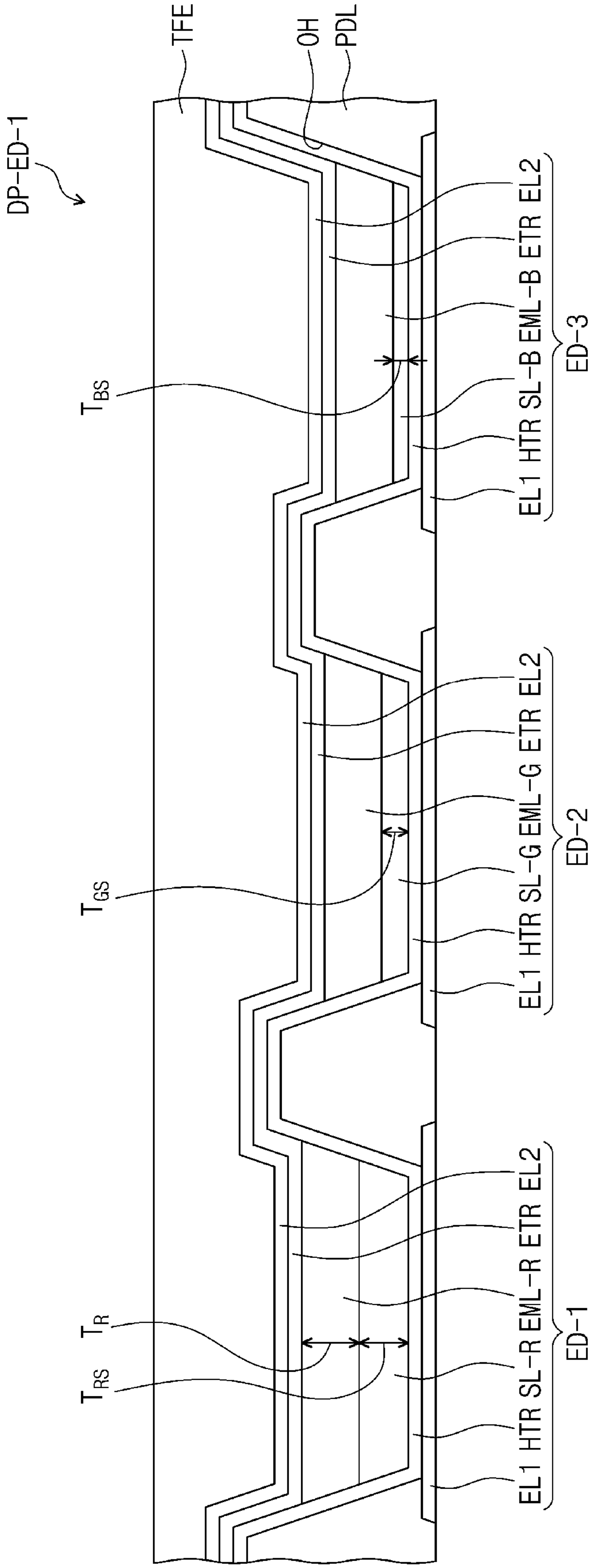
FIG. 8 is a schematic cross-sectional view of a display element layer according to an embodiment.
Figure 9:
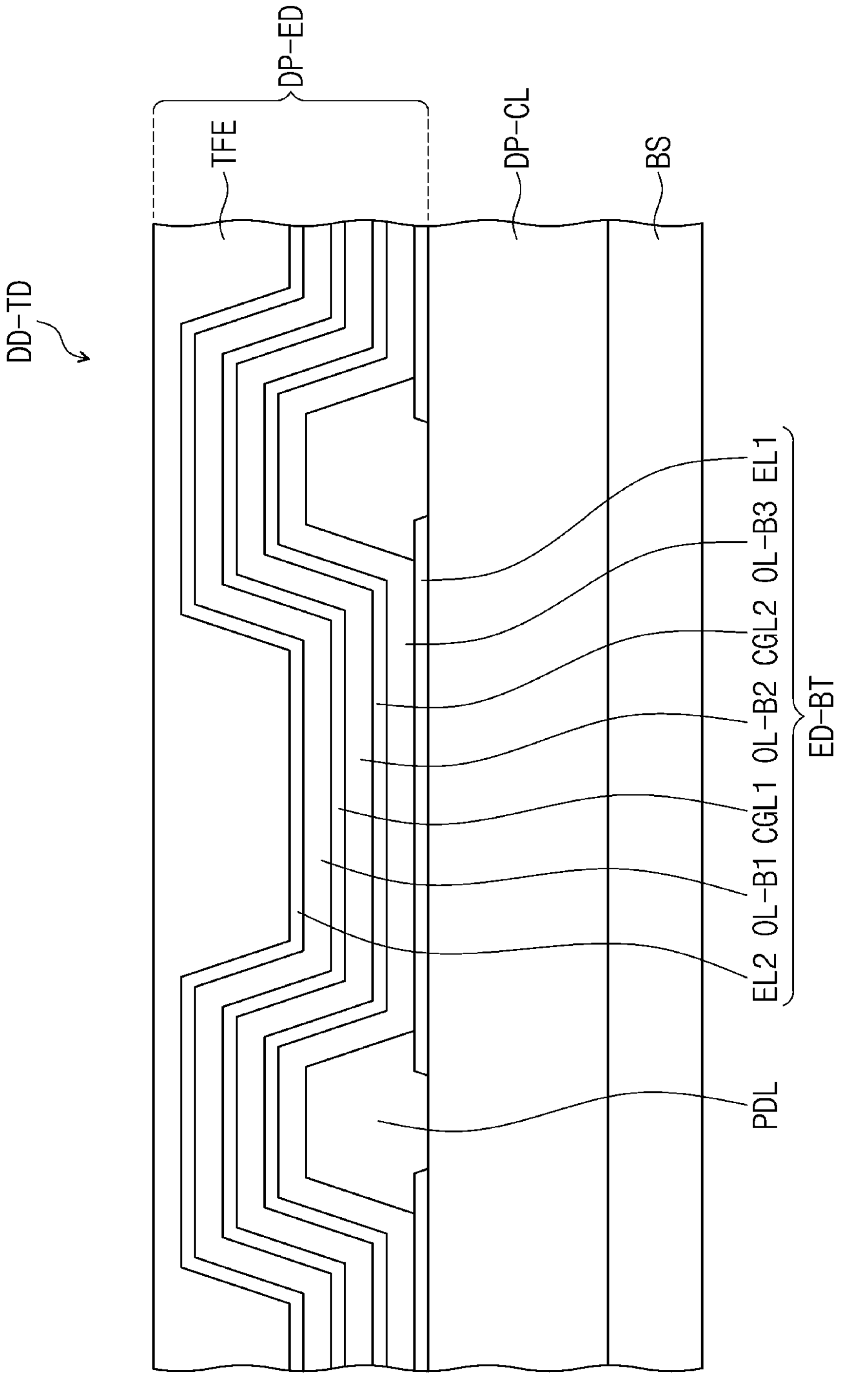
FIG. 9 is a schematic cross-sectional view of a display device according to an embodiment.

FIGS. 7 and 9 are each schematic a cross-sectional view of a display device according to an embodiment, and FIG. 8 is a schematic cross-sectional view of a display element layer according to an embodiment. Hereinafter, in the description of the display device according to an embodiment with reference to FIGS. 7 and 9, content which overlaps with the descriptions of FIGS. 1 to 6 will not be described again, and the differences will be described.

Referring to FIG. 7, a display device DD according to an embodiment may include a display panel DP having a display element layer DP-ED, a light control layer CCL disposed on the display panel DP, and a color filter layer CFL.

In an embodiment illustrated in FIG. 7, the display panel DP may include a base layer BS, a circuit layer DP-CL provided on the base layer BS, and a display element layer DP-ED, and the element layer DP-ED may include a light emitting element ED.

The light emitting element ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. A structure of the light emitting element ED shown in FIG. 7 may be the same as a structure of the light emitting element of FIGS. 3 to 6 described above.

Referring to FIG. 7, the emission layer EML may be disposed in the openings OH defined in the pixel defining films PDL. For example, the emission layer EML which is separated by the pixel defining films PDL and provided corresponding to each of the light emitting regions PXA-R, PXA-G, and PXA-B may emit light in a same wavelength range. In the display device DD of an embodiment, the emission layer EML may emit blue light. Although not shown in the drawings, in an embodiment, the emission layer EML may be provided as a common layer throughout the light emitting regions PXA-R, PXA-G, and PXA-B.

The light control layer CCL may be disposed on the display panel DP. The light control layer CCL may include a photoconverter. The photoconverter may be a quantum dot or a phosphor. The photoconverter may convert the wavelength of a provided light and may emit the converted light. For example, the light control layer CCL may be a layer containing quantum dots or phosphors.

The light control layer CCL may include light control units CCP1, CCP2, and CCP3. The light control units CCP1, CCP2, and CCP3 may be spaced apart from each other.

Referring to FIG. 7, a division pattern BMP may be disposed between the light control units CCP1, CCP2, and CCP3 spaced apart from each other, but embodiments are not limited thereto. In FIG. 7, the division pattern BMP is shown so that it does not overlap the light control units CCP1, CCP2, and CCP3, but the edges of the light control units CCP1, CCP2, and CCP3 may overlap at least a portion of the division pattern BMP.

The light control layer CCL may include a first light control unit CCP1 including a first quantum dot QD1 for converting first color light provided from the light emitting element ED into second color light, a second light control unit CCP2 including a second quantum dot QD2 for converting the first color light provided from the light emitting element ED into third color light, and a third light control unit CCP3 transmitting the first color light provided from the light emitting element ED.

In an embodiment, the first light control unit CCP1 may provide red light, which is the second color light, and the second light control unit CCP2 may provide green light, which is the third color light. The third light control unit CCP3 may transmit and provide blue light, which is the first color light provided from the light emitting element ED. For example, the first quantum dot QD1 may be a red quantum dot and the second quantum dot QD2 may be a green quantum dot. The same descriptions as provided above with respect to quantum dots may be applied to the quantum dots QD1 and QD2.

The light control layer CCL may further include scatterers SP. The first light control unit CCP1 may include the first quantum dot QD1 and the scatterers SP, the second light control unit CCP2 may include the second quantum dot QD2 and the scatterers SP, and the third light control unit CCP3 may not include a quantum dot but may include the scatterers SP.

The scatterers SP may be inorganic particles. For example, the scatterers SP may include at least one of $TiO_2$, ZnO, $Al_2O_3$, $SiO_2$, or hollow silica. The scatterers SP may include any one of $TiO_2$, ZnO, $Al_2O_3$, $SiO_2$, or hollow silica, or may be a mixture of two or more materials selected from $TiO_2$, ZnO, $Al_2O_3$, $SiO_2$, and hollow silica.

The first light control unit CCP1, the second light control unit CCP2, and the third light control unit CCP3 may each include base resins BR1, BR2, and BR3 for dispersing the quantum dots QD1 and QD2 and the scatterers SP. In an embodiment, the first light control unit CCP1 may include the first quantum dot QD1 and the scatterers SP dispersed in the first base resin BR1, the second light control unit CCP2 may include the second quantum dot QD2 and the scatterers SP dispersed in the second base resin BR2, and the third light control unit CCP3 may include the scatterers SP dispersed in the third base resin BR3. The base resins BR1, BR2, and BR3 may each be a medium in which the quantum dots QD1 and QD2 and the scatterers SP are dispersed, and may be formed of various resin compositions, which may be generally referred to as a binder. For example, the base resins BR1, BR2, and BR3 may each independently be an acrylic resin, a urethane-based resin, a silicone-based resin, an epoxy-based resin, etc. The base resins BR1, BR2, and BR3 may each be a transparent resin. In an embodiment, the first base resin BR1, the second base resin BR2, and the third base resin BR3 may each be the same as or different from each other.

The light control layer CCL may include a barrier layer BFL1. The barrier layer BFL1 may prevent moisture and/or oxygen (hereinafter referred to as "moisture/oxygen") from being introduced. The barrier layer BFL1 may be disposed on the light control units CCP1, CCP2, and CCP3 to prevent the light control units CCP1, CCP2, and CCP3 from being exposed to moisture/oxygen. The barrier layer BFL1 may cover the light control units CCP1, CCP2, and CCP3. A barrier layer BFL2 may be provided between the light control units CCP1, CCP2, and CCP3 and the color filter layer CFL.

The barrier layers BFL1 and BFL2 may each include at least one inorganic layer. For example, the barrier layers BFL1 and BFL2 may each be formed of an inorganic material. For example, the barrier layers BFL1 and BFL2 may each independently include silicon nitride, aluminum nitride, zirconium nitride, titanium nitride, hafnium nitride, tantalum nitride, silicon oxide, aluminum oxide, titanium oxide, tin oxide, cerium oxide, silicon oxynitride, or a metal thin film in which light transmittance is secured, etc. The barrier layers BFL1 and BFL2 may each further include an organic film. The barrier layers BFL1 and BFL2 may be formed of a single layer or of multiple layers.

In the display device DD of an embodiment, the color filter layer CFL may be disposed on the light control layer CCL. In an embodiment, the color filter layer CFL may be directly disposed on the light control layer CCL. For example, the barrier layer BFL2 may be omitted.

The color filter layer CFL may include alight blocking unit BM and filters CF1, CF2, and CF3. For example, the color filter layer CFL may include a first filter CF1 transmitting second color light, a second filter CF2 transmitting third color light, and a third filter CF3 transmitting first color light. For example, the first filter CF1 may be a red filter, the second filter CF2 may be a green filter, and the third filter CF3 may be a blue filter. The filters CF1, CF2, and CF3 may each include a polymer photosensitive resin, a pigment, or a dye. The first filter CF1 may include a red pigment or a red dye, the second filter CF2 may include a green pigment or a green dye, and the third filter CF3 may include a blue pigment or a blue dye. However, embodiments are not limited thereto, and the third filter CF3 may not include a pigment or a dye. The third filter CF3 may include a polymer photosensitive resin and may not include a pigment or a dye. The third filter CF3 may be transparent. The third filter CF3 may be formed of a transparent photosensitive resin.

In an embodiment, the first filter CF1 and the second filter CF2 may each be yellow filters. The first filter CF1 and the second filter CF2 may not be separated from each other and may be provided as a single body.

The light blocking unit BM may be a black matrix. The light blocking unit BM may include an organic light blocking material or an inorganic light blocking material, each including a black pigment or a black dye. The light blocking unit BM may prevent light leakage, and may distinguish boundaries between the adjacent filters CF1, CF2, and CF3. In an embodiment, the light blocking unit BM may be formed of a blue filter.

The first to third filters CF1, CF2, and CF3 may be disposed corresponding to the red light emitting region PXA-R, green light emitting region PXA-G, and blue light emitting region PXA-B, respectively.

The base substrate BL may be disposed on the color filter layer CFL. The base substrate BL may provide a base surface on which the color filter layer CFL and the light control layer CCL are disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawings, in an embodiment, the base substrate BL may be omitted.

In an embodiment shown in FIG. 8, a light emitting element layer DP-ED-1 may further include resonance auxiliary layers SL-R, SL-G, and SL-B disposed between the emission layers EML-R, EML-G, and EML-B and the hole transport region HTR. In an embodiment, the first to third emission layers EML-R, EML-G, and EML-B may be disposed to be spaced apart from each other in a plan view. The first emission layer EML-R may be spaced apart from the second emission layer EML-G, and the second emission layer EML-G may be spaced apart from the third emission layer EML-B. The resonance auxiliary layers SL-R, SL-G, and SL-B may control for a distance between the first electrode EL1 and the second electrode EL2 to assist in the generation of constructive interference of the light emitted from the emission layers EML-R, EML-G, and EML-B and the light reflected from the first electrode EL1.

The display device DD of an embodiment may have a structure in which light emitted from the emission layers EML-R, EML-G, and EML-B resonates. As for the resonance structure, the resonance distance may vary according to a wavelength of light emitted from the emission layers EML-R, EML-G, and EML-B. Accordingly, the resonance distance may be controlled by disposing the resonance auxiliary layers SL-R, SL-G, and SL-B below the emission layers EML-R, EML-G, and EML-B and the hole transport region HTR. The resonance auxiliary layers SL-R, SL-G, and SL-B may have different thicknesses according to a wavelength of light emitted from each of the emission layers EML-R, EML-G, and EML-B. A thickness $T_{RS}$ of the first resonance auxiliary layer SL-R is greater than the thickness TGs of the second resonance auxiliary layer SL-G, and the thickness TGs of the second resonance auxiliary layer SL-G may be greater than the thickness TBS of the third resonance auxiliary layer SL-B. For example, thickness may decrease in the order of the first resonance auxiliary layer SL-R, the second resonance auxiliary layer SL-G, and the third resonance auxiliary layer SL-B. However, this is presented as an example, and the embodiment is not limited thereto. In an embodiment, when the emission layers EML-R, EML-G, and EML-B emit light of a same wavelength, the resonance auxiliary layers SL-R, SL-G, and SL-B may have a same thickness.

FIG. 9 is a schematic cross-sectional view showing a portion of a display device according to an embodiment. FIG. 9 shows a schematic cross-sectional view of a portion corresponding to the display panel DP of FIG. 7. In a display device DD-TD of an embodiment, a light emitting element ED-BT may include light emitting structures OL-B1, OL-B2, and OL-B3. The light emitting element ED-BT may include the first electrode EL1 and the second electrode EL2 facing each other, and the light emitting structures OL-B1, OL-B2, and OL-B3 provided by being sequentially stacked in a thickness direction between the first electrode EL1 and the second electrode EL2. The light emitting structures OL-B1, OL-B2, and OL-B3 may each include the emission layer EML (FIG. 7), a hole transport region HTR, and an electron transport region ETR disposed with the emission layer EML (FIG. 7) therebetween.

For example, the light emitting element ED-BT included in the display device DD-TD of an embodiment may be a light emitting element having a tandem structure and including multiple emission layers.

In an embodiment illustrated in FIG. 9, light emitted from each of the light emitting structures OL-B1, OL-B2, and OL-B3 may all be blue light. However, embodiments are not limited thereto, and wavelength ranges of light emitted from each of the light emitting structures OL-B1, OL-B2, and OL-B3 may be different from each other. For example, the light emitting element ED-BT including the light emitting structures OL-B1, OL-B2, and OL-B3 emitting light in different wavelength ranges may emit white light.

Charge generation layers CGL1 and CGL2 may be disposed between neighboring light emitting structures OL-B1, OL-B2, and OL-B3. The charge generation layers CGL1 and CGL2 may each independently include a p-type charge generation layer and/or an n-type charge generation layer.

At least one of the light emitting structures OL-B1, OL-B2, and OL-B3 included in the display device DD-TD of an embodiment may include the amine compound of an embodiment described above.

The light emitting element ED according to an embodiment may include the first hole transport layer HTL1 having a low refractive index and including the first amine compound, the second hole transport layer HTL2 including the second amine compound having a high refractive index, and the third hole transport layer HTL3 including the third amine compound having a low refractive index. The light emitting element ED of an embodiment includes the three hole transport layers HTL1, HTL2, and HTL3, which are disposed in the order of a low refractive hole transport layer/high refractive hole transport layer/low refractive hole transport layer, and these hole transport layers bring about constructive interference of light to increase external light extraction efficiency.

Hereinafter, with reference to the Examples and the Comparative Examples, an amine compound according to an embodiment and a light emitting element of an embodiment will be described. The Examples are only provided as illustrations for understanding the disclosure, and the scope thereof is not limited thereto.

EXAMPLES

1. Synthesis of First and Third Amine Compounds

A method of synthesizing first and third amine compounds according to an embodiment of the inventive will be described in detail by providing a method of synthesizing Compounds 1, 22, 41, 42, and 46 as an example. A process of synthesizing the first and third amine compounds, which will be described hereinafter, is provided as an example, and thus a process of synthesizing the first and third amine compounds according to an embodiment of the inventive is not limited to Examples below.

(1) Synthesis of Compound 1

Amine compound 1 according to an embodiment may be synthesized by, for example, processes of a reaction below.

Synthesis of Intermediate A

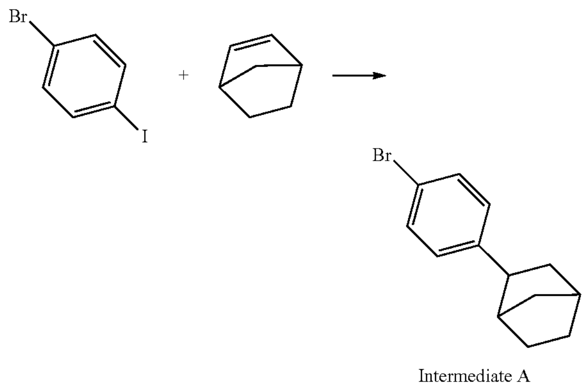

Intermediate A 2,6-difluoroaniline (12.9 g, 100 mmol), 2-iodoanisole (23.3 g), CuI (19.5 g, 100 mmol), $K_2CO_3$ (25.8 g, 200 mmol) were added to 200 ml of DMF solution and stirred at 150° C. for 96 hours. After the reaction was completed, the temperature was lowered to room temperature, and extraction was performed three times with ethyl acetate/$H_2O$. The resulting product was dried over anhydrous magnesium sulfate and purified through column chromatography using a mixed solvent of MC:HEX (1:10), thereby obtaining 18.8 g of Intermediate A (yield 80%).

Synthesis of Intermediate B

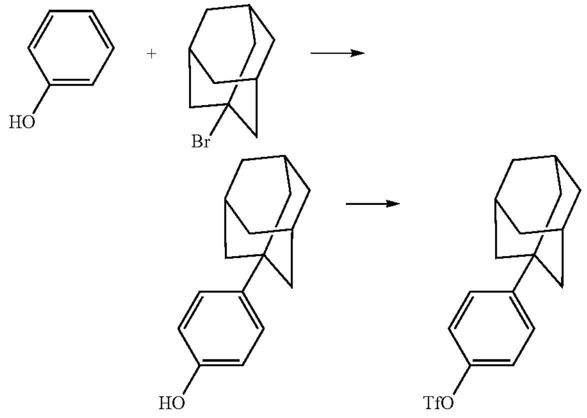

Intermediate B-1 Intermediate B

Synthesis of Intermediate B-1

1. Bromoadamantan (21.4 g, 100 mmol) was added to 100 ml of phenol, and stirred at 110° C. for 24 hours. After the reaction was completed, the resulting solid was washed 3 times with $H_2O$ at 60° C. After being dissolved in MC, the resulting product was dried over anhydrous magnesium sulfate to obtain 22 g of Intermediate B-1 (yield 100%).

Synthesis of Intermediate B

After dissolving 22 g of Intermediate B-1 and 10 g of $Et_3N$ in MC, the solution temperature was lowered to 0° C. 50 g of trifluoromethanesulfonic anhydride was added. The temperature was raised to room temperature, and the mixture was stirred for 4 hours. After the reaction was completed, the resulting solid was extracted 3 times with $H_2O$ at 60° C. The resulting product was dried over anhydrous magnesium sulfate, and separated and purified through column chromatography, thereby obtaining 33 g of Intermediate B (yield 90%).

Synthesis of Compound 1

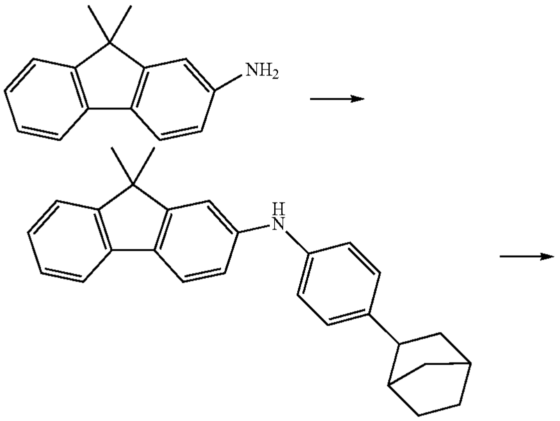

Intermediate 1-1

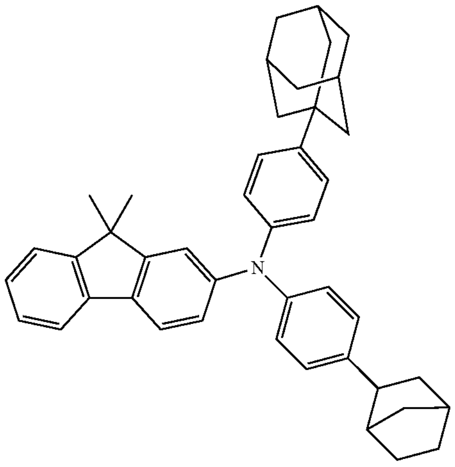

1

Synthesis of Intermediate 1-1

9,9-dimethyl-9H-fluoren-2-amine (4.2 g, 20 mmol), Intermediate A (5 g, 20 mmol), $Pd_2(dba)_3$ (0.915 g, 1 mol), Sphos (0.410 g, 1 ml), and $NaO^tBu$ (3.6 g, 40 mmol) were dissolved in 200 ml of toluene and stirred at 90° C. for 2 hours. After the reaction was completed, the resulting solid was extracted 3 times with $Et_2O/H_2O$. The resulting product was dried over anhydrous magnesium sulfate, and separated and purified through column chromatography, thereby obtaining 6.8 g of Intermediate 1-1 (18 mmol, yield 90%).

Synthesis of Compound 1

5.3 g of Compound 1 (9 mmol, yield 90%) was obtained in the same manner as in the synthesis of Intermediate 1-1, except that Intermediate 1-1 instead of 9,9-dimethyl-9H-fluoren-2-amine, and Intermediate B instead of Intermediate A were used.

Molecular weight and NMR results were shown as follows to confirm that it was Compound 1. [$C_{44}H_{47}N$ M+1: 590.45, $^1H$ NMR (500 MHz, $CDCl_3$) δ=7.80 (m, 2H), 7.60 (d, 1H), 7.55-7.10 (m, 12H), 2.5-0.9 (m, 32H)]

(2) Synthesis of Compound 22

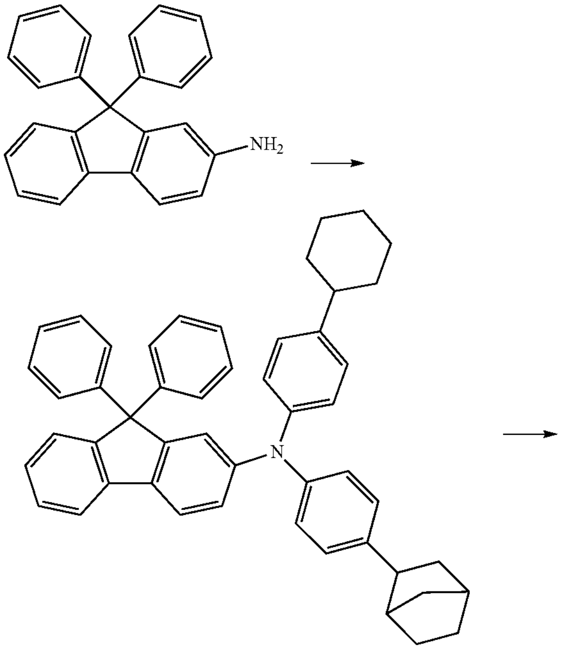

intermediate 1-2

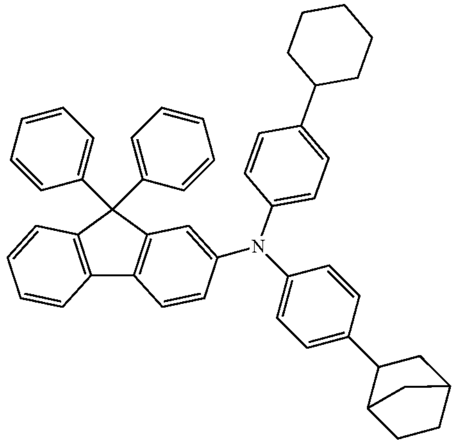

22

Synthesis of Intermediate 1-2

9,9-diphenyl-9H-fluoren-2-amine (6.6 g, 20 mmol), Intermediate A (5 g, 20 mmol), $Pd_2(dba)_3$ (0.915 g, 1 mol), Sphos (0.410 g, 1 ml), and NaO$^t$Bu (3.6 g, 40 mmol) were dissolved in 200 ml of toluene and stirred at 90° C. for 2 hours. After the reaction was completed, the resulting solid was extracted 3 times with $Et_2O/H_2O$. The resulting product was dried over anhydrous magnesium sulfate, and separated and purified through column chromatography, thereby obtaining 7.5 g of Intermediate 1-2 (15 mmol, yield 75%).

Synthesis of Compound 22

5.6 g of Compound 1 (8.5 mmol, yield 85%) was obtained in the same manner as in the synthesis of Intermediate 1-1, except that Intermediate 1-2 instead of 9,9-dimethyl-9H-fluoren-2-amine, and 1-bromo-4-cyclohexylbenzene instead of Intermediate A were used.

Molecular weight and NMR results were shown as follows to confirm that it was Compound 1. [$C_{44}H_{47}N$ M+1: 662.45, $^1H$ NMR (300 MHz, $CDCl_3$) δ=7.90 (d, 1H), 7.86 (d, 1H), 7.55-7.10 (m, 22H), 2.5-0.9 (m, 20H)]

(3) Synthesis of Compound 41

Amine compound 41 according to an embodiment may be synthesized by, for example, processes of a reaction below.

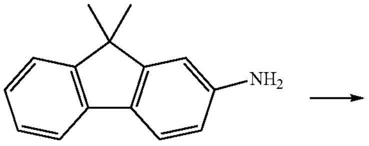

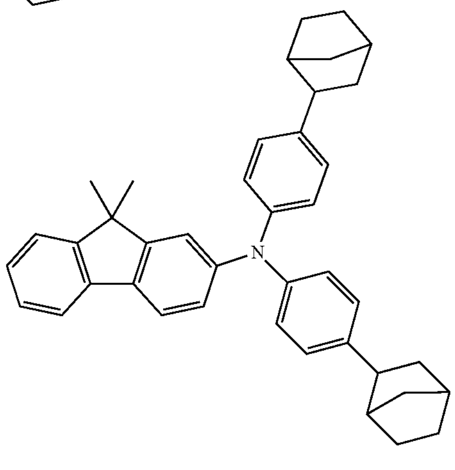

41

5.2 g of Compound 41 (9 mmol, yield 90%) was obtained in the same manner as in the synthesis of Intermediate 1-1, except that 9,9-dimethyl-9H-fluoren-2-amine (2.1 g, 10 mmol) was used.

Molecular weight and NMR results were shown as follows to confirm that it was Compound 41. [$C_{41}H_{43}N$ M+1: 550.52, 1H NMR (500 MHz, CDC13) δ=7.80 (m, 2H), 7.60 (d, 1H), 7.55-7.10 (m, 12H), 2.5-1.5 (m, 22H), 1.3 (d, 6H)]

(4) Synthesis of Compound 42

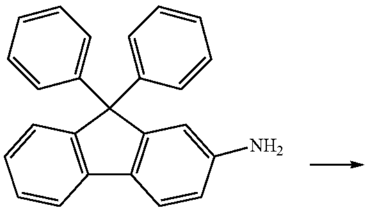

-continued

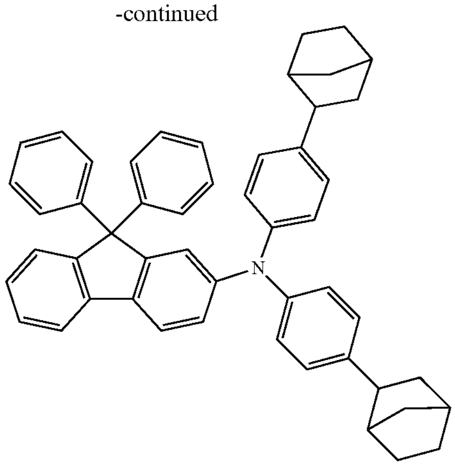

42

6.0 g of Compound 42 (9 mmol, yield 90%) was obtained in the same manner as in the synthesis of Intermediate 1-1, except that 9,9-diphenyl-9H-fluoren-2-amin (3.3 g, 10 mmol) was used.

Molecular weight and NMR results were shown as follows to confirm that it was Compound 42. [$C_{44}H_{47}N$ M+1: 674.37, $^1H$ NMR (300 MHz, $CDCl_3$) δ=7.90 (d, 1H), 7.86 (d, 1H), 7.55-7.10 (m, 22H), 2.5-0.9 (m, 20H)]

(5) Synthesis of Compound 46

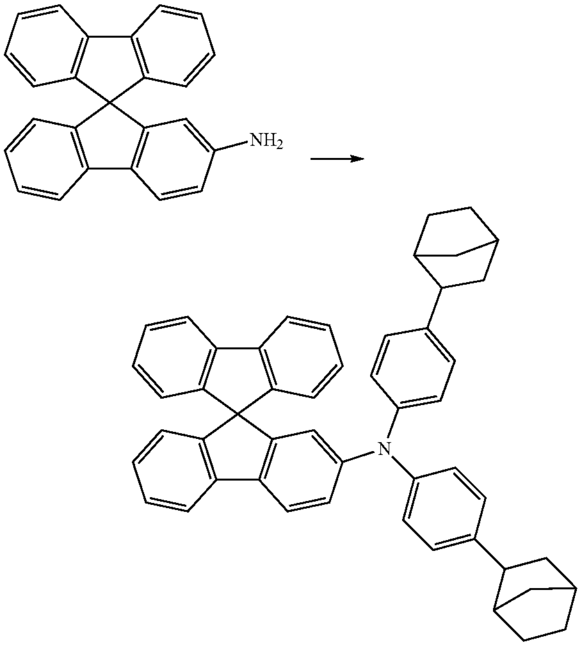

46

6.0 g of Compound 46 (9 mmol, yield 90%) was obtained in the same manner as in the synthesis of Intermediate 1-1, except that 9,9'spiro[fluoren]-2-amine (3.3 g, 10 mmol) was used.

Molecular weight and NMR results were shown as follows to confirm that it was Compound 46. [$C_{44}H_{47}N$ M+1: 672.36, $^1H$ NMR (300 MHz, $CDCl_3$) δ=7.90 (d, 1H), 7.86 (d, 1H), 7.55-7.10 (m, 19H), 2.5-0.9 (m, 20H)]

2. Synthesis of Second Amine Compound

A method of synthesizing the second amine compound according to an embodiment will be described in detail by providing a method of synthesizing Compounds 77 and 105 of Compound Group 2 as an example. A process of synthesizing the second amine compound, which will be described hereinafter, is provided as an example, and thus a process of synthesizing the second amine compound according to an embodiment is not limited to Examples below.

(1) Synthesis of Compound 77

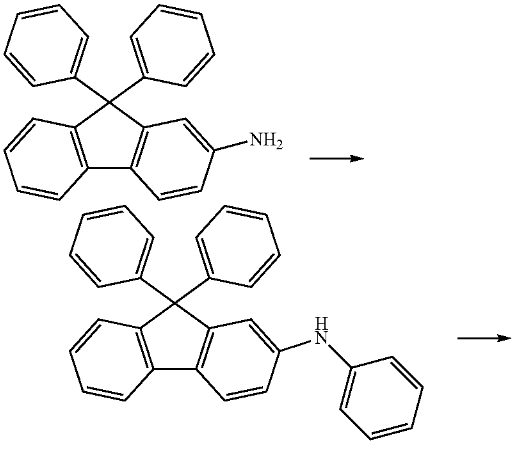

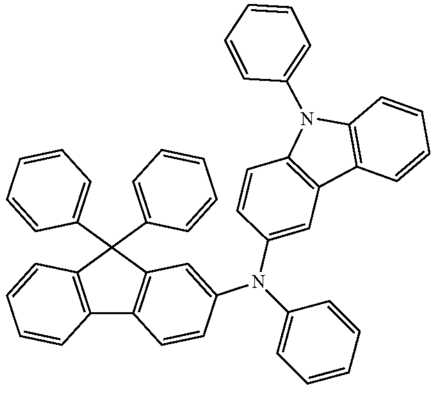

77

Synthesis of Intermediate 1-3

9,9-diphenyl-9H-fluoren-2-amine (6.6 g, 20 mmol), bromobenzene (3.1 g, 20 mmol), $Pd_2(dba)_3$ (0.915 g, 1 mol), Sphos (0.410 g, 1 ml), and NaO$^t$Bu (3.6 g, 40 mmol) were dissolved in 200 ml of toluene and stirred at 90° C. for 2 hours. After the reaction was completed, the resulting solid was extracted 3 times with $Et_2O/H_2O$. The resulting product was dried over anhydrous magnesium sulfate, and separated and purified through column chromatography, thereby obtaining 7.4 g of Intermediate 1-3 (18 mmol, yield 90%).

Synthesis of Compound 77

5.8 g of Compound 77 (9 mmol, yield 90%) was obtained in the same manner as in the synthesis of Intermediate 1-1, except that Intermediate 1-3 instead of 9,9-dimethyl-9H-fluoren-2-amine, and 3-bromo-9-phenyl-9H-carbazole instead of Intermediate A were used.

Molecular weight and NMR results were shown as follows to confirm that it was Compound 77. [$C_{44}H_{47}N$ M+1: 651.28, $^1H$ NMR (300 MHz, $CDCl_3$) δ=8.55 (d, 1H), 7.94-7.86 (m, 3H), 7.62-7.50 (m, 7H), 7.35-7.00 (m, 23H)]

(2) Synthesis of Compound 105

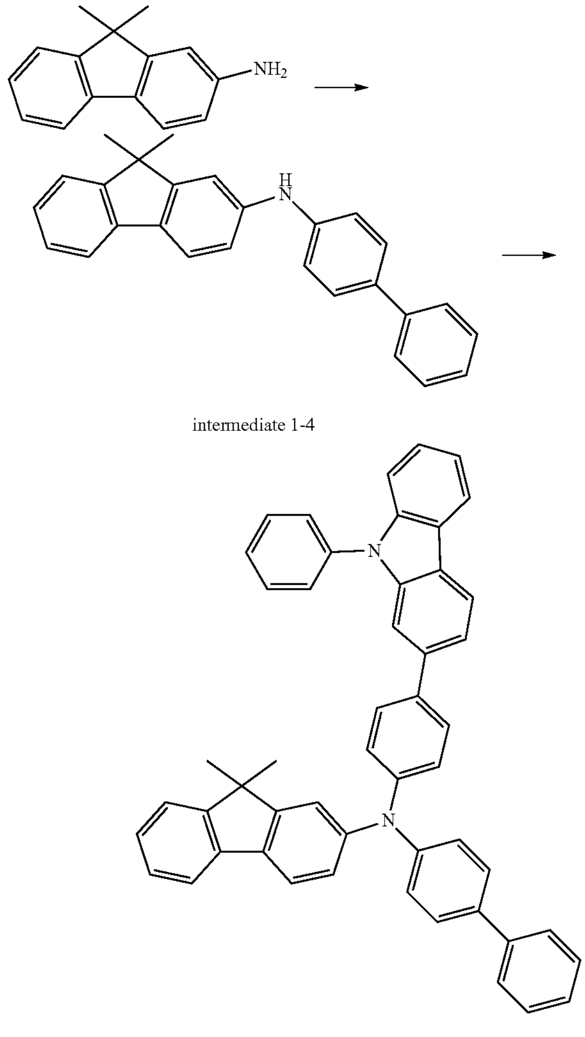
intermediate 1-4

105

Synthesis of Intermediate 1-4

9,9-dimethyl-9H-fluoren-2-amine (4.2 g, 20 mmol), 4-bromo-1,1'-biphenyl (4.6 g 20 mmol), $Pd_2(dba)_3$ (0.915 g, 1 mol), Sphos (0.410 g, 1 ml), and $NaO^tBu$ (3.6 g, 40 mmol) were dissolved in 200 ml of toluene and stirred at 90° C. for 2 hours. After the reaction was completed, the resulting solid was extracted 3 times with $Et_2O/H_2O$. The resulting product was dried over anhydrous magnesium, sulfate and separated and purified through column chromatography, thereby obtaining 6.2 g of Intermediate 1-4 (17 mmol, yield 85%).

Synthesis of Compound 105

6.1 g of Compound 105 (9 mmol, yield 90%) was obtained in the same manner as in the synthesis of Intermediate 1-1, except that Intermediate 1-4 instead of 9,9-dimethyl-9H-fluoren-2-amine, and 2-(4-bromophenyl)-9-phenyl-9H-carbazole instead of Intermediate A were used.

Molecular weight and NMR results were shown as follows to confirm that it was Compound 105. [$C_{44}H_{47}N$ M+1: 679.31, $^1H$ NMR (300 MHz, $CDCl_3$) δ=8.62 (d, 1H), 8.22 (d, 1H), 8.19 (d, 1H), 7.90 (d, 1H), 7.86 (d, 1H), 7.75-7.74 (m, 3H), 7.65-7.20 (m, 24H), 1.69 (s, 6H)

2. Manufacture and Evaluation of Light Emitting Elements (1) Manufacture of Light Emitting Elements of Examples 1 to 10

A substrate in which ITO/Ag/ITO was laminated to be 70 Å/1500 Å/70 Å thick on a glass substrate was washed with ultrapure water, subjected to ultrasonic cleaning, irradiated with UV for 30 minutes, and ozone-treated to form a first electrode. Thereafter, a first amine compound of an embodiment was deposited to be 300 Å thick to form a first hole transport layer, a second amine compound of an embodiment was deposited to be 600 Å thick to form a second hole transport layer, and a third amine compound of an embodiment was deposited to be 300 Å thick to form a third hole transport layer, thereby forming a hole transport region. ADN and blue fluorescent dopant, DPAVBi were co-deposited at a weight ratio of 98:2 on the hole transport region to form an emission layer having a thickness of 300 Å. $Alq_3$ was deposited to be 300 Å thick to form an electron transport layer, and LiF was deposited to be 10 Å thick to form an electron injection layer. Al was provided at a thickness of 3000 Å to form a second electrode.

In an embodiment, the hole injection layer, the hole transport layer, the emission layer, the electron transport layer, the electron injection layer, and the second electrode were formed using a vacuum deposition apparatus.

(2) Manufacture of Light Emitting Elements of Examples 11 to 15

The light emitting elements of Examples 11 to 15 were manufactured in the same manner as in the manufacturing method of the light emitting elements of Examples 1 to 10, except that ADN and blue fluorescent dopant, DABNA were co-deposited at a weight ratio of 98:2 on the hole transport region to form an emission layer having a thickness of 300 Å.

(3) Manufacture of Light Emitting Elements of Comparative Examples 1 to 7

A substrate in which ITO/Ag/ITO was laminated to be 70 Å/1500 Å/70 Å thick on a glass substrate was washed with ultrapure water, subjected to ultrasonic cleaning, irradiated with UV for 30 minutes, and ozone-treated to form a first electrode. Thereafter, a first amine compound or a second amine compound of an embodiment was deposited to be 1200 Å thick to form a single hole transport layer, thereby forming a hole transport region. ADN and blue fluorescent dopant, DPAVBi were co-deposited at a weight ratio of 98:2 on the hole transport region to form an emission layer having a thickness of 300 Å. $Alq_3$ was deposited to be 300 Å thick to form an electron transport layer, and LiF was deposited to be 10 Å thick to form an electron injection layer. Al was provided at a thickness of 3000 Å to form a second electrode.

In an embodiment, the hole transport layer, the emission layer, the electron transport layer, the electron injection layer, and the second electrode were formed using a vacuum deposition apparatus.

(4) Manufacture of Light Emitting Elements of Comparative Examples 8 to 12

The light emitting elements of Comparative Examples 8 to 12 were manufactured in the same manner as in the manufacturing method of the light emitting elements of Examples 1 to 10, except that on the first electrode, sequentially a second amine compound was deposited to be 900 Å thick to form a high refractive hole transport layer, and a third amine compound was deposited to be 300 Å thick to form a low refractive hole transport layer.

(5) Manufacture of Light Emitting Elements of Comparative Examples 13 to 17

The light emitting elements of Comparative Examples 13 to 17 were manufactured in the same manner as in the manufacturing method of the light emitting elements of Examples 1 to 10, except that on the first electrode, sequentially a first amine compound was deposited to be 300 Å thick to form a low refractive hole transport layer, and a second amine compound was deposited to be 900 Å thick to form a high refractive hole transport layer.

(6) Manufacture of Light Emitting Element of Comparative Example 18

The light emitting element of Comparative Example 18 was manufactured in the same manner as in the manufacturing method of the light emitting elements of Examples 1 to 10, except that on the first electrode, sequentially a second amine compound was deposited to be 300 Å thick to form a high refractive hole transport layer, a first amine compound was deposited to be 600 Å thick to form a low refractive hole transport layer, and a second amine compound was deposited to be 300 Å thick to form a high refractive hole transport layer.

(7) Manufacture of Light Emitting Element of Comparative Example 19

The light emitting element of Comparative Example 19 was manufactured in the same manner as in the manufacturing method of the light emitting elements of Comparative Examples 1 to 7, except that ADN and blue fluorescent dopant, DABNA were co-deposited at a weight ratio of 98:2 on the hole transport region to form an emission layer having a thickness of 300 Å.

Figure 10:
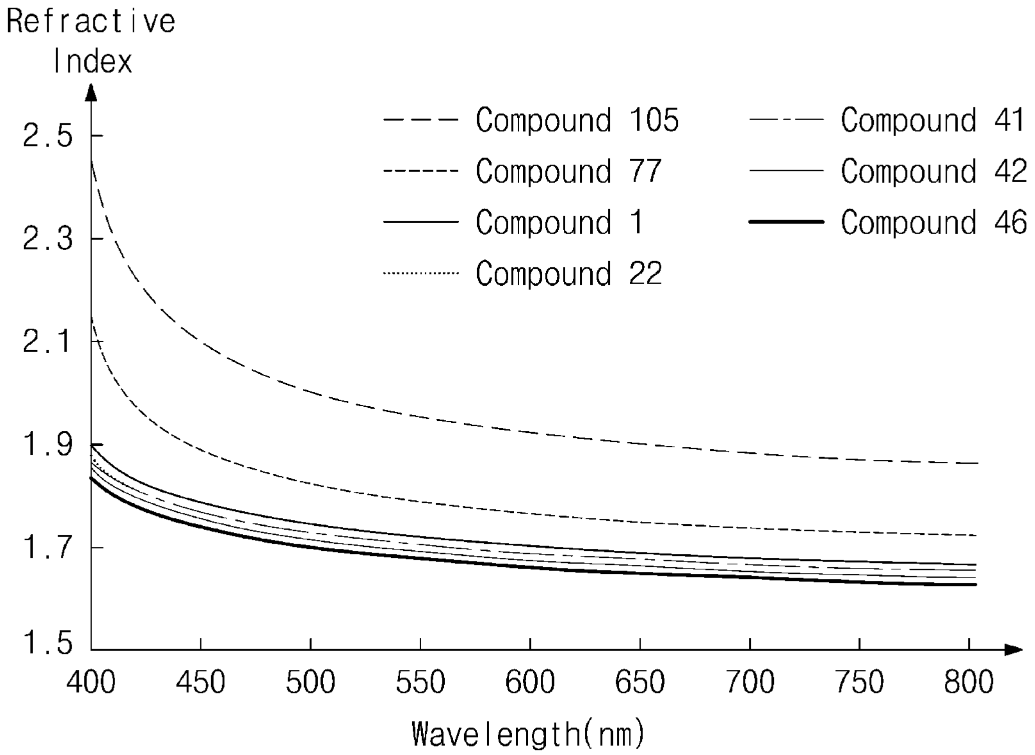
FIG. 10 is a graph showing changes in refractive index values of compounds of an embodiment in a wavelength range of the visible light region.

FIG. 10 is a graph showing changes in refractive index values of compounds of an embodiment in a wavelength range of the visible light region. Table 1 shows refractive index values of compounds of an embodiment in the wavelength of about 460 nm, about 550 nm, and about 650 nm among the changes in the refractive index values shown in FIG. 10.

Table 1 shows the refractive indices of Compound 1, Compound 22, Compound 41, Compound 42, Compound 46, Compound 77, and Compound 105. Table 1 shows the refractive indices of the compounds with respect to light having a central wavelength of about 460 nm, about 550 nm, and about 650 nm.

TABLE 1

| | Refractive Index (460 nm) | Refractive Index (550 nm) | Refractive Index (650 nm) |
|---|---|---|---|
| Compound 1 | 1.75 | 1.70 | 1.66 |
| Compound 22 | 1.73 | 1.69 | 1.66 |
| Compound 41 | 1.76 | 1.71 | 1.69 |
| Compound 42 | 1.78 | 1.73 | 1.70 |
| Compound 46 | 1.76 | 1.71 | 1.69 |
| Compound 77 | 1.88 | 1.80 | 1.77 |
| Compound 105 | 2.08 | 1.97 | 1.92 |

Referring to FIG. 10 and Table 1, it can be seen that Compound 1, Compound 22, Compound 41, Compound 42, and Compound 46 have a refractive index of about 1.3 to about 1.8 with respect to light having a central wavelength of about 460 nm, about 550 nm, or about 650 nm. It can be seen that Compound 77 and Compound 105 have a refractive index of about 1.8 to about 2.4 with respect to light having a central wavelength of about 460 nm, about 550 nm, or about 650 nm.

Compounds Used when Manufacturing Elements

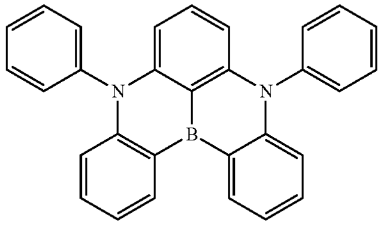

DABNA

-continued

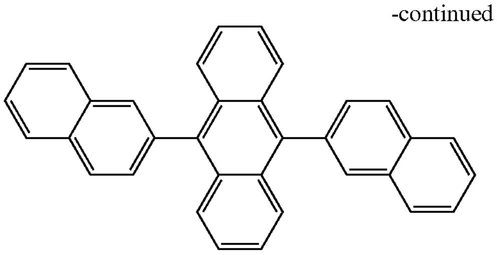

ADN

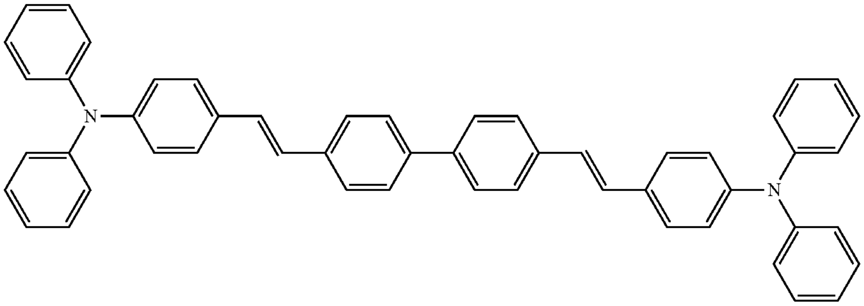

DPAVBi

Property Evaluation of Light Emitting Elements

Table 2 shows results of evaluation on light emitting elements for Examples 1 to 10, and Comparative Examples 1 to 18. Table 3 shows results of evaluation on light emitting elements for Examples 11 to 15, and Comparative Example 19. Tables 2 and 3 compare and show the luminous efficiency of the manufactured light emitting elements. In the property evaluation results of Examples shown in Tables 2 and 3, the luminous efficiency represents an efficiency value at a current density of 5 mA/$cm^2$. Tables 2 and 3 show color coordinate values of Examples 1 to 15 and Comparative Examples 1 to 19. It was confirmed that Examples 1 to 15 and Comparative Examples 1 to 19 exhibited a color coordinate value of about 0.042 corresponding to blue light.

The luminous efficiency evaluation of Examples and Comparative Examples was carried out in a dark room using PC Program LabVIEW 2.0 for measurement (National Instrument Co., Japan).

TABLE 2

| | First hole transport layer | Second hole transport layer | Third hole transport layer | Emission layer material | Efficiency (cd/A) | Color coordinate (By) |
|---|---|---|---|---|---|---|
| Comparative Example 1 | | 105 | | ADN:DPAVBi | 6.54 | 0.042 |
| Comparative Example 2 | | 1 | | | 7.32 | 0.042 |
| Comparative Example 3 | | 77 | | | 7.19 | 0.042 |
| Comparative Example 4 | | 41 | | | 7.32 | 0.042 |
| Comparative Example 5 | | 22 | | | 7.35 | 0.042 |
| Comparative Example 6 | | 42 | | | 7.28 | 0.042 |
| Comparative Example 7 | | 46 | | | 7.29 | 0.042 |
| Comparative Example 8 | — | 105 | 1 | | 7.49 | 0.042 |
| Comparative Example 9 | — | 105 | 41 | | 7.48 | 0.042 |
| Comparative Example 10 | — | 105 | 22 | | 7.51 | 0.042 |
| Comparative Example 11 | — | 105 | 42 | | 7.46 | 0.042 |
| Comparative Example 12 | — | 105 | 46 | | 7.48 | 0.042 |
| Comparative Example 13 | 1 | 105 | — | | 6.92 | 0.042 |
| Comparative Example 14 | 41 | 105 | — | | 6.87 | 0.042 |
| Comparative Example 15 | 22 | 105 | — | | 6.99 | 0.042 |

TABLE 2-continued

| | First hole transport layer | Second hole transport layer | Third hole transport layer | Emission layer material | Efficiency (cd/A) | Color coordinate (By) |
|---|---|---|---|---|---|---|
| Comparative Example 16 | 42 | 105 | — | | 7.12 | 0.042 |
| Comparative Example 17 | 46 | 105 | — | | 7.01 | 0.042 |
| Comparative Example 18 | 105 | 1 | 105 | | 5.69 | 0.042 |
| Example 1 | 1 | 105 | 1 | | 7.68 | 0.042 |
| Example 2 | 41 | 105 | 41 | | 7.74 | 0.042 |
| Example 3 | 22 | 105 | 22 | | 7.62 | 0.042 |
| Example 4 | 42 | 105 | 42 | | 7.82 | 0.042 |
| Example 5 | 46 | 105 | 46 | | 7.88 | 0.042 |
| Example 6 | 1 | 77 | 1 | | 7.78 | 0.042 |
| Example 7 | 41 | 77 | 41 | | 7.81 | 0.042 |
| Example 8 | 22 | 77 | 22 | | 7.72 | 0.042 |
| Example 9 | 42 | 77 | 42 | | 7.86 | 0.042 |
| Example 10 | 46 | 77 | 46 | | 7.87 | 0.042 |

TABLE 3

| | First hole transport layer | Second hole transport layer | Third hole transport layer | Emission layer material | Efficiency (cd/A) | Color coordinate (By) |
|---|---|---|---|---|---|---|
| Comparative Example 19 | | 105 | | ADN:DABNA | 8.50 | 0.042 |
| Example 11 | 1 | 105 | 1 | | 9.98 | 0.042 |
| Example 12 | 41 | 105 | 41 | | 10.21 | 0.042 |
| Example 13 | 22 | 105 | 22 | | 9.91 | 0.042 |
| Example 14 | 42 | 105 | 42 | | 10.14 | 0.042 |
| Example 15 | 46 | 105 | 46 | | 10.27 | 0.042 |

Referring to the results of Tables 2 and 3, it can be seen that the light emitting elements of Examples exhibited higher element efficiency than the light emitting elements of Comparative Examples when the same emission layer was used.

In Table 2, the light emitting elements of Examples 1 to 10 and the light emitting elements of Comparative Examples 1 to 18 using ADN:DPAVBi as an emission layer material are compared and described. It can be seen that the light emitting elements of Examples 1 to 10 including three hole transport layers, which are disposed in the order of a low refractive hole transport layer/high refractive hole transport layer/low refractive hole transport layer showed higher luminous efficiency than the light emitting elements of Comparative Examples 1 to 7 including a single hole transport layer, and the light emitting elements of Comparative Examples 8 to 17 including two hole transport layers. It can be seen that the light emitting elements of Examples 1 to 10 including three hole transport layers, which are disposed in the order of a low refractive hole transport layer/high refractive hole transport layer/low refractive hole transport layer showed higher luminous efficiency than the light emitting element of Comparative Example 18 including three hole transport layers disposed in the order of a high refractive hole transport layer/low refractive hole transport layer/high refractive hole transport layer. Against this backdrop, it is confirmed that the light emitting elements of Examples 1 to 10 include three hole transport layers disposed in the order of a low refractive hole transport layer/high refractive hole transport layer/low refractive hole transport layer, and thus have higher luminous efficiency than the light emitting elements of Comparative Examples 1 to 18.

In Table 3, the light emitting elements of Examples 11 to 15 and the light emitting elements of Comparative Example 19 using ADN:DABNA as an emission layer material are compared and described. It can be seen that the light emitting elements of Examples 11 to 15 have higher luminous efficiency than the light emitting elements of Comparative Example 19. Against this backdrop, it is confirmed that the luminous efficiency of the light emitting elements is improved when the three hole transport layers disposed in the order of a low refractive hole transport layer/high refractive hole transport layer/low refractive hole transport layer are included even when the type of an emission material is different.

Examples 1 to 10 show improved luminous efficiency compared to Comparative Examples 1 to 18, and Examples 11 to 15 show improved luminous efficiency compared to Comparative Example 19. The luminous efficiency of the light emitting element of an embodiment may be improved when the three hole transport layers disposed in the order of a low refractive hole transport layer/high refractive hole transport layer/low refractive hole transport layer are included.

A light emitting element of an embodiment includes a first hole transport layer including a first amine compound having a low refractive index, a second hole transport layer including a second amine compound having a high refractive index, and a third hole transport layer including a third amine compound having a low refractive index, which are sequentially staked, and thus may exhibit high efficiency characteristics.

A light emitting element and a display device including the same according to an embodiment may include a hole transport layer having a low refractive index, a hole transport layer having a high refractive index, and a hole transport layer having a low refractive index, which are sequentially stacked, and thus, may exhibit high efficiency characteristics.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the following claims.

What is claimed is:

1. A light emitting element comprising:

a first electrode;

a hole transport region disposed on the first electrode;

an emission layer disposed on the hole transport region;

an electron transport region disposed on the emission layer; and a second electrode disposed on the electron transport region, wherein the hole transport region includes:

a first hole transport layer disposed adjacent to the first electrode and including a first amine compound having a first refractive index;

a second hole transport layer disposed between the first hole transport layer and the emission layer, and including a second amine compound having a second refractive index greater than the first refractive index; and a third hole transport layer disposed between the second hole transport layer and the emission layer, and including a third amine compound having a third refractive index less than the second refractive index, and the first amine compound and the third amine compound are each independently a compound represented by Formula 1:

[Formula 1]

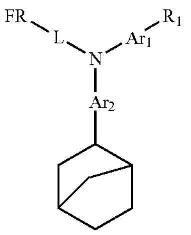

wherein in Formula 1, $R_1$ is a substituted or unsubstituted adamantyl group, a substituted or unsubstituted cyclohexyl group, or a substituted or unsubstituted bicycloheptyl group, $Ar_1$ and $Ar_2$ are each independently a substituted or unsubstituted arylene group having 6 to 30 ring-forming carbon atoms, L is a direct linkage, a substituted or unsubstituted arylene group having 6 to 30 ring-forming carbon atoms, or a substituted or unsubstituted heteroarylene group having 2 to 30 ring-forming carbon atoms, and FR is a group represented by Formula 2:

[Formula 2]

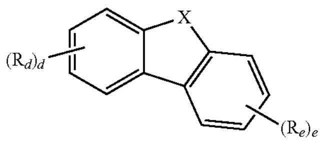

wherein in Formula 2,

X is $C(R_a)(R_b)$, N, $N(R_c)$, O, or S, $R_a$ to $R_c$ are each independently a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring, d and e are each independently an integer from 0 to 4, and $R_d$ and $R_e$ are each independently a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring.

2. The light emitting element of claim 1, wherein a difference between the second refractive index and the first refractive index is in a range of about 0.1 to about 1.1, and a difference between the second refractive index and the third refractive index is in a range of about 0.1 to about 1.1.

3. The light emitting element of claim 1, wherein the first refractive index and the third refractive index are each independently in a range of about 1.3 to about 1.8.

4. The light emitting element of claim 1, wherein the second refractive index is in a range of about 1.8 to about 2.4.

5. The light emitting element of claim 1, wherein a thickness ratio of the first hole transport layer to the second hole transport layer to the third hole transport layer is in a range of about 4.50:1.00:4.50 to about 0.125:1.00:0.125.

6. The light emitting element of claim 1, wherein the compound represented by Formula 1 is represented by Formula 1-1 or Formula 1-2:

[Formula 1-1]

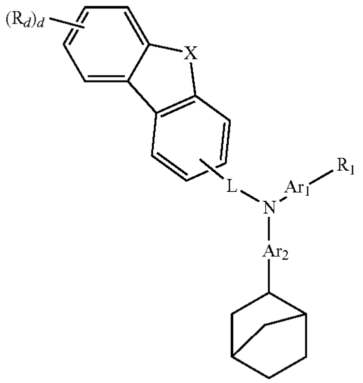

[Formula 1-2]

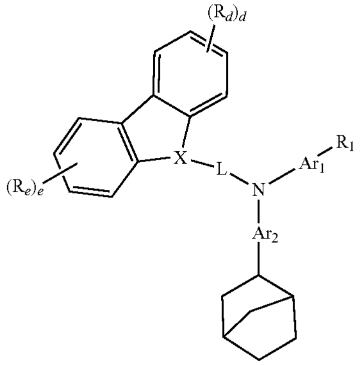

wherein in Formulas 1-1 and 1-2, $R_1$, L, $Ar_1$, and $Ar_2$ are the same as defined in Formula 1, and X, $R_d$, $R_e$, d, and e are the same as defined in Formula 2.

7. The light emitting element of claim 6, wherein the compound represented by Formula 1-2 is represented by Formula 1-2A:

[Formula 1-2A]

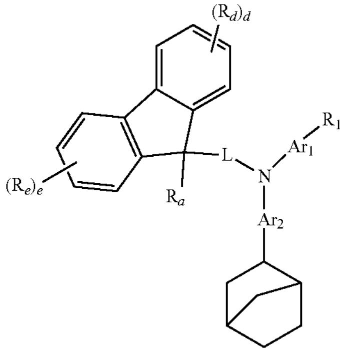

wherein in Formula 1-2A, $R_1$, L, $Ar_1$, and $Ar_2$ are the same as defined in Formula 1, and $R_a$, $R_d$, $R_e$, d, and e are the same as defined in Formula 2.

8. The light emitting element of claim 1, wherein the compound represented by Formula 1 is represented by Formula 1A:

[Formula 1A]

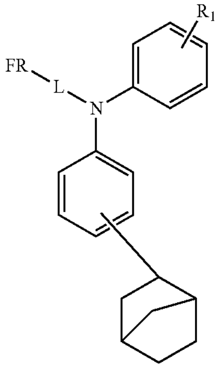

wherein in Formula 1A, $R_1$, L, and FR are the same as defined in Formula 1.

9. The light emitting element of claim 1, wherein the first amine compound and the third amine compound are each independently selected from Compound Group 1:

[Compound Group 1]

1

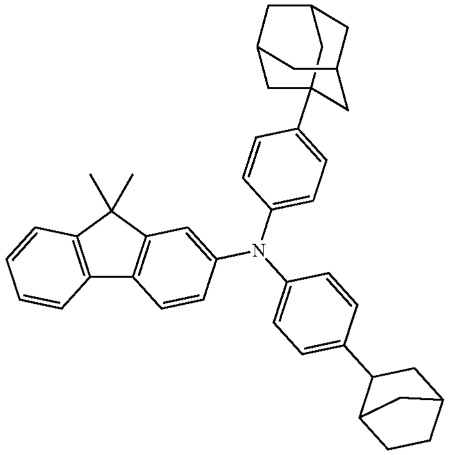

2

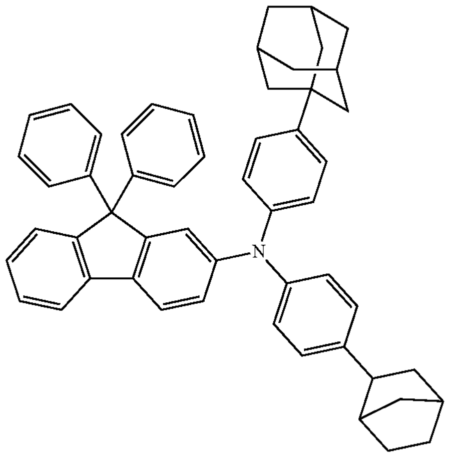

-continued
3
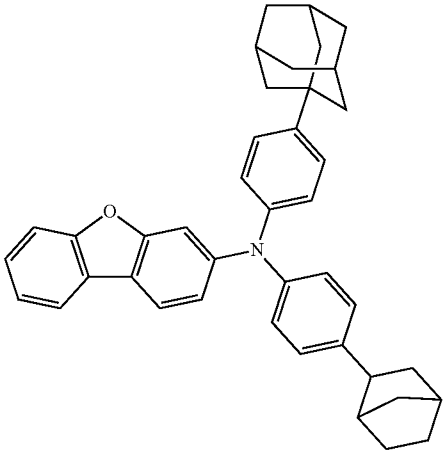
4
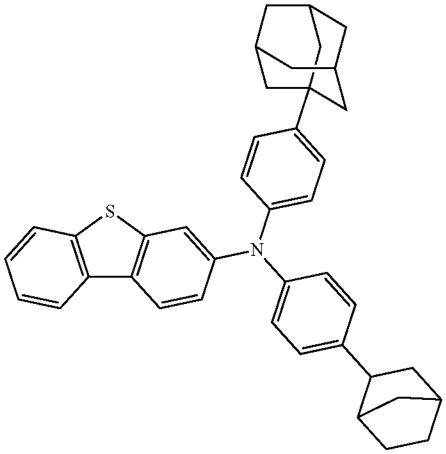
5
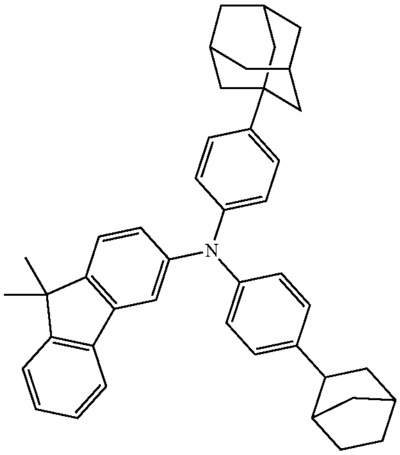
-continued
6
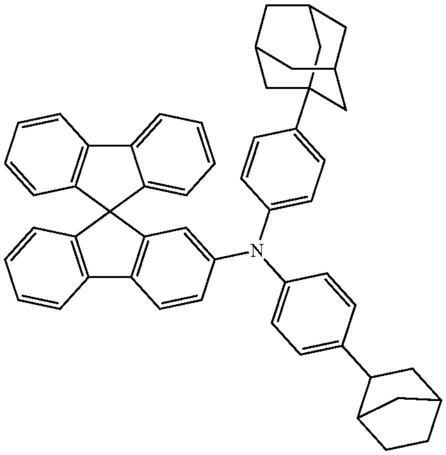
7
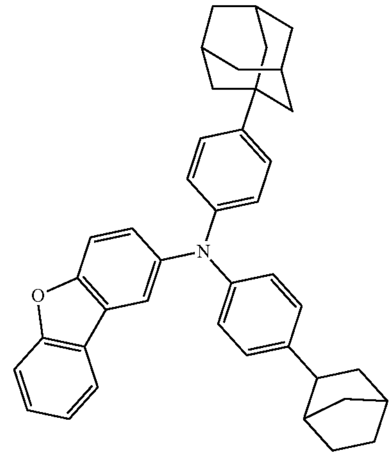
8
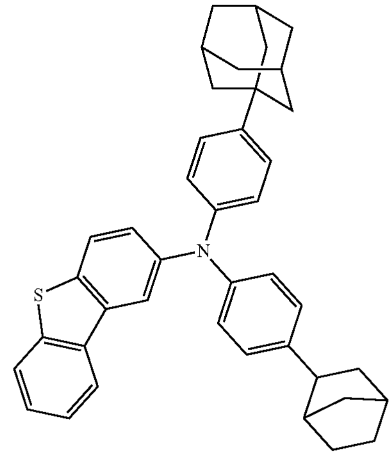

9
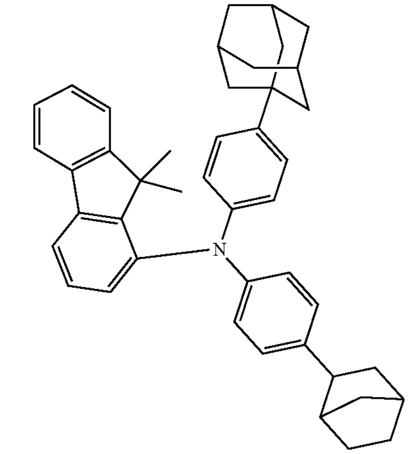
10
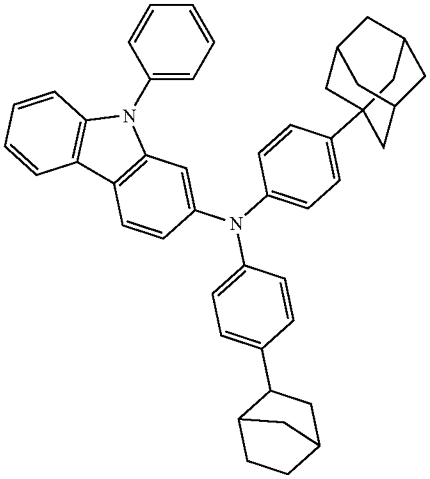
11
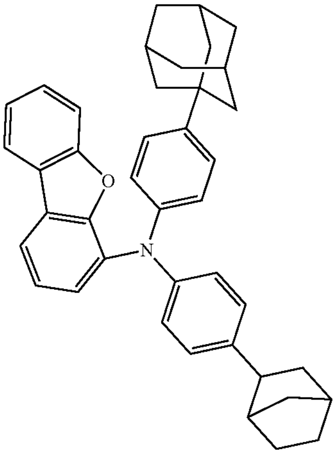
12
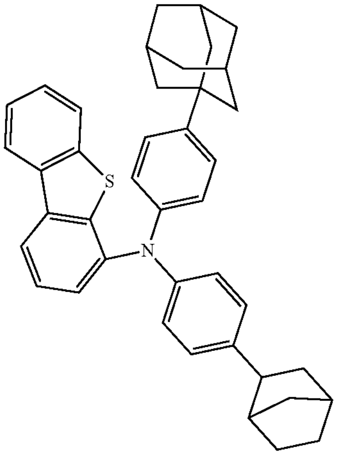
13
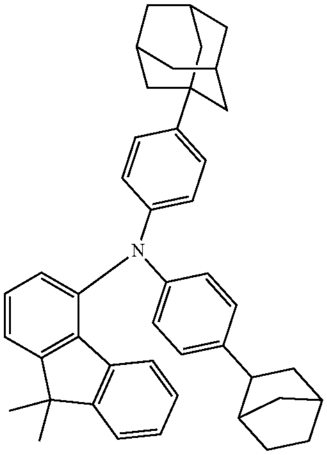
14
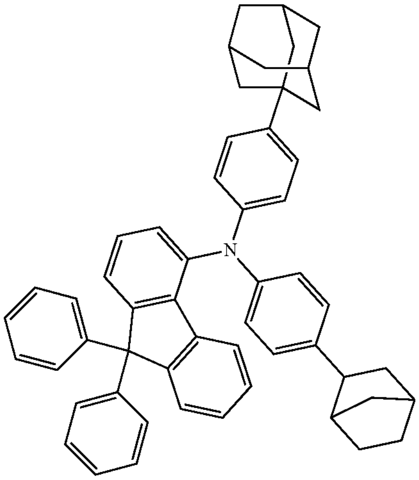

-continued
15
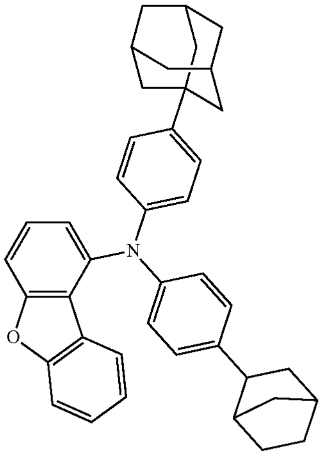
16
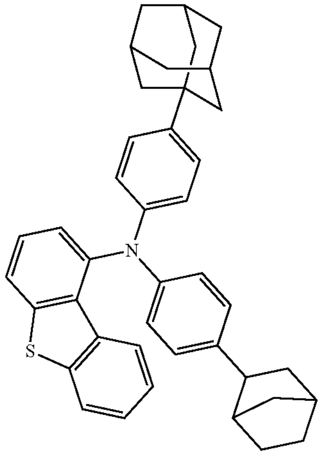
17
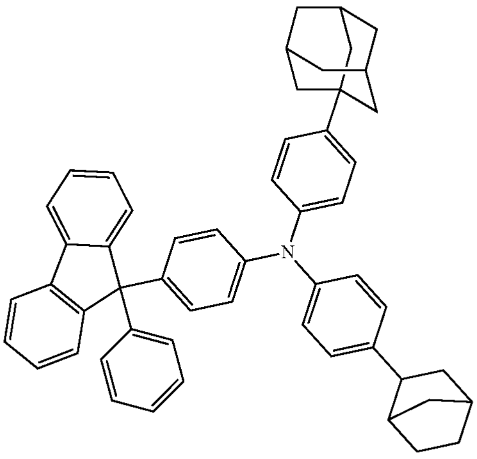
-continued
18
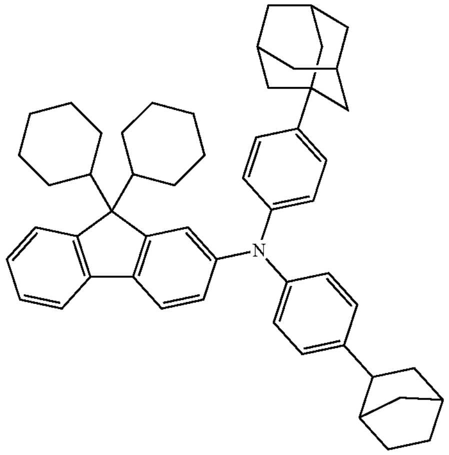
19
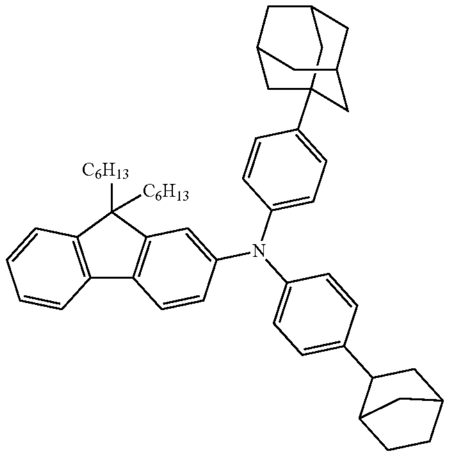
20
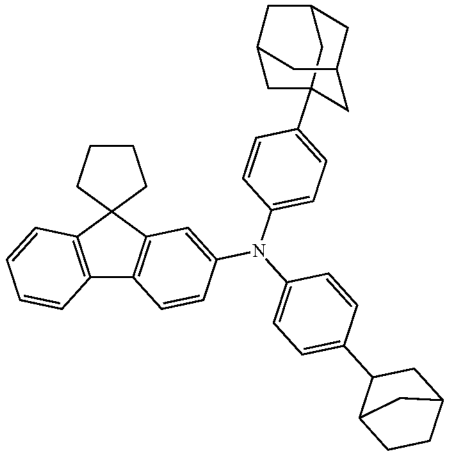

-continued
21
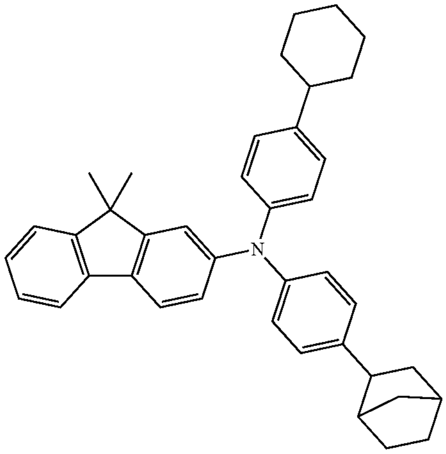
22
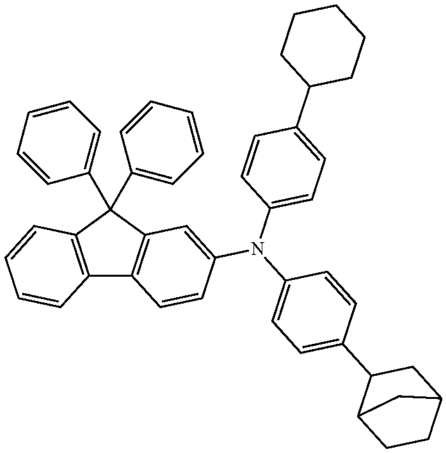
23
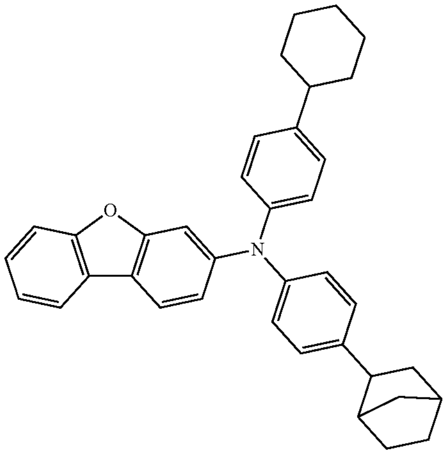
-continued
24
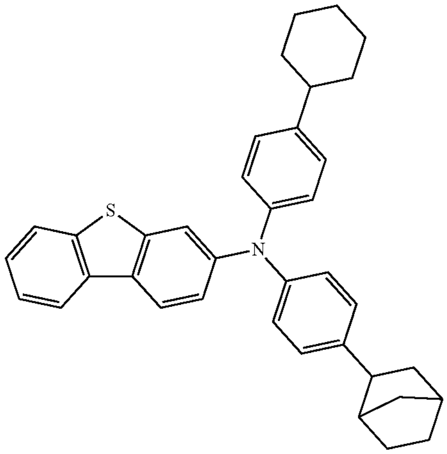
25
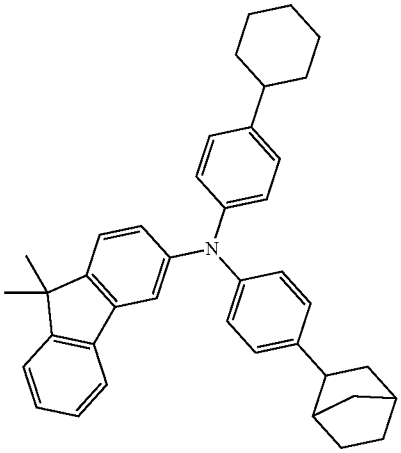
26
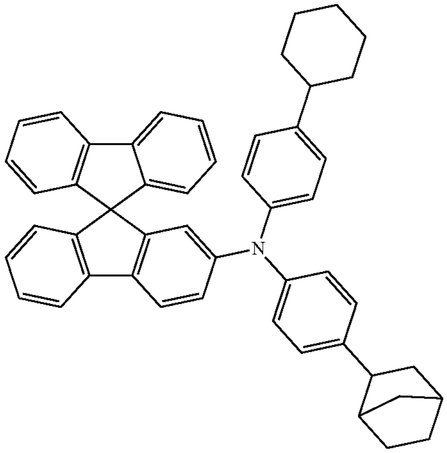

-continued
27
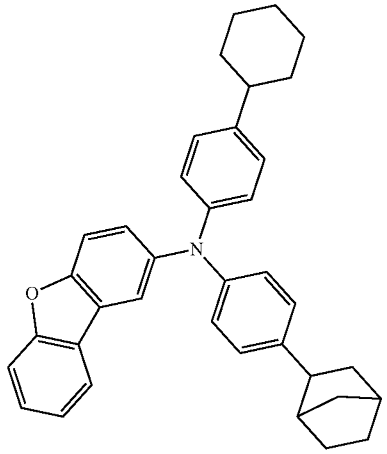
28
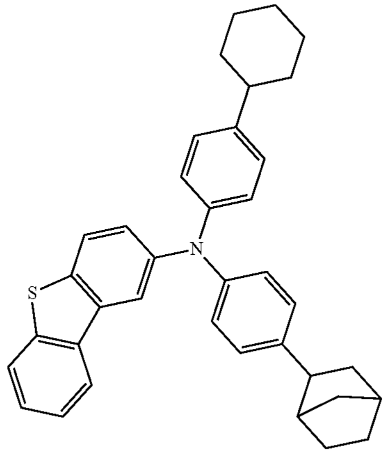
29
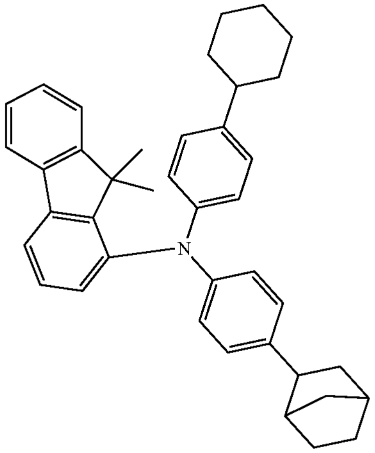
-continued
30
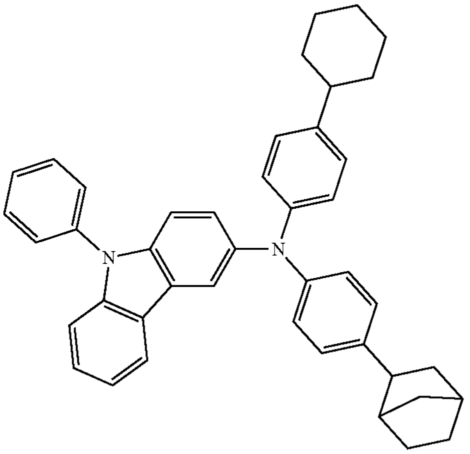
31
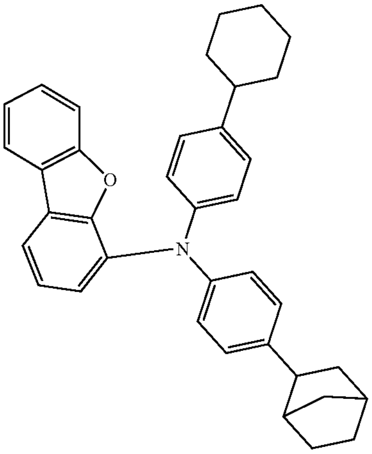
32
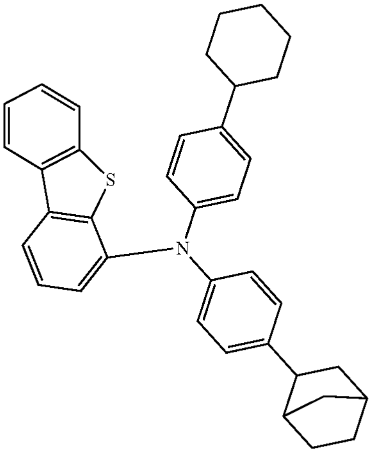

-continued
33
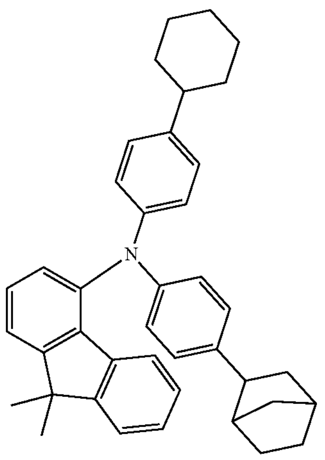
34
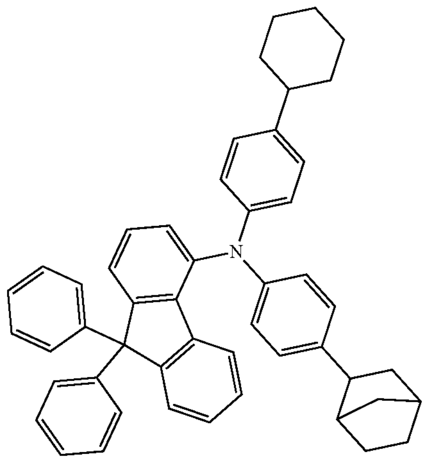
35
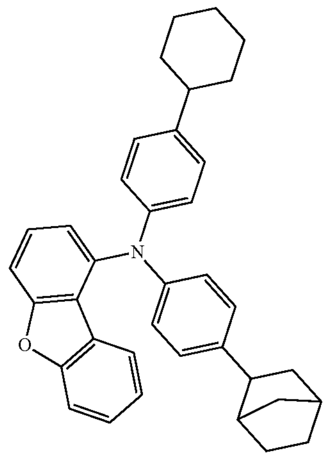
-continued
36
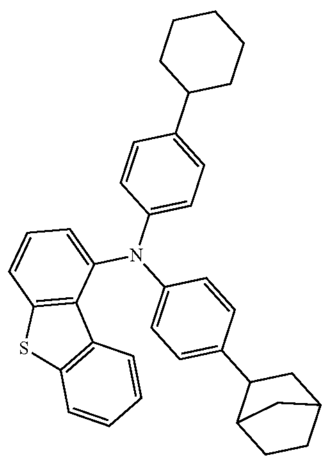
37
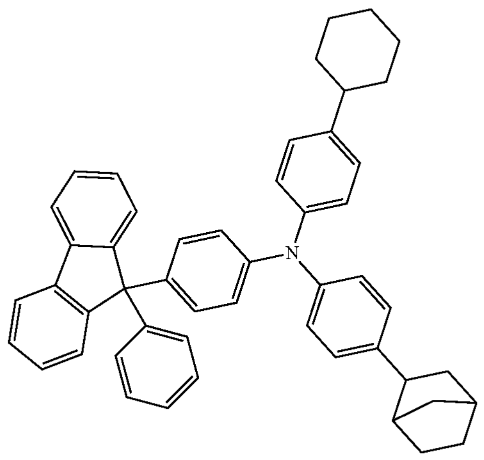
38
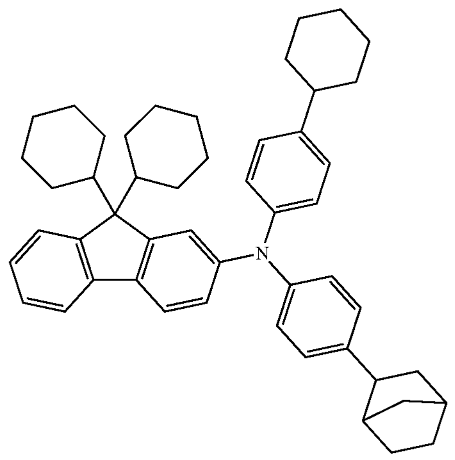

-continued
39
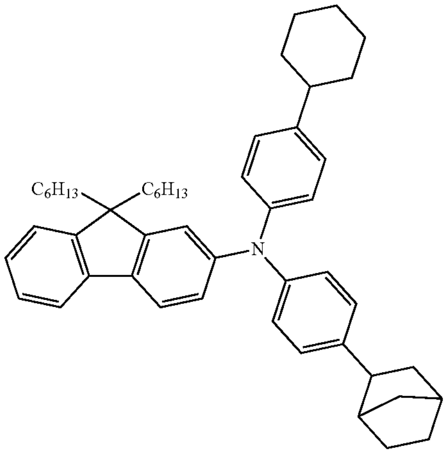
40
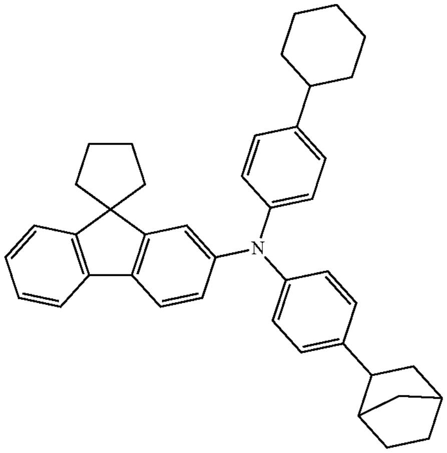
41
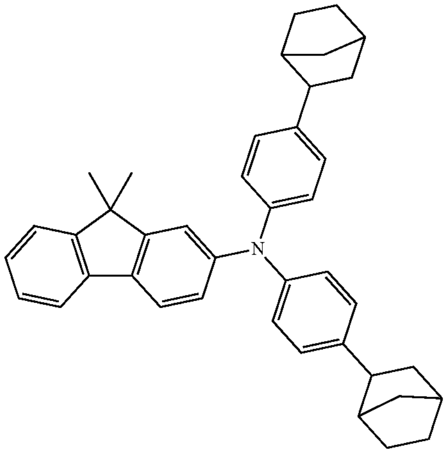
-continued
42
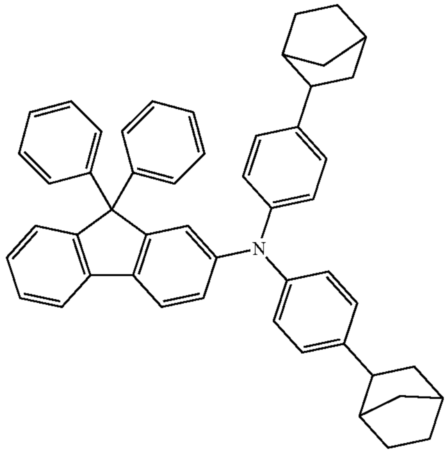
43
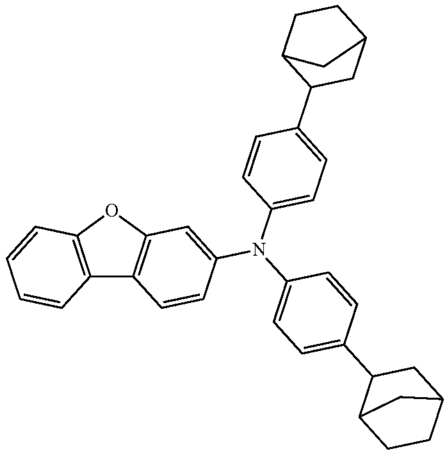
44
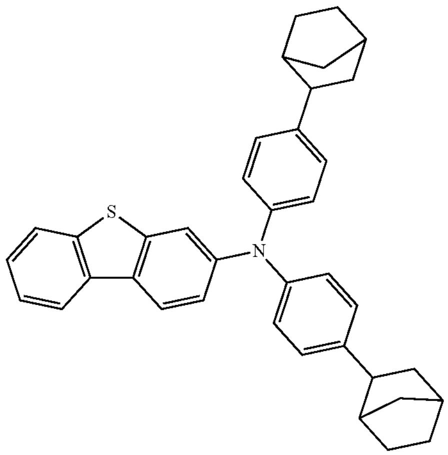

-continued
45
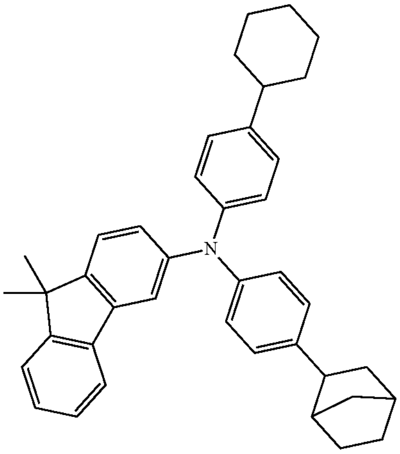
46
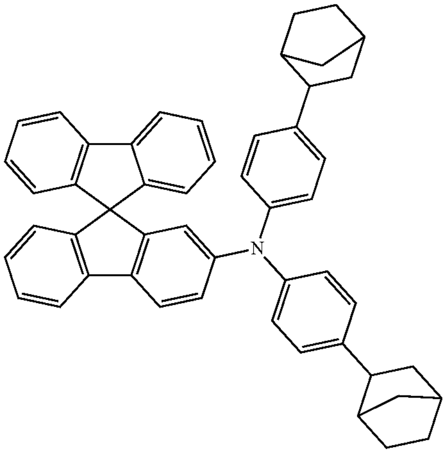
47
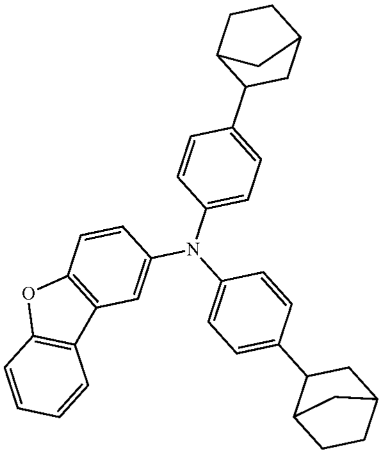
-continued
48
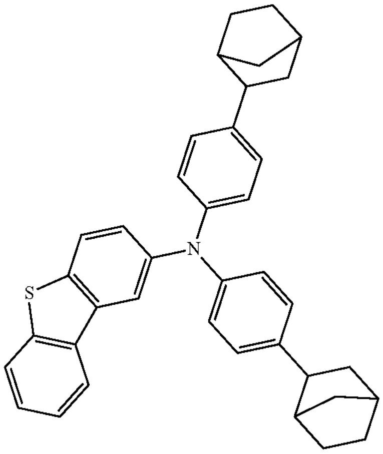
49
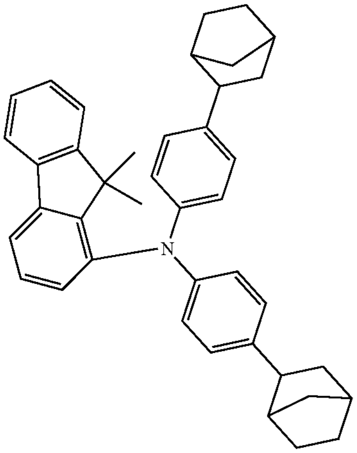
50
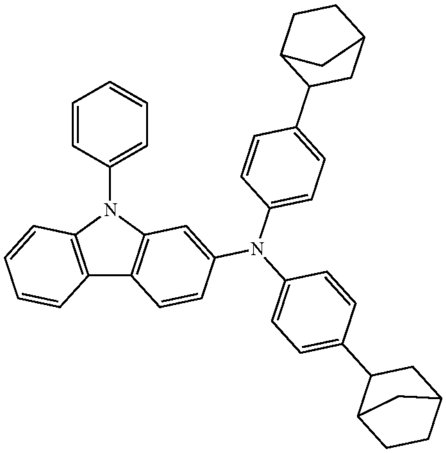

-continued
51
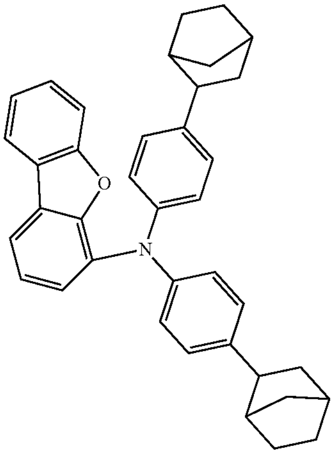
52
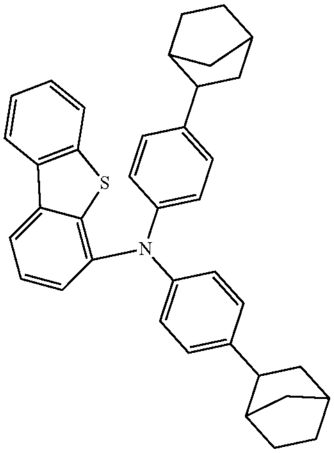
53
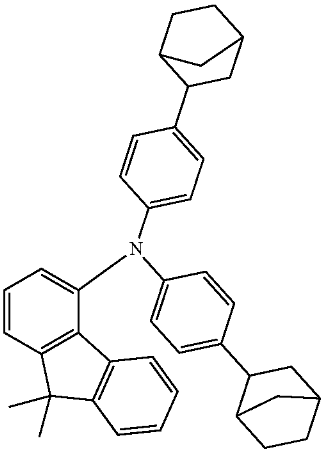
-continued
54
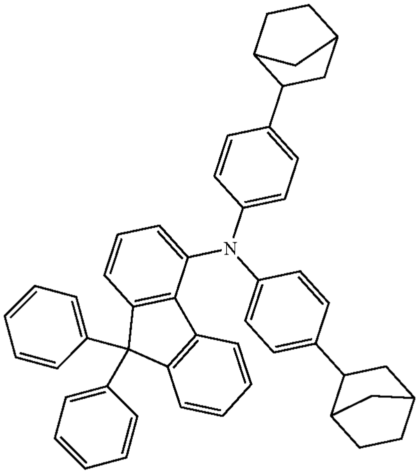
55
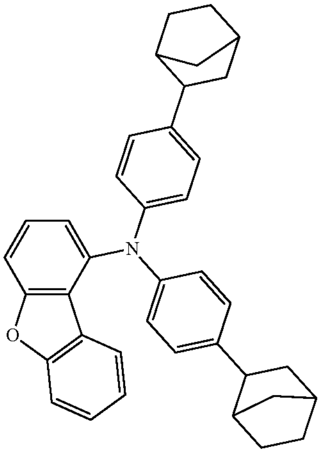
56
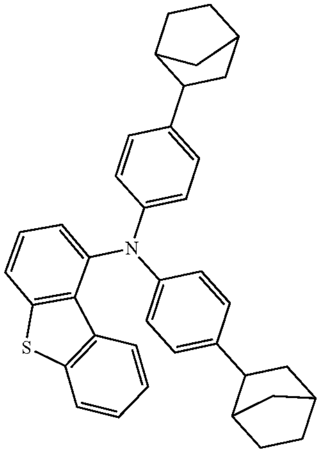

57
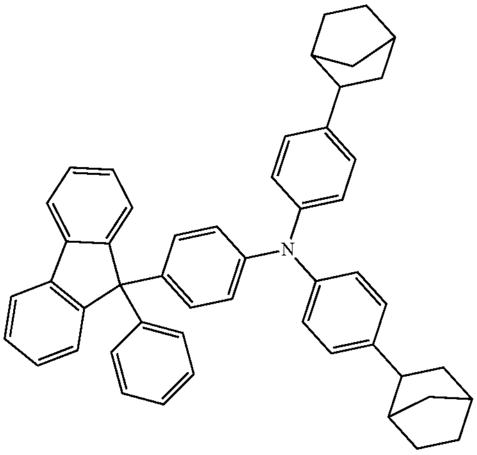
58
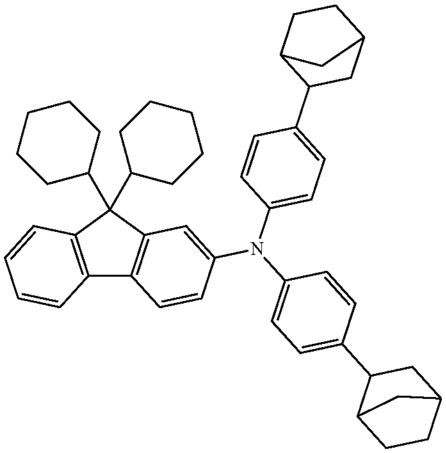
59
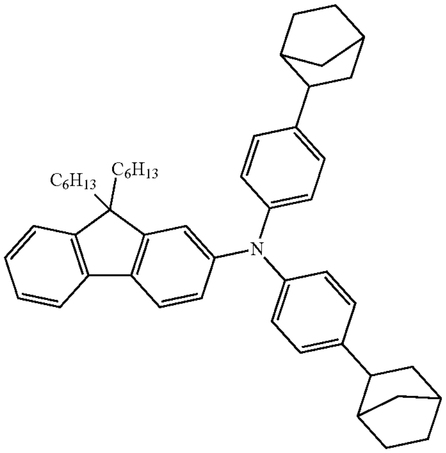
60
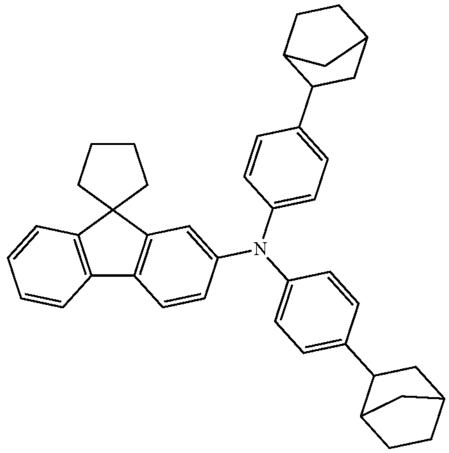
61
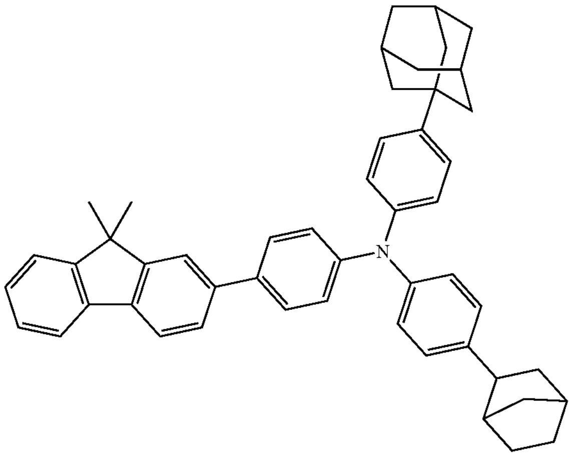
62
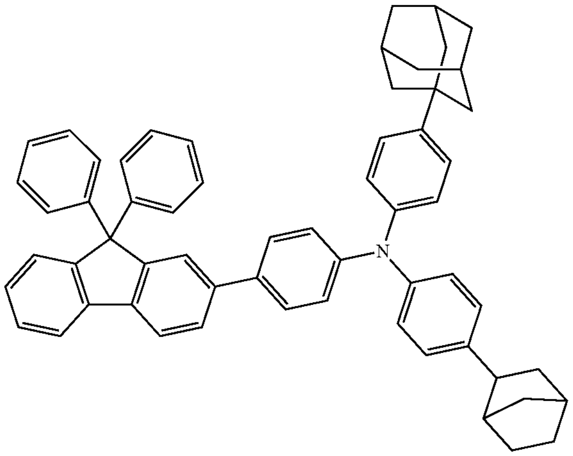

63
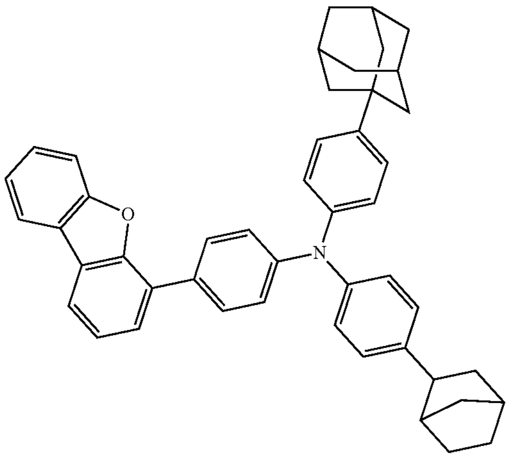
64
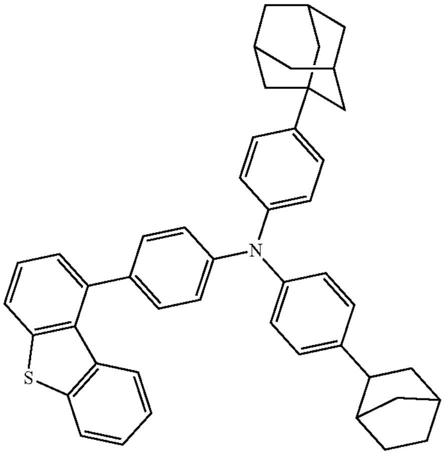
65
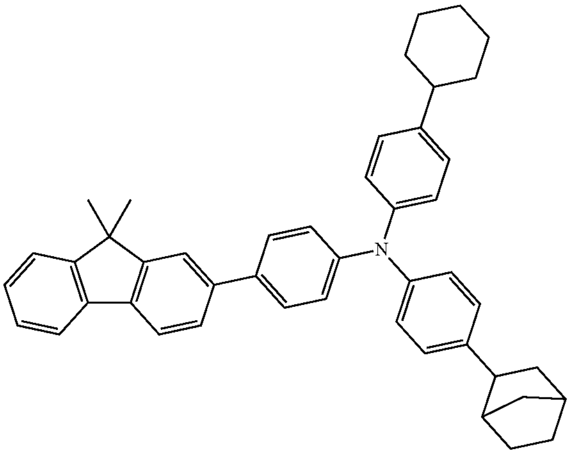
66
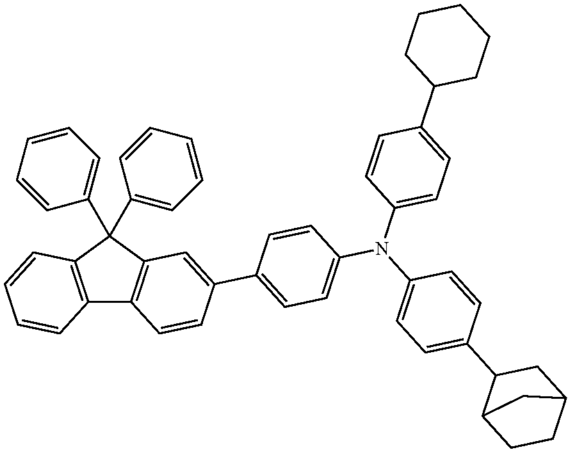
67
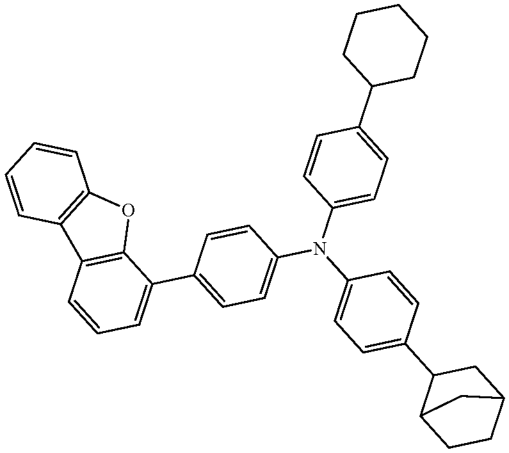
68
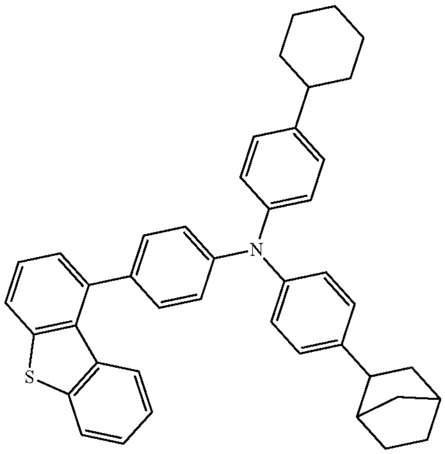

-continued

69

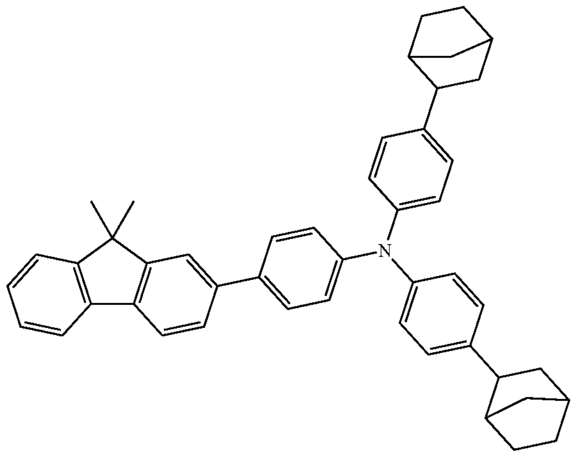

70

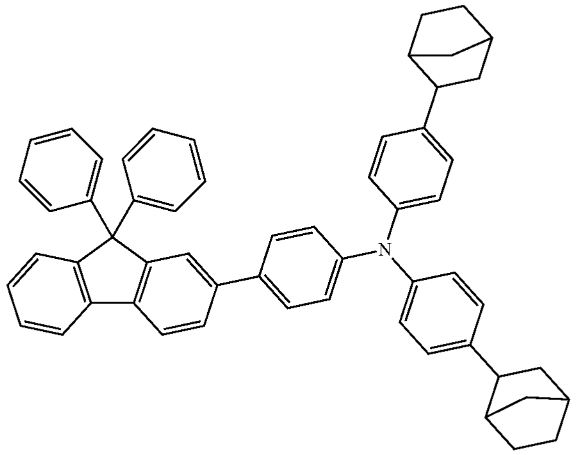

71

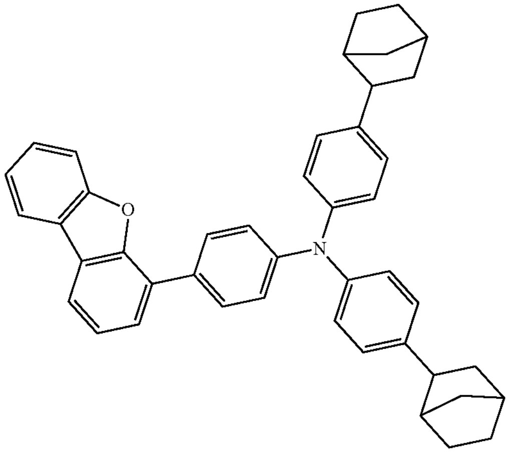

-continued

72

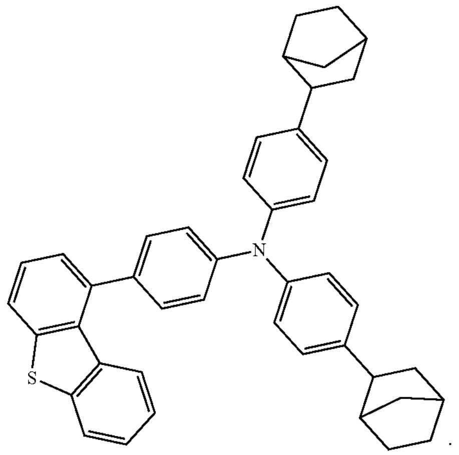

10. The light emitting element of claim 1, wherein the second amine compound is represented by Formula 3:

[Formula 3]

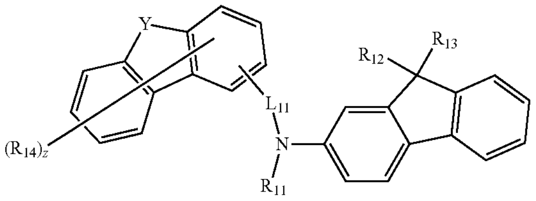

wherein in Formula 3, z is an integer from 0 to 7,

Y is $C(R_f)(R_g)$, $N(R_h)$, O, or S, $L_{11}$ is a direct linkage, a substituted or unsubstituted arylene group having 6 to 30 ring-forming carbon atoms, or a substituted or unsubstituted heteroarylene group having 2 to 30 ring-forming carbon atoms, and $R_f$ to $R_h$ and $R_{11}$ to $R_{14}$ are each independently a hydrogen atom, a deuterium atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring.

11. The light emitting element of claim 10, wherein the second amine compound represented by Formula 3 is represented by one of Formulas 3-1 to 3-3:

[Formula 3-1]

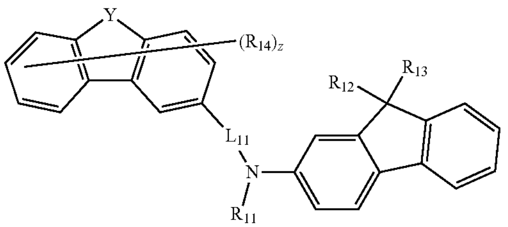

-continued
[Formula 3-2]
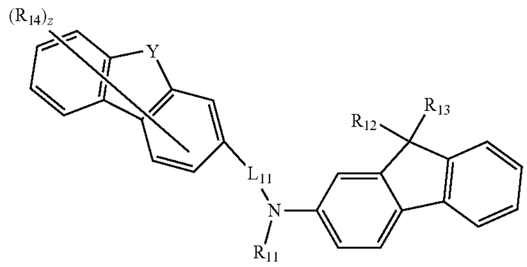
[Formula 3-3]
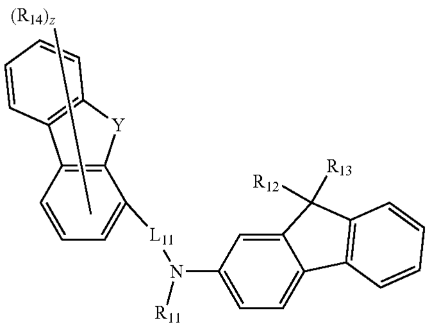
wherein in Formulas 3-1 to 3-3,
z, $L_{11}$, Y, and $R_{11}$ to $R_{14}$ are the same as defined in Formula 3.
12. The light emitting element of claim 10, wherein the second amine compound represented by Formula 3 is one selected from Compound Group 2:
[Compound Group 2]
73
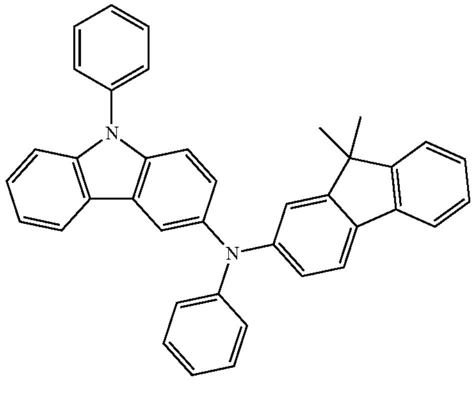
-continued
74
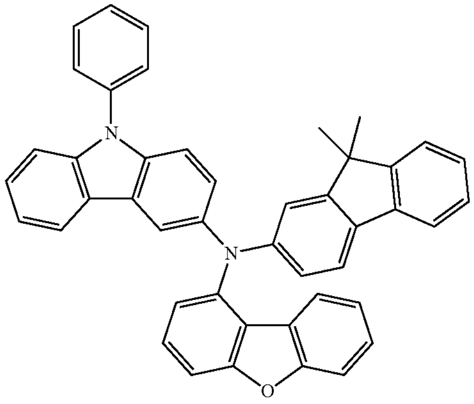
75
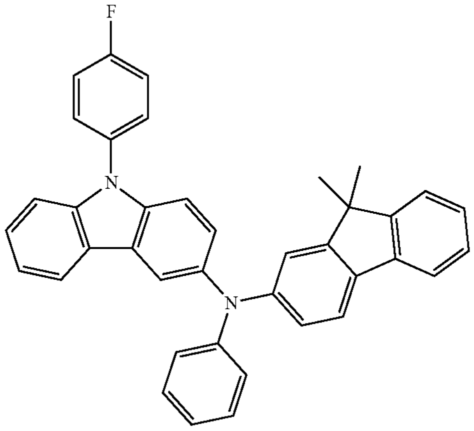
76
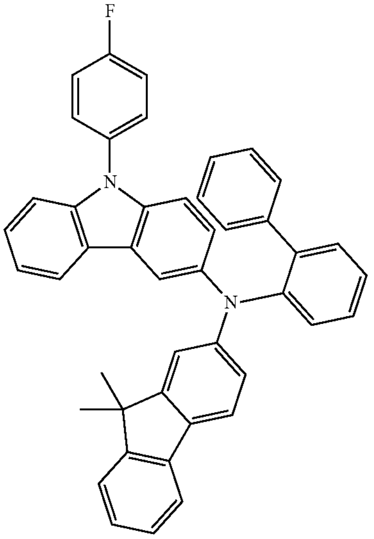

-continued
77
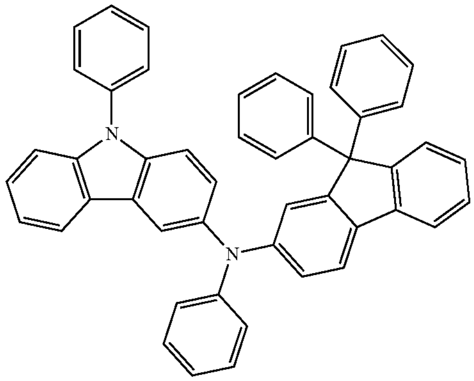
78
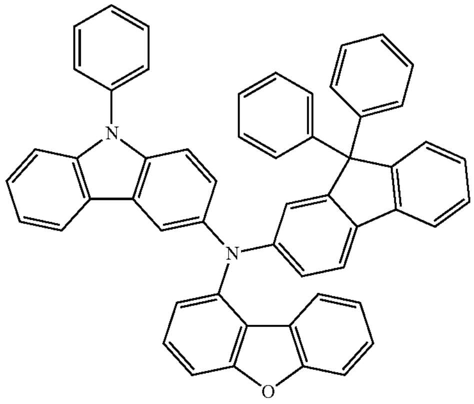
79
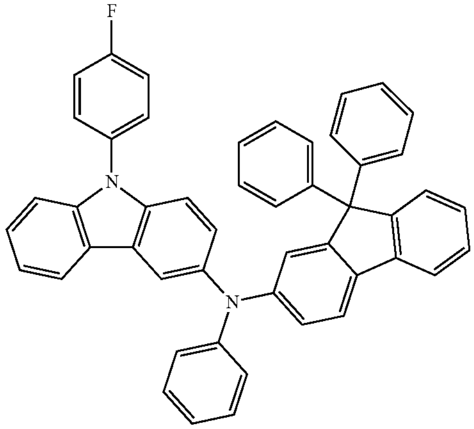
80
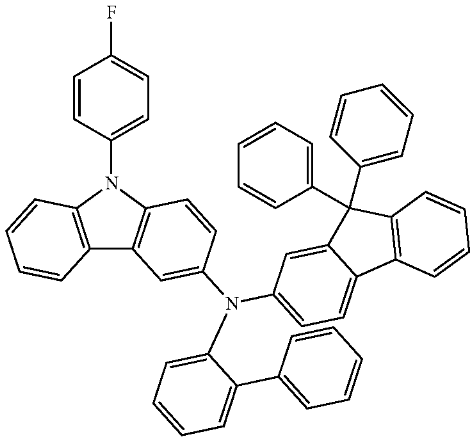
-continued
81
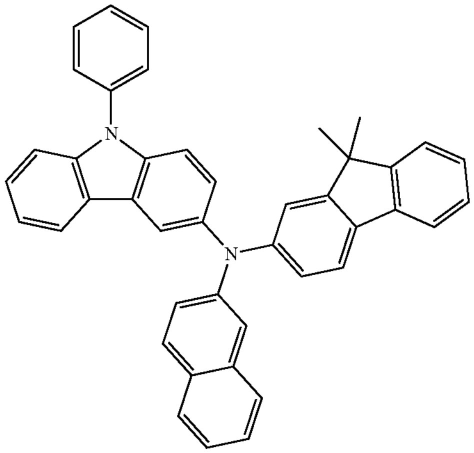
82
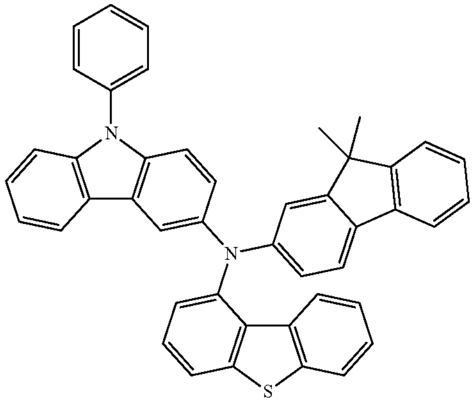
83
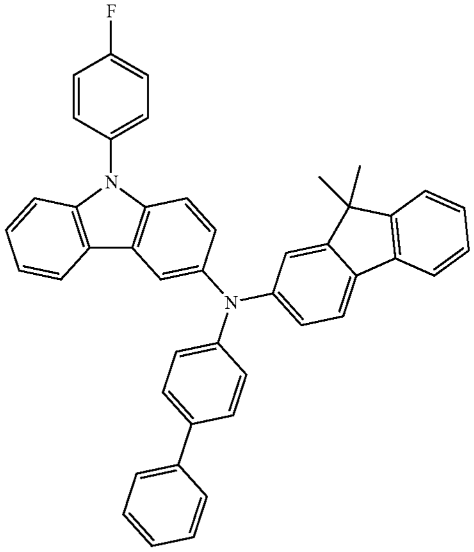

-continued
84
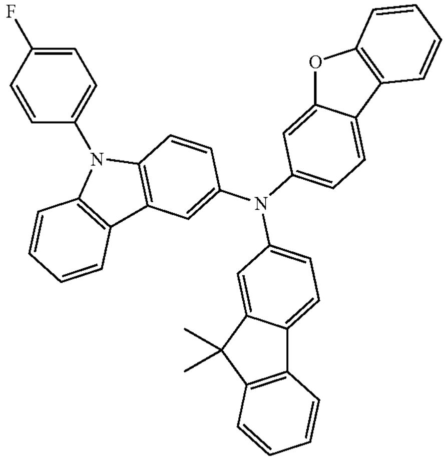
85
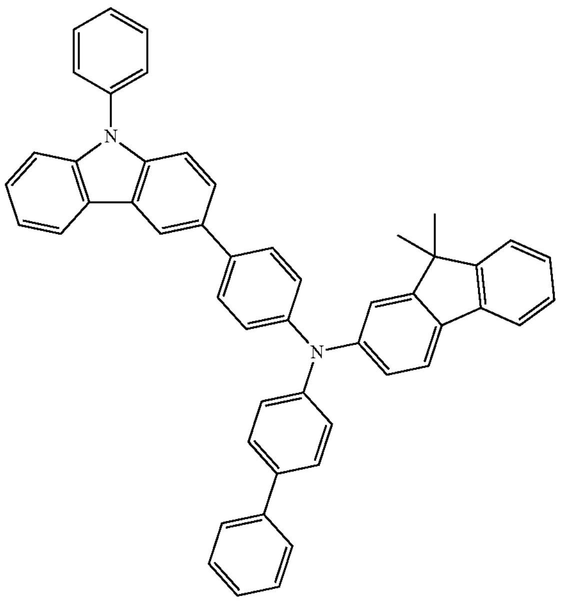
86
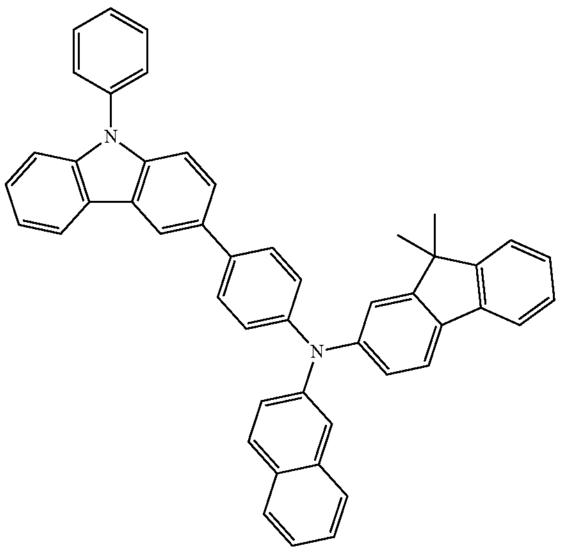
-continued
87
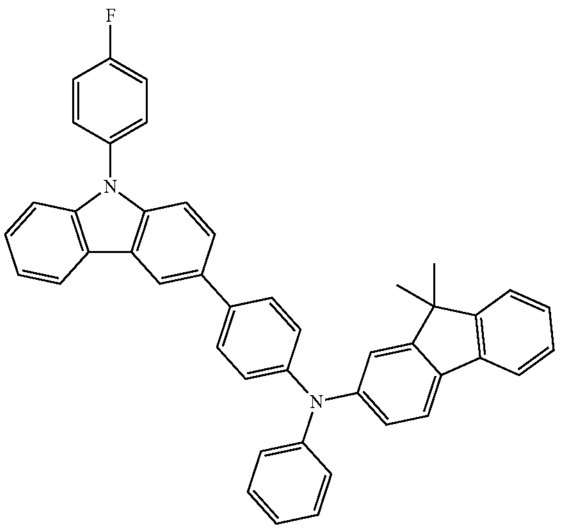
88
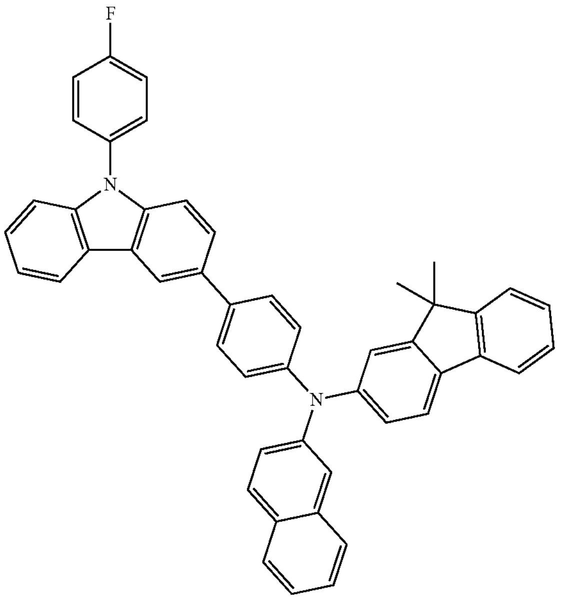

-continued
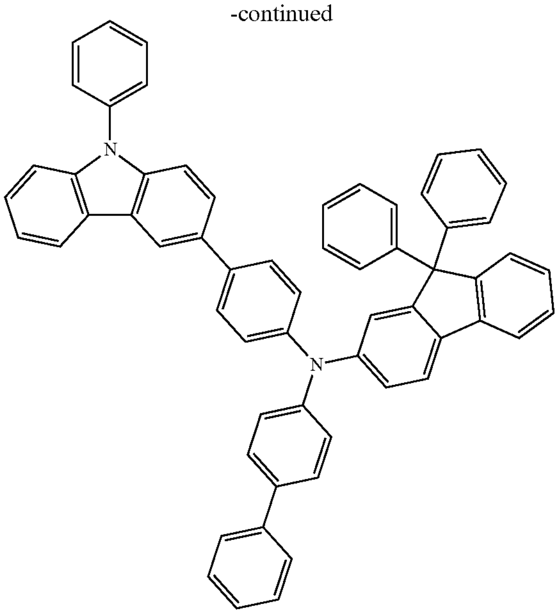
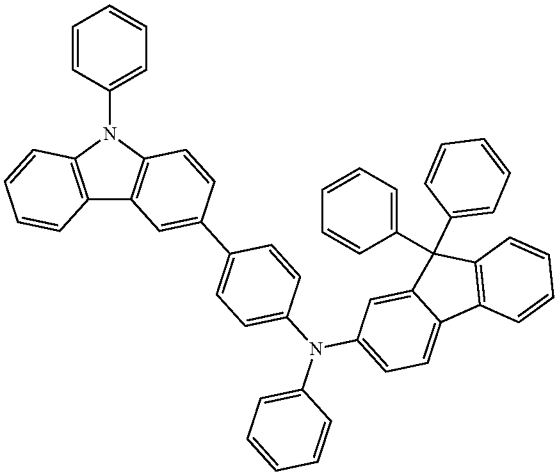
91
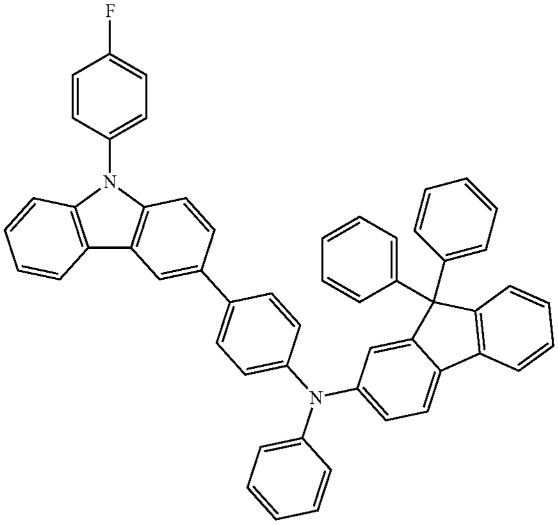
-continued
92
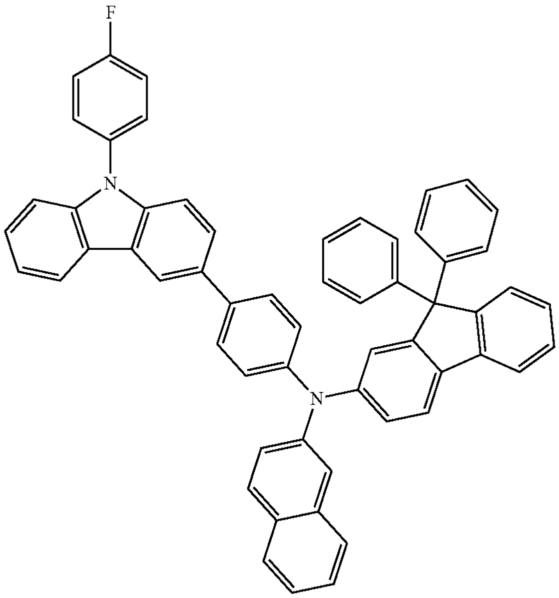
93
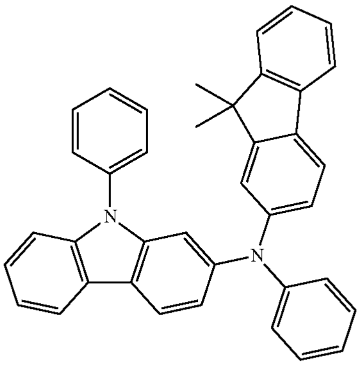
94
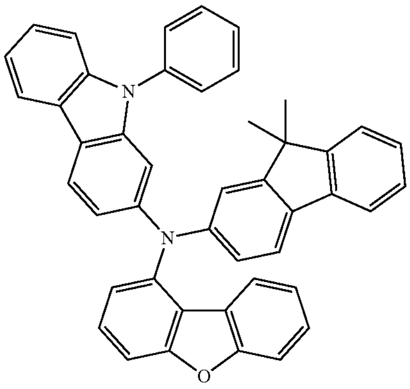

95
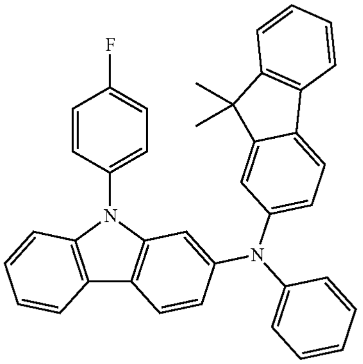
96
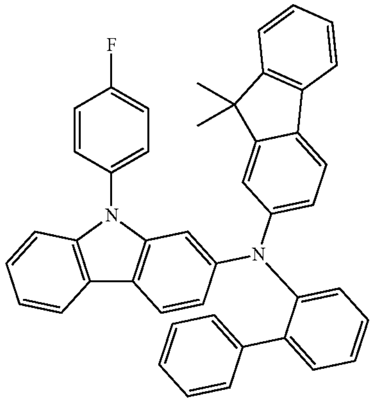
97
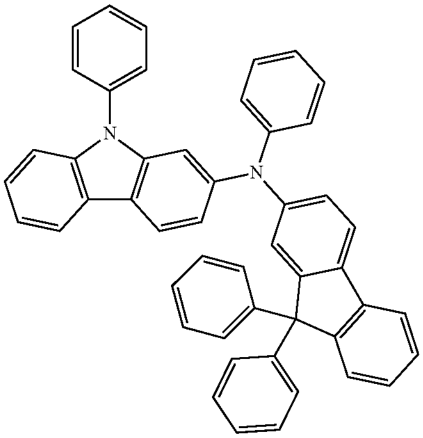
98
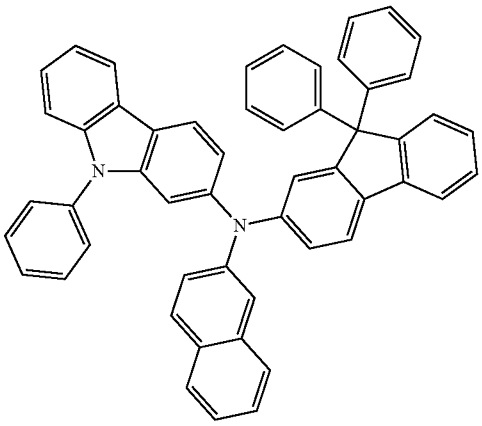
99
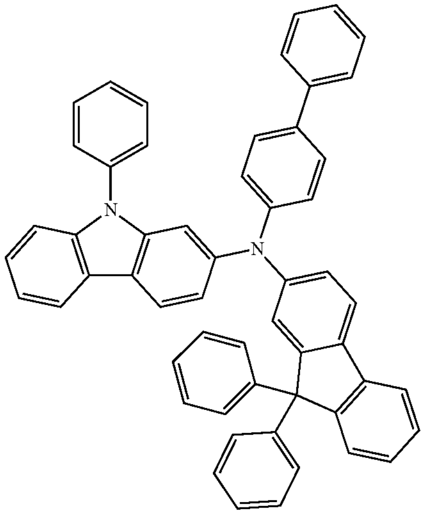
100
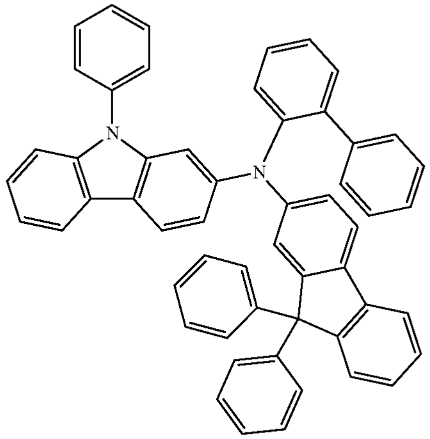
101
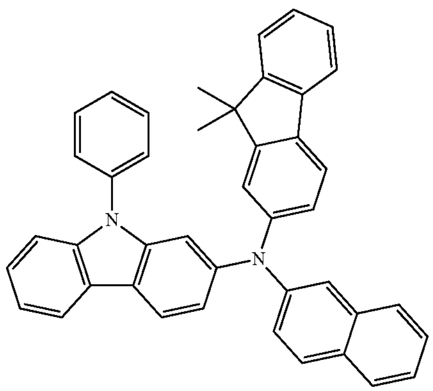

-continued
102
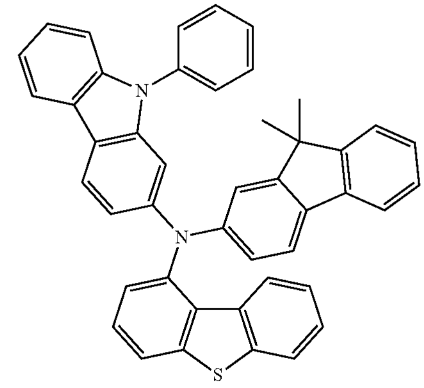
103
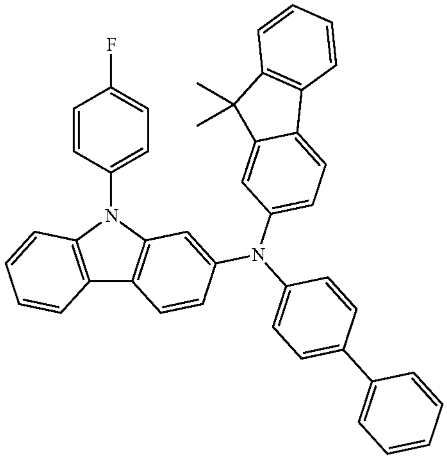
104
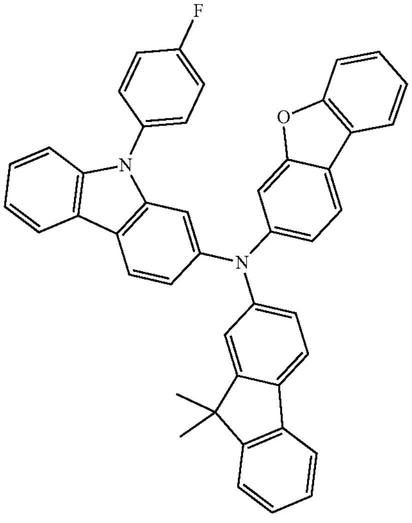
-continued
105
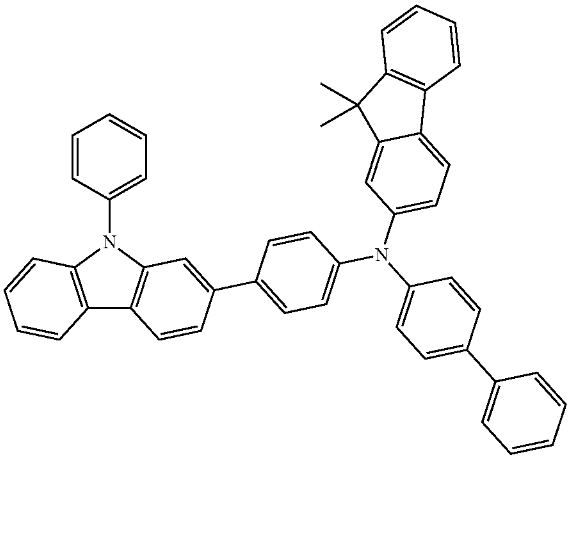
106
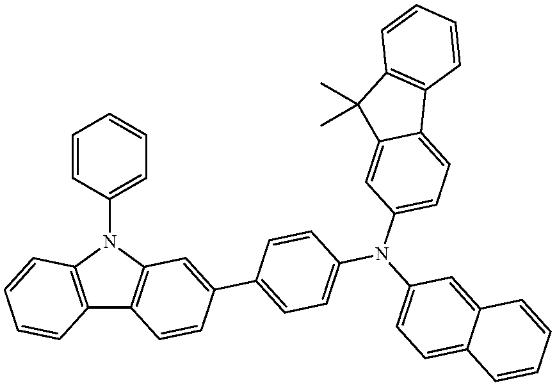
107
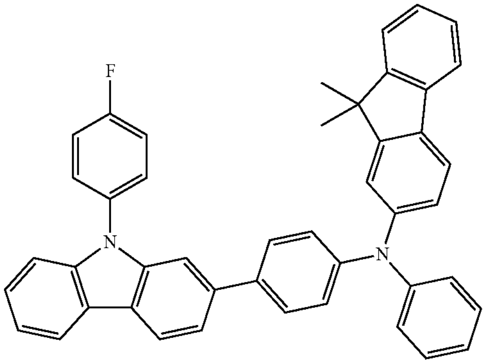

-continued
108
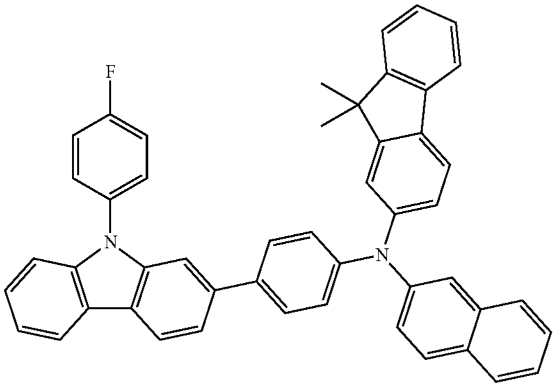
109
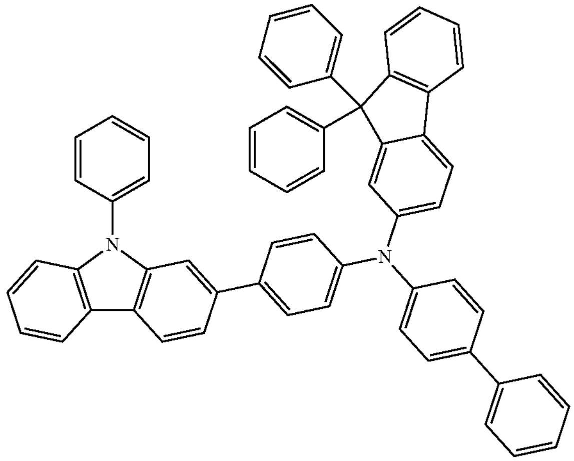
110
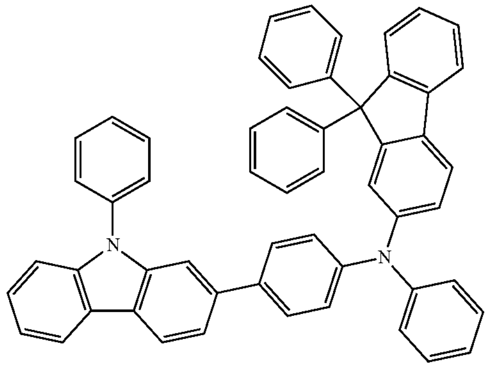
111
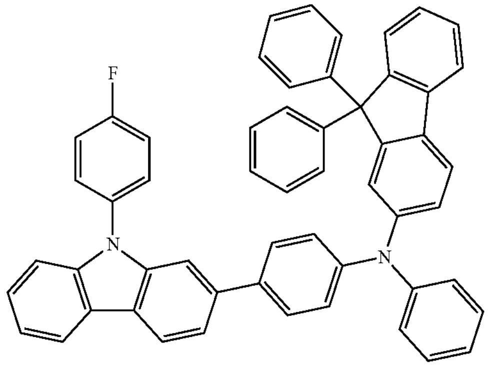
-continued
112
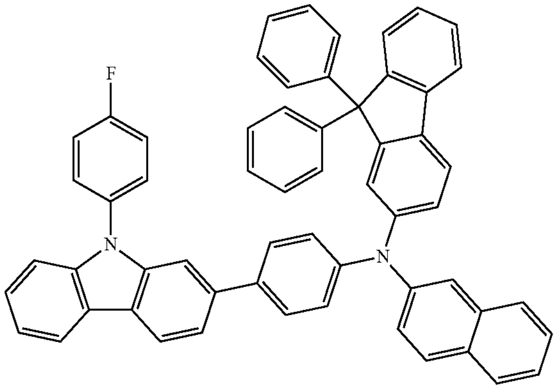
113
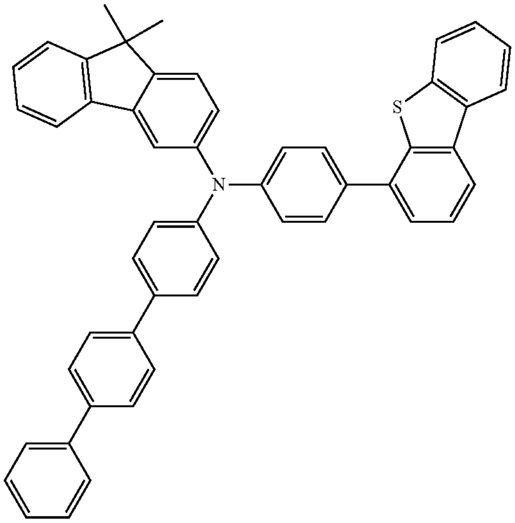
114
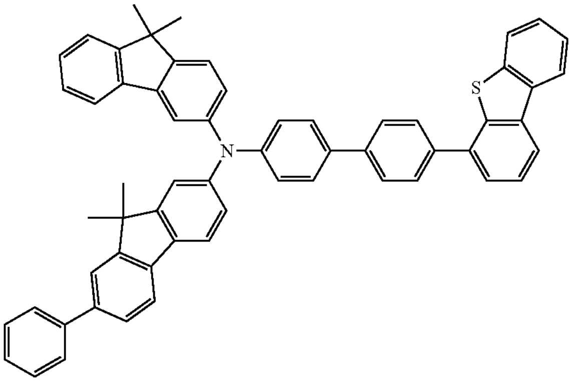

-continued

115

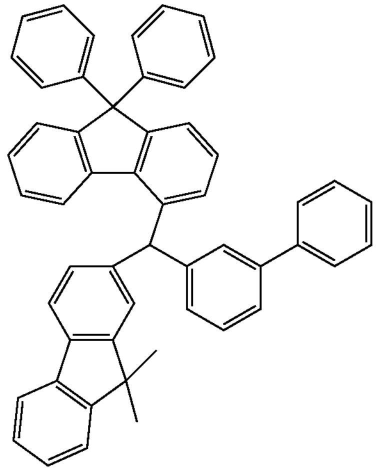

116

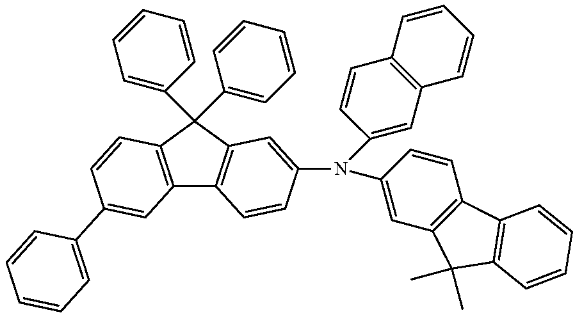

117

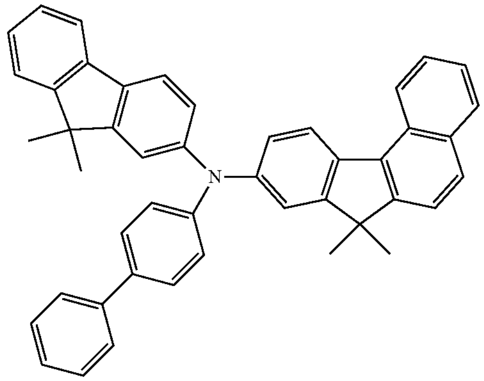

-continued

118

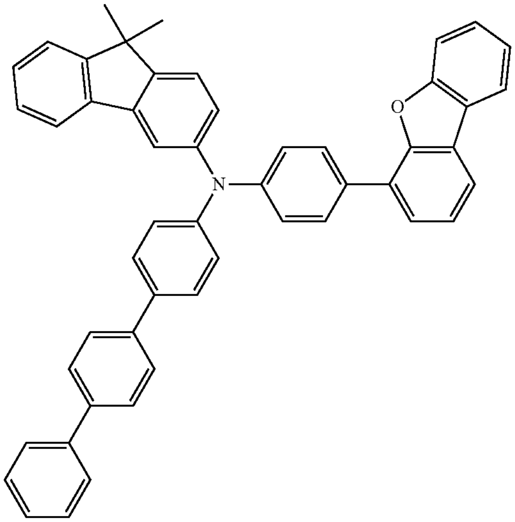

119

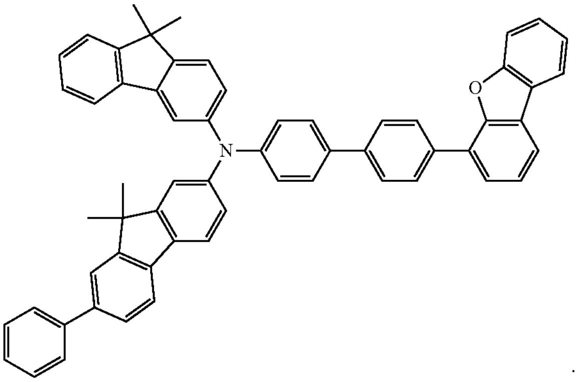

.

13. A light emitting element comprising:

a first electrode;

a hole transport region disposed on the first electrode;

an emission layer disposed on the hole transport region;

an electron transport region disposed on the emission layer; and a second electrode disposed on the electron transport region, wherein the hole transport region includes:

a first hole transport layer disposed adjacent to the first electrode and including a first amine compound having a first refractive index;

a second hole transport layer disposed between the first hole transport layer and the emission layer and including a second amine compound having a second refractive index; and a third hole transport layer disposed between the second hole transport layer and the emission layer and including a third amine compound having a third refractive index, the second amine compound is represented by Formula 3, and the first amine compound and the third amine compound are each independently a compound represented by Formula 4:

[Formula 3]

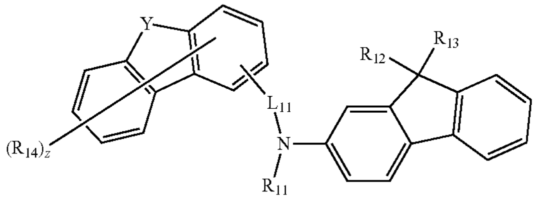

wherein in Formula 3, z is an integer from 0 to 7,

Y is $C(R_f)(R_g)$, $N(R_h)$, O, or S, $L_{11}$ is a direct linkage, a substituted or unsubstituted arylene group having 6 to 30 ring-forming carbon atoms, or a substituted or unsubstituted heteroarylene group having 2 to 30 ring-forming carbon atoms, and $R_f$ to $R_h$ and $R_{11}$ to $R_{14}$ are each independently a hydrogen atom, a deuterium atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring,

[Formula 4]

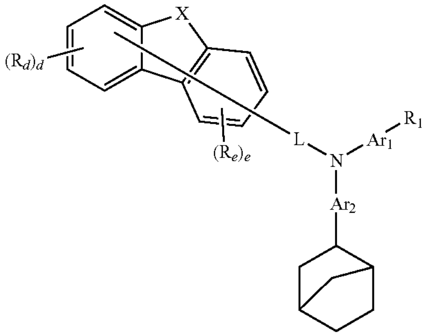

wherein in Formula 4, $R_1$ is a substituted or unsubstituted adamantyl group, a substituted or unsubstituted cyclohexyl group, or a substituted or unsubstituted bicycloheptyl group, $Ar_1$ and $Ar_2$ are each independently a substituted or unsubstituted arylene group having 6 to 30 ring-forming carbon atoms, L is a direct linkage, a substituted or unsubstituted arylene group having 6 to 30 ring-forming carbon atoms, or a substituted or unsubstituted heteroarylene group having 2 to 30 ring-forming carbon atoms, X is $C(R_a)(R_b)$, N, $N(R_c)$, O, or S, $R_a$ to $R_c$ are each independently a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring, d and e are each independently an integer from 0 to 4, and $R_d$ and $R_e$ are each independently a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring.

14. The light emitting element of claim 13, wherein the first refractive index and the third refractive index are each independently in a range of about 1.3 to about 1.8;

the second refractive index is in a range of about 1.8 to about 2.4; and the first refractive index and the third refractive index are each less than the second refractive index.

15. The light emitting element of claim 14, wherein a difference between the second refractive index and the first refractive index is in a range of about 0.1 to about 1.1, and a difference between the second refractive index and the third refractive index is in a range of about 0.1 to about 1.1.

16. The light emitting element of claim 13, wherein the compound represented by Formula 4 is represented by Formula 4-1 or Formula 4-2:

[Formula 4-1]

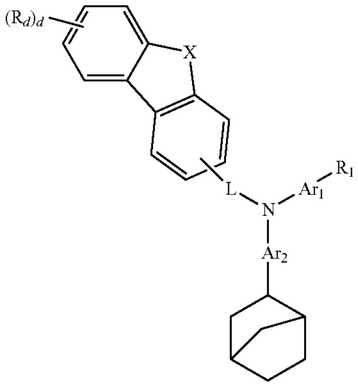

[Formula 4-2]

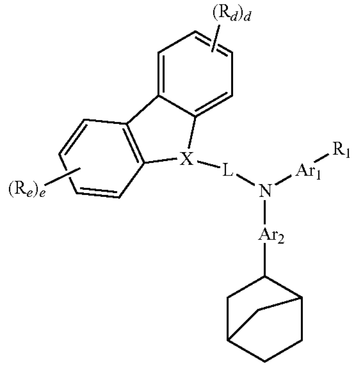

wherein in Formulas 4-1 and 4-2, $R_1$, L, $Ar_1$, $Ar_2$, X, $R_d$, Re, d, and e are the same as defined in Formula 4.

17. The light emitting element of claim 16, wherein the compound represented by Formula 4-2 is represented by Formula 4-2A:

[Formula 4-2A]

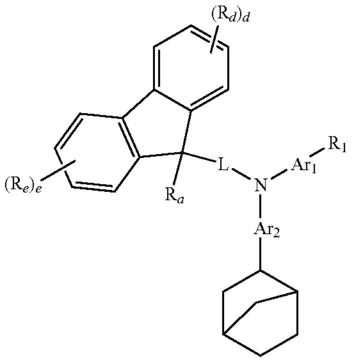

wherein in Formulas 4-2A, $R_1$, L, $Ar_1$, $Ar_2$, $R_a$, $R_d$, $R_e$, d, and e are the same as defined in Formula 4.

18. The light emitting element of claim 13, wherein the compound represented by Formula 4 is represented by Formula 4A:

[Formula 4A]

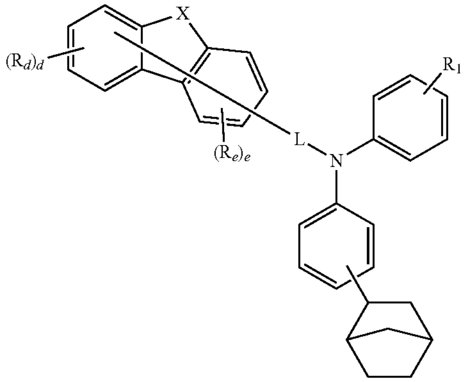

wherein in Formula 4A, $R_1$, L, X, $R_d$, $R_e$, d, and e are the same as defined in Formula 4.

19. The light emitting element of claim 13, wherein the first amine compound and the third amine compound are each independently selected from Compound Group 1:

[Compound Group 1]

1

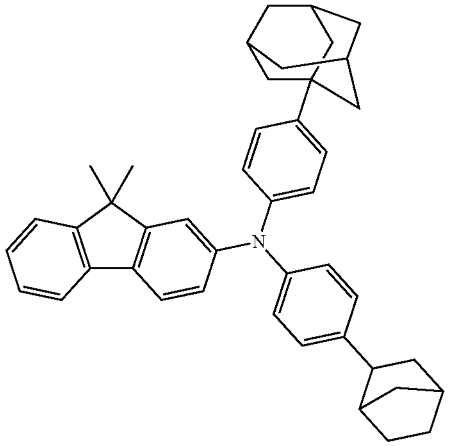

2

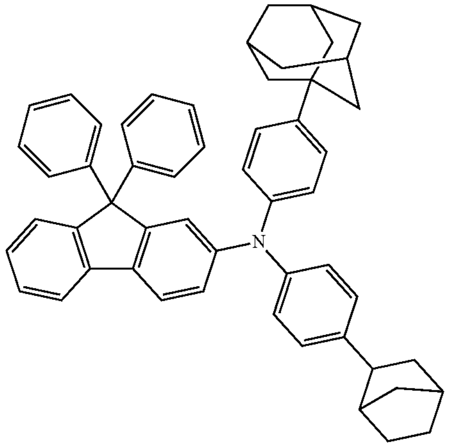

3

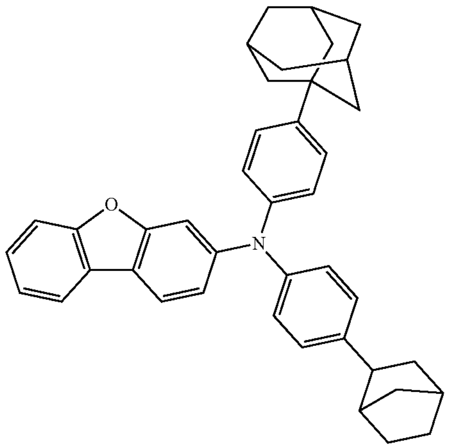

-continued
4
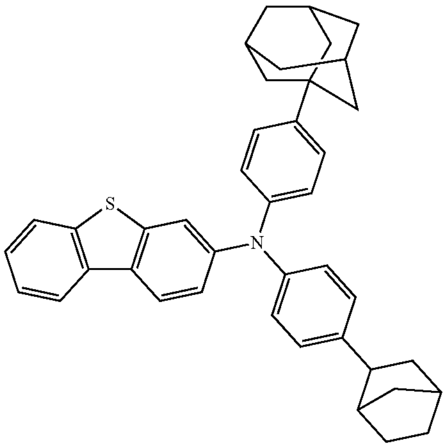
5
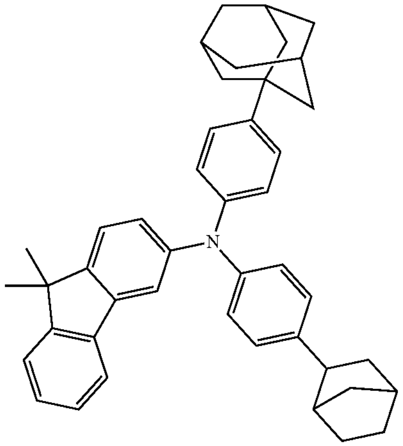
6
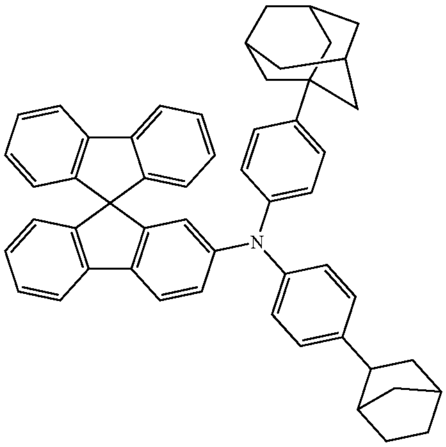
-continued
7
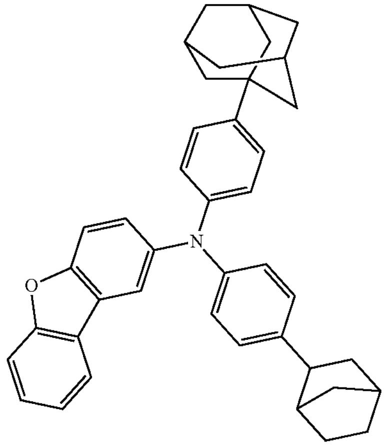
8
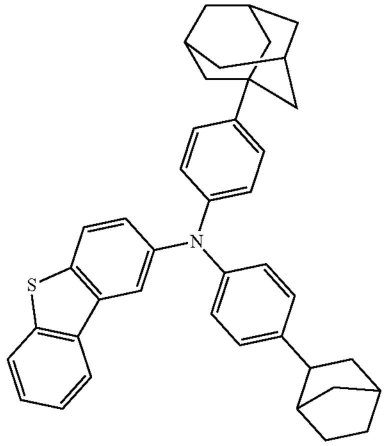
9
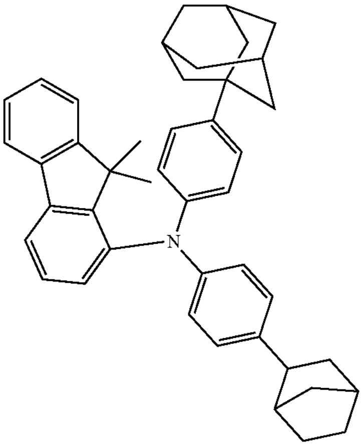

-continued
10
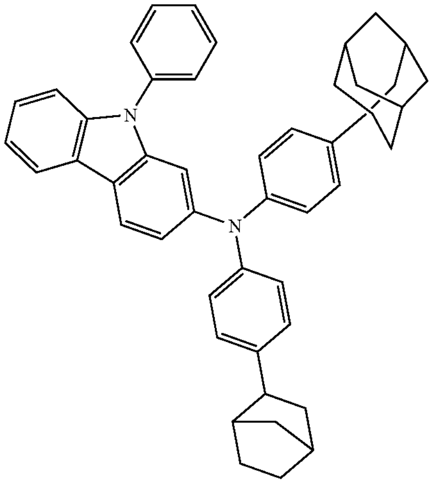
11
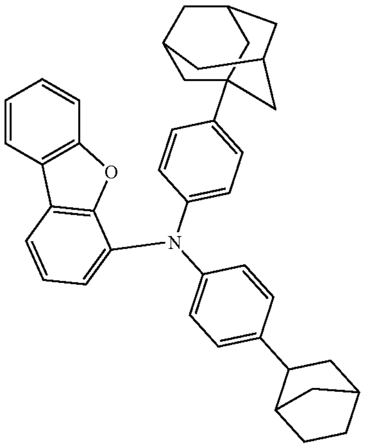
12
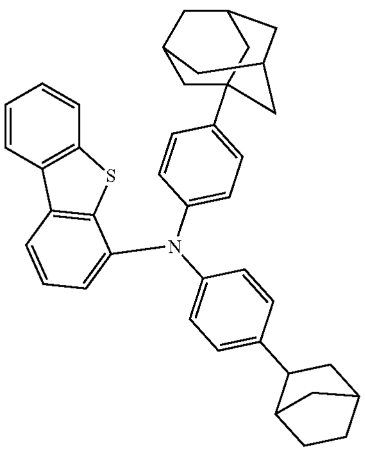
-continued
13
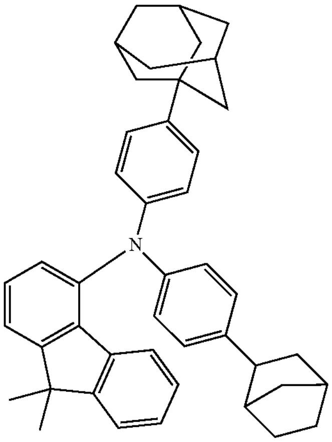
14
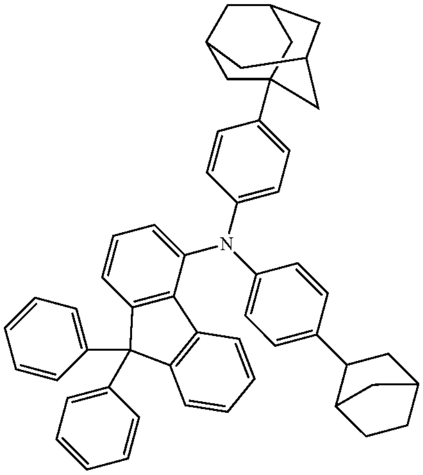
15
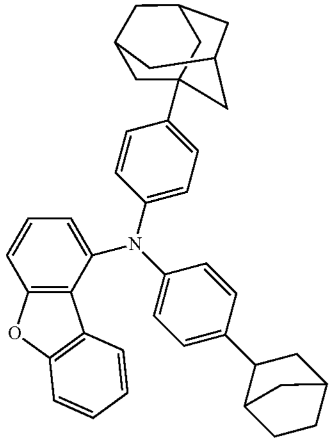

16
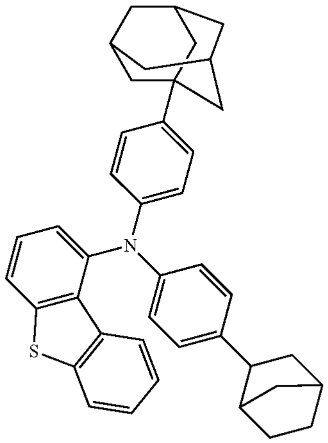
17
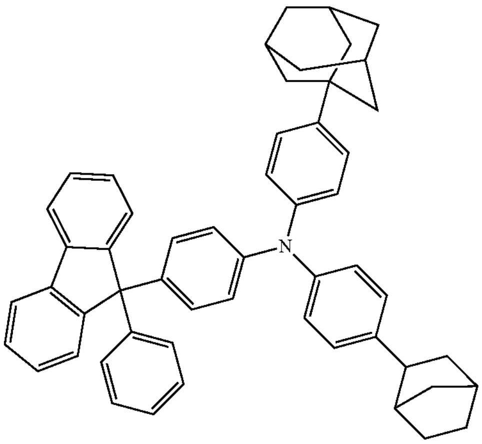
18
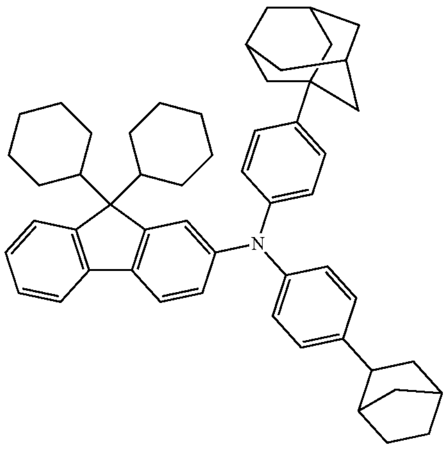
19
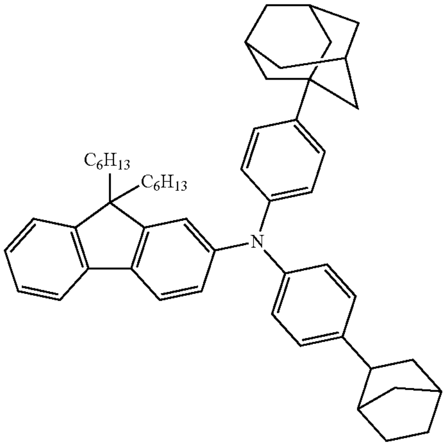
20
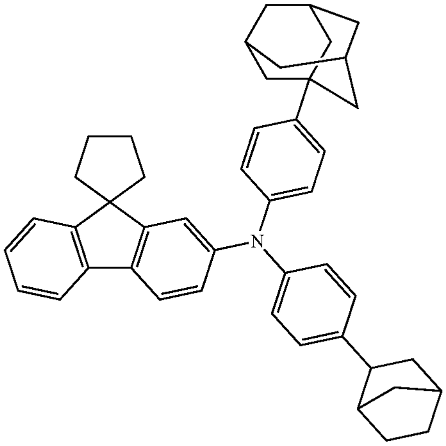
21
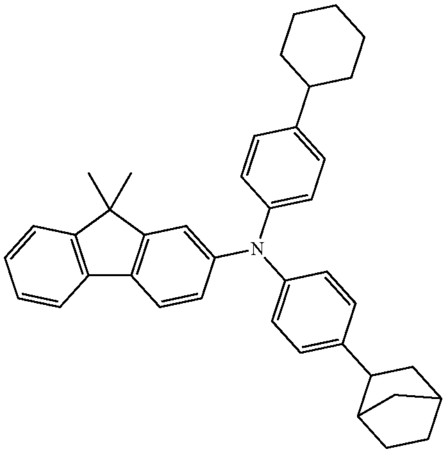

-continued
22
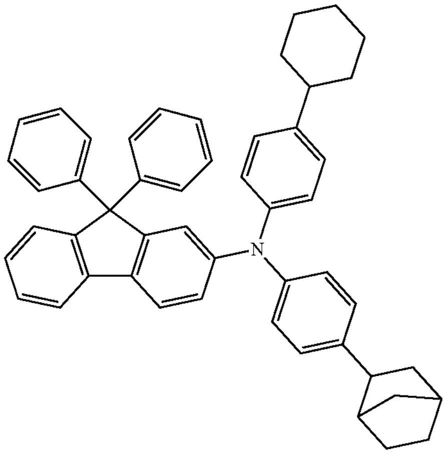
23
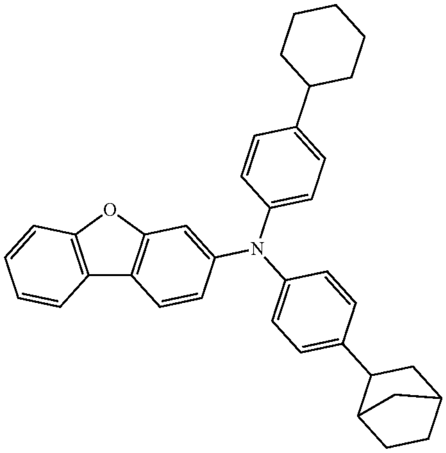
24
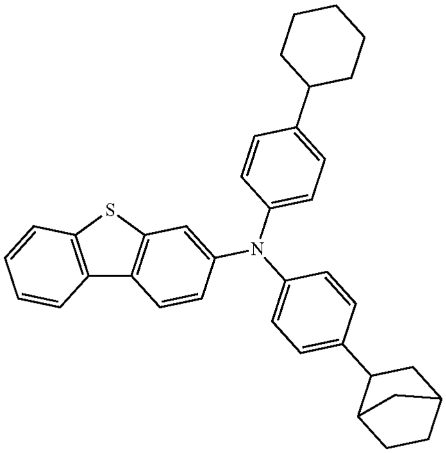
-continued
25
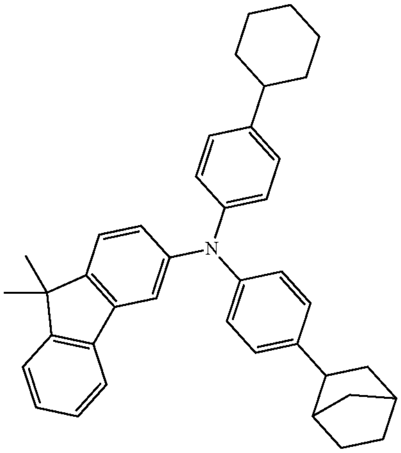
26
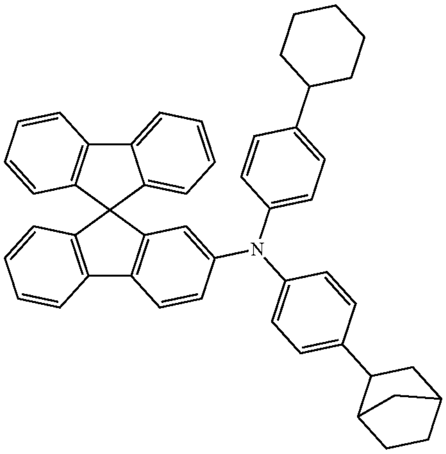
27
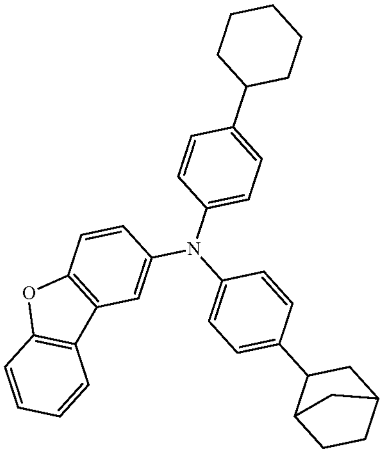

-continued
28
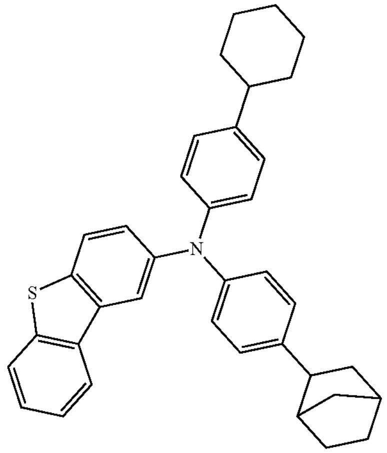
29
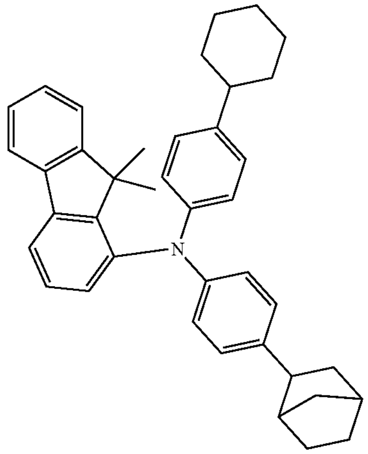
30
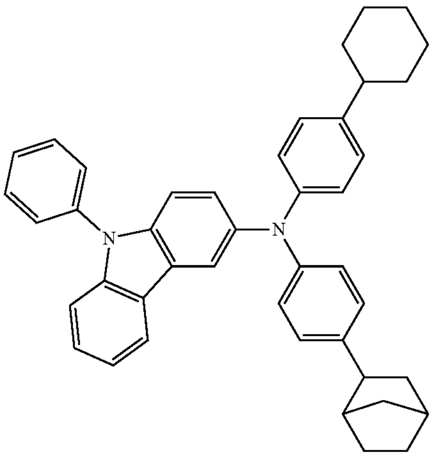
-continued
31
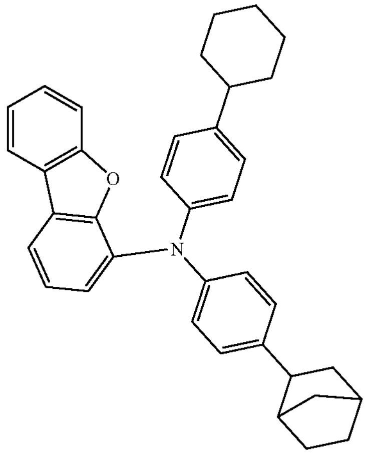
32
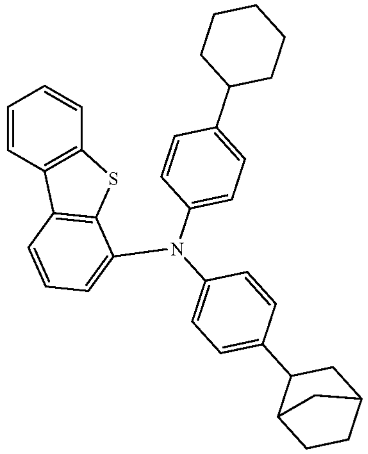
33
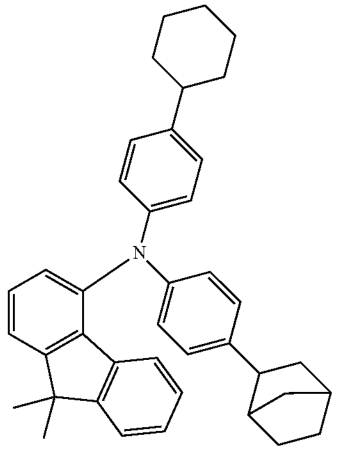

-continued
34
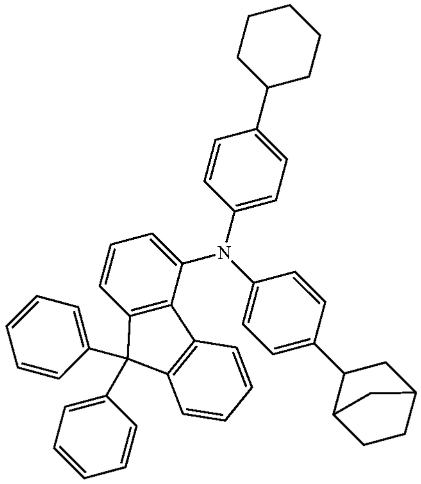
35
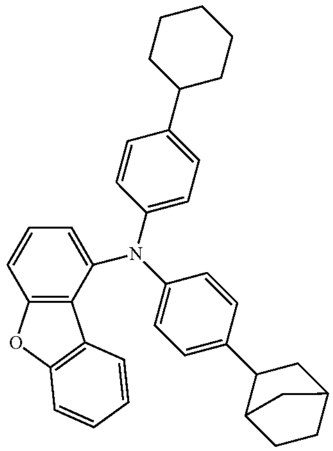
36
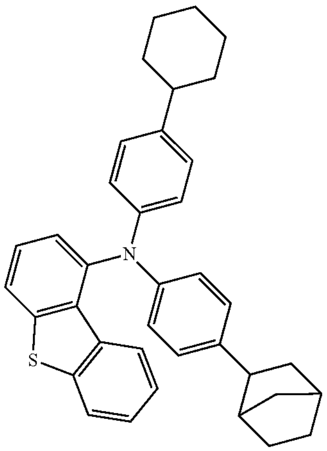
-continued
37
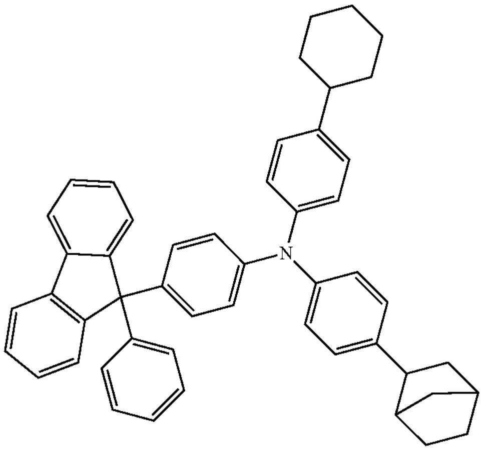
38
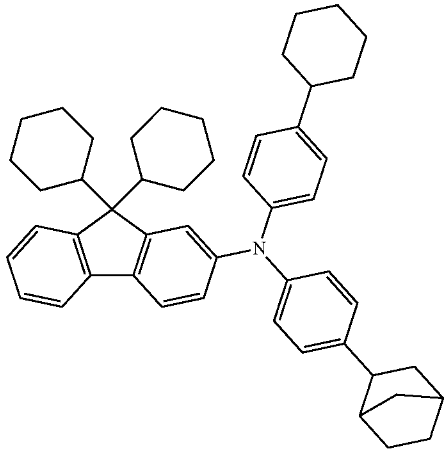
39
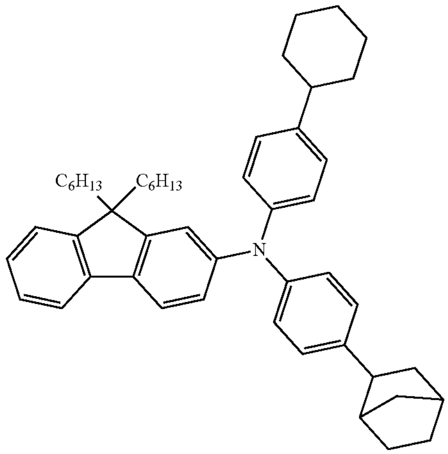

-continued
40
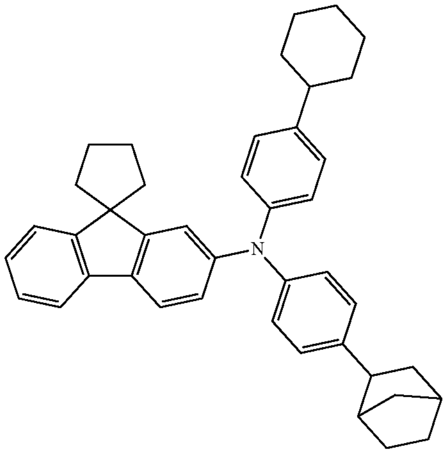
41
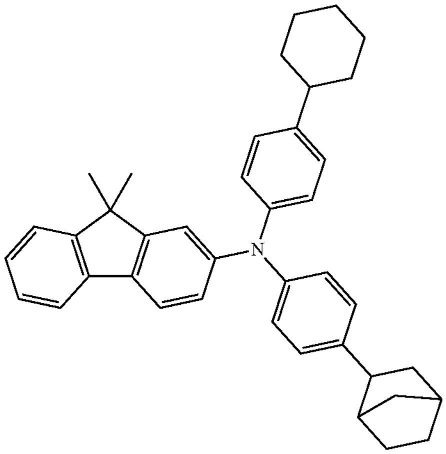
42
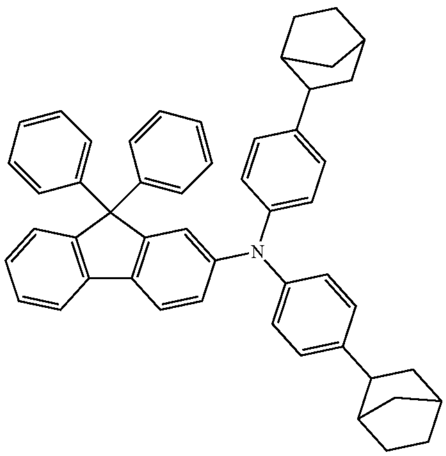
-continued
43
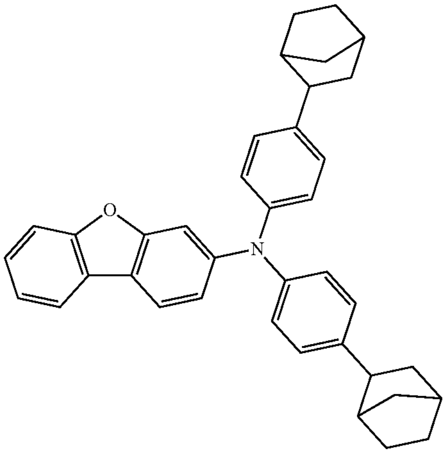
44
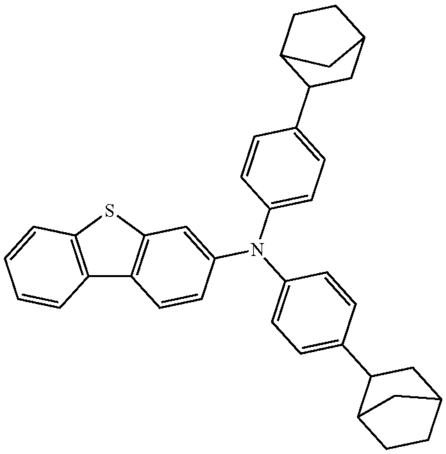
45
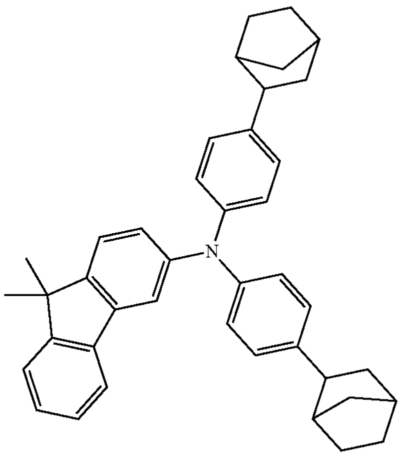

-continued
46
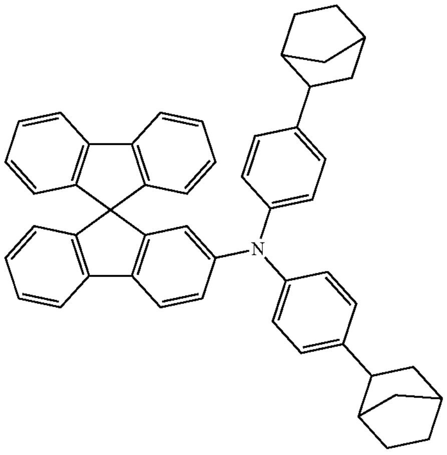
47
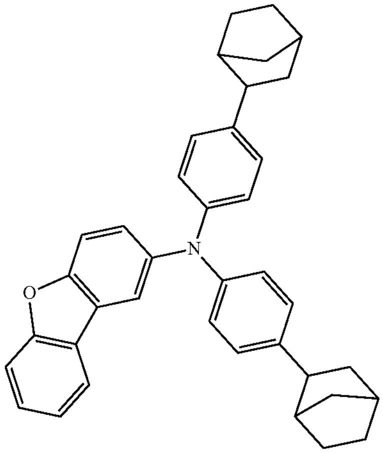
48
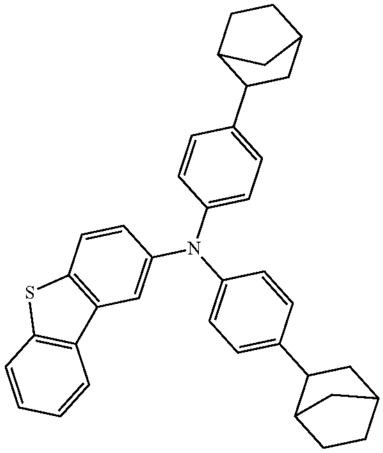
-continued
49
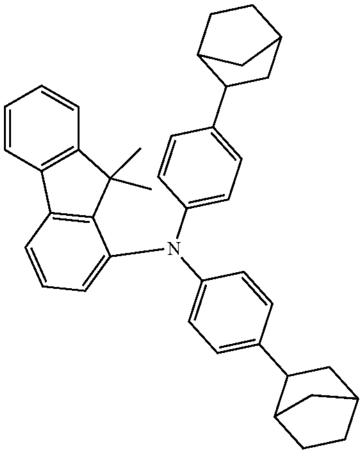
50
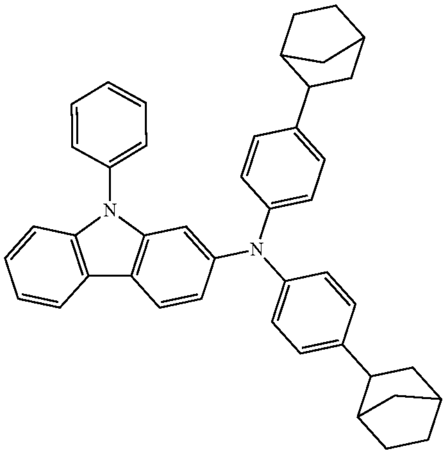
51
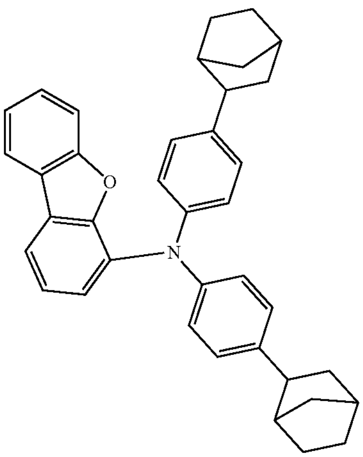

-continued
52
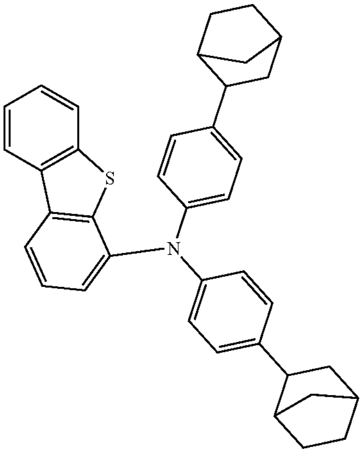
53
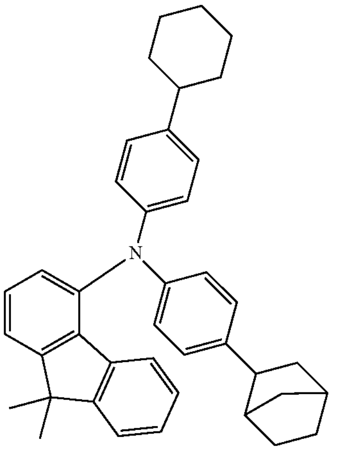
54
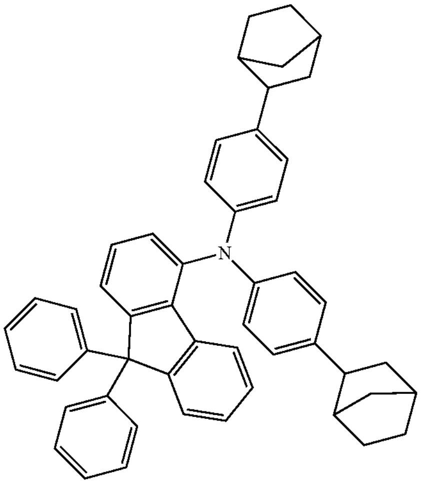
-continued
55
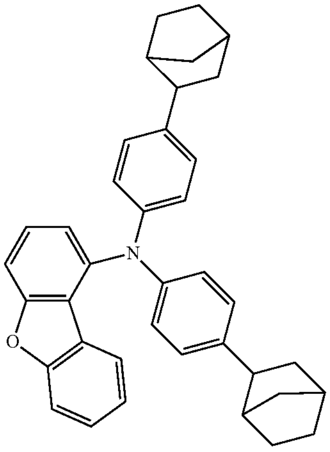
56
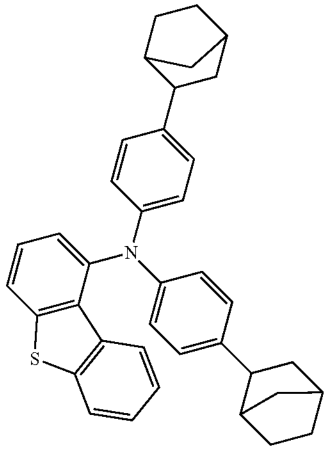
57
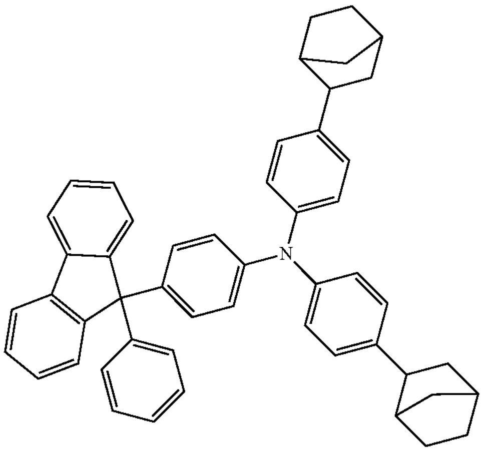

-continued
58
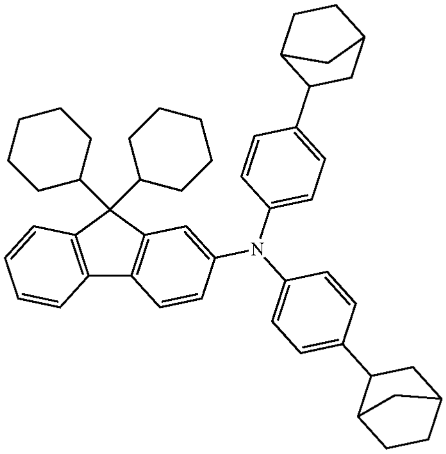
59
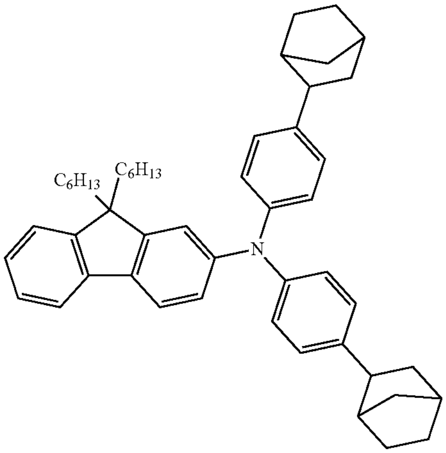
60
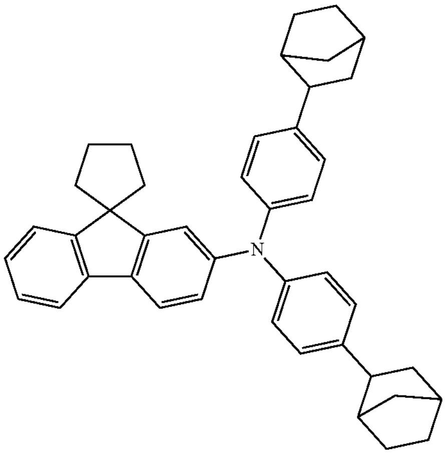
-continued
61
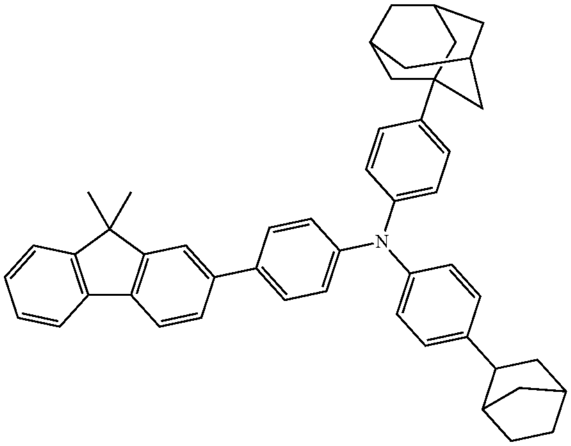
62
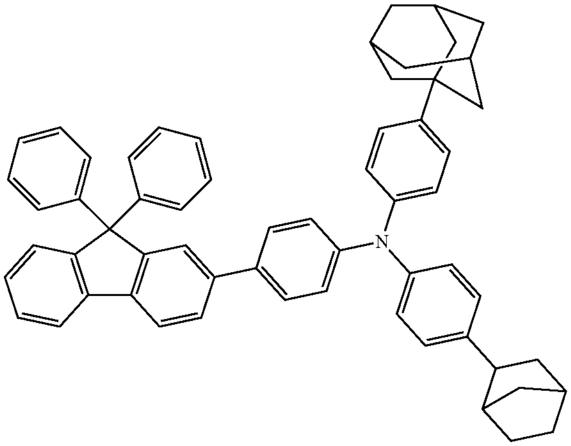
63
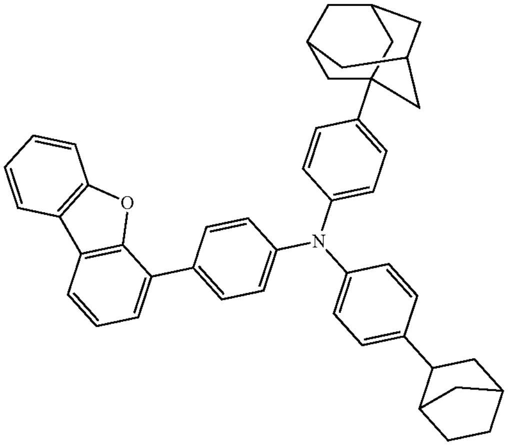

-continued
64
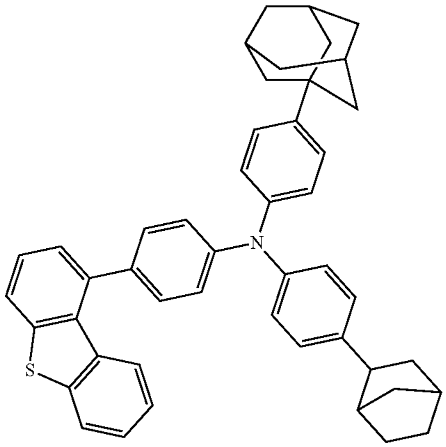
65
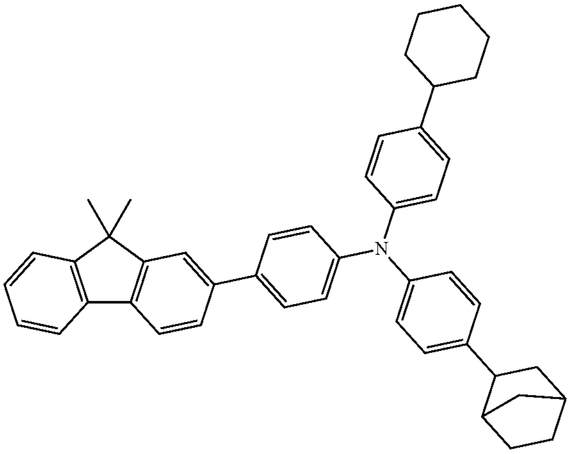
66
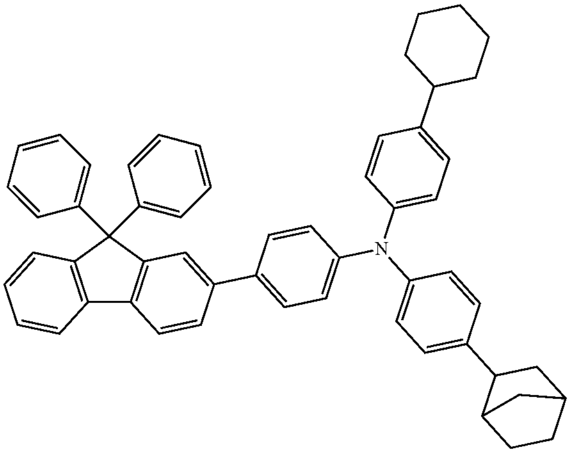
-continued
67
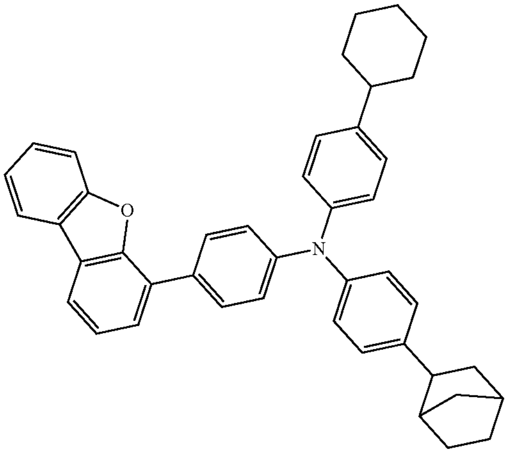
68
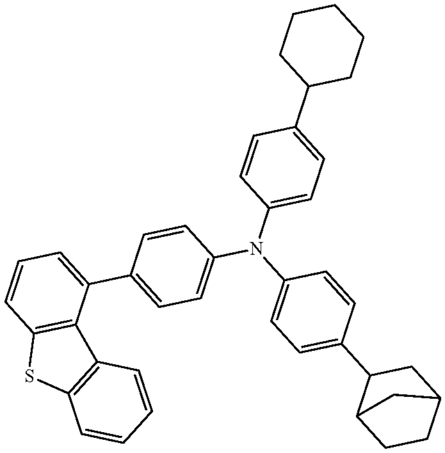
69
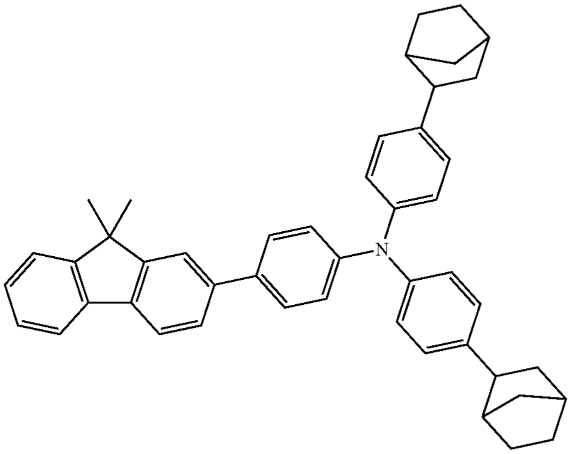

-continued

70

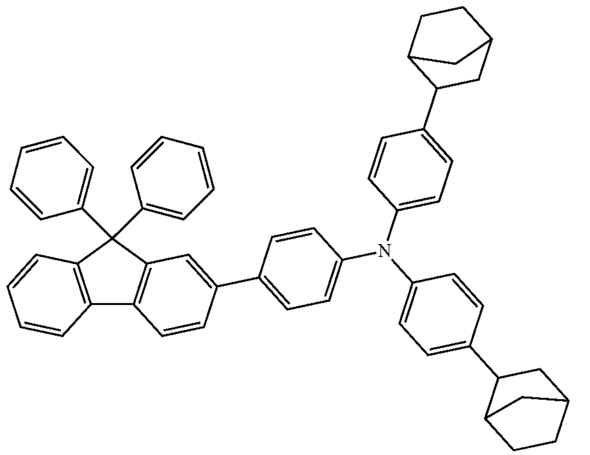

71

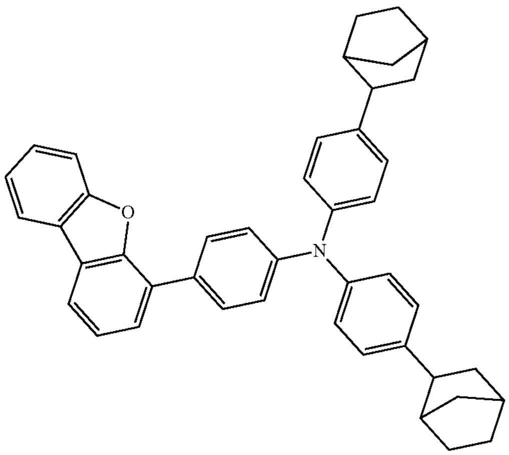

72

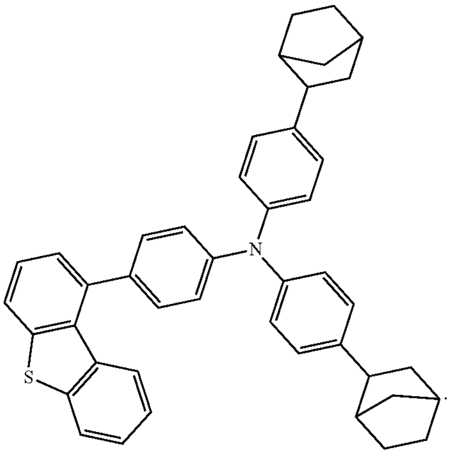

20. The light emitting element of claim 13, wherein the second amine compound represented by Formula 3 is represented by one of Formulas 3-1 to 3-3:

[Formula 3-1]

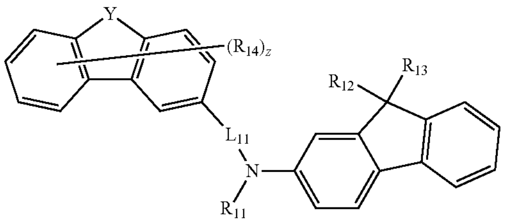

[Formula 3-2]

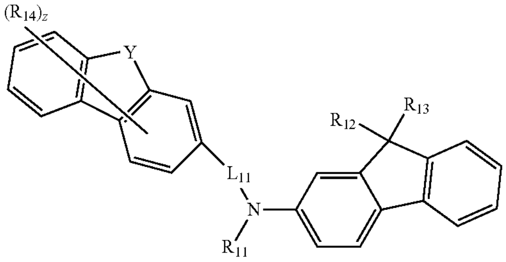

[Formula 3-3]

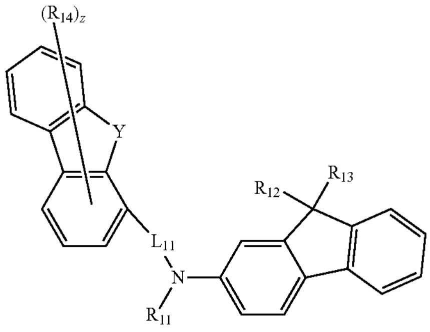

wherein in Formulas 3-1 to 3-3, z, $L_{11}$, Y, and $R_{11}$ to $R_{14}$ are the same as defined in Formula 3.

21. The light emitting element of claim 13, wherein the second amine compound represented by Formula 3 is selected from Compound Group 2:

[Compound Group 2]

73

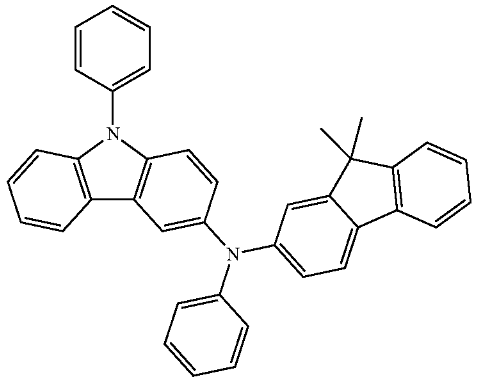

-continued
74
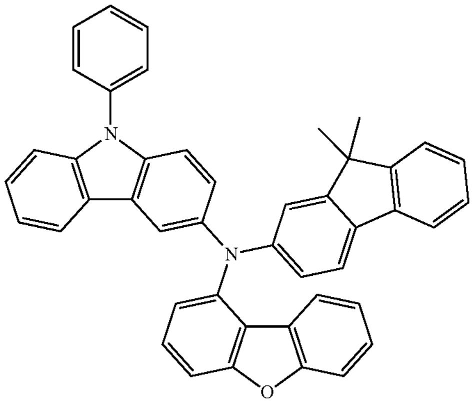
75
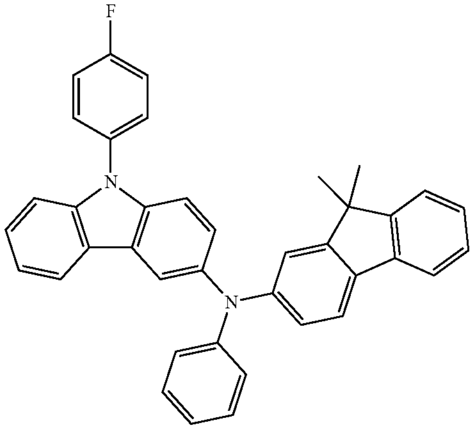
76
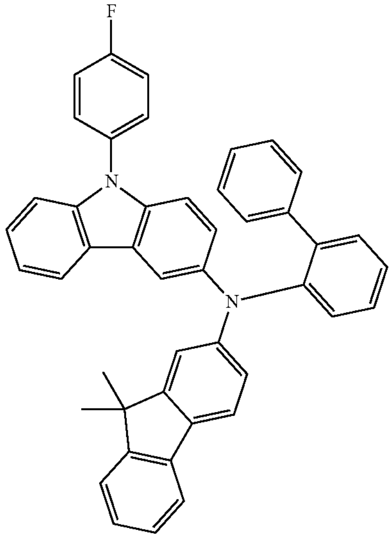
-continued
77
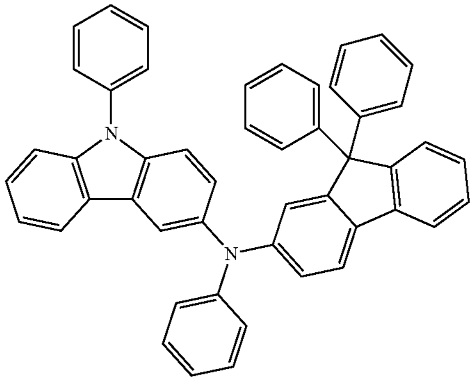
78
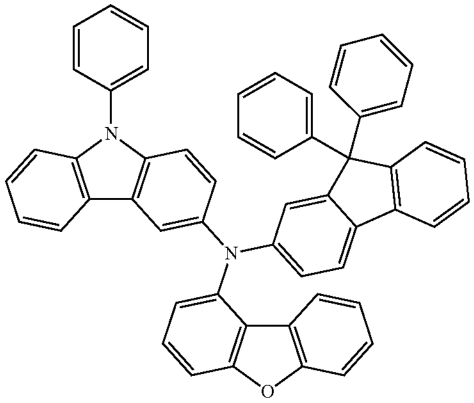
79
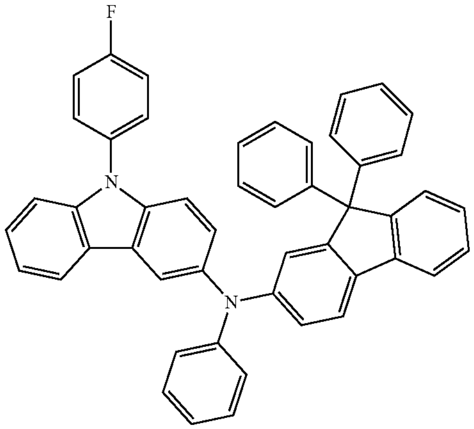

-continued
80
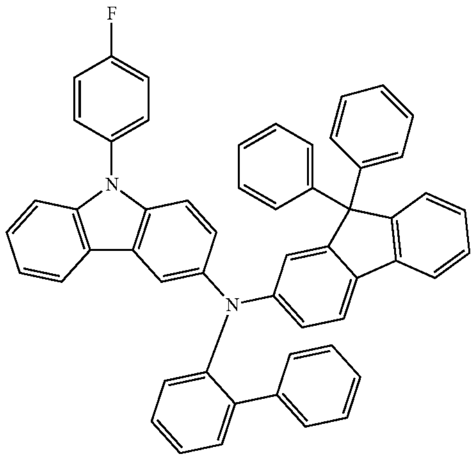
81
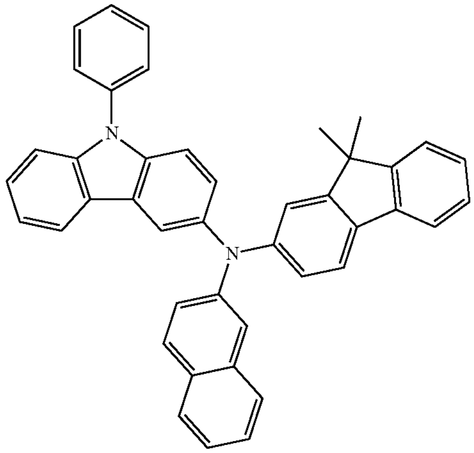
82
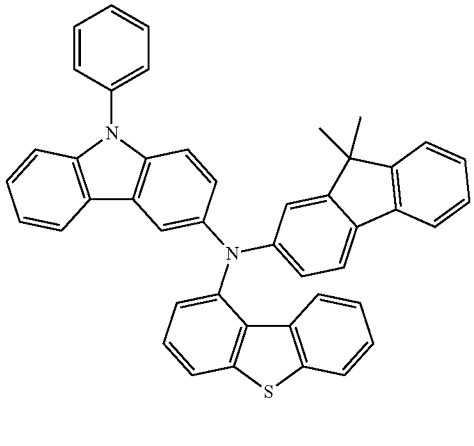
-continued
83
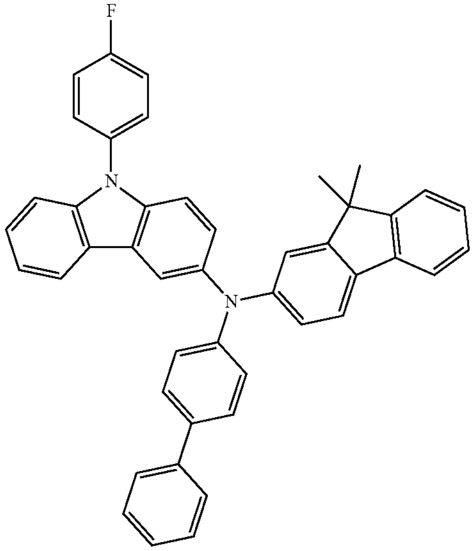
84
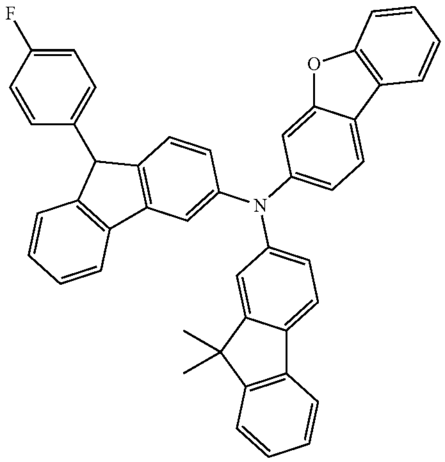
85
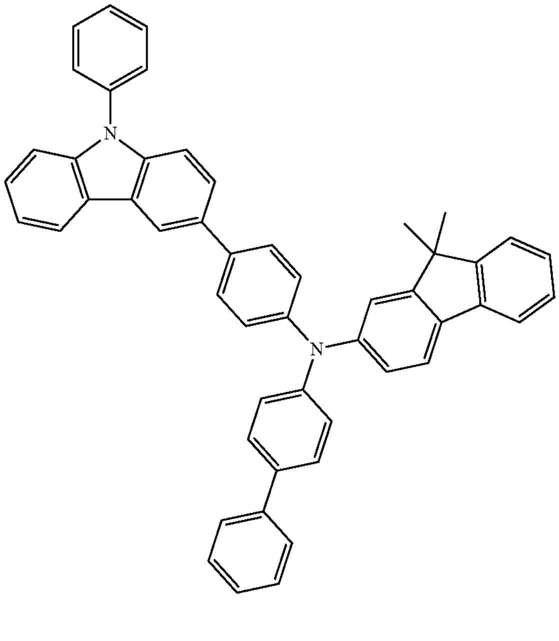

86
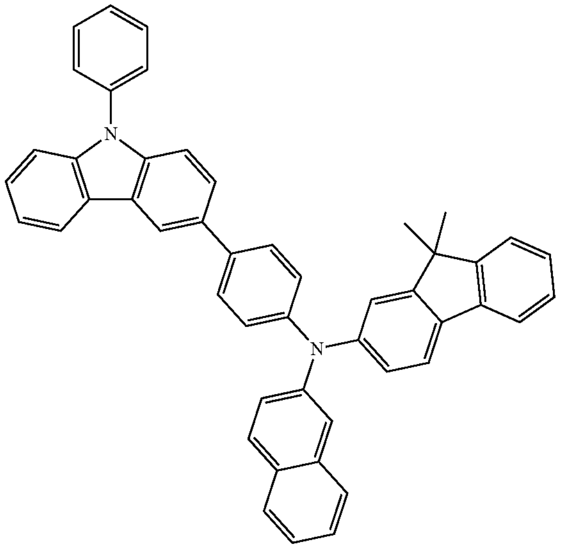
88
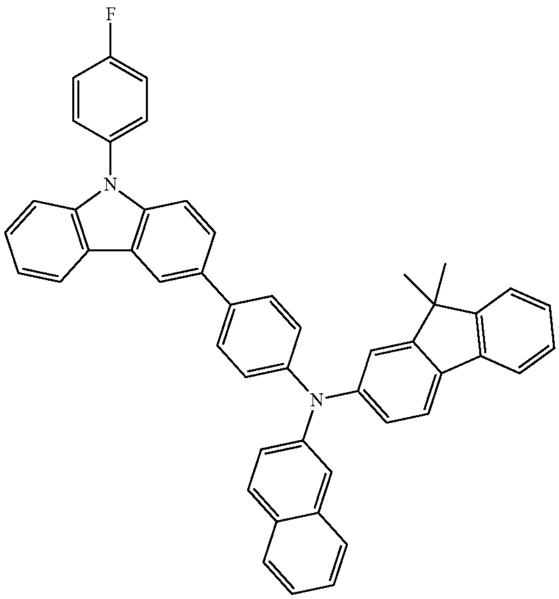
87
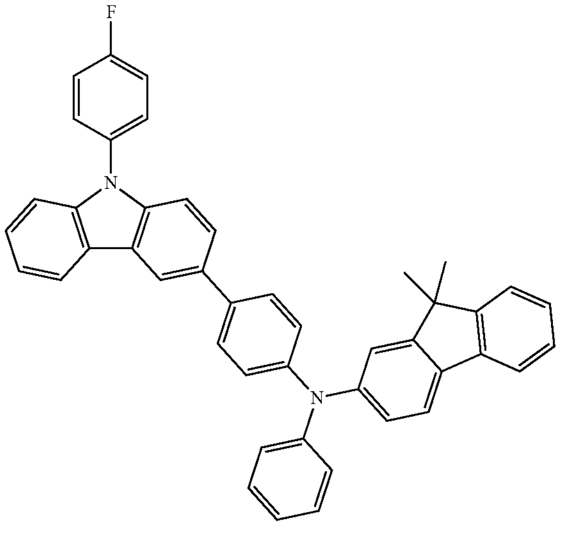
89
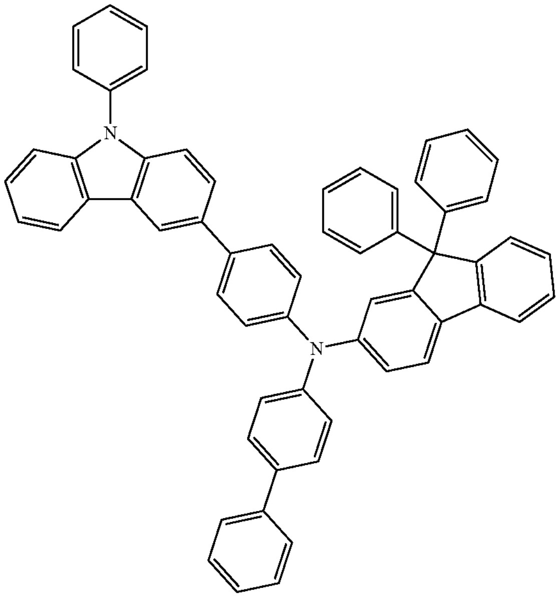

90
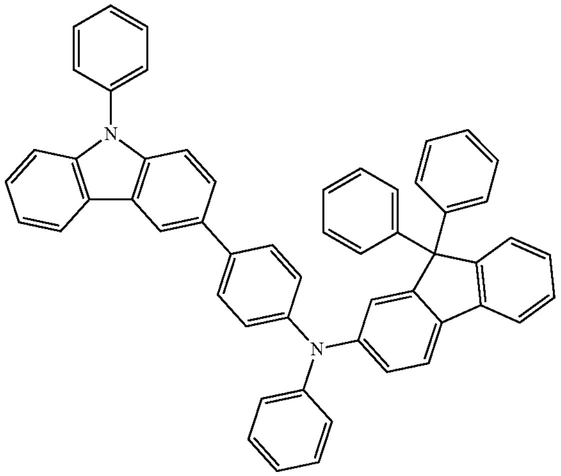
91
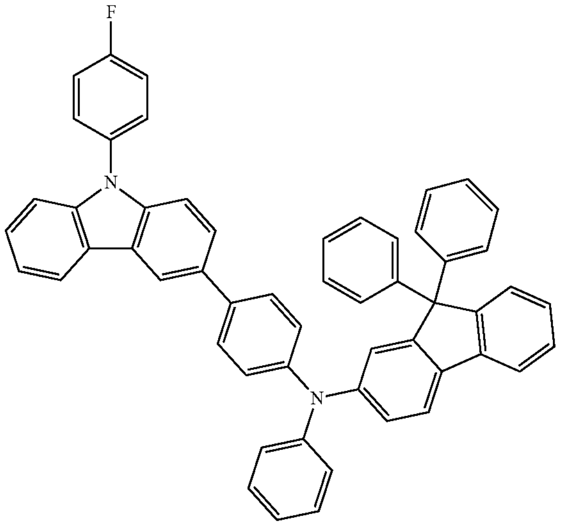
92
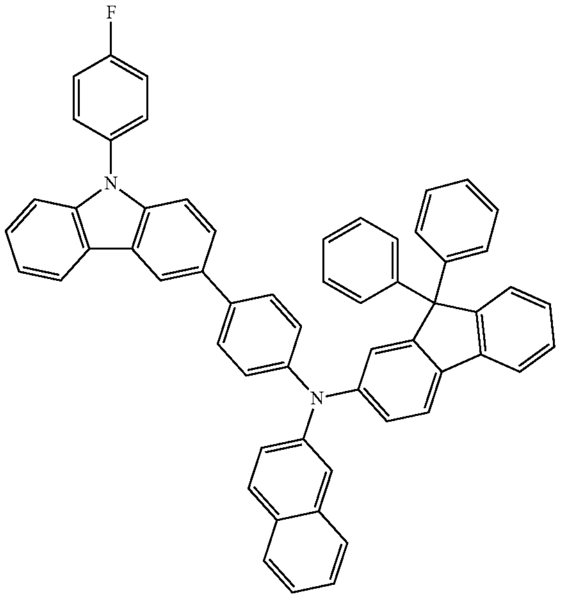
93
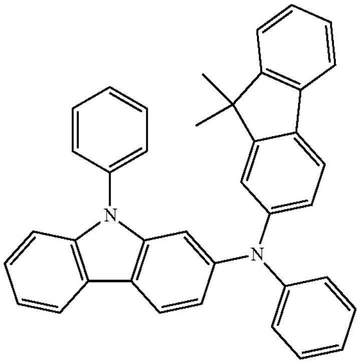
94
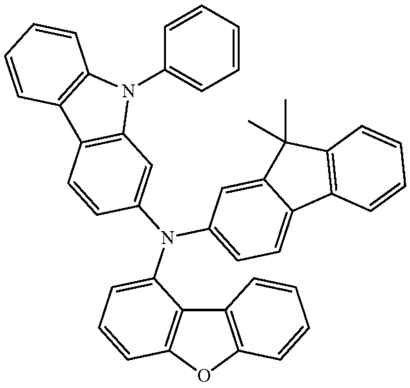
95
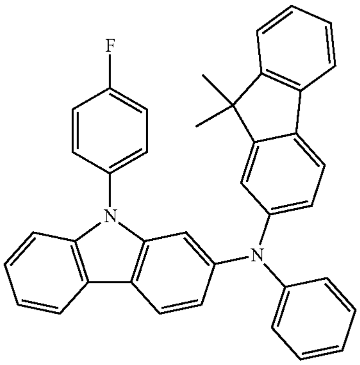
96
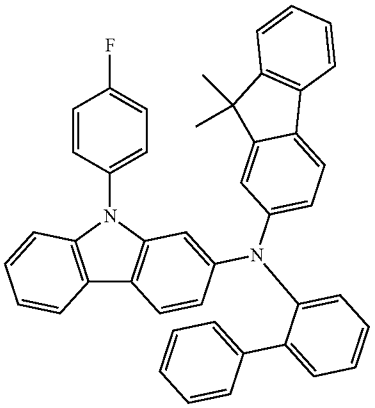

-continued
97
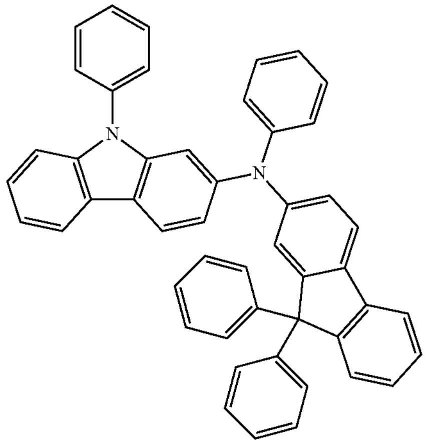
98
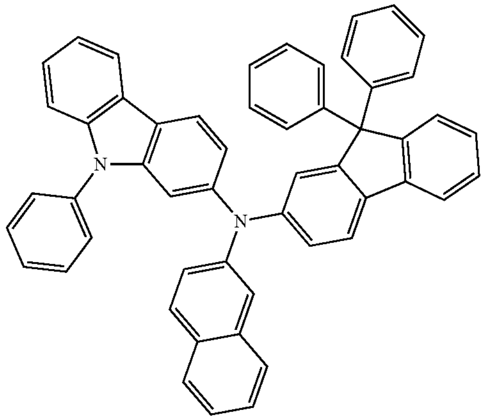
99
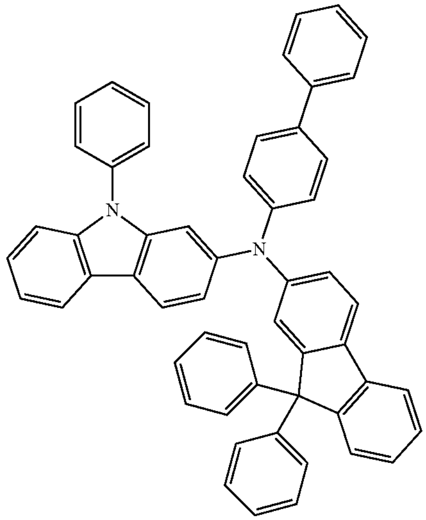
-continued
100
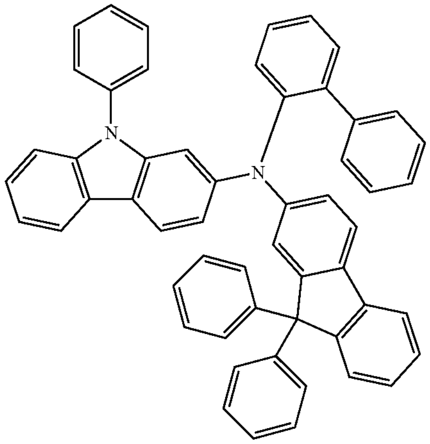
101
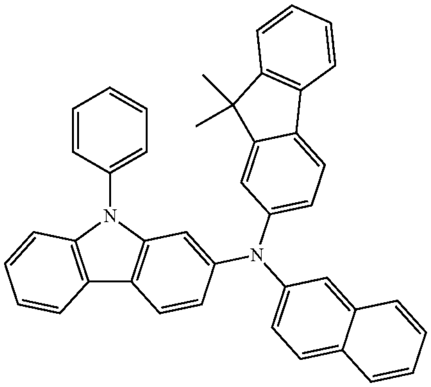
102
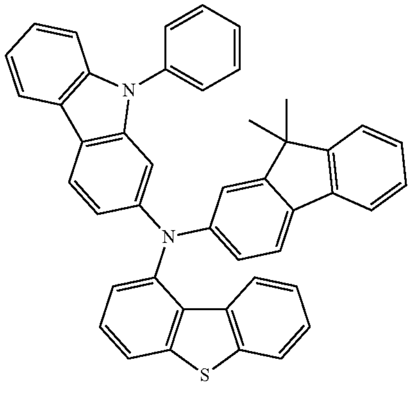

-continued
103
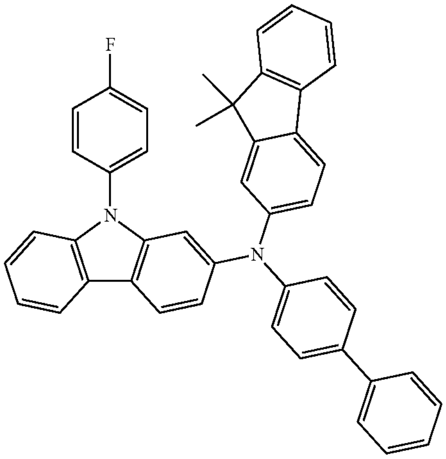
104
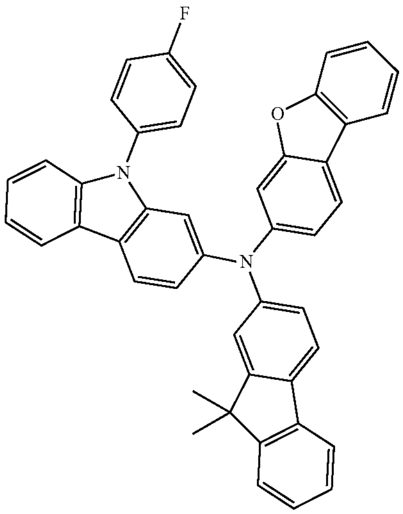
105
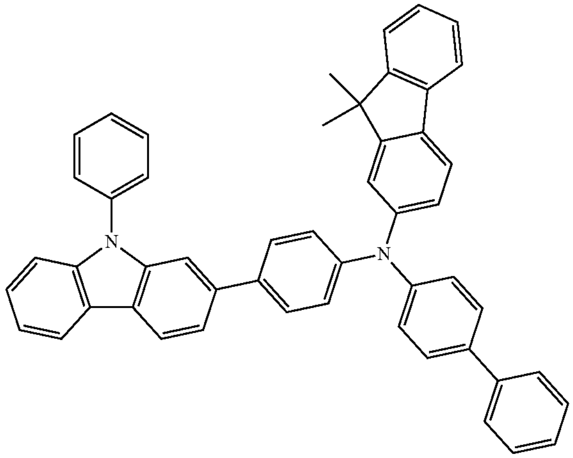
-continued
106
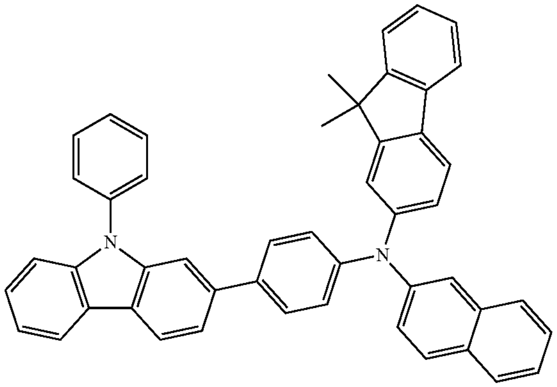
107
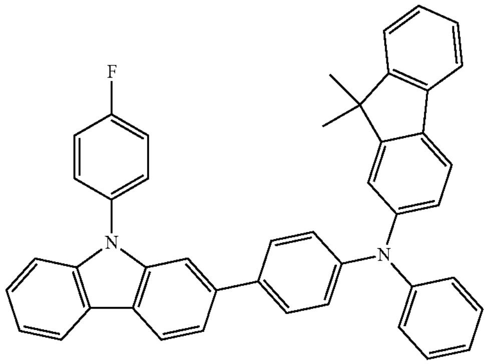
108
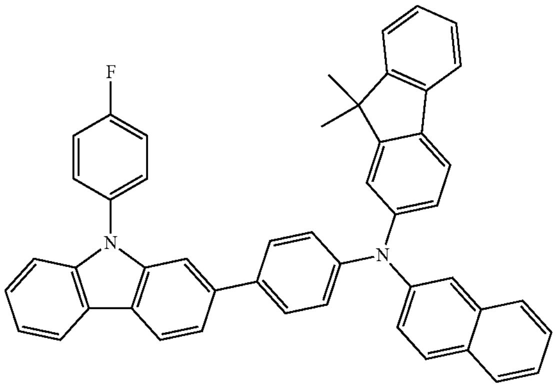

-continued
109
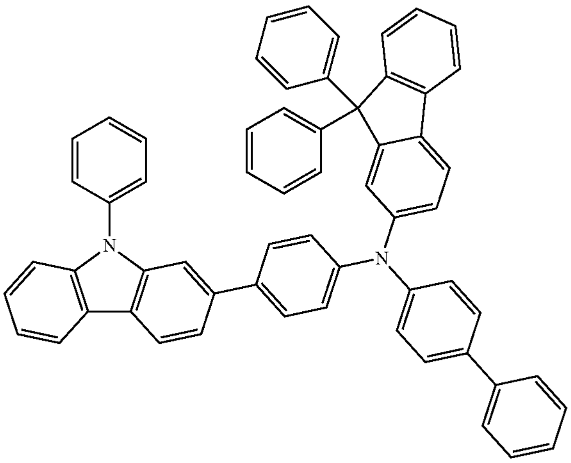
110
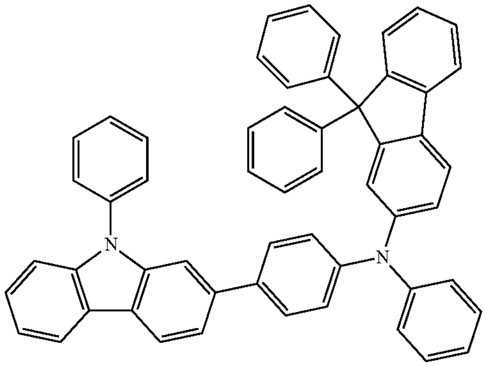
111
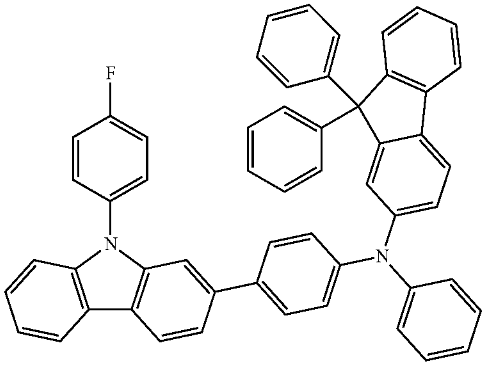
112
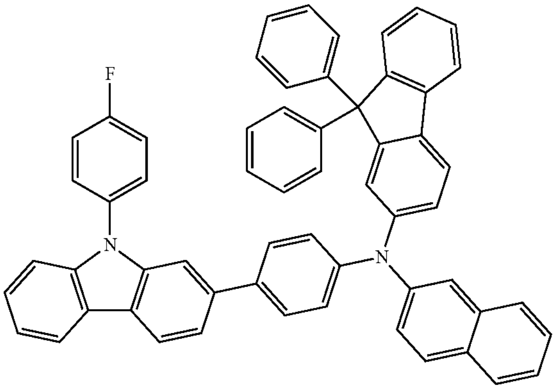
-continued
113
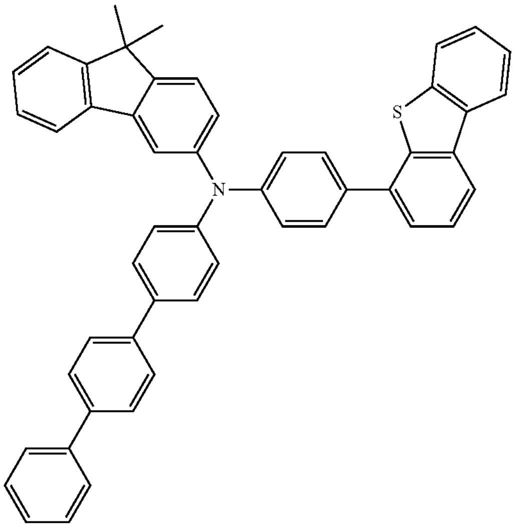
114
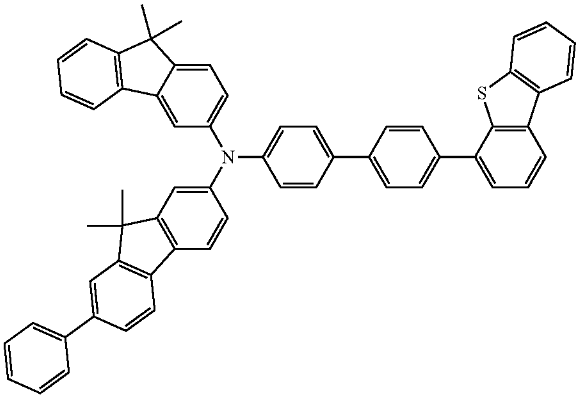
115
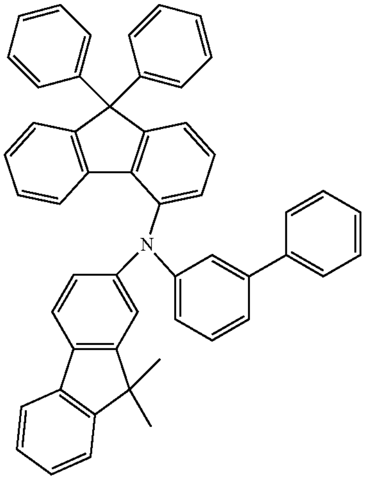

-continued

116

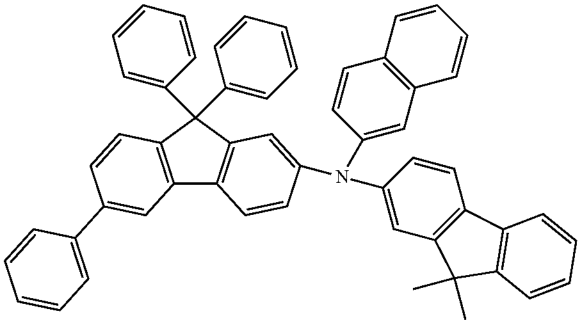

117

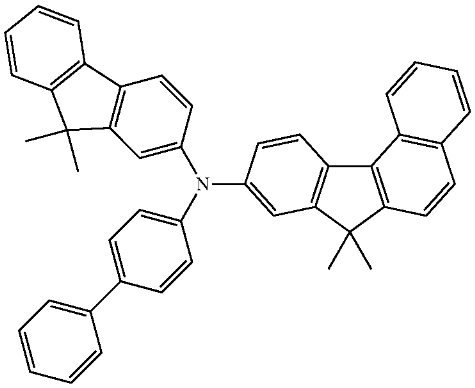

118

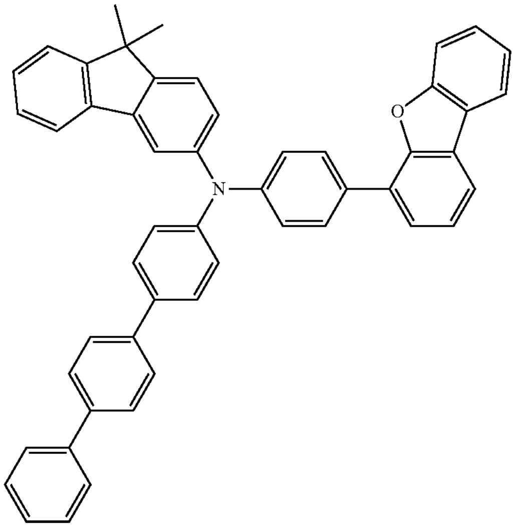

-continued

119

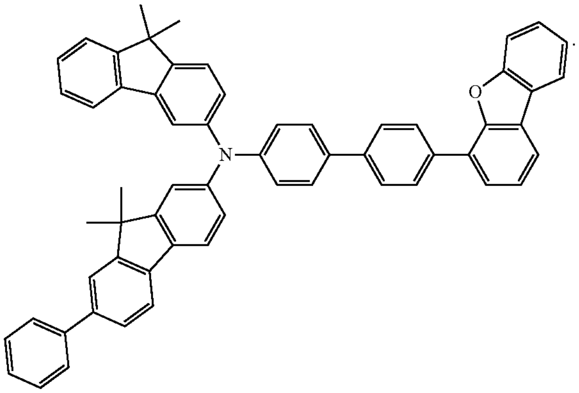

22. A display device comprising:

a plurality of light emitting elements, wherein the plurality of light emitting elements each include:

a first electrode;

a hole transport region disposed on the first electrode;

an emission layer disposed on the hole transport region;

an electron transport region disposed on the emission layer; and a second electrode disposed on the electron transport region, the hole transport region includes:

a first hole transport layer disposed adjacent to the first electrode and including a first amine compound having a first refractive index;

a second hole transport layer disposed between the first hole transport layer and the emission layer, and including a second amine compound having a second refractive index greater than the first refractive index; and a third hole transport layer disposed between the second hole transport layer and the emission layer, and including a third amine compound having a third refractive index less than the second refractive index, and the first amine compound and the third amine compound are each independently a compound represented by Formula 1:

[Formula 1]

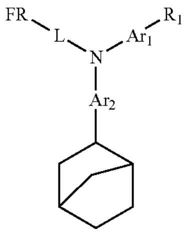

wherein in Formula 1, $R_1$ is a substituted or unsubstituted adamantyl group, a substituted or unsubstituted cyclohexyl group, or a substituted or unsubstituted bicycloheptyl group, $Ar_1$ and $Ar_2$ are each independently a substituted or unsubstituted arylene group having 6 to 30 ring-forming carbon atoms, L is a direct linkage, a substituted or unsubstituted arylene group having 6 to 30 ring-forming carbon atoms, or a substituted or unsubstituted heteroarylene group having 2 to 30 ring-forming carbon atoms, and FR is a group represented by Formula 2:

[Formula 2]

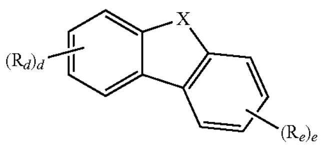

wherein in Formula 2,

X is $C(R_a)(R_b)$, N, $N(R_c)$, O, or S, $R_a$ to $R_c$ are each independently a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring, d and e are each independently an integer from 0 to 4, and $R_d$ and $R_e$ are each independently a hydrogen atom, a deuterium atom, a halogen atom, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring.

23. The display device of claim 22, wherein the first refractive index and the third refractive index are each independently in a range of about 1.3 to about 1.8, and the second refractive index is in a range of about 1.8 to about 2.4.

24. The display device of claim 23, wherein a difference between the second refractive index and the first refractive index is in a range of about 0.1 to about 1.1, and a difference between the second refractive index and the third refractive index is in a range of about 0.1 to about 1.1.

25. The display device of claim 22, wherein the plurality of light emitting elements comprise:

a first light emitting element including a first emission layer emitting light of a first wavelength;

a second light emitting element emitting light of a second wavelength different from the first wavelength and including a second emission layer spaced apart from the first emission layer in a plan view; and a third light emitting element emitting light of a third wavelength different from the first wavelength and the second wavelength, and including a third emission layer spaced apart from the first emission layer and the second emission layer in a plan view.

26. The display device of claim 25, wherein at least one emission layer of the first to third emission layers comprises a polycyclic compound represented by Formula F-c:

[Formula F-c]

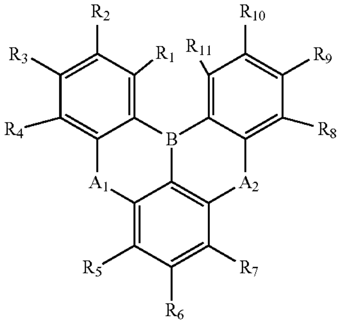

wherein in Formula F-c, $A_1$ and $A_2$ are each independently O, S, Se, or $N(R_m)$, $R_m$ is a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and $R_1$ to $R_{11}$ are each independently a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring.

27. The display device of claim 25, wherein the first wavelength is longer than the second wavelength, the second wavelength is longer than the third wavelength, the display device further comprises:

a first resonance auxiliary layer disposed between the first emission layer and the hole transport region;

a second resonance auxiliary layer disposed between the second emission layer and the hole transport region and having a smaller thickness than the first resonance auxiliary layer; and a third resonance auxiliary layer disposed between the third emission layer and the hole transport region and having a smaller thickness than the second resonance auxiliary layer.

28. The display device of claim 22, wherein the first electrode is a reflective electrode, and the second electrode is a transflective electrode or a transmissive electrode.

* * * * *